Figure 2A:
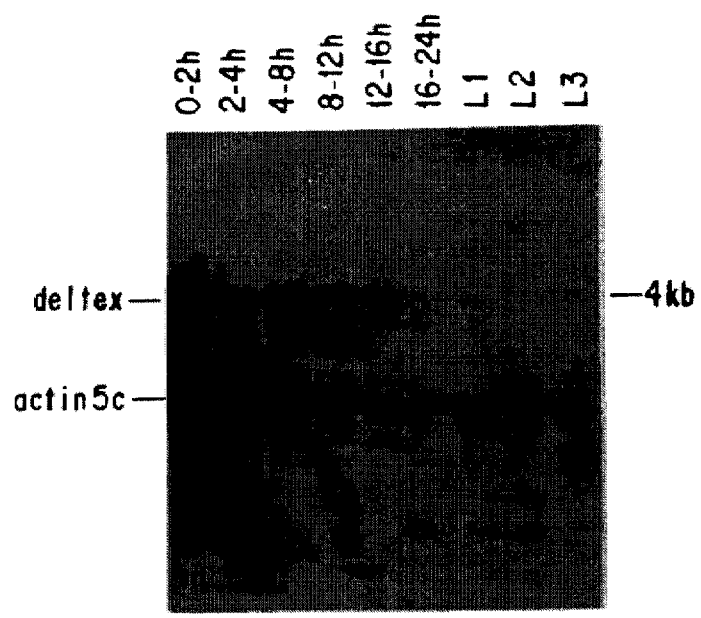

United States Patent [19]
Artavanis-Tsakonas et al.

[11] Patent Number: 5,750,652
[45] Date of Patent: May 12, 1998

[54] DELTEX PROTEINS

[75] Inventors: Spyridon Artavanis-Tsakonas, Hamden, Conn.; Isabelle Busseau, Bures-Sur-Yvette, France; Robert J. Diederich, New Haven, Conn.; Tian Xu, Guilford, Conn.; Kenji Matsuno, New Haven, Conn.

[73] Assignee: Yale University, New Haven, Conn.

[21] Appl. No.: 185,432

[22] Filed: Jan. 21, 1994

[51] Int. Cl.$^6$ .................................................. C07K 14/705
[52] U.S. Cl. ...................... 530/350; 530/300; 530/326; 530/328; 514/2; 930/10
[58] Field of Search .............................. 530/350, 326, 530/328; 930/10; 514/2

[56] References Cited

FOREIGN PATENT DOCUMENTS

WO 89/12690  12/1989  WIPO.
WO 92/19734  11/1992  WIPO.
WO 92/19737  11/1992  WIPO.

OTHER PUBLICATIONS

Duboule et al "DNA Sequences Homologous to the *Drosophila* Opa Repeat . . . " *Mol. Cell. Biol.* 7(5):2003–2006 (May 1987).

Peterson et al "Functional Domains and Upstream Activation Properties of Cloned Human TATA Binding Protein", *Science* 248:1625–1630 (Jun. 1990).

Karson et al., 1992, "Prospect for human gene therapy," J. Reproductive Medicine 37(6):508–514.

Roemer and Friedmann, 1992, "Concepts and strategies for human gene therapy," Eur. J. Biochem. 208:211–225.

Uhlmann and Peyman, 1990, "Antisense oligonucleotides: a new therapeutic principle" Chemical Reviews 90(4):544–584.

Artavanis–Tsakonas and Simpson, 1991, "Choosing a cell fate: a view from the Notch locus," Trends Genet. 7:403–408.

Artavanis–Tsakonas et al., 1991, "The Notch locus and the cell biology of neuroblast segregation," Ann. Rev. Cell Biol. 7:427–452.

Bennett, 1992, J. Biol. Chem. "Adaptors between diverse plasma membrane proteins and the cytoplasm," 267:8703–8706.

Blank et al., 1992, "NF–κB and related proteins: rel/dorsal homologies meet ankyrin–like repeats," Trends Biochem. Sci. 17:135–140.

Breeden and Nasmyth, 1987, "Similarity between cell–cycle genes of budding yeast and fisson yeast and the Notch1 gene of Drosophila, "Nature 329:651–654.

Bunch et al., 1988, "Characterization and use of the Drosophila metallothionein promoter in cultured *Drosophila melanogaster* cells,", Nucl. Acids Res. 16:1043–1061.

Burns et al., 1984, "Isolation and characterization of cloned DNA sequences containing ribosomal protein genes of *Drosophila melanogaster*, " Mol. Cell. Biol. 4:2643–4652.

Cagan and Ready, "Notch is required for successive cell decisions in the developing Drosophilaretina," Genes Dev. 3:1099–1112.

Chirgwin et al. 1979, "Isolation of biologically active ribonucleic acid from sources enriched in ribonuclease." Biochemisty 18:5294–5299.

Coffman et al., 1990, "Xotch, the Xenopus homolog of Drosophila notch," Science 249:1438–1441.

Coffman et al. 1993, "Expression of an extracellular deletion of Xotch diverts cell fate in Xenopus embryos," Cell 73:659–671.

Delidakis et al., 1991, "Two genetically and molecularly distinct functions involved in early neurogenesis reside with the Enhancer of split locus of *Drosophila melanogaster*, " Genetics 129:803–823.

Demerec et al., 11942, "The gene," Yearbook–Carnegie Institution 41:190–199.

Ellisen et al. 1991, "*TAN–1*, the human homolog of the Drosophila Notch gene, is broken by chromosomal translocations in T lymphoblastic neoplasms," Cell 66:649–661.

Fehon et al., 1990, "Molecular interactions between the protein products of the neurogenic loci Notch and Delta, two EGF–homologous genes in Drosophila," Cell 61:523–534.

Fehon et al., 1991, "Complex cellular and subcellular regulation of Notch expression during embryonic and imaginal development of Drosophila: implications for Notch function," J. Cell Biol. 113:657–669.

Feinberg and Vogelstein, 1984, "A technique for radiolabeling DNA restriction endonuclease fragments to high specific activity," Anal. Biochem. 137:266–267.

Fortini and Artavanis–Tsakonas, 1993, "Notch: neurogensis is only part of the picture," Cell 75:1245–1247.

Fortini et al, 1993, "An activated Notch receptor blocks cell–fate commitment in the developing Drosophila eye," Nature 365:555–557.

Foster, 1975, "Negative complementation at the Notch locus of *Drosophila melanogaster*, " Genetics 81:99–120.

Franco del Amo et al., 1992, "Expression pattern of Motch, a mouse homolog of *Drosophila Notch*, suggests an important role in early postimplantation mouse development," Development 115:737–744.

(List continued on next page.)

*Primary Examiner*—Stephen Walsh
*Assistant Examiner*—Kenneth A. Sorensen
*Attorney, Agent, or Firm*—Pennie & Edmonds LLP

[57] ABSTRACT

The present invention relates to amino acid sequences of the encoded deltex protein. The invention further relates to fragments and other derivatives, and analogs, of deltex proteins. In specific embodiments, the invention relates to deltex protein derivatives and analogs of the invention which are functionally active, or which comprise one or more domains of a deltex protein, including but not limited to the Gln-rich clusters, SH3 binding domains, domains which mediate binding to Notch or to a Notch derivative containing Notch cdc10/SW16/ankyrin ("ANK") repeats, domains which mediate binding to a second deltex protein, or any combination of the foregoing. The present invention also relates to compositions based on deltex proteins.

27 Claims, 40 Drawing Sheets

OTHER PUBLICATIONS

Franco del Amo et al., 1993, "Cloning, analysis, and chromosomal localization of Notch-1, a mouse homolog of Drosophila Notch," Genomics 15:259–264.

Frischauf et al., 1983, "Lambda replacement vectors carrying polylinker sequences," J. Biol. 170:827–842.

Geiser et al., 1992, "cactus, a gene involved in dorsoventral pattern formation of Drosophila, is related to the IKB gene family of vertebrates," Cell 71:613–621.

Gietz et al., "Improved method for high efficiency transformation of intact yeast cells," Nucl. Acids Res. 20:1425.

Golubovsky, 1983, "Recessive sex–linked female–specific lethals at deltex locus discovered in natural populations of D. melanogaster," Dros. Inf. Ser. 59:42–43.

Gorman and Girton, 1992, "A genetic analysis of deltex and its interaction with the Notch locus in Drosophila melanogaster," Genetics 131:99–112.

Hartley et al., 1987, "The embryonic expression of the Notch locus of Drosophila melanogaster and the implications of point mutations in the extracellular EGF–like domain of the predicted protein," EMBO J. 6:3407–3417.

Hartley et al., 1988, "A deduced gene product from the Drosophila neurogenic locus, Enhancer of split, shows homology to mammalian G–protein β subunit," Cell 55:785–795.

Heitzler and Simpson, 1991, "The choice of cell fate in the epidermis of Drosophila," Cell 64:1083–1092.

Heitzler and Simpson, 1993, "Altered epidermal growth factor–like sequences provide evidence for a role of Notch as a receptor in cell fate decisions," Development 117:1113–1123.

Hultmark et al., 1986, "Translational and transcriptional control elements in the untranslated leader of the heat–shock gene hsp22," Cell 44:429–438.

Kelley et al., 1987, "Mutations altering the structure of epidermal growth factor–like coding sequences at the Drosophila Notch locus," Cell 51:539–548.

Kidd et al., 1986, "Sequence of the Notch locus of Drosophila melanogaster: relationship of the encoded protein to mammalian clotting and growth factors," Mol. Cell. Biol. 6:3094–3108.

Kidd, 1992, "Characterization of the Drosophila cactus locus and analysis of interactions between cactus and dorsal proteins," Cell 71:623–635.

Klambt et al., 1989, "Closely related transcripts encoded by the neurogenic gene complex Enhancer of split of Drosophila melanogaster," EMBO J. 8:203–210.

Knust et al., 1987, "Molecular analysis of the neurogenic locus Enhancer of split of Drosophila melanogaster," EMBO J. 6:4113–4123.

Koch et al., 1991, "SH2 and SH3 domains: elements that control interactions of cytoplasmic signaling proteins," Science 252:668–674.

Kodoyianni et al., 1992, "Molecular basis of loss–of–function mutations in the glp-1 gene of Caenorhabitis elegans," Molec. Biol. Cell 3:1199–1213.

Kongsuwan et al., 1985, "A Drosophila Minute gene encodes a ribosomal protein," Nature 317:555–558.

Kopan and Weintraub, 1993, "Mouse Notch: expression in hair follicles correlates with cell fate determination," J. Cell Biol. 121:631–641.

LaMarco et al., 1991, "Identification of Ets–and Notch–related subunits in GA binding protein," Science 253:789–792.

Lefevre, 1974, "The one–band gene hypothesis: evidence from a cytogenetic analysis of mutant and nonmutant rearrangement breakpoints in Drosophila melanogaster," Cold Spring Harbor Symp. Quant. Biol. 38:591–599.

Lux et al., 1990, "Analysis of cDNa for human erythrocyte ankyrin indicates a repeated structure with homology to tissue–differentiation and cell–cycle control proteins," Nature 344:36–42.

Maine et al., 1985, "The sex–lethal gene of Drosophila: DNA alterations associated with sex–specific letal mutations," Cell 43:521–529.

McGinnis et al., 1984, "A conserved DNA sequence in homoeotic genes of the Drosophila antennapedia and bithorax complexes," Nature 308:428–433.

Michaely and Bennett, 1992, "The ANK repeat: a ubiquitous motif involved in macromolecular recognition," Trends Cell Biol. 2:127–129.

Morgan et al., "The constitution of the germinal material in relation to heredity," Year book—Carnegie Institution 30:408–415.

Oliver et al., 1993, "A Drosophila SH2–SH3 adaptor protein implicatred in coupling the sevenless tyrosine kinase to an activator of Ras guanine nucleotide exchange, Sos," Cell 73:179–191.

Palka et al., 1990, "Neurogenic and antineurogenic effects from modifications at the Notch locus," Development 109:167–175.

Pawson and Gish, 1992, "SH2 and SH3 domains: from structure to function," Cell 71:359–362.

Poole et al., 1985, "The engrailed Locus of Drosophila: structural analysis of an embryonic transcript," Cell 40:37–43.

Preiss et al., 1988, "The molecular genetics of Enhancer of split, a gene required for embryonic neural development in Drosophila," EMBO J. 7:3917–3927.

Rebay et al., 1991, "Specific EGF repeats of Notch mediated interactions with Delta and Serrate: implications for Notch as a multifunctional receptor," Cell 67:687–699.

Rebay et al., 1993, "Specific truncations of Drosophila Notch define dominant activated and dominant negative forms of the receptor," Cell 74:319–329.

Ren et al., 1993, "Identification of a ten–amino acid proline–rich SH3 binding site," Science 259:1157–1161.

Robbins et al., 1992, "Mouse mammary tumor gene int-3: a member of the notch gene family transforms mammary epithelial cells," J. Virol. 66:2594–2599.

Schneider, 1972, "Cell lines derived from late embryonic stages of Drosophula melanogaster," J. Embryol. Exp. Morph. 27:353–365.

Simon et al., 1993, "An SH3–SH2–SH3 protein is required for $p21^{Ras1}$ activation and binds to sevenless and Sos proteins in vitro," Cell 73:169–177.

Smith and Johnson, 1988, "Single–step purification of polypeptides expressed in Escherichia coli as fusions with glutathione S–transferase," Gene 67:31–40.

Smoller et al., 1990, "The Drosophila neurogenic locus mastermind encodes a nuclear protein unusually rich in amino acid homopolymers," Genes Dev. 4:1688–1700.

Sprading, 1986, "P element–mediated transformation,"in Glover, D.M. (ed.), Drosophila A Practical Approach, IRL Press, Oxford, pp. 175–197.

Stephenson and Mahowald, 1987, "Isolation of Drosophila clones encoding maternally restricted RNAs," Dev. Biol. 124:1–8.

Stifani et al., 1992, "Human homologs of a Drosophila Enhancer of split gene product define a novel family of nuclear proteins," Nature Genetics 2:119–127.

Struhl et al., 1993, "Intrinsic activity of the Lin–12 and Notch intracellular domains in vivo," Cell 74:331–345.

Tamkun et al., 1992, "brahma: a regulator of Drosophila homeotic genes structurally related to the yeast transcriptional activator SNF2/SW12," Cell 68:561–572.

Thummel and Pirrotta, 1991, "New pCaSpeR P element vectors," Dros. Info. Svc. 71:150.

Weinmaster et al., 1991, "A homolog of Drosophila Notch expressed during mammalian development," Development 113:199–205.

Weinmaster et al., 1992, "Notch2: a second mammalian Notch gene," Development 116:931–941.

Wharton et al., 1985, "Opa: a novel family of transcribed repeats shared by the Notch locus amd other developmentally regulated loci in D. melanogaster," Cell 40:55–62.

Wharton et al., 1985, "Nucleotide sequence from the neurogenic locus Notch implies a gene product that shares homology with proteins containing EGF–like repeats," Cell 43:567–581.

Xu et al., 1990, "The Notch Locus and the genetic circuitry involved in early Drosophila neurogenesis," Genes Dev. 4:464–475.

Xu and Artavanis–Tsakonas, 1990, "deltex, a locus interacting with the interacting with the neurogenic genes, Notch, Dalta and mastermind in Drosophila melanogaster," Genetics 126:665–677.

Xu et al., 1992, "The involvement of the Notch locus in Drosophila oogenesis," Development 115:913–922.

Zervos et al., 1993, "Mxi1, a protein that specifically interacts with Max to bind Myc–Max recognition sites," Cell 72:223–232.

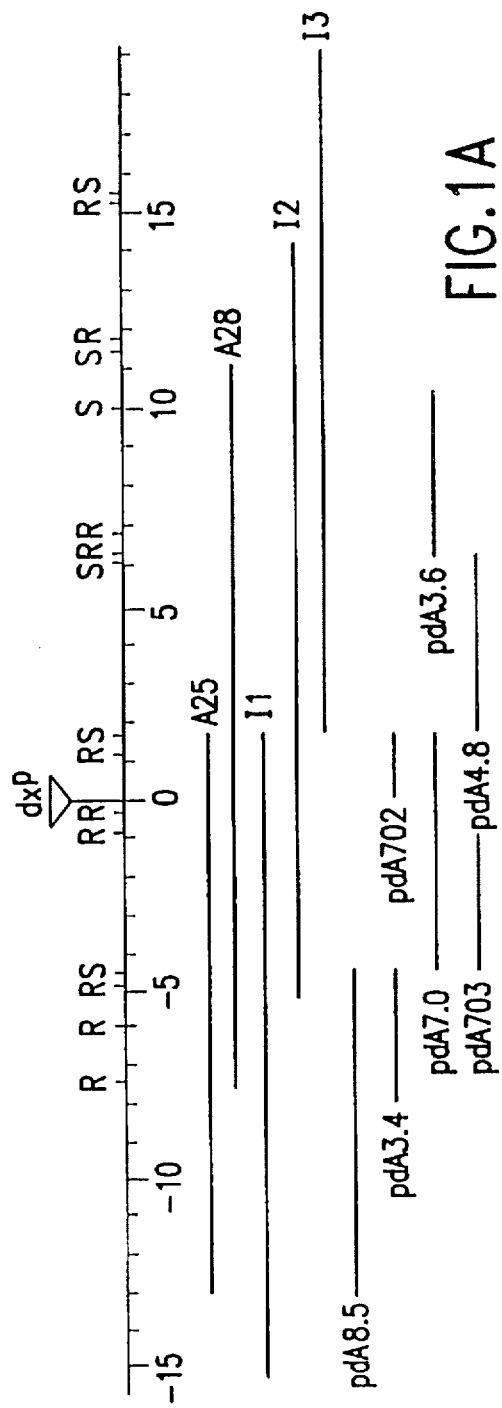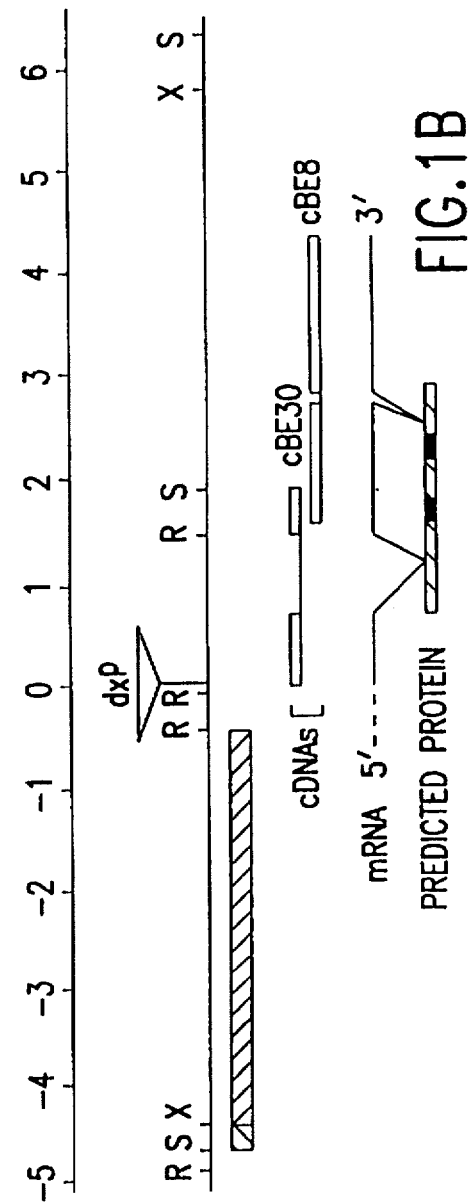

FIG.3A tttcaaaatttccatctttacaacatcaaaatggacaaaaaaatttaatttcactttgtaaaagtttgaatgatgcaggaatttccgctttgaaataaagctagaaatcagtcga cttaaatcgctggagtttggctgagttatgtattatgtatcaaatttagggctatataaatgtattcttcttgcacaaatccaactgcaactgatattctagcttcaatcata gatgtaacttaacctattcctactccttgcaggGCCAACAAACCTGGACCTGTGCAACACATCGGGCTACCCTGCCTGTGTCAACACCATTAATTTTGCAATCTCACCCACGTGCGCAACCC 191
                                                G  E  Q  T  L  D  L  C  N  T  H  I  G  L  P  Y  T  I  N  F  C  N  L  T  H  V  R  Q  P 927  AGCGGACCATGCCAGCATTCGGGTACCCAACAGGCCCGTATCCCTTGGTGAAACTAACGCCAACAGGCCAACAACTCAAGTCGAATTCCGCCAGCGTGACGCAGCCAGTACAAC 231
      S  G  P  M  R  S  I  R  R  T  Q  Q  A  P  Y  P  L  V  K  L  T  P  Q  A  N  Q  L  K  S  N  A  S  V  S  S  Q  Y  N 1047 ACTCTACCCAAACTGGCCACACACCAGAGCCTGCACAGAGTGCCCATGACCAGGCAACAACAGCAGCAACATGCCAACAAGTCACGCAGCAGCAGCAGTCAGCTCCAGCATCAACAG 271
      T  L  P  K  L  G  D  T  K  S  L  H  R  V  P  M  T  R  Q  Q  H  P  L  P  T  S  H  Q  V  Q  Q  Q  Q  L  Q  Q  Q 1167 CACCAGCAGCAACATCACCAGCAGCAACATCAGCAACAACAGCAGCAACATCAGATCCAGCACCATCAGATCATCAGAACGGCGCCAGGAAGCCCCCAAGAAC 311
      Q  Q  Q  Q  X  X  X  Q  X  Q  Q  Q  X  Q  Q  Q  Q  X  Q  X  X  Q  I  X  X  Q  T  A  P  R  K  P  P  K  K 1287 CACACCAGACGATCCACCACCAATCTACGCCAGATACTCAACAACATCTTCAGCAGCAGCACTAAGCAGCAGCACTGAACATGTCGACGGCGCCAGTGCCAGTCATCCTCCTCA 351
      H  S  E  I  S  T  T  N  L  R  Q  I  L  N  N  L  N  I  F  S  S  S  T  K  H  Q  S  N  M  S  T  A  A  S  S  S  S  S 1407 TCGGCCTGCTGCTGCACCATGCCAACCATCGTGTGGCCATGCCCACTTTTGCGCACGCCAAGAACAACATGTGACTGCCTCGATGAACACAGTCATCATATGCTGCCTCCGAGGCATCGCTCCTGCAGTCG 391
      S  A  S  L  H  H  A  N  H  L  S  H  A  H  F  S  H  A  K  N  M  L  T  A  S  M  N  S  H  H  S  R  C  S  E  G  S  L  Q  S 1527 CAAAGCAGCAGCGGGATGGGCTCGCATCGCTCCAGATCGTCCAGAATCGTCCAGAGTCGAACCGGACACGGACACTCGGACACTCGAAATCCATCGGCGGAGACCCAGTGTGACACCGTGTCCACTTAC 431
      Q  R  S  S  R  M  G  S  H  R  R  S  R  T  R  T  S  D  T  D  T  N  S  V  K  S  H  R  R  R  P  S  V  D  T  V  S  T  Y

FIG.3B

1647 CTCAGCCACGAGGAGCAAGGAGACCCTGCCAGCAGGAACCTGCCATTTGCCGTCAATGATCCTGCTGGACTGCTCGCTTGGCACCGATGAAGTTTTTGTGCCCTCCTGCCCCATGTCG 471
L S H E S K E S L R S R N F A I S V N D L L D C S L G S D E V F V P S V P P S S

1767 CTGGGCGAAAGGGCCCCGGTGCCCCGGCCCCATTACCACTGCCCGCACAGCAGCAACAGCAGCAACAGCAGCAGCAACAGGCCAGCAGCAGCAG 511
L G E R A P V P P P L P L H P R Q Q Q Q Q Q Q Q Q L X Q Q Q Q X Q Q Q Q Q Q Q

1887 CAGCAATCAATCCCGGTTCGATTGTGGGCGTGGACCCTGCCAGCGACATGATATCGGCGTTTGTCAAGGTGGTGGAGCCACCCCTGTGGCCCAATGCCCAGCCCTGTCCCATGTGCATG 551
Q Q S I A G S I V G V D P A S D M I S R F V K V V E P P L W P N A Q P C P M C M

2007 GAGGAGCTGGTGCACTCGGCCCAGAATCCGGCCATTTCGCTGAGTCTCCGCAGCATCTCATGCATGCATCTGCAGCTCAATGGGATGATAATTGCCCAGCAAAACGAAATGAACAAGAAC 591
E E L V H S A Q N P A I S L S R C Q H L M H L Q C L N G M I I A Q Q N E M N K N

2127 CTTTTCATCGAGTGCCCTGTATGCGGGATCGTTTACGGGGAGAAGGTCGGCAATGGGCAGCCCATTGGCAGCATGTCGTGGAGCATAATTAGCAAGAATCTGCCAGGACACGAGGGTCAGAAC 631
L F I E C P V C G I V Y G E K V G N G Q P I G S M S W S I I S K N L P G H E G Q N

2247 ACCATACAGATTGTTTACGAgtaagtgtgaatgtgcctgtggccactggcaatcaactataatcactctttttcattgcatggcagCATTGCATCGGGACTGCAGACGGAGGACCATC
T I Q I V Y D                                                                I A S G L Q T E E H P 649

2299 CGGCATCCAGGTCGTGCCTCCTGTTCCCGCGGCATCGTCCTACTGCCGGACTGCCTTCCTCAAGATTGCATTGCGGTTCCTCCGGCTCTGCTTT 689
H P G R A F F A V G F P P R I C Y L P D C P L G R K V L R F L K I A F D R R L L F

2419 TCTCGATGGACCATCGGTGACCACCGGCGAGGACGTGGTCATCTGGAACAGTGTGGATCACAAGACCCAGTTCAATATGTTTCCGGATCCCACCTATTTGCAGCGGACCAACATGCAAC 729
S I G R S V T T G R E D V V I W N S V D H K T Q F N M F P D P T Y L Q R T M Q Q

FIG.3C

FIG.3D

```
2539  AGCTGGTGCACCTGGGCGTGACGGATTAAGGATTAGTTCCCTGTCCCCAAGTAGAACTACCAACCACCGAGTCCCCTGATCATTCTCTTCCATTCGTC
         L  V  H  L  G  V  T  D                                                                            737

2659  GTTAAGTTACTTCTACATAATCTCAGTGTGTGTCCAATCCTCGTTTACTATGATATATTTTTTTATAGATATATTGTAATAGCCGTTCGAGCTGCTCGAACCCTAAAACAACAGCAAAC

2779  CACAATTGCAATTGTAGCTTCCTTCCGCTCTCCAATTCGTATTGTACCCACATAAGTTGGCCTACATACATATGTATTAGCTAGTAGTTAGTTAGTTGTAGC

2899  TGTAGTTCCCAAGAGAATCTTGACCAAGACACCTACTAGTATTAGGCATTATCCTGATTCCTGATTCGATTCAACCCAAGCCAGCCATTCAGTGCAAGCTGTGCC

3019  AAAATCGTAGCCTCCCGTTTATAGGATATGTATATGTGATATAGCTACGTATAACCATTGCCCATCTCTCCGTTTCGAATTGTCTCTTTCATCAGATCCATGTGAA

3139  TTTTCTTTATATCGGATTTATATAGGATTAAAATAGTATTTTGAGAGGAAATGGGTAAATTCGATAGACTGTCTCACTGTCTGTCTGTTAATCTCTTCATTCAGCCA

3259  ATTTGATGTGATTTAATTGAATTATTCATTATTATTAAACGGAGCATTACGAAGCCATAGTGTAACGCATAATCCAGCCAGATATCCATTACCGATACATATCATATATATACACATATAC

3379  ATAAACATATATTTAACATAGCCCCATAGGCCATATAACAATATAATTTTTTTTATCGAATCCCTTGCATACATTTGATGAATTGTTGCTTTCATATTGATATCATCGAGCATCGAACG

3499  AACTATCGTATACATCGCCATATGTCCCATATATTAGCATATATTCGAGATCGTACTGACTGACCCGCCACCATATTTGATATGATATGATATGATTTACT

3619  AAGTTGTATTTAGCCACTCGATTAGTTATTAAAGTTCATTTGACGAATATTCCAACACAAATTCCACACCATTTCTGTATGCATATTACCGCATATATAATACAGTACATTTATATAGTTC

3739  AAATAAAGTAACTTTCATTCATGTTCaaattaagtcttcttttggatatttatttcactcatgtctaaaaggaaatcttcttttggactttttcacttatgtatgtatgtatgttcgaatg
      ================================
      cgttcttctttttgggacttttttcttatgc
```

| allele | Su(dx)$^{sp}$/+ | Su(dx)/+ | Su(dx)$^2$/+ |
|---|---|---|---|
| dx$^{ENU}$ | +++ | +++ | +++ |
| dx$^{SM}$ | +++ | +++ | + |
| dx | ++ | ++ | + |
| dx$^p$ | + | + | + |

FIG.5

2044
I N A A D N S G K T A L H W A A A V N N T E A V N I L L M H H A N

V

```
          10         20         30         40         50         60
           *          *          *          *          *          *
      AAATGCTAGA AAAACCGTTT TTACCATCAA ACGTGAATTC TTAAGCTGCG CCTAAACGAA
      TTTACGATCT TTTTGGCAAA AATGGTAGTT TGCACTTAAG AATTCGACGC GGATTTGCTT 70         80         90        100        110        120
           *          *          *          *          *          *
      ACCGAGTGAC TAAAGAACCA GAACGAAAAC TTCGGGAAAA TGGAAGCCAG GGAAAATCAG
      TGGCTCACTG ATTTCTTGGT CTTGCTTTTG AAGCCCTTTT ACCTTCGGTC CCTTTTAGTC 130        140        150        160        170        180
           *          *          *          *          *          *
      GGATAACTAA CGCTGGCAGC GGGTCCACCA TTTTTAATTT CTTTGTTTAT TTTGTGCCCA
      CCTATTGATT GCGACCGTCG CCCAGGTGGT AAAAATTAAA GAAACAAATA AAACACGGGT 190        200        210        220        230        240
           *          *          *          *          *          *
      TCTTCGCCAG CGAGCCAGAT AGCGCGACAG CAACAGCAAG AGAGAGCGAG AGAGAGAGTG
      AGAAGCGCTC GCTCGCTCTA TCGCGCTGTC GTTGTCGTTC TCTCTCGCTC TCTCTCTCAC 250        260        270        280        290        300
           *          *          *          *          *          *
      AGTGAGTGAG AGCTAGTGAA GAGAGCGCAG GAGGAGTTGG ATATGGAAAT GGGCATGGAT
      TCACTCACTC TCGATCACTT CTCTCGCGTC CTCCTCAACC TATACCTTTA CCCGTACCTA 310        320        330        340        350        360
           *          *          *          *          *          *
      ATGGCAATGG GCTCACTCCA CGGATAACGG ATCAACTGCA AGCAATGGCC AGCAGCGCCG
      TACCGTTACC CGAGTGAGGT GCCTATTGCC TAGTTGACGT TCGTTACCGG TCGTCGCGGC
                                                    M  A  S  S  A>

370        380        390        400        410        420
           *          *          *          *          *          *
      GAAGTGCGGC ATCCGGATCC GTTGTTCCCG GTGGCGGAGG TAGCGCCGCC TCCAGTTGTG
      CTTCACGCCG TAGGCCTAGG CAACAAGGGC CACCGCCTCC ATCGCGGCGG AGGTCAACAC
      G  S  A  A   S  G  S   V  V  P   G  G  G    S  A  A   S  S  C>

430        440        450        460        470        480
           *          *          *          *          *          *
      CCACCATGGC CCTGTCCACC GCCGGATCCG GTGGGCCGCC CGTGAACCAC GCCCACGCCG
      GGTGGTACCG GGACAGGTGG CGGCCTAGGC CACCCGGCGG GCACTTGGTG CGGGTGCGGC
      A  T  M  A   L  S  T   A  G  S   G  G  P  P   V  N  H   A  H  A>
```

FIG.12A

```
         490        500        510        520        530        540
          •    •     •    •     •    •     •    •     •    •     •    •
    TCTGCGTGTG GGAGTTCGAG TCGCGCGGCA AGTGGCTGCC CTATTCGCCG GCGGTGTCGC
    AGACGCACAC CCTCAAGCTC AGCGCGCCGT TCACCGACGG GATAAGCGGC CGCCACAGCG
      V C V   W E F    S R G     K W L     P Y S P    A V S>

550        560        570        580        590        600
          •    •     •    •     •    •     •    •     •    •     •    •
    AGCACTTGGA ACGCGCCCAC GCCAAGAAAC TGACGCGCGT CATGCTGAGC GATGCGGATC
    TCGTGAACCT TGCGCGGGTG CGGTTCTTTG ACTGCGCGCA GTACGACTCG CTACGCCTAG
      Q H L E    R A H    A K K    L T R V    M L S    D A D>

610        620        630        640        650        660
          •    •     •    •     •    •     •    •     •    •     •    •
    CCAGCCTGGA GCAGTACTAC GTCAACGTGC GCACAATGAC CCAGGAATCG GAGGCGGAAA
    GGTCGGACCT CGTCATGATG CAGTTGCACG CGTGTTACTG GGTCCTTAGC CTCCGCCTTT
      P S L E    Q Y Y    V N V    R T M T    Q E S    E A E>

670        680        690        700        710        720
          •    •     •    •     •    •     •    •     •    •     •    •
    CGCGCTCCGG CCTGCTGACC ATCGGTGTTC GGCGCATGTT ATACGCACCC AGCTCGCCGG
    GCGCGAGGCC GGACGACTGG TAGCCACAAG CCGCGTACAA TATGCGTGGG TCGAGCGGCC
      T R S G    L L T    I G V    R R M L    Y A P    S S P>

730        740        750        760        770        780
          •    •     •    •     •    •     •    •     •    •     •    •
    CGGGCAAGGG CACCAAGTGG GAGTGGTCGG GCGGCAGTGC CGATAGCAAC AACGACTGGC
    GCCCGTTCCC GTGGTTCACC CTCACCAGCC CGCCGTCACG GCTATCGTTG TTGCTGACCG
      A G K G    T K W    E W S    G G S A    D S N    N D W>

790        800        810        820        830        840
          •    •     •    •     •    •     •    •     •    •     •    •
    GGCCCTACAA CATGCACGTC CAGTGCATCA TCGAGGACGC CTGGGCGAGG GGCGAACAAA
    CCGGGATGTT GTACGTGCAG GTCACGTAGT AGCTCCTGCG GACCCGCTCC CCGCTTGTTT
      R P Y N    M H V    Q C I    I E D A    W A R    G E Q>

850        860        870        880        890        900
          •    •     •    •     •    •     •    •     •    •     •    •
    CCTTGGACCT GTGCAACACC CACATCGGCC TGCCGTACAC CATTAATTTT TGCAATCTCA
    GGAACCTGGA CACGTTGTGG GTGTAGCCGG ACGGCATGTG GTAATTAAAA ACGTTAGAGT
      T L D L    C N T    H I G    L P Y T    I N F    C N L>
```

FIG.12B

```
         910        920        930        940        950        960
          *          *          *          *          *          *
     CCCACGTGCG CCAACCCAGC GGACCCATGC GCAGCATTCG GCCTACCCAA CAGGCGCCGT
     GGGTGCACGC GGTTGGGTCG CCTGGGTACG CGTCGTAAGC CGGATGGGTT GTCCGCGGCA
      T  H  V  R  Q  P  S  G  P  M  R  S  I  R  R  T  Q  Q  A  P>

970        980        990       1000       1010       1020
          *          *          *          *          *          *
     ATCCCTTGGT GAAACTAACG CCACAACAGG CCAACCAACT CAAGTCGAAT TCCGCCAGCG
     TAGGGAACCA CTTTGATTGC GGTGTTGTCC GGTTGGTTGA GTTCAGCTTA AGGCGGTCGC
      Y  P  L  V  K  L  T  P  Q  Q  A  N  Q  L  K  S  N  S  A  S>

1030       1040       1050       1060       1070       1080
          *          *          *          *          *          *
     TGAGCAGCCA GTACAACACT CTACCCAAAC TGGGCGACAC CAAGAGCCTG CACAGAGTGC
     ACTCGTCGGT CATGTTGTGA GATGGGTTTG ACCCGCTGTG GTTCTCGGAC GTGTCTCACG
      V  S  S  Q  Y  N  T  L  P  K  L  G  D  T  K  S  L  H  R  V>

1090       1100       1110       1120       1130       1140
          *          *          *          *          *          *
     CCATGACCAG GCAACAGCAC CCATTGCCCA CCAGCCATCA GTGCAGCAG CAGCAGCATC
     GGTACTGGTC CGTTGTCGTG GGTAACGGGT GGTCGGTAGT TCACGTCGTC GTCGTCGTAG
      P  M  T  R  Q  Q  H  P  L  P  T  S  H  Q  V  Q  Q  Q  Q  H>

1150       1160       1170       1180       1190       1200
          *          *          *          *          *          *
     AGCTCCAGCA TCAACAGCAG CAGCAGCAGC AACATCATCA CCAGCATCAG CAACAACAGC
     TCGAGGTCGT AGTTGTCGTC GTCGTCGTCG TTGTAGTAGT GGTCGTAGTC GTTGTTGTCG
      Q  L  Q  H  Q  Q  Q  Q  Q  Q  H  H  H  Q  H  Q  Q  Q  Q>

1210       1220       1230       1240       1250       1260
          *          *          *          *          *          *
     ATCAGCAACA GCAGCAACAT CAGATGCAGC ACCATCAGAT CCATCATCAG ACGGCGCCCA
     TAGTCGTTGT CGTCGTTGTA GTCTACGTCG TGGTAGTCTA GGTAGTAGTC TGCCGCGGGT
      H  Q  Q  Q  Q  Q  H  Q  M  Q  H  H  Q  I  H  H  Q  T  A  P>

1270       1280       1290       1300       1310       1320
          *          *          *          *          *          *
     GGAAGCCGCC CAAGAAGCAC AGCGAGATCT CCACCACCAA TCTACGCCAG ATACTCAACA
     CCTTCGGCGG GTTCTTCGTG TCGCTCTAGA GGTGGTGGTT AGATGCGGTC TATGAGTTGT
      R  K  P  P  K  K  H  S  E  I  S  T  T  N  L  R  Q  I  L  N>
```

FIG.12C

```
              1330       1340       1350       1360       1370       1380
               *  *       *  *       *  *       *  *       *  *       *  *
          ACCTAAACAT CTTCAGCAGC AGCACTAAGC ACCAATCGAA CATGTCGACG GCGGCCAGTG
          TGGATTTGTA GAAGTCGTCG TCGTGATTCG TGGTTAGCTT GTACAGCTGC CGCCGGTCAC
           N  L  N  I  F  S  S   S  T  K   H  Q  S  N  M  S  T   A  A  S>

1390       1400       1410       1420       1430       1440
               *  *       *  *       *  *       *  *       *  *       *  *
          CCAGTTCATC CTCCTCATCG GCCTCGCTGC ACCATGCCAA CCATCTGTCG CATGCGCACT
          GGTCAAGTAG GAGGAGTAGC CGGAGCGACG TGGTACGGTT GGTAGACAGC GTACGCGTGA
           A  S  S  S   S  S  S   A  S  L   H  H  A  N   H  L  S   H  A  H>

1450       1460       1470       1480       1490       1500
               *  *       *  *       *  *       *  *       *  *       *  *
          TTTCGCACGC CAAGAACATG CTGACTGCCT CGATGAACAG TCATCATAGT CGCTGCTCGG
          AAAGCGTGCG GTTCTTGTAC GACTGACGGA GCTACTTGTC AGTAGTATCA GCGACGAGCC
           F  S  H  A   K  N  M   L  T  A   S  M  N  S   H  H  S   R  C  S>

1510       1520       1530       1540       1550       1560
               *  *       *  *       *  *       *  *       *  *       *  *
          AGGGATCGCT GCAGTCGCAA AGGAGCAGCC GGATGGGCTC GCATCGCTCG AGATCGCGAA
          TCCCTAGCGA CGTCAGCGTT TCCTCGTCGG CCTACCCGAG CGTAGCGAGC TCTAGCGCTT
           E  G  S  L   Q  S  Q   R  S  S   R  M  G  S   H  R  S   R  S  R>

1570       1580       1590       1600       1610       1620
               *  *       *  *       *  *       *  *       *  *       *  *
          CGCGGACCTC GGACACGGAC ACGAACAGTG TGAAATCGCA TCGGCGGAGA CCCAGTGTGG
          GCGCCTGGAG CCTGTGCCTG TGCTTGTCAC ACTTTAGCGT AGCCGCCTCT GGGTCACACC
           T  R  T  S   D  T  D   T  N  S   V  K  S  H   R  R  R   P  S  V>

1630       1640       1650       1660       1670       1680
               *  *       *  *       *  *       *  *       *  *       *  *
          ACACCGTGTC CACTTACCTC AGCCACGAGA GCAAGGAGAG CCTGCGCAGC AGGAACTTTG
          TGTGGCACAG GTGAATGGAG TCGGTGCTCT CGTTCCTCTC GGACGCGTCG TCCTTGAAAC
           D  T  V  S   T  Y  L   S  H  E   S  K  E  S   L  R  S   R  N  F>

1690       1700       1710       1720       1730       1740
               *  *       *  *       *  *       *  *       *  *       *  *
          CCATTTCGGT CAATGATCTG CTGGACTGCT CGCTTGGCAG CGATGAAGTT TTTGTGCCCT
          GGTAAAGCCA GTTACTAGAC GACCTGACGA GCGAACCGTC GCTACTTCAA AAACACGGGA
           A  I  S  V   N  D  L   L  D  C   S  L  G  S   D  E  V   F  V  P>
```

FIG.12D

```
        1750       1760       1770       1780       1790       1800
          *          *          *          *          *          *
     CCGTGCCGCC ATCGTCGCTG GGCGAAAGGG CGCCGGTGCC GCCGCCATTA CCACTGCATC
     GGCACGGCGG TAGCAGCGAC CCGCTTTCCC GCGGCCACGG CGGCGGTAAT GGTGACGTAG
      S V P P    S S L      G E R      A P V P    P P L      P L H>

1810       1820       1830       1840       1850       1860
          *          *          *          *          *          *
     CGCGACAGCA ACAGCAGCAG CAACAACAGC AGCAACAGCT GCAGATGCAA CAGCAGCAAC
     GCGCTGTCGT TGTCGTCGTC GTTGTTGTCG TCGTTGTCGA CGTCTACGTT GTCGTCGTTG
      P R Q Q    Q Q Q Q    Q Q Q L    Q M Q      Q Q Q>

1870       1880       1890       1900       1910       1920
          *          *          *          *          *          *
     AGGCGCAGCA GCAGCAGCAG CAATCAATCG CCGGTTCGAT TGTGGGCCTG GACCCGGCCA
     TCCGCGTCGT CGTCGTCGTC GTTAGTTAGC GGCCAAGCTA ACACCCGGCAC CTGGGCCGGT
      Q A Q Q    Q Q Q      Q S I      A G S I    V G V      D P A>

1930       1940       1950       1960       1970       1980
          *          *          *          *          *          *
     GCGATATGAT ATCGCGTTTT GTCAAGGTGG TGGAGCCACC GCTGTGGCCC AATGCCCAGC
     CGCTATACTA TAGCGCAAAA CAGTTCCACC ACCTCGGTGG CGACACCGGG TTACGGGTCG
      S D M I    S R F      V K V      V E P P    L W P      N A Q>

1990       2000       2010       2020       2030       2040
          *          *          *          *          *          *
     CCTGTCCCAT GTGCATGGAG GAGCTCGTGC ACTCCGCCCA GAATCCGGCC ATTTCGCTGA
     GGACAGGGTA CACGTACCTC CTCGAGCACG TGAGGCGGGT CTTAGGCCGG TAAAGCGACT
      P C P M    C M E      E L V      H S A Q    N P A      I S L>

2050       2060       2070       2080       2090       2100
          *          *          *          *          *          *
     GTCGCTGCCA GCATCTCATG CATTTGCAGT GCCTCAATGG GATGATAATT GCCCAGCAAA
     CAGCGACGGT CGTAGAGTAC GTAAACGTCA CGGAGTTACC CTACTATTAA CGGGTCGTTT
      S R C Q    H L M      H L Q      C L N G    M I I      A Q Q>

2110       2120       2130       2140       2150       2160
          *          *          *          *          *          *
     ACGAAATGAA CAAGAACCTT TTCATCGAGT GCCCTGTATG CGGCATCGTT TACGGCGAGA
     TGCTTTACTT GTTCTTGGAA AAGTAGCTCA CGGGACATAC GCCGTAGCAA ATGCCGCTCT
      N E M N    K N L      F I E      C P V C    G I V      Y G E>
```

FIG.12E

```
         2170       2180       2190       2200       2210       2220
           *          *  *       *  *       *  *       *  *       *  *
       AGGTCGGCAA TCAGCCCATT GGCAGCATGT CGTGGAGCAT AATTAGCAAG AATCTGCCAG
       TCCAGCCGTT AGTCGGGTAA CCGTCGTACA GCACCTCGTA TTAATCGTTC TTAGACGGTC
        K  V  G  N  Q  P  I  G  S  M   S  W  S  I   I  S  K   N  L  P>

2230       2240       2250       2260       2270       2280
           *  *       *  *       *  *       *  *       *  *       *  *
       GACACGAGGG TCAGAACACC ATACAGATTG TTTACGACAT TGCATCGGGA CTGCAGACGG
       CTGTGCTCCC AGTCTTGTGG TATGTCTAAC AAATGCTGTA ACGTAGCCCT GACGTCTGCC
        G  H  E  G  Q  N  T  I  Q  I   V  Y  D  I   A  S  G   L  Q  T>

2290       2300       2310       2320       2330       2340
           *  *       *  *       *  *       *  *       *  *       *  *
       AGGAGCATCC GCATCCAGGT CGTGCCTTCT TCCCCGTGGG ATTCCCGCGG ATCTGCTACT
       TCCTCGTAGG CGTAGGTCCA GCACGGAAGA AGGGGCACCC TAAGGGCGCC TAGACGATGA
        E  E  H  P  H  P  G  R  A  F   F  A  V  G   F  P  R   I  C  Y>

2350       2360       2370       2380       2390       2400
           *  *       *  *       *  *       *  *       *  *       *  *
       TGCCGGACTG CCCGCTGGGG CGAAAGGTTT TGCCGCTTCCT CAAGATTGCA TTCGATCGTC
       ACGGCCTGAC GGGCGACCCC GCTTTCCAAA ACGCGAAGGA GTTCTAACGT AAGCTAGCAG
        L  P  D  C  P  L  G  R  K  V   L  R  F  L   K  I  A   F  D  R>

2410       2420       2430       2440       2450       2460
           *  *       *  *       *  *       *  *       *  *       *  *
       GGCTGCTTTT CTCGATCGGA CGATCGGTGA CCACCGGACG CGAGGATGTG GTGATCTGGA
       CCGACGAAAA GAGCTAGCCT GCTAGCCACT GGTGGCCTGC GCTCCTACAC CACTAGACCT
        R  L  L  F  S  I  G  R  S  V   T  T  G  R   E  D  V   V  I  W>

2470       2480       2490       2500       2510       2520
           *  *       *  *       *  *       *  *       *  *       *  *
       ACAGTGTGGA TCACAAGACG CAGTTCAATA TGTTTCCGGA TCCCACCTAT TTGCAGCGAA
       TGTCACACCT AGTGTTCTGC GTCAAGTTAT ACAAAGGCCT AGGGTGGATA AACGTCGCTT
        N  S  V  D  H  K  T  Q  F  N   M  F  P  D   P  T  Y   L  Q  R>

2530       2540       2550       2560       2570       2580
           *  *       *  *       *  *       *  *       *  *       *  *
       CCATGCAACA GCTGGTGCAC CTGGGCGTGA CGGATTAAGG ATTAGTTCCC TGTCCCCAAC
       GGTACGTTGT CGACCACGTG GACCCGCACT GCCTAATTCC TAATCAAGGG ACAGGGGTTC
        T  M  Q  Q  L  V  H  L  G  V   T  D  *>
```

FIG.12F

```
            2590       2600       2610       2620       2630       2640
              *          *          *          *          *          *
              *          *          *          *          *          *
         TAGAACTACC AACCAACCAA TCAACCACCC ACCCACCGAA GTCCCCTCGA TCATTCTCTT
         ATCTTGATGG TTGGTTGGTT AGTTGGTGGG TGGGTGGCTT CAGGGGAGCT AGTAAGAGAA 2650       2660       2670       2680       2690       2700
              *          *          *          *          *          *
              *          *          *          *          *          *
         CCATTCGTCG TTAAGTTACT TTCTACATAA TCTCAGTGTG TGTGCAATCC TCGTTTACTA
         GGTAAGCAGC AATTCAATGA AAGATGTATT AGAGTCACAC ACACGTTAGG AGCAAATGAT 2710       2720       2730       2740       2750       2760
              *          *          *          *          *          *
              *          *          *          *          *          *
         TGATATATTT TTTTTATAGA TATATTGTAA TAGCGTTCGA GCTGCTCGAA CCCTAAAACA
         ACTATATAAA AAAAATATCT ATATAACATT ATCGCAAGCT CGACGAGCTT GGGATTTTGT 2770       2780       2790       2800       2810       2820
              *          *          *          *          *          *
              *          *          *          *          *          *
         ACAGCAAACC ACAATTGCAA TTGTAGCTTC CTTTCCGCTC TTCCAATTCG TATTTGTACG
         TGTCGTTTGG TGTTAACGTT AACATCGAAG GAAAGGCGAG AAGGTTAAGC ATAAACATGC 2830       2840       2850       2860       2870       2880
              *          *          *          *          *          *
              *          *          *          *          *          *
         CACATACGCA ATAAGTTGGC GTACATCATA TGTATTAGCT AGTTAGTTAG TTAGTTAGTT
         GTGTATGCGT TATTCAACCG CATGTAGTAT ACATAATCGA TCAATCAATC AATCAATCAA 2890       2900       2910       2920       2930       2940
              *          *          *          *          *          *
              *          *          *          *          *          *
         AGTTGTAGCT GTAGTTCCCA AGAGAATCTT GACCCAAGAC ACCTACTAGT ATTAGGCATT
         TCAACATCGA CATCAAGGGT TCTCTTAGAA CTGGGTTCTG TGGATGATCA TAATCCGTAA 2950       2960       2970       2980       2990       3000
              *          *          *          *          *          *
              *          *          *          *          *          *
         ATCCTGATTC TTGATTCCTG ATTCGATTCA AGCCAAGCCA AGCCACGCCA TTCGAGTGCA
         TAGGACTAAG AACTAAGGAC TAAGCTAAGT TCGGTTCGGT TCGGTGCGGT AAGCTCACGT 3010       3020       3030       3040       3050       3060
              *          *          *          *          *          *
              *          *          *          *          *          *
         AGCTGTGCCA AAATCGTAGC GCTCCCGTTT ATAGGATATG TATATTGTTG ATATAGCTAG
         TCGACACGGT TTTAGCATCG CGAGGGCAAA TATCCTATAC ATATAACAAC TATATCGATC
```

FIG.12G

```
      3070       3080       3090       3100       3110       3120
        *  *       *  *       *  *       *  *       *  *       *  *
   CTATAACCAT TGCCCATCTC TCCATCTCTC TCGGTTTCGA ATTTGTCTCT TTCATCAGAT
   GATATTGGTA ACGGGTAGAG AGGTAGAGAG AGCCAAAGCT TAAACAGAGA AAGTAGTCTA 3130       3140       3150       3160       3170       3180
        *  *       *  *       *  *       *  *       *  *       *  *
   CCATGTGAAT TTTCTTTATA TCGGATTTAT ATAGGATTAA AATAGTATTT TGAGAGAGGA
   GGTACACTTA AAAGAAATAT AGCCTAAATA TATCCTAATT TTATCATAAA ACTCTCTCCT 3190       3200       3210       3220       3230       3240
        *  *       *  *       *  *       *  *       *  *       *  *
   AATGGAGATG GGTAAATTCG ATAGACTTGT CTCACTTGTC TTGGCCATTT AATCTCTTTC
   TTACCTCTAC CCATTTAAGC TATCTGAACA GAGTGAACAG AACCGGTAAA TTAGAGAAAG 3250       3260       3270       3280       3290       3300
        *  *       *  *       *  *       *  *       *  *       *  *
   ATTCAGCGAA TTTGATGTGA TTTTAATTTG AATTATTCAT TATTAAACGG AGCATTTAGG
   TAAGTCGCTT AAACTACACT AAAATTAAAC TTAATAAGTA ATAATTTGCC TCGTAAATCC 3310       3320       3330       3340       3350       3360
        *  *       *  *       *  *       *  *       *  *       *  *
   AAGCATAGTT GTAACGCAGC CAGATATTCC ATTACGCATA TACATATACA TATACATATA
   TTCGTATCAA CATTGCGTCG GTCTATAAGG TAATGCGTAT ATGTATATGT ATATGTATAT 3370       3380       3390       3400       3410       3420
        *  *       *  *       *  *       *  *       *  *       *  *
   CATACATACA TAAACATATT TTAACATAGC CCCATAGCCA TACGACATAA CAATAATTTT
   GTATGTATGT ATTTGTATAA AATTGTATCG GGGTATCGGT ATGCTGTATT GTTATTAAAA 3430       3440       3450       3460       3470       3480
        *  *       *  *       *  *       *  *       *  *       *  *
   TTTTATCGAA TCCCTTGCAT ACATTTGATG AATTGTTGCT TTCATATTGA TATCATCGAG
   AAAATAGCTT AGGGAACGTA TGTAAACTAC TTAACAACGA AAGTATAACT ATAGTAGCTC 3490       3500       3510       3520       3530       3540
        *  *       *  *       *  *       *  *       *  *       *  *
   CATCGAACGA ACTATCGTAT ACATCGCCAA TATATAGCAT ATATAGCATA TAGTATGTAG
   GTAGCTTGCT TGATAGCATA TGTAGCGGTT ATATATCGTA TATATCGTAT ATCATACATC
```

FIG.12H

```
        3550       3560       3570       3580       3590       3600
         •    •     •    •     •    •     •    •     •    •     •    •
    AGATCGTACG GACAGCTAGC GGCTACTGAC CGCGCCACCA TATTTGATAT GATATGATAT
    TCTAGCATGC CTGTCGATCG CCGATGACTG GCGCGGTGGT ATAAACTATA CTATACTATA 3610       3620       3630       3640       3650       3660
         •    •     •    •     •    •     •    •     •    •     •    •
    GATTTTACTA AGTTGTATTT AGCACTGATT AGTTATTAAA GTTCATTTGA CGAATATTCC
    CTAAAATGAT TCAACATAAA TCGTGACTAA TCAATAATTT CAAGTAAACT GCTTATAAGG 3670       3680       3690       3700       3710       3720
         •    •     •    •     •    •     •    •     •    •     •    •
    ACAACAAATT CCACACCATT TATGTATGCA TATTACGCAT ATATAATACA GTACATTTAT
    TGTTGTTTAA GGTGTGGTAA ATACATACGT ATAATGCGTA TATATTATGT CATGTAAATA 3730       3740       3750       3760       3770
         •    •     •    •     •    •     •    •     •    •
    ATATAGTTCA AATAAAGTAA CTTCATTCAT GTTCAAAAAA AAAAAAAAAA A
    TATATCAAGT TTATTTCATT GAAGTAAGTA CAAGTTTTTT TTTTTTTTTT T
```

FIG.12I

```
         10         20         30         40         50         60
          *          *          *          *          *          *
    MASSAGSAAS GSVVPGGGGS AASSCATMAL STAGSGGPPV NHAHAVCVWE FESRGKWLPY
    _____A_____>
    _____D_____>

70         80         90        100        110        120
          *          *          *          *          *          *
    SPAVSQHLER AHAKKLTRVM LSDADPSLEQ YYVNVRTMTQ ESEAETRSGL LTIGVRRMLY
    _____A_____>
    _____D_____>

130        140        150        160        170        180
          *          *          *          *          *          *
    APSSPAGKGT KWEWSGGSAD SNNDWRPYNM HVQCIIEDAW ARGEQTLDLC NTHIGLPYTI
    _____A_____>
    _____D_____>

190        200        210        220        230        240
          *          *          *          *          *          *
    NFCNLTHVRQ PSGPMRSIRR TQQAPYPLVK LTPQQANQLK SNSASVSSQY NTLPKLGDTK
    _____A_____>
    _____D_____>

250        260        270        280        290        300
          *          *          *          *          *          *
    SLHRVPMTRQ QHPLPTSHQV QQQQHQLQHQ QQQQQQHHHQ HQQQQHQQQQ QHQMQHHQIH
    _____A_____>

310        320        330        340        350        360
          *          *          *          *          *          *
    HQTAPRKPPK KHSEISTTNL RQILNNLNIF SSSTKHQSNM STAASASSSS SSASLHHANH
    ___>
                  _____B_____>

370        380        390        400        410        420
          *          *          *          *          *          *
    LSHAHFSHAK NMLTASMNSH HSRCSEGSLQ SQRSSRMGSH RSRSRTRTSD TDTNSVKSHR
    _____B_____>
```

FIG.14A

```
            430         440         450         460         470         480
             .  .        .  .        .  .        .  .        .  .        .  .
           RRPSVDTVST YLSHESKESL RSRNFAISVN DLLDCSLGSD EVFVPSVPPS SLGERAPVPP
                                         B
           _____>

490         500         510         520         530         540
             .  .        .  .        .  .        .  .        .  .        .  .
           PLPLHPRQQQ QQQQQQQQLQ MQQQQQAQQQ QQQSIAGSIV GVDPASDMIS RFVKVVEPPL
           ____>
                                                        _____C_____>

550         560         570         580         590         600
             .  .        .  .        .  .        .  .        .  .        .  .
           WPNAQPCPMC MEELVHSAQN PAISLSRCQH LMHLQCLNGM IIAQQNEMNK NLFIECPVCG
           _____C_____>

610         620         630         640         650         660
             .  .        .  .        .  .        .  .        .  .        .  .
           IVYGEKVGNQ PIGSMSWSII SKNLPGHEGQ NTIQIVYDIA SGLQTEEHPH PGRAFFAVGF
           _____C_____>

670         680         690         700         710         720
             .  .        .  .        .  .        .  .        .  .        .  .
           PRICYLPDCP LGRKVLRFLK IAFDRRLLFS IGRSVTTGRE DVVIWNSVDH KTQFNMFPDP
           _____C_____>

730
             .  .  .
           TYLQRTMQQL VHLGVTD
           _____C_____>
```

FIG. 14B

| | REGION | CORE | SEQ. ID NO. |
|---|---|---|---|
| MOUSE 3BP-1 (GAP) | | RAPTMPPPLPPVPPQP | 9 |
| FLY DELTEX | 1 (58aa)<br>2 | RAP-VPPPLPLHPRQQ...<br>FVKVVEPPLWPNA-QP | 10<br>11 |
| FLY SON OF SEVENLESS (GNEF) | 1 (37aa)<br>2 | RA---VPPPLPPRRKER<br>DAPTLPPR<br>DGELSPPPIPPRLNHS | 12<br>13 |
| FLY HAIRLESS | 1 | SYPPLPPPLPANLSRT | 14 |
| FLY DISABLED | 1 | SVDAPPIPLPSRRVGR | 15 |

FIG. 16

FIG. 17A

```
                    Potential signal cleavage site
                                    ↓                              ┌─EGF-like Repeats
hum N   MP........  ..........  ALRPAL LWALLALWLC CA.....APA HA.........┌ QCRDGYEPCV NEGMCVTYHN GIGYCKCPEG FLGEYCQHRD PCE-KNRCQN GGTC--VAQA    83
TAN-1   MP........  ..........PL LAPLLCLALL PA.....LAA RC............. P RCSQPGETCL NGGKCEA-AN GTEACVCGGA FVGPRCQDPN PCL-STPCKN AGTCHVVDRR    80
Xen N   MD........  ..............  RIGLAVLLCS LP.....VLT QG........... L RCTQTAEMCL NGGRCEMTPG GTGVCLCGNL YFGERCQFPN PCTIKNCCMN FGTCEPVLCG    80
Dros N  MQSQRSRRRS RAPNTWICFW INKMHAVASL PASLPLLLLT LAFANLPNIV RGTDTALVAA SCTSVG--CQ NGGTCVTQLN GKTYCACDSH YVGDYCEHRN PCN-SWRCQN GGTCQVTFRN   117 hum N   MLGKATCRCA SGFTGEDCQY STSHPCFVSR PCLNGGTCHM LSRDT-YECT CQVGFTGKEC QWTDACLSHP CANGSTCTTV --ANQFSCKC LTGFTGQKCE TDVNEC-DIP GHCQHGGTCL    199
TAN-1   GVADYACSCA LGFSGPLCLT PLDNAC-LTN PCRNGGTCDL LT-LTEYKCR CPPGWSGKSC QQADPCASNP CANGGQCLPF --EASYICHC PPSFHGPTCR QDVNECGQKP RLCRHGGTCH    196
Xen N   NAIDFICHCP VGFTDKVCLT PVDNAC-VNN PCRNGGTCEL LNSVTEYKCR CPPGWTGDSC CQADPCASNP CANGGKCLPF --EIQYTCKC PPGFHGATCK QDINEC-S-Q NPCKNGGQCI    195
Dros N  GRPCISCKCP LGFDESLCEI AVPNAC-DHV TCLNGGTCQL KT-LEEYTCA CANGYTGERC ETKNLCASSP CRNGATCTAL AGSSSFTCSC PPGFTGDTCS YDIEEC-Q-S NPCKYGGICV    233 hum N   NLPGSYQCQC PQGFTGQYCD SLYVPCAPSP CVNGGTCRQT GDFTFECNCL PGFEQSTCER NIDDCPNHRC QNGGVCVDGV NTYNCRCPPQ WTGQFCTEDV DECLLQPNA- CQNGGTCANR    318
TAN-1   NEVGSYRCVC RATHTGPNCE RPYVPCSPSP CQNGGTCRPT CQVTHECACL PGFTGONCND NIDDCPGNNC KNGACVDGV NTYNCPCPPE WTGQYCTEDV DECQLMPNA- CQNGGTCHNT    315
Xen N   NEFGSYRCTC QNRFTGRNCD EPYVPCNPSP CLNGGTCRQT DDTSYDCTCL PGFSGONCEN NIDDCPSNNC RNGTCVDGV NTYNCQCPPD WTGQYCTEDV DECQLMPNA- CQNGGTCHNI    314
Dros N  NTHGSYQCMC PIGYTGKDCD TKYNPCSPSP CQNAGICRSN G-LSYECKCP KGFEGKNCEQ NYDDCLGHLC QNGGTCIDGI SDYTCRCPPN FTGRFCQDDV DECARDHPV CQNGATCINT    352 hum N   NGGYGYCVCV NGWSGDDCSEN IDDCAFASCT PGSTCIDRVA SFSCMCPEGK AGILLCHLDD A CISNPCHKGA LCDTNPLNGQ YICTCPQGYK GADCTEDVDE CAMANSNPCE HAGKCVNTDG    438
TAN-1   HGGYNCVCVN GWTGEDCSEN IDDCASAACF HGATCHDRVA SFYCECPHGR TGLLCHLNDA CISNPCNEGS NCDTNPVNGK AICTCPSGYT GPACSQDVDE CSLG-ANPCE HAGKCINTLG    434
Xen N   YGGYNCVCVN GWTGEDCSEN IDDCANAACH SGATCHDRVA SFYCECPHGR TGLLCHLDNA CISNPCNEGS NCDTNPVNGK AICTCPPGYT GPACNNDVDE CSLG-ANPCE HGGRCINTLG    433
Dros N  HGSYSCICVN TDDCKQAACF YGATCIDGVG SFYCQCPEGK TGLLCHLDDA CTSNPCHADA ICDTSPSINGS YACSCATGYK GVDCSEDIDE CDQG--SPCE HNGICVNTPG    470 hum N   AFHCECLKGY AGPRCEMDIN ECHSDPCQND ATCLDKIGGF TCLCMPGFKG VHCELEINEC QSNPCVNNCQ CVDKVNRFQC LCPPGFTGPV CQIDIDDCSS TPCLNGAKCI DHPNGYECQC    558
SFECQCLQGY TGPRCEIDVN ECVSNPCQND ECVSNPCQND ECLSNPCQND STCLDQIGEF QCKCMPAGYEG QCIQMPGYEG LYCETNIDEC ASNPCLHNGK CIDKINEFRC CLDKINEFCC CIDKINEFCC DCPTGFTGHL CQYDVDECAS TPCKNGAKCL DCPNTYTCVD    554
Xen N   SFCQNCPGGY AGPRCEIDVN ECLSNPCQND STCLDQIGEF QCIQMPGYEG LYCETNIDEC ASNPCLHNGK CIDKINEFRC DCPTGFSGNL CQHDFDECTS TPCKNGAKCL DGPNSYTCQC    553
Dros N  SYRCNCSSGF TGPRCETNIN ECESHPCQNE GSCLDDPGTF RCVCMPGFTG TQCEIDIDEC CHDKINGFKC SCALGFTGAR CQINIDDCQS QPCRNRGTCH DSIAGYSCEC    590
```

FIG. 17B

| | | | | | | |
|---|---|---|---|---|---|---|
| hum N | SNPCONGATC | SDFIGGYRCE | CVPGYCGVNC | EYEVDECONQ | PCONGGTCID | LVNHFKCSCP PCTRGLLCEE NIDDCAR———GPHCLN GGQCMDRIGG YSCRCLPGFA GERCEGDINE | 1267 |
| TAN-1 | PSPCONGATC | TDYLGGYSCK | CVAGYHGVNC | SEEIDECLSH | PCONGGTCLD | LPNTYKCSCP RGTQGVHCEI NVDDCNPPVD PVSRSPKCFN NGTCVDQVGG YSCTCPPGFV GERCEGDVNE | 1271 |
| Xen N | PNPCONGATC | TDYLGGYSCE | CVAGYHGVNC | SEEINECLSH | PCONGGTCID | LINTYKCSCP RGTQGVHCEI NVDDCTPFYD SFTLEPKCFN NGKCIDRVGG YNCICPPGFV GERCEGDVNE | 1269 |
| Dros N | SQPCONGGTC | RDLIGAYECQ | CROGFCGQNC | ELNIDDCAPN | PCONGGTCHD | RVMAFSCSCP PCTHGIICEI NKDDCKP———GACHN NGSCIDRVGG FECVCQPGFV GARCEGDINE | 1300 |
| | | | | | | |
| hum N | CLSNPCSSEG | SLDCIQLTND | YLCVCRSAFT | GRHCETFVDV | CPQMPCLNGG | TCAVASNMPD GFICRCPPGF SGARCQS———SCGQVKCRKG EQCVHTAS———GPRCFCPSP——RDCES——— | 1376 |
| TAN-1 | CLSNPCDARG | TQNCVCRVND | FHCECRAGHT | GRRCESVING | CKGKPCKNGG | TCAVASNTAR GFICKCPAGF EGATCENDAR TCGSLRCLNG GTCISGPR——SPTCLCLGPF TGPECQFPAS | 1389 |
| Xen N | CLSNPCDSRG | TQNCIQLVND | YRCECRCGFT | GRRCESWDG | CKGMPCRNGG | TCAVASNTER GFICKCPPGF DGATCEYDSR TCSNLRCQNG GTCISVLI——SSKCVCSEGY TGATCQYPVI | 1387 |
| Dros N | CLSNPCSNAG | TLDCVQLVNN | YHCNCRPGHM | GRHCEHKVDF | CAQSPCONGG | GHHCICNNGF YGKNCELSGQ DCDSNPCRVG —NCVVADEGF GYRCECPRGT LGEHCEIDTL | 1415 |
| | | | | LNR(Notch/Lin-12 Repeats) | | |
| hum N | —GC-ASSPCQ | HGGSCHPQRQ | PPYYSCQCAP | PFSGSRCEL | —YTAPP———S———A—TCL SQYCADKARD GVCDEACNSH ACMQDGDCS LTMENPWANC SSPLPCMDYI | 1476 |
| TAN-1 | SPCLGGMPCY | NGGTCEPTSE | SPFYRCLCPA | KFNGLLCHIL | DYSFGG————ACE——LPECQEDAGN KVCSLQCNNH ACWQGGDCS LNFNDPWKNC TQSLQCWKYF | 1501 |
| SPC N | SPC-ASHPCY | NGGTCFFAE | EPFFQCFCPK | NFNGLFCHIL | DYEFPG——————ICE NEQCSELADN KVCNANCNNH ACWQGGDCS LNFNDPWKNC TQSLQCWKYF | 1498 |
| Dros N | DEC-SPAPCA | QGAACEDLLG | D—YECLCPS | KWKGKRCDIY | DANYPGWACG SGSNDRYAA DLEQGRAMCD KRCCTEKCQN GICDSOCNTY ACNFDGNDCS LGI-NPWANC TAN-ECMNKF | 1531 |
| | | | | | | |
| hum N | NN-QCDELCN | TVECLFDNFE | CGGNSKTCK- | -YDKYCADHF | KONHCNQGCN | SEECMDGLD CAADQPEN-L AEGTLVIVVL MPPEQLLQDA R-SFLRALGT LLHTNLRIKR DSQGELMVYP | 1591 |
| TAN-1 | SDGHCDSOCN | SAGCLFDGFD | CQRAEGCONP | LYDQYCKDHF | SDGHCDSOGN | SAECEWDGLD CAEHVPER-L AAGTL-VVV LMPPEQLRNS SFHFLRELSR VLHTNVVFKR DAHGQOMIFP | 1619 |
| Xen N | NDGKCDSOCN | NTGCLYDGFD | CQKVEVCONP | LYDQYCKDHF | ODCHCDSOCN | NAECEWDGLD C-ANMPEN-L AEGTLVLVVL MPPERLKNNS V-NFLRELSR VLHTNVVFKK DSKGEYKIYP | 1615 |
| Dros N | KNGKONEECN | NAACHYDGHD | CERKLKSCDS | LFDAYCQKHY | GGGFCDYGCN | NAECSMDGLD CENKTQSPVL AEGAMSVVML MVVEAFREIQ A-QFLRMSH MLRTTVRLKK DALGHDIIIN | 1650 |
| | | | | | | TM |
| hum N | YYGEKSAAMK | KQ——R——— | ————————— | ————————— | MTRRSL PGEQ——E QEVAGSKVFL EIDNRCCVQD SDHCFKNTDA AAALLASHAI CC———TLSYP LVSVVSESLT PERT-Q-LY | 1680 |
| TAN-1 | YYGREEELRK | HPIKRAAEGN | AAPDALLGQV | KASLLPGGSE | CGRRRRELDP MDVRGSIVYL EIDNRCCVQA SSQCFQSATD VAAFLGALAS LGSL-NIPYK IEAVQSETVE PPPPAQ-LHF | 1737 |
| Xen N | YYGNEELKK | HHIKRSTDYW | SDAPSAI— | -FSTMKESIL | LGRHRRELDE MEVRGSIVYL EIDNRCCYKS SSQCFNSATD VAAFLGALAS LGSLDTLSYK IEAVKSENME TPKPST-LYP | 1730 |
| Dros N | WKQNVRVPEI | EDTDFARKNK | ILYTQQVHQ- | ————————— | ——————————TGIQIYL EIDNRKCTEC FTHAVEAAEF LAATAAKHQL RNDFQ-IHSV RGIKNPGDED NGEPPANVKY | 1745 |

FIG.17C

FIG. 17D

```
hum N                                                         -PLAHGASTV LPSVSQLLSH HHIVSPQS---  2235
TAN-1        ITSPGILQAS PNPML--ATA APPAPVHAQH ALSFSNLHEM Q---                                    2306
Xen N        LFSPF---QQS PSVPLNHLPG MPDTHLGIGH LNVAA-KPEM AALGGGGRLA FETGPPRLSH LPVASGTSTV LGSSSGGALN FTVGGSTSLN  2294
Dros N  MECCIKNAQS MQSLCCNGLD MIKLDNYAYS MCSPF--QCE LLNCQGLGMN GNCQRNGVGP GVLPGGLCCH SHECQLSPPY SNQSPPHSVQ SSLALSPHAY LGSPSPAKSR  2445
             CK II                      cdc2 hum N   GSAGSLSRLH PYPVPADW--- MNRMEVNETQ YNEMFGMVLA PAEG-THPGI APQSRPPEGK                                                      2320
TAN-1   QQCEWLSRLQ SCMVPNQYNP LRGSVAPGPL STQAPSLQHS -HMCPLIHSSL AASALSQMMS       ---HITTPRE PLPP-IV-TF QLIPKGSIAQ PAG---        2414
Xen N   SQCDWLARLQ NGM/QNQYDP IRNGIQCQN- AQQAQALQHG LMTS-LHNCL PATTLSQMHT        -YQCLPSTRL ATQPHLVQTQ QVQPQNLQMQ QQNLQPANIQ QQQSLQPPPP  2384
Dros N  PSLPTSPTHI QAMRHATQQK QFGGSNLNSL LGGANGGGVV GGQQNSPVS LGIISPTGSD MGIMLAPPQS SKMSAIMQTI SPQQQQQQQQ QQQQHQQQQ QQQQQQQQQQ ---LQLHQS  2565

PEST-containing Region
hum N   APQPQSTCPP AVAGPLPTMY QIP----EM ARL-PSVAFP TAMMPQQQCQ VAQTILPAYH PFPASVGKYP | TPPSQHSYAS SNAAERTPSH SQHLCQEHPY LTPSPESPDQ WSSSPHSA-   | 2433
TAN-1   PPQPHLGVSS AASGHLGRSF LSGEPSQADV QPLGPSSLAV HTILPQ-ESP ALPTSLPSSL VPPVTAAQFL | TPPSQHSY-S S-PVENTPSH QLQVP-EHPF LTPSPESPDQ WSSSPHSNV   | 2520
Xen N   HQQQHHN-SS TTSTHINSPF CSSDISQTDL QQM--SSNNI HSVMPQ-DTQ IFAASLPSNL TQSMTTAQFL | TPPSQHSY-S S-PMONTPSH QLQVP-DHFF LTPSPESPDQ WSSSPHSNM   | 2497
Dros N  QQQLGGLEFG SAGLDLNG-F CCSPDSFHSG QMAPPS---I QSSMSG-SSP STMMLSPSSQ HNQQAFYQYL | ---CGHTPQH LVQTL-Q-SY PTPSPESPGH WSSSPRSN-               | 2671 hum N   SDMSDVTTSP TFGGAGGGQR GPGTHMSEPPHNN MQVYA            2471
TAN-1   SDMSEGVSSP PT------SMQ SQIARIPEAFK                  2556
Xen N   SDMSEGISSP PT------SMQ PQRTHIPEAFK                  2523
Dros N  SDMSEGVQSP AAMNLYISGG HQANKGSEAIYI                  2703
```

FIG.17E

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
( A ) LENGTH: 5063 base pairs
( B ) TYPE: nucleic acid
( C ) STRANDEDNESS: double
( D ) TOPOLOGY: unknown ( i i ) MOLECULE TYPE: cDNA/DNA (genomic)

( i x ) FEATURE:
( A ) NAME/KEY: CDS
( B ) LOCATION: 864..1349

( i x ) FEATURE:
( A ) NAME/KEY: CDS
( B ) LOCATION: 1944..3370

( i x ) FEATURE:
( A ) NAME/KEY: CDS
( B ) LOCATION: 3439..3736

( x i ) SEQUENCE DESCRIPTION: SEQ ID NO:1:

```
ACATACACCA  CAAATGTGAT  CGTTACAGCA  AAGACATGCT  CAAATTATGA  ATTTCTTAAA     60

AGTGACCGAT  TTGTATTACC  GAAAATCTTG  AAAAGAAATA  CTAAATAGAA  AGAAACTTTG    120

GAAGCAGCCA  GTGTTGGAGG  CTGCGTTGCT  TAAGAAAAGT  AGCTTAAACT  TGCCAAAGTA    180

AATAAAAAAT  ATTGAAATTA  ATATCAAGTA  AAATCATTGC  AAGTTCTTAT  TTTTTTCATT    240

TCAATATAGA  ATTCAATTAC  ACATATATTA  ATTGATTAAT  TAACAAGCTA  AAAATAGTAT    300

CTGTTTATAT  TCAAGTGCAA  GAAAAGAAAA  TAAAAAATAT  TAAACATTTA  GCTAGATCTA    360

GCTAGCAACC  AGTTATGCCA  ACCCTGAAAC  TACCGAATCC  AACTGGTGGC  TGCGAGATGC    420

AGTGCGGTAT  TTTCATCCGG  CCTTATTTAG  CCATTTTCCG  CTGTTGTCTC  TCATTAAATC    480

GCTGTCCAAC  AATAAAAATT  TCTCGCCTGC  GCTTCGCGTA  AATGCTAGAA  AAACCGTTTT    540
```

```
TACCATCAAA CGTGAATTCT TAAGCTGCGC CTAAACGAAA CCGAGTGACT AAAGAACCAG      600

AACGAAAACT TCGGGAAAAT GGAAGCCAGG GAAAATCAGG GATAACTAAC GCTGGCAGCG      660

GGTCCACCAT TTTTAATTTC TTTGTTTATT TTGTGCCCAT CTTCGCGAGC GAGCGAGATA      720

GCGCGACAGC AACAGCAAGA GAGAGCGAGA GAGAGAGTGA GTGAGTGAGA GCTAGTGAAG      780

AGAGCGCAGG AGGAGTTGGA TATGGAAATG GGCATGGATA TGGCAATGGG CTCACTCCAC      840

GGATAACGGA TCAACTGCAA GCA ATG GCC AGC AGC GCC GGA AGT GCG GCA          890
                         Met Ala Ser Ser Ala Gly Ser Ala Ala
                          1                   5

TCC GGA TCC GTT GTT CCC GGT GGC GGA GGT AGC GCC GCC TCC AGT TGT        938
Ser Gly Ser Val Val Pro Gly Gly Gly Gly Ser Ala Ala Ser Ser Cys
 10              15                  20                  25

GCC ACC ATG GCC CTG TCC ACC GCC GGA TCC GGT GGG CCG CCC GTG AAC        986
Ala Thr Met Ala Leu Ser Thr Ala Gly Ser Gly Gly Pro Pro Val Asn
             30                  35                  40

CAC GCC CAC GCC GTC TGC GTG TGG GAG TTC GAG TCG CGC GGC AAG TGG       1034
His Ala His Ala Val Cys Val Trp Glu Phe Glu Ser Arg Gly Lys Trp
         45                  50                  55

CTG CCC TAT TCG CCG GCG GTG TCG CAG CAC TTG GAA CGC GCC CAC GCC       1082
Leu Pro Tyr Ser Pro Ala Val Ser Gln His Leu Glu Arg Ala His Ala
             60                  65                  70

AAG AAA CTG ACG CGC GTC ATG CTG AGC GAT GCG GAT CCC AGC CTG GAG       1130
Lys Lys Leu Thr Arg Val Met Leu Ser Asp Ala Asp Pro Ser Leu Glu
 75                  80                  85

CAG TAC TAC GTC AAC GTG CGC ACA ATG ACC CAG GAA TCG GAG GCG GAA       1178
Gln Tyr Tyr Val Asn Val Arg Thr Met Thr Gln Glu Ser Glu Ala Glu
 90                  95                 100                 105

ACG CGC TCC GGC CTG CTG ACC ATC GGT GTT CGG CGC ATG TTA TAC GCA       1226
Thr Arg Ser Gly Leu Leu Thr Ile Gly Val Arg Arg Met Leu Tyr Ala
             110                 115                 120

CCC AGC TCG CCG GCG GGC AAG GGC ACC AAG TGG GAG TGG TCG GGC GGC       1274
Pro Ser Ser Pro Ala Gly Lys Gly Thr Lys Trp Glu Trp Ser Gly Gly
             125                 130                 135

AGT GCC GAT AGC AAC AAC GAC TGG CGG CCC TAC AAC ATG CAC GTC CAG       1322
Ser Ala Asp Ser Asn Asn Asp Trp Arg Pro Tyr Asn Met His Val Gln
     140                 145                 150

TGC ATC ATC GAG GAC GCC TGG GCG AGG GTGAGTGCCG TGCAGAATCG             1369
Cys Ile Ile Glu Asp Ala Trp Ala Arg
 155                 160

AATGTTTTCC CATTGGCAGT CTAGTTGGAA TTTGAGTTG CTCAGGAATT TTTTTATCGG      1429

TAGAATATAT AGGGAATCTT TAAAGAGTGT GGGTTTACCA CTGATCCTGA AGAATTGGCT     1489

AAGGATGCAC CAGTCTGTGA TGTGTCCATA GGTGGTTAAA TAGTACATAT TAGCCAAATT     1549

CCACAGTTCA CATCTCAGCC AAAAAACGTA GTAGATCGAA GAAGTGTACC TTTTTGAATT     1609

TCTGATGCTT AGACAAATAA ATCTGCATTT AATTTTTTAA CTAAAATCAA ATTAATTTTT     1669

TTTTCAAAAT TTCCATCTTT ACAACATCAA AATTGGACAA AAAAATTTTA ATTTTCACTT     1729

TTGTAAAAGT TTGAATGCAG AAATTTTCCG CTTTGAAATA AAGACTAGAA AATCAGTCGC     1789

ACTTAAATCG CTGGAGTTTG GCTGAGTTAT GGTATTATGA TCAAATTTTA GGGGCTATAT     1849

AAATGTATTC TTCTTCTTGC ACAAATTCCA ACTGCAACTG CATATTCTAG CTTCAATCAT     1909

AGATTGTAAC TTAACCTATT CCTACTCCTT GCAG GGC GAA CAA ACC TTG GAC         1961
                                      Gly Glu Gln Thr Leu Asp
                                                     165

CTG TGC AAC ACC CAC ATC GGC CTG CCG TAC ACC ATT AAT TTT TGC AAT       2009
Leu Cys Asn Thr His Ile Gly Leu Pro Tyr Thr Ile Asn Phe Cys Asn
 170                 175                 180
```

```
CTC ACC CAC GTG CGC CAA CCC AGC GGA CCC ATG CGC AGC ATT CGG CGT    2057
Leu Thr His Val Arg Gln Pro Ser Gly Pro Met Arg Ser Ile Arg Arg
185                 190                 195                 200

ACC CAA CAG GCG CCG TAT CCC TTG GTG AAA CTA ACG CCA CAA CAG GCC    2105
Thr Gln Gln Ala Pro Tyr Pro Leu Val Lys Leu Thr Pro Gln Gln Ala
                    205                 210                 215

AAC CAA CTC AAG TCG AAT TCC GCC AGC GTG AGC AGC CAG TAC AAC ACT    2153
Asn Gln Leu Lys Ser Asn Ser Ala Ser Val Ser Ser Gln Tyr Asn Thr
                220                 225                 230

CTA CCC AAA CTG GGC GAC ACC AAG AGC CTG CAC AGA GTG CCC ATG ACC    2201
Leu Pro Lys Leu Gly Asp Thr Lys Ser Leu His Arg Val Pro Met Thr
            235                 240                 245

AGG CAA CAG CAC CCA TTG CCC ACC AGC CAT CAA GTG CAG CAG CAG CAG    2249
Arg Gln Gln His Pro Leu Pro Thr Ser His Gln Val Gln Gln Gln Gln
        250                 255                 260

CAT CAG CTC CAG CAT CAA CAG CAG CAG CAG CAA CAT CAT CAC CAG        2297
His Gln Leu Gln His Gln Gln Gln Gln Gln Gln His His His Gln
265                 270                 275                 280

CAT CAG CAA CAA CAG CAT CAG CAA CAG CAG CAA CAT CAG ATG CAG CAC    2345
His Gln Gln Gln Gln His Gln Gln Gln Gln Gln His Gln Met Gln His
                    285                 290                 295

CAT CAG ATC CAT CAT CAG ACG GCG CCC AGG AAG CCG CCC AAG AAG CAC    2393
His Gln Ile His His Gln Thr Ala Pro Arg Lys Pro Pro Lys Lys His
            300                 305                 310

AGC GAG ATC TCC ACC ACC AAT CTA CGC CAG ATA CTC AAC AAC CTA AAC    2441
Ser Glu Ile Ser Thr Thr Asn Leu Arg Gln Ile Leu Asn Asn Leu Asn
        315                 320                 325

ATC TTC AGC AGC AGC ACT AAG CAC CAA TCG AAC ATG TCG ACG GCG GCC    2489
Ile Phe Ser Ser Ser Thr Lys His Gln Ser Asn Met Ser Thr Ala Ala
330                 335                 340

AGT GCC AGT TCA TCC TCC TCA TCG GCC TCG CTG CAC CAT GCC AAC CAT    2537
Ser Ala Ser Ser Ser Ser Ser Ser Ala Ser Leu His His Ala Asn His
345                 350                 355                 360

CTG TCG CAT GCG CAC TTT TCG CAC GCC AAG AAC ATG CTG ACT GCC TCG    2585
Leu Ser His Ala His Phe Ser His Ala Lys Asn Met Leu Thr Ala Ser
                    365                 370                 375

ATG AAC AGT CAT CAT AGT CGC TGC TCG GAG GGA TCG CTG CAG TCG CAA    2633
Met Asn Ser His His Ser Arg Cys Ser Glu Gly Ser Leu Gln Ser Gln
                380                 385                 390

AGG AGC AGC CGG ATG GGC TCG CAT CGC TCG AGA TCG CGA ACG CGG ACC    2681
Arg Ser Ser Arg Met Gly Ser His Arg Ser Arg Ser Arg Thr Arg Thr
        395                 400                 405

TCG GAC ACG GAC ACG AAC AGT GTG AAA TCG CAT CGG CGG AGA CCC AGT    2729
Ser Asp Thr Asp Thr Asn Ser Val Lys Ser His Arg Arg Arg Pro Ser
410                 415                 420

GTG GAC ACC GTG TCC ACT TAC CTC AGC CAC GAG AGC AAG GAG AGC CTG    2777
Val Asp Thr Val Ser Thr Tyr Leu Ser His Glu Ser Lys Glu Ser Leu
425                 430                 435                 440

CGC AGC AGG AAC TTT GCC ATT TCG GTC AAT GAT CTG CTG GAC TGC TCG    2825
Arg Ser Arg Asn Phe Ala Ile Ser Val Asn Asp Leu Leu Asp Cys Ser
                    445                 450                 455

CTT GGC AGC GAT GAA GTT TTT GTG CCC TCC GTG CCG CCA TCG TCG CTG    2873
Leu Gly Ser Asp Glu Val Phe Val Pro Ser Val Pro Pro Ser Ser Leu
                460                 465                 470

GGC GAA AGG GCG CCG GTG CCG CCG CCA TTA CCA CTG CAT CCG CGA CAG    2921
Gly Glu Arg Ala Pro Val Pro Pro Pro Leu Pro Leu His Pro Arg Gln
        475                 480                 485

CAA CAG CAG CAG CAA CAA CAG CAG CAA CAG CTG CAG ATG CAA CAG CAG    2969
Gln Gln Gln Gln Gln Gln Gln Gln Gln Gln Leu Gln Met Gln Gln Gln
490                 495                 500
```

-continued

| | | | | | | | | | | | | | | | | |
|---|---|---|---|---|---|---|---|---|---|---|---|---|---|---|---|---|
|CAA|CAG|GCG|CAG|CAG|CAG|CAG|CAG|CAA|TCA|ATC|GCC|GGT|TCG|ATT|GTG|3017|
|Gln|Gln|Ala|Gln|Gln|Gln|Gln|Gln|Gln|Ser|Ile|Ala|Gly|Ser|Ile|Val||
|505| | | |510| | | | |515| | | | |520| | |

|GGC|GTG|GAC|CCG|GCC|AGC|GAT|ATG|ATA|TCG|CGT|TTT|GTC|AAG|GTG|GTG|3065|
|---|---|---|---|---|---|---|---|---|---|---|---|---|---|---|---|---|
|Gly|Val|Asp|Pro|Ala|Ser|Asp|Met|Ile|Ser|Arg|Phe|Val|Lys|Val|Val||
| | | | |525| | | | |530| | | | |535| | |

|GAG|CCA|CCG|CTG|TGG|CCC|AAT|GCC|CAG|CCC|TGT|CCC|ATG|TGC|ATG|GAG|3113|
|---|---|---|---|---|---|---|---|---|---|---|---|---|---|---|---|---|
|Glu|Pro|Pro|Leu|Trp|Pro|Asn|Ala|Gln|Pro|Cys|Pro|Met|Cys|Met|Glu||
| | | |540| | | | |545| | | | |550| | | |

|GAG|CTG|GTG|CAC|TCC|GCC|CAG|AAT|CCG|GCC|ATT|TCG|CTG|AGT|CGC|TGC|3161|
|---|---|---|---|---|---|---|---|---|---|---|---|---|---|---|---|---|
|Glu|Leu|Val|His|Ser|Ala|Gln|Asn|Pro|Ala|Ile|Ser|Leu|Ser|Arg|Cys||
| | |555| | | |560| | | |565| | | | | | |

|CAG|CAT|CTC|ATG|CAT|TTG|CAG|TGC|CTC|AAT|GGG|ATG|ATA|ATT|GCC|CAG|3209|
|---|---|---|---|---|---|---|---|---|---|---|---|---|---|---|---|---|
|Gln|His|Leu|Met|His|Leu|Gln|Cys|Leu|Asn|Gly|Met|Ile|Ile|Ala|Gln||
|570| | | | |575| | | | |580| | | | | | |

|CAA|AAC|GAA|ATG|AAC|AAG|AAC|CTT|TTC|ATC|GAG|TGC|CCT|GTA|TGC|GGC|3257|
|---|---|---|---|---|---|---|---|---|---|---|---|---|---|---|---|---|
|Gln|Asn|Glu|Met|Asn|Lys|Asn|Leu|Phe|Ile|Glu|Cys|Pro|Val|Cys|Gly||
|585| | | | |590| | | | |595| | | | |600| |

|ATC|GTT|TAC|GGC|GAG|AAG|GTC|GGC|AAT|CAG|CCC|ATT|GGC|AGC|ATG|TCG|3305|
|---|---|---|---|---|---|---|---|---|---|---|---|---|---|---|---|---|
|Ile|Val|Tyr|Gly|Glu|Lys|Val|Gly|Asn|Gln|Pro|Ile|Gly|Ser|Met|Ser||
| | | | |605| | | | |610| | | | |615| | |

|TGG|AGC|ATA|ATT|AGC|AAG|AAT|CTG|CCA|GGA|CAC|GAG|GGT|CAG|AAC|ACC|3353|
|---|---|---|---|---|---|---|---|---|---|---|---|---|---|---|---|---|
|Trp|Ser|Ile|Ile|Ser|Lys|Asn|Leu|Pro|Gly|His|Glu|Gly|Gln|Asn|Thr||
| | | |620| | | | |625| | | | |630| | | |

|ATA|CAG|ATT|GTT|TAC|GA|GTAAGTGTGA|ATGTGCCTGT|GGCCACTGAG| | | | | | | |3400|
|---|---|---|---|---|---|---|---|---|---|---|---|---|---|---|---|---|
|Ile|Gln|Ile|Val|Tyr|As| | | | | | | | | | | |
| | | |635| | | | | | | | | | | | | |

|CAATCAACTA|TAATCACTCT|TTTTCATTTG|CATGGCAG|C|ATT|GCA|TCG|GGA|CTG|3454|
|---|---|---|---|---|---|---|---|---|---|---|
| | | | |p|Ile|Ala|Ser|Gly|Leu| |
| | | | | | | | |640| | |

|CAG|ACG|GAG|GAG|CAT|CCG|CAT|CCA|GGT|CGT|GCC|TTC|TTC|GCC|GTG|GGA|3502|
|---|---|---|---|---|---|---|---|---|---|---|---|---|---|---|---|---|
|Gln|Thr|Glu|Glu|His|Pro|His|Pro|Gly|Arg|Ala|Phe|Phe|Ala|Val|Gly||
| | | |645| | | | |650| | | | |655| | | |

|TTC|CCG|CGG|ATC|TGC|TAC|TTG|CCG|GAC|TGC|CCG|CTG|GGG|CGA|AAG|GTT|3550|
|---|---|---|---|---|---|---|---|---|---|---|---|---|---|---|---|---|
|Phe|Pro|Arg|Ile|Cys|Tyr|Leu|Pro|Asp|Cys|Pro|Leu|Gly|Arg|Lys|Val||
|660| | | | |665| | | | |670| | | | |675| |

|TTG|CGC|TTC|CTC|AAG|ATT|GCA|TTC|GAT|CGT|CGG|CTG|CTT|TTC|TCG|ATC|3598|
|---|---|---|---|---|---|---|---|---|---|---|---|---|---|---|---|---|
|Leu|Arg|Phe|Leu|Lys|Ile|Ala|Phe|Asp|Arg|Arg|Leu|Leu|Phe|Ser|Ile||
| | | | |680| | | | |685| | | | |690| | |

|GGA|CGA|TCG|GTG|ACC|ACC|GGA|CGC|GAG|GAT|GTG|GTG|ATC|TGG|AAC|AGT|3646|
|---|---|---|---|---|---|---|---|---|---|---|---|---|---|---|---|---|
|Gly|Arg|Ser|Val|Thr|Thr|Gly|Arg|Glu|Asp|Val|Val|Ile|Trp|Asn|Ser||
| | | |695| | | | |700| | | | |705| | | |

|GTG|GAT|CAC|AAG|ACG|CAG|TTC|AAT|ATG|TTT|CCG|GAT|CCC|ACC|TAT|TTG|3694|
|---|---|---|---|---|---|---|---|---|---|---|---|---|---|---|---|---|
|Val|Asp|His|Lys|Thr|Gln|Phe|Asn|Met|Phe|Pro|Asp|Pro|Thr|Tyr|Leu||
| | |710| | | | |715| | | | |720| | | | |

|CAG|CGA|ACC|ATG|CAA|CAG|CTG|GTG|CAC|CTG|GGC|GTG|ACG|GAT| | |3736|
|---|---|---|---|---|---|---|---|---|---|---|---|---|---|---|---|---|
|Gln|Arg|Thr|Met|Gln|Gln|Leu|Val|His|Leu|Gly|Val|Thr|Asp| | ||
|725| | | |730| | | | |735| | | | | | | |

| | | | | | |
|---|---|---|---|---|---|
|TAAGGATTAG|TTCCCTGTCC|CCAAGTAGAA|CTACCAACCA|ACCAATCAAC|CACCCACCCA|3796|
|CCGAAGTCCC|CTCGATCATT|CTCTTCCATT|CGTCGTTAAG|TTACTTTCTA|CATAATCTCA|3856|
|GTGTGTGTGC|AATCCTCGTT|TACTATGATA|TATTTTTTTT|ATAGATATAT|TGTAATAGCG|3916|
|TTCGAGCTGC|TCGAACCCTA|AAACAACAGC|AAACCACAAT|TGCAATTGTA|GCTTCCTTTC|3976|
|CGCTCTTCCA|ATTCGTATTT|GTACGCACAT|ACGCAATAAG|TTGGCGTACA|TCATATGTAT|4036|
|TAGCTAGTTA|GTTAGTTAGT|TAGTTAGTTG|TAGCTGTAGT|TCCCAAGAGA|ATCTTGACCC|4096|
|AAGACACCTA|CTAGTATTAG|GCATTATCCT|GATTCTTGAT|TCCTGATTCG|ATTCAAGCCA|4156|
|AGCCAAGCCA|CGCCATTCGA|GTGCAAGCTG|TGCCAAAATC|GTAGCGCTCC|CGTTTATAGG|4216|

```
ATATGTATAT TGTTGATATA GCTAGCTATA ACCATTGCCC ATCTCTCCAT CTCTCTCGGT    4276

TTCGAATTTG TCTCTTTCAT CAGATCCATG TGAATTTTCT TTATATCGGA TTTATATAGG    4336

ATTAAAATAG TATTTTGAGA GAGGAAATGG AGATGGGTAA ATTCGATAGA CTTGTCTCAC    4396

TTGTCTTGGC CATTTAATCT CTTTCATTCA GCGAATTTGA TGTGATTTTA ATTGAATTA     4456

TTCATTATTA AACGGAGCAT TTAGGAAGCA TAGTTGTAAC GCAGCCAGAT ATTCCATTAC    4516

GCATATACAT ATACATATAC ATATACATAC ATACATAAAC ATATTTTAAC ATAGCCCCAT    4576

AGCCATACGA CATAACAATA ATTTTTTTTA TCGAATCCCT TGCATACATT TGATGAATTG    4636

TTGCTTTCAT ATTGATATCA TCGAGCATCG AACGAACTAT CGTATACATC GCCAATATAT    4696

AGCATATATA GCATATAGTA TGTAGAGATC GTACGGACAG CTAGCGGCTA CTGACCGCGC    4756

CACCATATTT GATATGATAT GATATGATTT TACTAAGTTG TATTTAGCAC TGATTAGTTA    4816

TTAAAGTTCA TTTGACGAAT ATTCCACAAC AAATTCCACA CCATTTCTGT ATGCATATTA    4876

CGCATATATA ATACAGTACA TTTATATATA GTTCAAATAA AGTAACTTTC ATTCATGTTC    4936

AAATTAAGTC TTTCTTTTGG GATATTTATT CACTCATGTC TAAAAGGAAA TCTTTCTTTT    4996

TGGACTTTTT CACTTATGTA TGTATGTTCG AATGCGTTCT TTCTTTTGGG ACTTTTTTTC    5056

TTTATGC                                                              5063
```

( 2 ) INFORMATION FOR SEQ ID NO:2:

( i ) SEQUENCE CHARACTERISTICS:
    ( A ) LENGTH: 737 amino acids
    ( B ) TYPE: amino acid
    ( D ) TOPOLOGY: unknown ( i i ) MOLECULE TYPE: protein ( x i ) SEQUENCE DESCRIPTION: SEQ ID NO:2:

```
Met Ala Ser Ser Ala Gly Ser Ala Ala Ser Gly Ser Val Val Pro Gly
 1               5                  10                  15

Gly Gly Gly Ser Ala Ala Ser Ser Cys Ala Thr Met Ala Leu Ser Thr
                20                  25                  30

Ala Gly Ser Gly Gly Pro Pro Val Asn His Ala His Ala Val Cys Val
                35                  40                  45

Trp Glu Phe Glu Ser Arg Gly Lys Trp Leu Pro Tyr Ser Pro Ala Val
        50                  55                  60

Ser Gln His Leu Glu Arg Ala His Ala Lys Lys Leu Thr Arg Val Met
65                  70                  75                  80

Leu Ser Asp Ala Asp Pro Ser Leu Glu Gln Tyr Tyr Val Asn Val Arg
                85                  90                  95

Thr Met Thr Gln Glu Ser Glu Ala Glu Thr Arg Ser Gly Leu Leu Thr
            100                 105                 110

Ile Gly Val Arg Arg Met Leu Tyr Ala Pro Ser Ser Pro Ala Gly Lys
        115                 120                 125

Gly Thr Lys Trp Glu Trp Ser Gly Gly Ser Ala Asp Ser Asn Asn Asp
    130                 135                 140

Trp Arg Pro Tyr Asn Met His Val Gln Cys Ile Ile Glu Asp Ala Trp
145                 150                 155                 160

Ala Arg Gly Glu Gln Thr Leu Asp Leu Cys Asn Thr His Ile Gly Leu
                165                 170                 175

Pro Tyr Thr Ile Asn Phe Cys Asn Leu Thr His Val Arg Gln Pro Ser
            180                 185                 190

Gly Pro Met Arg Ser Ile Arg Arg Thr Gln Gln Ala Pro Tyr Pro Leu
```

```
                    195                         200                          205
Val  Lys  Leu  Thr  Pro  Gln  Gln  Ala  Asn  Gln  Leu  Lys  Ser  Asn  Ser  Ala
     210                      215                     220

Ser  Val  Ser  Ser  Gln  Tyr  Asn  Thr  Leu  Pro  Lys  Leu  Gly  Asp  Thr  Lys
225                           230                     235                     240

Ser  Leu  His  Arg  Val  Pro  Met  Thr  Arg  Gln  Gln  His  Pro  Leu  Pro  Thr
                    245                     250                     255

Ser  His  Gln  Val  Gln  Gln  Gln  His  Gln  Leu  Gln  His  Gln  Gln  Gln
               260                      265                     270

Gln  Gln  Gln  Gln  His  His  His  Gln  His  Gln  Gln  Gln  Gln  His  Gln  Gln
          275                      280                     285

Gln  Gln  Gln  His  Gln  Met  Gln  His  His  Gln  Ile  His  His  Gln  Thr  Ala
290                      295                               300

Pro  Arg  Lys  Pro  Pro  Lys  Lys  His  Ser  Glu  Ile  Ser  Thr  Thr  Asn  Leu
305                      310                     315                          320

Arg  Gln  Ile  Leu  Asn  Asn  Leu  Asn  Ile  Phe  Ser  Ser  Ser  Thr  Lys  His
                    325                     330                     335

Gln  Ser  Asn  Met  Ser  Thr  Ala  Ala  Ala  Ser  Ser  Ser  Ser  Ser  Ser  Ser
               340                      345                     350

Ala  Ser  Leu  His  His  Ala  Asn  His  Leu  Ser  His  Ala  His  Phe  Ser  His
               355                      360                     365

Ala  Lys  Asn  Met  Leu  Thr  Ala  Ser  Met  Asn  Ser  His  His  Ser  Arg  Cys
370                           375                     380

Ser  Glu  Gly  Ser  Leu  Gln  Ser  Gln  Arg  Ser  Ser  Arg  Met  Gly  Ser  His
385                      390                     395                          400

Arg  Ser  Arg  Ser  Arg  Thr  Arg  Thr  Ser  Asp  Thr  Asp  Thr  Asn  Ser  Val
                    405                     410                     415

Lys  Ser  His  Arg  Arg  Arg  Pro  Ser  Val  Asp  Thr  Val  Ser  Thr  Tyr  Leu
               420                      425                     430

Ser  His  Glu  Ser  Lys  Glu  Ser  Leu  Arg  Ser  Arg  Asn  Phe  Ala  Ile  Ser
               435                      440                     445

Val  Asn  Asp  Leu  Leu  Asp  Cys  Ser  Leu  Gly  Ser  Asp  Glu  Val  Phe  Val
450                           455                     460

Pro  Ser  Val  Pro  Pro  Ser  Ser  Leu  Gly  Glu  Arg  Ala  Pro  Val  Pro  Pro
465                      470                     475                          480

Pro  Leu  Pro  Leu  His  Pro  Arg  Gln  Gln  Gln  Gln  Gln  Gln  Gln  Gln  Gln
               485                      490                     495

Gln  Gln  Leu  Gln  Met  Gln  Gln  Gln  Gln  Ala  Gln  Gln  Gln  Gln  Gln
          500                      505                     510

Gln  Ser  Ile  Ala  Gly  Ser  Ile  Val  Gly  Val  Asp  Pro  Ala  Ser  Asp  Met
          515                      520                     525

Ile  Ser  Arg  Phe  Val  Lys  Val  Val  Glu  Pro  Pro  Leu  Trp  Pro  Asn  Ala
          530                      535                     540

Gln  Pro  Cys  Pro  Met  Cys  Met  Glu  Glu  Leu  Val  His  Ser  Ala  Gln  Asn
545                           550                     555                     560

Pro  Ala  Ile  Ser  Leu  Ser  Arg  Cys  Gln  His  Leu  Met  His  Leu  Gln  Cys
                    565                     570                          575

Leu  Asn  Gly  Met  Ile  Ile  Ala  Gln  Gln  Asn  Glu  Met  Asn  Lys  Asn  Leu
               580                      585                     590

Phe  Ile  Glu  Cys  Pro  Val  Cys  Gly  Ile  Val  Tyr  Gly  Glu  Lys  Val  Gly
          595                      600                     605

Asn  Gln  Pro  Ile  Gly  Ser  Met  Ser  Trp  Ser  Ile  Ile  Ser  Lys  Asn  Leu
610                           615                     620
```

| | | | | | | | | | | | | | | | |
|---|---|---|---|---|---|---|---|---|---|---|---|---|---|---|---|
| Pro | Gly | His | Glu | Gly | Gln | Asn | Thr | Ile | Gln | Ile | Val | Tyr | Asp | Ile | Ala |
| 625 | | | | | 630 | | | | | 635 | | | | | 640 |
| Ser | Gly | Leu | Gln | Thr | Glu | Glu | His | Pro | His | Pro | Gly | Arg | Ala | Phe | Phe |
| | | | | 645 | | | | | 650 | | | | | 655 | |
| Ala | Val | Gly | Phe | Pro | Arg | Ile | Cys | Tyr | Leu | Pro | Asp | Cys | Pro | Leu | Gly |
| | | | | 660 | | | | | 665 | | | | 670 | | |
| Arg | Lys | Val | Leu | Arg | Phe | Leu | Lys | Ile | Ala | Phe | Asp | Arg | Arg | Leu | Leu |
| | | | 675 | | | | | 680 | | | | | 685 | | |
| Phe | Ser | Ile | Gly | Arg | Ser | Val | Thr | Thr | Gly | Arg | Glu | Asp | Val | Val | Ile |
| | | 690 | | | | 695 | | | | | 700 | | | | |
| Trp | Asn | Ser | Val | Asp | His | Lys | Thr | Gln | Phe | Asn | Met | Phe | Pro | Asp | Pro |
| 705 | | | | | 710 | | | | | 715 | | | | | 720 |
| Thr | Tyr | Leu | Gln | Arg | Thr | Met | Gln | Gln | Leu | Val | His | Leu | Gly | Val | Thr |
| | | | | 725 | | | | | 730 | | | | | 735 | |

Asp ( 2 ) INFORMATION FOR SEQ ID NO:3:

( i ) SEQUENCE CHARACTERISTICS:
      ( A ) LENGTH: 3771 base pairs
      ( B ) TYPE: nucleic acid
      ( C ) STRANDEDNESS: double
      ( D ) TOPOLOGY: unknown ( i i ) MOLECULE TYPE: cDNA ( i x ) FEATURE:
      ( A ) NAME/KEY: CDS
      ( B ) LOCATION: 345..2558

( x i ) SEQUENCE DESCRIPTION: SEQ ID NO:3:

| | | |
|---|---|---|
| AAATGCTAGA AAAACCGTTT TTACCATCAA ACGTGAATTC TTAAGCTGCG CCTAAACGAA | | 60 |
| ACCGAGTGAC TAAAGAACCA GAACGAAAAC TTCGGGAAAA TGGAAGCCAG GGAAAATCAG | | 120 |
| GGATAACTAA CGCTGGCAGC GGGTCCACCA TTTTTAATTT CTTTGTTTAT TTTGTGCCCA | | 180 |
| TCTTCGCGAG CGAGCGAGAT AGCGCGACAG CAACAGCAAG AGAGAGCGAG AGAGAGAGTG | | 240 |
| AGTGAGTGAG AGCTAGTGAA GAGAGCGCAG GAGGAGTTGG ATATGGAAAT GGGCATGGAT | | 300 |

| | | | | | | | | | | | | | | |
|---|---|---|---|---|---|---|---|---|---|---|---|---|---|---|
| ATGGCAATGG GCTCACTCCA CGGATAACGG ATCAACTGCA AGCA ATG GCC AGC AGC | | | | | | | | | | | | | | 356 |
| | | | | | | | | | | | Met | Ala | Ser | Ser |
| | | | | | | | | | | | 1 | | | |
| GCC GGA AGT GCG GCA TCC GGA TCC GTT GTT CCC GGT GGC GGA GGT AGC | | | | | | | | | | | | | | 404 |
| Ala | Gly | Ser | Ala | Ala | Ser | Gly | Ser | Val | Val | Pro | Gly | Gly | Gly | Gly | Ser |
| 5 | | | | | 10 | | | | | 15 | | | | | 20 |
| GCC GCC TCC AGT TGT GCC ACC ATG GCC CTG TCC ACC GCC GGA TCC GGT | | | | | | | | | | | | | | 452 |
| Ala | Ala | Ser | Ser | Cys | Ala | Thr | Met | Ala | Leu | Ser | Thr | Ala | Gly | Ser | Gly |
| | | | | 25 | | | | | 30 | | | | | 35 | |
| GGG CCG CCC GTG AAC CAC GCC CAC GCC GTC TGC GTG TGG GAG TTC GAG | | | | | | | | | | | | | | 500 |
| Gly | Pro | Pro | Val | Asn | His | Ala | His | Ala | Val | Cys | Val | Trp | Glu | Phe | Glu |
| | | | 40 | | | | | 45 | | | | | 50 | | |
| TCG CGC GGC AAG TGG CTG CCC TAT TCG CCG GCG GTG TCG CAG CAC TTG | | | | | | | | | | | | | | 548 |
| Ser | Arg | Gly | Lys | Trp | Leu | Pro | Tyr | Ser | Pro | Ala | Val | Ser | Gln | His | Leu |
| | | 55 | | | | | 60 | | | | | 65 | | | |
| GAA CGC GCC CAC GCC AAG AAA CTG ACG CGC GTC ATG CTG AGC GAT GCG | | | | | | | | | | | | | | 596 |
| Glu | Arg | Ala | His | Ala | Lys | Lys | Leu | Thr | Arg | Val | Met | Leu | Ser | Asp | Ala |
| | 70 | | | | | 75 | | | | | 80 | | | | |
| GAT CCC AGC CTG GAG CAG TAC TAC GTC AAC GTG CGC ACA ATG ACC CAG | | | | | | | | | | | | | | 644 |
| Asp | Pro | Ser | Leu | Glu | Gln | Tyr | Tyr | Val | Asn | Val | Arg | Thr | Met | Thr | Gln |
| 85 | | | | | 90 | | | | | 95 | | | | | 100 |
| GAA TCG GAG GCG GAA ACG CGC TCC GGC CTG CTG ACC ATC GGT GTT CGG | | | | | | | | | | | | | | 692 |
| Glu | Ser | Glu | Ala | Glu | Thr | Arg | Ser | Gly | Leu | Leu | Thr | Ile | Gly | Val | Arg |

-continued

|   |   |   | 105 |   |   |   | 110 |   |   |   | 115 |   |   |   |     |
|---|---|---|---|---|---|---|---|---|---|---|---|---|---|---|-----|

```
CGC  ATG  TTA  TAC  GCA  CCC  AGC  TCG  CCG  GCG  GGC  AAG  GGC  ACC  AAG  TGG    740
Arg  Met  Leu  Tyr  Ala  Pro  Ser  Ser  Pro  Ala  Gly  Lys  Gly  Thr  Lys  Trp
               120                 125                      130

GAG  TGG  TCG  GGC  GGC  AGT  GCC  GAT  AGC  AAC  AAC  GAC  TGG  CGG  CCC  TAC    788
Glu  Trp  Ser  Gly  Gly  Ser  Ala  Asp  Ser  Asn  Asn  Asp  Trp  Arg  Pro  Tyr
          135                      140                           145

AAC  ATG  CAC  GTC  CAG  TGC  ATC  ATC  GAG  GAC  GCC  TGG  GCG  AGG  GGC  GAA    836
Asn  Met  His  Val  Gln  Cys  Ile  Ile  Glu  Asp  Ala  Trp  Ala  Arg  Gly  Glu
     150                      155                      160

CAA  ACC  TTG  GAC  CTG  TGC  AAC  ACC  CAC  ATC  GGC  CTG  CCG  TAC  ACC  ATT    884
Gln  Thr  Leu  Asp  Leu  Cys  Asn  Thr  His  Ile  Gly  Leu  Pro  Tyr  Thr  Ile
165                      170                      175                      180

AAT  TTT  TGC  AAT  CTC  ACC  CAC  GTG  CGC  CAA  CCC  AGC  GGA  CCC  ATG  CGC    932
Asn  Phe  Cys  Asn  Leu  Thr  His  Val  Arg  Gln  Pro  Ser  Gly  Pro  Met  Arg
                    185                      190                      195

AGC  ATT  CGG  CGT  ACC  CAA  CAG  GCG  CCG  TAT  CCC  TTG  GTG  AAA  CTA  ACG    980
Ser  Ile  Arg  Arg  Thr  Gln  Gln  Ala  Pro  Tyr  Pro  Leu  Val  Lys  Leu  Thr
               200                      205                      210

CCA  CAA  CAG  GCC  AAC  CAA  CTC  AAG  TCG  AAT  TCC  GCC  AGC  GTG  AGC  AGC   1028
Pro  Gln  Gln  Ala  Asn  Gln  Leu  Lys  Ser  Asn  Ser  Ala  Ser  Val  Ser  Ser
          215                      220                      225

CAG  TAC  AAC  ACT  CTA  CCC  AAA  CTG  GGC  GAC  ACC  AAG  AGC  CTG  CAC  AGA   1076
Gln  Tyr  Asn  Thr  Leu  Pro  Lys  Leu  Gly  Asp  Thr  Lys  Ser  Leu  His  Arg
     230                      235                      240

GTG  CCC  ATG  ACC  AGG  CAA  CAG  CAC  CCA  TTG  CCC  ACC  AGC  CAT  CAA  GTG   1124
Val  Pro  Met  Thr  Arg  Gln  Gln  His  Pro  Leu  Pro  Thr  Ser  His  Gln  Val
245                      250                      255                      260

CAG  CAG  CAG  CAG  CAT  CAG  CTC  CAG  CAT  CAA  CAG  CAG  CAG  CAG  CAG  CAA   1172
Gln  Gln  Gln  Gln  His  Gln  Leu  Gln  His  Gln  Gln  Gln  Gln  Gln  Gln  Gln
                    265                      270                      275

CAT  CAT  CAC  CAG  CAT  CAG  CAA  CAA  CAG  CAT  CAG  CAA  CAG  CAG  CAA  CAT   1220
His  His  His  Gln  His  Gln  Gln  Gln  Gln  His  Gln  Gln  Gln  Gln  Gln  His
               280                      285                      290

CAG  ATG  CAG  CAC  CAT  CAG  ATC  CAT  CAT  CAG  ACG  GCG  CCC  AGG  AAG  CCG   1268
Gln  Met  Gln  His  His  Gln  Ile  His  His  Gln  Thr  Ala  Pro  Arg  Lys  Pro
          295                      300                      305

CCC  AAG  AAG  CAC  AGC  GAG  ATC  TCC  ACC  ACC  AAT  CTA  CGC  CAG  ATA  CTC   1316
Pro  Lys  Lys  His  Ser  Glu  Ile  Ser  Thr  Thr  Asn  Leu  Arg  Gln  Ile  Leu
     310                      315                      320

AAC  AAC  CTA  AAC  ATC  TTC  AGC  AGC  AGC  ACT  AAG  CAC  CAA  TCG  AAC  ATG   1364
Asn  Asn  Leu  Asn  Ile  Phe  Ser  Ser  Ser  Thr  Lys  His  Gln  Ser  Asn  Met
325                      330                      335                      340

TCG  ACG  GCG  GCC  AGT  GCC  AGT  TCA  TCC  TCC  TCA  TCG  GCC  TCG  CTG  CAC   1412
Ser  Thr  Ala  Ala  Ser  Ala  Ser  Ser  Ser  Ser  Ser  Ser  Ala  Ser  Leu  His
                    345                      350                      355

CAT  GCC  AAC  CAT  CTG  TCG  CAT  GCG  CAC  TTT  TCG  CAC  GCC  AAG  AAC  ATG   1460
His  Ala  Asn  His  Leu  Ser  His  Ala  His  Phe  Ser  His  Ala  Lys  Asn  Met
               360                      365                      370

CTG  ACT  GCC  TCG  ATG  AAC  AGT  CAT  CAT  AGT  CGC  TGC  TCG  GAG  GGA  TCG   1508
Leu  Thr  Ala  Ser  Met  Asn  Ser  His  His  Ser  Arg  Cys  Ser  Glu  Gly  Ser
          375                      380                      385

CTG  CAG  TCG  CAA  AGG  AGC  AGC  CGG  ATG  GGC  TCG  CAT  CGC  TCG  AGA  TCG   1556
Leu  Gln  Ser  Gln  Arg  Ser  Ser  Arg  Met  Gly  Ser  His  Arg  Ser  Arg  Ser
     390                      395                      400

CGA  ACG  CGG  ACC  TCG  GAC  ACG  GAC  ACG  AAC  AGT  GTG  AAA  TCG  CAT  CGG   1604
Arg  Thr  Arg  Thr  Ser  Asp  Thr  Asp  Thr  Asn  Ser  Val  Lys  Ser  His  Arg
405                      410                      415                      420

CGG  AGA  CCC  AGT  GTG  GAC  ACC  GTG  TCC  ACT  TAC  CTC  AGC  CAC  GAG  AGC   1652
Arg  Arg  Pro  Ser  Val  Asp  Thr  Val  Ser  Thr  Tyr  Leu  Ser  His  Glu  Ser
```

-continued

```
                     425                              430                              435
AAG  GAG  AGC  CTG  CGC  AGC  AGG  AAC  TTT  GCC  ATT  TCG  GTC  AAT  GAT  CTG       1700
Lys  Glu  Ser  Leu  Arg  Ser  Arg  Asn  Phe  Ala  Ile  Ser  Val  Asn  Asp  Leu
               440                      445                      450

CTG  GAC  TGC  TCG  CTT  GGC  AGC  GAT  GAA  GTT  TTT  GTG  CCC  TCC  GTG  CCG       1748
Leu  Asp  Cys  Ser  Leu  Gly  Ser  Asp  Glu  Val  Phe  Val  Pro  Ser  Val  Pro
               455                      460                      465

CCA  TCG  TCG  CTG  GGC  GAA  AGG  GCG  CCG  GTG  CCG  CCG  CCA  TTA  CCA  CTG       1796
Pro  Ser  Ser  Leu  Gly  Glu  Arg  Ala  Pro  Val  Pro  Pro  Pro  Leu  Pro  Leu
     470                      475                      480

CAT  CCG  CGA  CAG  CAA  CAG  CAG  CAA  CAA  CAG  CAG  CAA  CAG  CTG  CAG            1844
His  Pro  Arg  Gln  Gln  Gln  Gln  Gln  Gln  Gln  Gln  Gln  Gln  Leu  Gln
485                      490                      495                      500

ATG  CAA  CAG  CAG  CAA  CAG  GCG  CAG  CAG  CAG  CAG  CAG  CAA  TCA  ATC  GCC       1892
Met  Gln  Gln  Gln  Gln  Gln  Ala  Gln  Gln  Gln  Gln  Gln  Gln  Ser  Ile  Ala
                    505                      510                      515

GGT  TCG  ATT  GTG  GGC  GTG  GAC  CCG  GCC  AGC  GAT  ATG  ATA  TCG  CGT  TTT       1940
Gly  Ser  Ile  Val  Gly  Val  Asp  Pro  Ala  Ser  Asp  Met  Ile  Ser  Arg  Phe
               520                      525                      530

GTC  AAG  GTG  GTG  GAG  CCA  CCG  CTG  TGG  CCC  AAT  GCC  CAG  CCC  TGT  CCC       1988
Val  Lys  Val  Val  Glu  Pro  Pro  Leu  Trp  Pro  Asn  Ala  Gln  Pro  Cys  Pro
          535                      540                      545

ATG  TGC  ATG  GAG  GAG  CTG  GTG  CAC  TCC  GCC  CAG  AAT  CCG  GCC  ATT  TCG       2036
Met  Cys  Met  Glu  Glu  Leu  Val  His  Ser  Ala  Gln  Asn  Pro  Ala  Ile  Ser
     550                      555                      560

CTG  AGT  CGC  TGC  CAG  CAT  CTC  ATG  CAT  TTG  CAG  TGC  CTC  AAT  GGG  ATG       2084
Leu  Ser  Arg  Cys  Gln  His  Leu  Met  His  Leu  Gln  Cys  Leu  Asn  Gly  Met
565                      570                      575                      580

ATA  ATT  GCC  CAG  CAA  AAC  GAA  ATG  AAC  AAG  AAC  CTT  TTC  ATC  GAG  TGC       2132
Ile  Ile  Ala  Gln  Gln  Asn  Glu  Met  Asn  Lys  Asn  Leu  Phe  Ile  Glu  Cys
                    585                      590                      595

CCT  GTA  TGC  GGC  ATC  GTT  TAC  GGC  GAG  AAG  GTC  GGC  AAT  CAG  CCC  ATT       2180
Pro  Val  Cys  Gly  Ile  Val  Tyr  Gly  Glu  Lys  Val  Gly  Asn  Gln  Pro  Ile
               600                      605                      610

GGC  AGC  ATG  TCG  TGG  AGC  ATA  ATT  AGC  AAG  AAT  CTG  CCA  GGA  CAC  GAG       2228
Gly  Ser  Met  Ser  Trp  Ser  Ile  Ile  Ser  Lys  Asn  Leu  Pro  Gly  His  Glu
          615                      620                      625

GGT  CAG  AAC  ACC  ATA  CAG  ATT  GTT  TAC  GAC  ATT  GCA  TCG  GGA  CTG  CAG       2276
Gly  Gln  Asn  Thr  Ile  Gln  Ile  Val  Tyr  Asp  Ile  Ala  Ser  Gly  Leu  Gln
     630                      635                      640

ACG  GAG  GAG  CAT  CCG  CAT  CCA  GGT  CGT  GCC  TTC  TTC  GCC  GTG  GGA  TTC       2324
Thr  Glu  Glu  His  Pro  His  Pro  Gly  Arg  Ala  Phe  Phe  Ala  Val  Gly  Phe
645                      650                      655                      660

CCG  CGG  ATC  TGC  TAC  TTG  CCG  GAC  TGC  CCG  CTG  GGG  CGA  AAG  GTT  TTG       2372
Pro  Arg  Ile  Cys  Tyr  Leu  Pro  Asp  Cys  Pro  Leu  Gly  Arg  Lys  Val  Leu
                    665                      670                      675

CGC  TTC  CTC  AAG  ATT  GCA  TTC  GAT  CGT  CGG  CTG  CTT  TTC  TCG  ATC  GGA       2420
Arg  Phe  Leu  Lys  Ile  Ala  Phe  Asp  Arg  Arg  Leu  Leu  Phe  Ser  Ile  Gly
               680                      685                      690

CGA  TCG  GTG  ACC  ACC  GGA  CGC  GAG  GAT  GTG  GTG  ATC  TGG  AAC  AGT  GTG       2468
Arg  Ser  Val  Thr  Thr  Gly  Arg  Glu  Asp  Val  Val  Ile  Trp  Asn  Ser  Val
          695                      700                      705

GAT  CAC  AAG  ACG  CAG  TTC  AAT  ATG  TTT  CCG  GAT  CCC  ACC  TAT  TTG  CAG       2516
Asp  His  Lys  Thr  Gln  Phe  Asn  Met  Phe  Pro  Asp  Pro  Thr  Tyr  Leu  Gln
     710                      715                      720

CGA  ACC  ATG  CAA  CAG  CTG  GTG  CAC  CTG  GGC  GTG  ACG  GAT  TAA                 2558
Arg  Thr  Met  Gln  Gln  Leu  Val  His  Leu  Gly  Val  Thr  Asp  *
725                      730                      735

GGATTAGTTC  CCTGTCCCCA  AGTAGAACTA  CCAACCAACC  AATCAACCAC  CCACCCACCG              2618
```

| | | | | | |
|---|---|---|---|---|---|
| AAGTCCCCTC | GATCATTCTC | TTCCATTCGT | CGTTAAGTTA | CTTTCTACAT | AATCTCAGTG | 2678 |
| TGTGTGCAAT | CCTCGTTTAC | TATGATATAT | TTTTTTTATA | GATATATTGT | AATAGCGTTC | 2738 |
| GAGCTGCTCG | AACCCTAAAA | CAACAGCAAA | CCACAATTGC | AATTGTAGCT | TCCTTTCCGC | 2798 |
| TCTTCCAATT | CGTATTTGTA | CGCACATACG | CAATAAGTTG | GCGTACATCA | TATGTATTAG | 2858 |
| CTAGTTAGTT | AGTTAGTTAG | TTAGTTGTAG | CTGTAGTTCC | CAAGAGAATC | TTGACCCAAG | 2918 |
| ACACCTACTA | GTATTAGGCA | TTATCCTGAT | TCTTGATTCC | TGATTCGATT | CAAGCCAAGC | 2978 |
| CAAGCCACGC | CATTCGAGTG | CAAGCTGTGC | CAAAATCGTA | GCGCTCCCGT | TTATAGGATA | 3038 |
| TGTATATTGT | TGATATAGCT | AGCTATAACC | ATTGCCCATC | TCTCCATCTC | TCTCGGTTTC | 3098 |
| GAATTTGTCT | CTTTCATCAG | ATCCATGTGA | ATTTCTTTA | TATCGGATTT | ATATAGGATT | 3158 |
| AAAATAGTAT | TTTGAGAGAG | GAAATGGAGA | TGGGTAAATT | CGATAGACTT | GTCTCACTTG | 3218 |
| TCTTGGCCAT | TTAATCTCTT | TCATTCAGCG | AATTGATGT | GATTTAATT | TGAATTATTC | 3278 |
| ATTATTAAAC | GGAGCATTTA | GGAAGCATAG | TTGTAACGCA | GCCAGATATT | CCATTACGCA | 3338 |
| TATACATATA | CATATACATA | TACATACATA | CATAAACATA | TTTTAACATA | GCCCCATAGC | 3398 |
| CATACGACAT | AACAATAATT | TTTTTATCG | AATCCCTTGC | ATACATTTGA | TGAATTGTTG | 3458 |
| CTTTCATATT | GATATCATCG | AGCATCGAAC | GAACTATCGT | ATACATCGCC | AATATATAGC | 3518 |
| ATATATAGCA | TATAGTATGT | AGAGATCGTA | CGGACAGCTA | GCGGCTACTG | ACCGCGCCAC | 3578 |
| CATATTTGAT | ATGATATGAT | ATGATTTAC | TAAGTTGTAT | TTAGCACTGA | TTAGTTATTA | 3638 |
| AAGTTCATTT | GACGAATATT | CCACAACAAA | TTCCACACCA | TTTATGTATG | CATATTACGC | 3698 |
| ATATATAATA | CAGTACATTT | ATATATAGTT | CAAATAAAGT | AACTTCATTC | ATGTTCAAAA | 3758 |
| AAAAAAAAAA | AAA | | | | | 3771 |

( 2 ) INFORMATION FOR SEQ ID NO:4:

( i ) SEQUENCE CHARACTERISTICS:
        ( A ) LENGTH: 737 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:4:

```
Met Ala Ser Ser Ala Gly Ser Ala Ala Ser Gly Ser Val Val Pro Gly
  1               5                  10                  15

Gly Gly Gly Ser Ala Ala Ser Ser Cys Ala Thr Met Ala Leu Ser Thr
                 20                  25                  30

Ala Gly Ser Gly Gly Pro Pro Val Asn His Ala His Ala Val Cys Val
             35                  40                  45

Trp Glu Phe Glu Ser Arg Gly Lys Trp Leu Pro Tyr Ser Pro Ala Val
 50                  55                  60

Ser Gln His Leu Glu Arg Ala His Ala Lys Lys Leu Thr Arg Val Met
 65                  70                  75                  80

Leu Ser Asp Ala Asp Pro Ser Leu Glu Gln Tyr Tyr Val Asn Val Arg
                 85                  90                  95

Thr Met Thr Gln Glu Ser Glu Ala Glu Thr Arg Ser Gly Leu Leu Thr
                100                 105                 110

Ile Gly Val Arg Arg Met Leu Tyr Ala Pro Ser Ser Pro Ala Gly Lys
            115                 120                 125

Gly Thr Lys Trp Glu Trp Ser Gly Gly Ser Ala Asp Ser Asn Asn Asp
        130                 135                 140

Trp Arg Pro Tyr Asn Met His Val Gln Cys Ile Ile Glu Asp Ala Trp
```

```
145                 150                 155                 160
Ala Arg Gly Glu Gln Thr Leu Asp Leu Cys Asn Thr His Ile Gly Leu
                165                 170                 175
Pro Tyr Thr Ile Asn Phe Cys Asn Leu Thr His Val Arg Gln Pro Ser
                180                 185                 190
Gly Pro Met Arg Ser Ile Arg Arg Thr Gln Gln Ala Pro Tyr Pro Leu
                195                 200                 205
Val Lys Leu Thr Pro Gln Gln Ala Asn Gln Leu Lys Ser Asn Ser Ala
    210                 215                 220
Ser Val Ser Ser Gln Tyr Asn Thr Leu Pro Lys Leu Gly Asp Thr Lys
225                 230                 235                 240
Ser Leu His Arg Val Pro Met Thr Arg Gln Gln His Pro Leu Pro Thr
                245                 250                 255
Ser His Gln Val Gln Gln Gln His Gln Leu Gln His Gln Gln Gln
                260                 265                 270
Gln Gln Gln Gln His His His Gln His Gln Gln Gln His Gln Gln
            275                 280                 285
Gln Gln Gln His Gln Met Gln His His Gln Ile His His Gln Thr Ala
    290                 295                 300
Pro Arg Lys Pro Pro Lys Lys His Ser Glu Ile Ser Thr Thr Asn Leu
305                 310                 315                 320
Arg Gln Ile Leu Asn Asn Leu Asn Ile Phe Ser Ser Ser Thr Lys His
                325                 330                 335
Gln Ser Asn Met Ser Thr Ala Ala Ser Ala Ser Ser Ser Ser Ser Ser
                340                 345                 350
Ala Ser Leu His His Ala Asn His Leu Ser His Ala His Phe Ser His
                355                 360                 365
Ala Lys Asn Met Leu Thr Ala Ser Met Asn Ser His Ser Arg Cys
    370                 375                 380
Ser Glu Gly Ser Leu Gln Ser Gln Arg Ser Ser Arg Met Gly Ser His
385                 390                 395                 400
Arg Ser Arg Ser Arg Thr Arg Thr Ser Asp Thr Asp Thr Asn Ser Val
                405                 410                 415
Lys Ser His Arg Arg Arg Pro Ser Val Asp Thr Val Ser Thr Tyr Leu
                420                 425                 430
Ser His Glu Ser Lys Glu Ser Leu Arg Ser Arg Asn Phe Ala Ile Ser
        435                 440                 445
Val Asn Asp Leu Leu Asp Cys Ser Leu Gly Ser Asp Glu Val Phe Val
    450                 455                 460
Pro Ser Val Pro Pro Ser Ser Leu Gly Glu Arg Ala Pro Val Pro Pro
465                 470                 475                 480
Pro Leu Pro Leu His Pro Arg Gln Gln Gln Gln Gln Gln Gln Gln Gln
                485                 490                 495
Gln Gln Leu Gln Met Gln Gln Gln Gln Ala Gln Gln Gln Gln
            500                 505                 510
Gln Ser Ile Ala Gly Ser Ile Val Gly Val Asp Pro Ala Ser Asp Met
        515                 520                 525
Ile Ser Arg Phe Val Lys Val Val Glu Pro Pro Leu Trp Pro Asn Ala
    530                 535                 540
Gln Pro Cys Pro Met Cys Met Glu Glu Leu Val His Ser Ala Gln Asn
545                 550                 555                 560
Pro Ala Ile Ser Leu Ser Arg Cys Gln His Leu Met His Leu Gln Cys
                565                 570                 575
```

-continued

| | | | | | | | | | | | | | | |
|---|---|---|---|---|---|---|---|---|---|---|---|---|---|---|
| Leu | Asn | Gly | Met<br>580 | Ile | Ile | Ala | Gln | Gln<br>585 | Asn | Glu | Met | Asn<br>590 | Lys | Asn | Leu |
| Phe | Ile | Glu<br>595 | Cys | Pro | Val | Cys | Gly<br>600 | Ile | Val | Tyr | Gly | Glu<br>605 | Lys | Val | Gly |
| Asn | Gln<br>610 | Pro | Ile | Gly | Ser | Met<br>615 | Ser | Trp | Ser | Ile | Ile<br>620 | Ser | Lys | Asn | Leu |
| Pro<br>625 | Gly | His | Glu | Gly | Gln<br>630 | Asn | Thr | Ile | Gln | Ile<br>635 | Val | Tyr | Asp | Ile | Ala<br>640 |
| Ser | Gly | Leu | Gln | Thr<br>645 | Glu | Glu | His | Pro | His<br>650 | Pro | Gly | Arg | Ala | Phe<br>655 | Phe |
| Ala | Val | Gly | Phe<br>660 | Pro | Arg | Ile | Cys | Tyr<br>665 | Leu | Pro | Asp | Cys | Pro<br>670 | Leu | Gly |
| Arg | Lys | Val<br>675 | Leu | Arg | Phe | Leu | Lys<br>680 | Ile | Ala | Phe | Asp | Arg<br>685 | Arg | Leu | Leu |
| Phe | Ser<br>690 | Ile | Gly | Arg | Ser | Val<br>695 | Thr | Thr | Gly | Arg | Glu<br>700 | Asp | Val | Val | Ile |
| Trp<br>705 | Asn | Ser | Val | Asp | His<br>710 | Lys | Thr | Gln | Phe | Asn<br>715 | Met | Phe | Pro | Asp | Pro<br>720 |
| Thr | Tyr | Leu | Gln | Arg<br>725 | Thr | Met | Gln | Gln | Leu<br>730 | Val | His | Leu | Gly | Val<br>735 | Thr |
| Asp | | | | | | | | | | | | | | | |

( 2 ) INFORMATION FOR SEQ ID NO:5:

( i ) SEQUENCE CHARACTERISTICS:
        ( A ) LENGTH: 303 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:5:

| | | | | | | | | | | | | | | |
|---|---|---|---|---|---|---|---|---|---|---|---|---|---|---|
| Met<br>1 | Ala | Ser | Ser | Ala<br>5 | Gly | Ser | Ala | Ala | Ser<br>10 | Gly | Ser | Val | Val | Pro<br>15 | Gly |
| Gly | Gly | Gly | Ser<br>20 | Ala | Ala | Ser | Ser | Cys<br>25 | Ala | Thr | Met | Ala | Leu<br>30 | Ser | Thr |
| Ala | Gly | Ser<br>35 | Gly | Gly | Pro | Pro | Val<br>40 | Asn | His | Ala | His | Ala<br>45 | Val | Cys | Val |
| Trp | Glu<br>50 | Phe | Glu | Ser | Arg | Gly<br>55 | Lys | Trp | Leu | Pro | Tyr<br>60 | Ser | Pro | Ala | Val |
| Ser<br>65 | Gln | His | Leu | Glu | Arg<br>70 | Ala | His | Ala | Lys | Lys<br>75 | Leu | Thr | Arg | Val | Met<br>80 |
| Leu | Ser | Asp | Ala | Asp<br>85 | Pro | Ser | Leu | Glu | Gln<br>90 | Tyr | Tyr | Val | Asn | Val<br>95 | Arg |
| Thr | Met | Thr | Gln<br>100 | Glu | Ser | Glu | Ala | Glu<br>105 | Thr | Arg | Ser | Gly | Leu<br>110 | Leu | Thr |
| Ile | Gly | Val<br>115 | Arg | Arg | Met | Leu | Tyr<br>120 | Ala | Pro | Ser | Ser | Pro<br>125 | Ala | Gly | Lys |
| Gly | Thr<br>130 | Lys | Trp | Glu | Trp | Ser<br>135 | Gly | Gly | Ser | Ala | Asp<br>140 | Ser | Asn | Asn | Asp |
| Trp<br>145 | Arg | Pro | Tyr | Asn | Met<br>150 | His | Val | Gln | Cys | Ile<br>155 | Ile | Glu | Asp | Ala | Trp<br>160 |
| Ala | Arg | Gly | Glu | Gln<br>165 | Thr | Leu | Asp | Leu | Cys<br>170 | Asn | Thr | His | Ile | Gly<br>175 | Leu |
| Pro | Tyr | Thr | Ile<br>180 | Asn | Phe | Cys | Asn | Leu<br>185 | Thr | His | Val | Arg | Gln<br>190 | Pro | Ser |

| | | | | | | | | | | | | | | |
|---|---|---|---|---|---|---|---|---|---|---|---|---|---|---|
| Gly | Pro | Met<br>195 | Arg | Ser | Ile | Arg | Arg<br>200 | Thr | Gln | Gln | Ala | Pro<br>205 | Tyr | Pro | Leu |
| Val | Lys | Leu<br>210 | Thr | Pro | Gln | Gln<br>215 | Ala | Asn | Gln | Leu | Lys<br>220 | Ser | Asn | Ser | Ala |
| Ser<br>225 | Val | Ser | Ser | Gln | Tyr<br>230 | Asn | Thr | Leu | Pro | Lys<br>235 | Leu | Gly | Asp | Thr | Lys<br>240 |
| Ser | Leu | His | Arg | Val<br>245 | Pro | Met | Thr | Arg | Gln<br>250 | Gln | His | Pro | Leu | Pro<br>255 | Thr |
| Ser | His | Gln | Val<br>260 | Gln | Gln | Gln | His<br>265 | Gln | Leu | Gln | His<br>270 | Gln | Gln | Gln |
| Gln | Gln | Gln<br>275 | Gln | His | His | His<br>280 | Gln | His | Gln | Gln | Gln<br>285 | His | Gln | Gln |
| Gln | Gln | Gln<br>290 | Gln | His | Gln | Met<br>295 | Gln | His | His | Gln | Ile<br>300 | His | His | Gln | Thr |

(2) INFORMATION FOR SEQ ID NO:6:

(i) SEQUENCE CHARACTERISTICS:
        (A) LENGTH: 181 amino acids
        (B) TYPE: amino acid
        (D) TOPOLOGY: unknown (ii) MOLECULE TYPE: protein (xi) SEQUENCE DESCRIPTION: SEQ ID NO:6:

| | | | | | | | | | | | | | | |
|---|---|---|---|---|---|---|---|---|---|---|---|---|---|---|
| Arg<br>1 | Lys | Pro | Pro | Lys<br>5 | Lys | His | Ser | Glu | Ile<br>10 | Ser | Thr | Thr | Asn | Leu<br>15 | Arg |
| Gln | Ile | Leu | Asn<br>20 | Asn | Leu | Asn | Ile | Phe<br>25 | Ser | Ser | Ser | Thr | Lys<br>30 | His | Gln |
| Ser | Asn | Met<br>35 | Ser | Thr | Ala | Ala | Ser<br>40 | Ala | Ser | Ser | Ser | Ser<br>45 | Ser | Ser | Ala |
| Ser | Leu | His<br>50 | His | Ala | Asn | His<br>55 | Leu | Ser | His | Ala | His<br>60 | Phe | Ser | His | Ala |
| Lys<br>65 | Asn | Met | Leu | Thr | Ala<br>70 | Ser | Met | Asn | Ser | His<br>75 | His | Ser | Arg | Cys | Ser<br>80 |
| Glu | Gly | Ser | Leu | Gln<br>85 | Ser | Gln | Arg | Ser | Ser<br>90 | Arg | Met | Gly | Ser | His<br>95 | Arg |
| Ser | Arg | Ser | Arg<br>100 | Thr | Arg | Thr | Ser | Asp<br>105 | Thr | Asp | Thr | Asn | Ser<br>110 | Val | Lys |
| Ser | His | Arg<br>115 | Arg | Arg | Pro | Ser | Val<br>120 | Asp | Thr | Val | Ser | Thr<br>125 | Tyr | Leu | Ser |
| His | Glu | Ser<br>130 | Lys | Glu | Ser | Leu<br>135 | Arg | Ser | Arg | Asn | Phe<br>140 | Ala | Ile | Ser | Val |
| Asn<br>145 | Asp | Leu | Leu | Asp | Cys<br>150 | Ser | Leu | Gly | Ser | Asp<br>155 | Glu | Val | Phe | Val | Pro<br>160 |
| Ser | Val | Pro | Pro | Ser<br>165 | Ser | Leu | Gly | Glu | Arg<br>170 | Ala | Pro | Val | Pro | Pro<br>175 | Pro |
| Leu | Pro | Leu | His<br>180 | Pro | | | | | | | | | | | |

(2) INFORMATION FOR SEQ ID NO:7:

(i) SEQUENCE CHARACTERISTICS:
        (A) LENGTH: 224 amino acids
        (B) TYPE: amino acid
        (D) TOPOLOGY: unknown (ii) MOLECULE TYPE: protein (xi) SEQUENCE DESCRIPTION: SEQ ID NO:7:

-continued

| | | | | | | | | | | | | | | |
|---|---|---|---|---|---|---|---|---|---|---|---|---|---|---|
| Ser<br>1 | Ile | Ala | Gly | Ser<br>5 | Ile | Val | Gly | Val | Asp<br>10 | Pro | Ala | Ser | Asp | Met<br>15 | Ile |
| Ser | Arg | Phe | Val<br>20 | Lys | Val | Val | Glu | Pro<br>25 | Pro | Leu | Trp | Pro | Asn<br>30 | Ala | Gln |
| Pro | Cys | Pro<br>35 | Met | Cys | Met | Glu | Glu<br>40 | Leu | Val | His | Ser | Ala<br>45 | Gln | Asn | Pro |
| Ala | Ile<br>50 | Ser | Leu | Ser | Arg | Cys<br>55 | Gln | His | Leu | Met | His<br>60 | Leu | Gln | Cys | Leu |
| Asn<br>65 | Gly | Met | Ile | Ile | Ala<br>70 | Gln | Gln | Asn | Glu | Met<br>75 | Asn | Lys | Asn | Leu | Phe<br>80 |
| Ile | Glu | Cys | Pro | Val<br>85 | Cys | Gly | Ile | Val | Tyr<br>90 | Gly | Glu | Lys | Val | Gly<br>95 | Asn |
| Gln | Pro | Ile | Gly<br>100 | Ser | Met | Ser | Trp | Ser<br>105 | Ile | Ile | Ser | Lys | Asn<br>110 | Leu | Pro |
| Gly | His | Glu<br>115 | Gly | Gln | Asn | Thr | Ile<br>120 | Gln | Ile | Val | Tyr | Asp<br>125 | Ile | Ala | Ser |
| Gly | Leu<br>130 | Gln | Thr | Glu | Glu | His<br>135 | Pro | His | Pro | Gly | Arg<br>140 | Ala | Phe | Phe | Ala |
| Val<br>145 | Gly | Phe | Pro | Arg | Ile<br>150 | Cys | Tyr | Leu | Pro | Asp<br>155 | Cys | Pro | Leu | Gly | Arg<br>160 |
| Lys | Val | Leu | Arg | Phe<br>165 | Leu | Lys | Ile | Ala | Phe<br>170 | Asp | Arg | Arg | Leu | Leu<br>175 | Phe |
| Ser | Ile | Gly | Arg<br>180 | Ser | Val | Thr | Thr | Gly<br>185 | Arg | Glu | Asp | Val | Val<br>190 | Ile | Trp |
| Asn | Ser | Val<br>195 | Asp | His | Lys | Thr | Gln<br>200 | Phe | Asn | Met | Phe | Pro<br>205 | Asp | Pro | Thr |
| Tyr | Leu<br>210 | Gln | Arg | Thr | Met | Gln<br>215 | Gln | Leu | Val | His | Leu<br>220 | Gly | Val | Thr | Asp |

( 2 ) INFORMATION FOR SEQ ID NO:8:

( i ) SEQUENCE CHARACTERISTICS:
      ( A ) LENGTH: 204 amino acids
      ( B ) TYPE: amino acid
      ( D ) TOPOLOGY: unknown ( i i ) MOLECULE TYPE: protein ( x i ) SEQUENCE DESCRIPTION: SEQ ID NO:8:

| | | | | | | | | | | | | | | |
|---|---|---|---|---|---|---|---|---|---|---|---|---|---|---|
| Met<br>1 | Ala | Ser | Ser | Ala<br>5 | Gly | Ser | Ala | Ala | Ser<br>10 | Gly | Ser | Val | Val | Pro<br>15 | Gly |
| Gly | Gly | Gly | Ser<br>20 | Ala | Ala | Ser | Ser | Cys<br>25 | Ala | Thr | Met | Ala | Leu<br>30 | Ser | Thr |
| Ala | Gly | Ser<br>35 | Gly | Gly | Pro | Pro | Val<br>40 | Asn | His | Ala | His | Ala<br>45 | Val | Cys | Val |
| Trp | Glu<br>50 | Phe | Glu | Ser | Arg | Gly<br>55 | Lys | Trp | Leu | Pro | Tyr<br>60 | Ser | Pro | Ala | Val |
| Ser<br>65 | Gln | His | Leu | Glu | Arg<br>70 | Ala | His | Ala | Lys | Lys<br>75 | Leu | Thr | Arg | Val | Met<br>80 |
| Leu | Ser | Asp | Ala | Asp<br>85 | Pro | Ser | Leu | Glu | Gln<br>90 | Tyr | Tyr | Val | Asn | Val<br>95 | Arg |
| Thr | Met | Thr | Gln<br>100 | Glu | Ser | Glu | Ala | Glu<br>105 | Thr | Arg | Ser | Gly | Leu<br>110 | Leu | Thr |
| Ile | Gly | Val<br>115 | Arg | Arg | Met | Leu | Tyr<br>120 | Ala | Pro | Ser | Ser | Pro<br>125 | Ala | Gly | Lys |
| Gly | Thr | Lys | Trp | Glu | Trp | Ser | Gly | Gly | Ser | Ala | Asp | Ser | Asn | Asn | Asp |

```
                    130                    135                      140
      Trp Arg Pro Tyr Asn Met His Val Gln Cys Ile Ile Glu Asp Ala Trp
      145                     150                 155                 160

Ala Arg Gly Glu Gln Thr Leu Asp Leu Cys Asn Thr His Ile Gly Leu
                      165                 170                 175

Pro Tyr Thr Ile Asn Phe Cys Asn Leu Thr His Val Arg Gln Pro Ser
                  180                 185                 190

Gly Pro Met Arg Ser Ile Arg Arg Thr Gln Gln Ala
                  195                 200
```

(2) INFORMATION FOR SEQ ID NO:9:

(i) SEQUENCE CHARACTERISTICS:
        (A) LENGTH: 16 amino acids
        (B) TYPE: amino acid
        (D) TOPOLOGY: unknown (ii) MOLECULE TYPE: peptide (xi) SEQUENCE DESCRIPTION: SEQ ID NO:9:

```
      Arg Ala Pro Thr Met Pro Pro Pro Leu Pro Val Pro Pro Gln Pro
      1                5                   10                  15              Pro
```

(2) INFORMATION FOR SEQ ID NO:10:

(i) SEQUENCE CHARACTERISTICS:
        (A) LENGTH: 15 amino acids
        (B) TYPE: amino acid
        (D) TOPOLOGY: unknown (ii) MOLECULE TYPE: peptide (xi) SEQUENCE DESCRIPTION: SEQ ID NO:10:

```
      Arg Ala Pro Val Pro Pro Pro Leu Pro Leu His Pro Arg Gln Gln
      1               5                   10                  15
```

(2) INFORMATION FOR SEQ ID NO:11:

(i) SEQUENCE CHARACTERISTICS:
        (A) LENGTH: 15 amino acids
        (B) TYPE: amino acid
        (D) TOPOLOGY: unknown (ii) MOLECULE TYPE: peptide (xi) SEQUENCE DESCRIPTION: SEQ ID NO:11:

```
      Phe Val Lys Val Val Glu Pro Pro Leu Trp Pro Asn Ala Gln Pro
      1               5                   10                  15
```

(2) INFORMATION FOR SEQ ID NO:12:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (xi) SEQUENCE DESCRIPTION: SEQ ID NO:12:

```
      Arg Ala Val Pro Pro Pro Leu Pro Pro Arg Arg Lys Glu Arg
      1               5                   10
```

(2) INFORMATION FOR SEQ ID NO:13:

(i) SEQUENCE CHARACTERISTICS:
        (A) LENGTH: 24 amino acids
        (B) TYPE: amino acid (D) TOPOLOGY: unknown (ii) MOLECULE TYPE: peptide (xi) SEQUENCE DESCRIPTION: SEQ ID NO:13:

```
Asp Ala Pro Thr Leu Pro Pro Arg Asp Gly Glu Leu Ser Pro Pro Pro
1               5                   10                  15

Ile Pro Pro Arg Leu Asn His Ser
            20
```

(2) INFORMATION FOR SEQ ID NO:14:

(i) SEQUENCE CHARACTERISTICS:
      (A) LENGTH: 16 amino acids
      (B) TYPE: amino acid
      (D) TOPOLOGY: unknown (ii) MOLECULE TYPE: peptide (xi) SEQUENCE DESCRIPTION: SEQ ID NO:14:

```
Ser Tyr Pro Pro Leu Pro Pro Pro Leu Pro Ala Asn Leu Ser Arg Thr
1               5                   10                  15
```

(2) INFORMATION FOR SEQ ID NO:15:

(i) SEQUENCE CHARACTERISTICS:
      (A) LENGTH: 16 amino acids
      (B) TYPE: amino acid
      (D) TOPOLOGY: unknown (ii) MOLECULE TYPE: peptide (xi) SEQUENCE DESCRIPTION: SEQ ID NO:15:

```
Ser Val Asp Ala Pro Pro Ile Pro Leu Pro Ser Arg Arg Val Gly Arg
1               5                   10                  15
```

(2) INFORMATION FOR SEQ ID NO:16:

(i) SEQUENCE CHARACTERISTICS:
      (A) LENGTH: 2471 amino acids
      (B) TYPE: amino acid
      (D) TOPOLOGY: unknown (ii) MOLECULE TYPE: protein (xi) SEQUENCE DESCRIPTION: SEQ ID NO:16:

```
Met Pro Ala Leu Arg Pro Ala Leu Leu Trp Ala Leu Leu Ala Leu Trp
1               5                   10                  15

Leu Cys Cys Ala Ala Pro Ala His Ala Leu Gln Cys Arg Asp Gly Tyr
                20                  25                  30

Glu Pro Cys Val Asn Glu Gly Met Cys Val Thr Tyr His Asn Gly Thr
            35                  40                  45

Gly Tyr Cys Lys Cys Pro Glu Gly Phe Leu Gly Glu Tyr Cys Gln His
        50                  55                  60

Arg Asp Pro Cys Glu Lys Asn Arg Cys Gln Asn Gly Gly Thr Cys Val
65                  70                  75                  80

Ala Gln Ala Met Leu Gly Lys Ala Thr Cys Arg Cys Ala Ser Gly Phe
                85                  90                  95

Thr Gly Glu Asp Cys Gln Tyr Ser Thr Ser His Pro Cys Phe Val Ser
            100                 105                 110

Arg Pro Cys Leu Asn Gly Gly Thr Cys His Met Leu Ser Arg Asp Thr
        115                 120                 125

Tyr Glu Cys Thr Cys Gln Val Gly Phe Thr Gly Lys Glu Cys Gln Trp
        130                 135                 140
```

```
Thr Asp Ala Cys Leu Ser His Pro Cys Ala Asn Gly Ser Thr Cys Thr
145                 150                 155                 160

Thr Val Ala Asn Gln Phe Ser Cys Lys Cys Leu Thr Gly Phe Gly
                165                 170                 175

Gln Lys Cys Glu Thr Asp Val Asn Glu Cys Asp Ile Pro Gly His Cys
            180                 185                 190

Gln His Gly Gly Thr Cys Leu Asn Leu Pro Gly Ser Tyr Gln Cys Gln
        195                 200                 205

Cys Pro Gln Gly Phe Thr Gly Gln Tyr Cys Asp Ser Leu Tyr Val Pro
    210                 215                 220

Cys Ala Pro Ser Pro Cys Val Asn Gly Gly Thr Cys Arg Gln Thr Gly
225                 230                 235                 240

Asp Phe Thr Phe Glu Cys Asn Cys Leu Pro Gly Phe Glu Gly Ser Thr
                245                 250                 255

Cys Glu Arg Asn Ile Asp Asp Cys Pro Asn His Arg Cys Gln Asn Gly
            260                 265                 270

Gly Val Cys Val Asp Gly Val Asn Thr Tyr Asn Cys Arg Cys Pro Pro
        275                 280                 285

Gln Trp Thr Gly Gln Phe Cys Thr Glu Asp Val Asp Glu Cys Leu Leu
    290                 295                 300

Gln Pro Asn Ala Cys Gln Asn Gly Gly Thr Cys Ala Asn Arg Asn Gly
305                 310                 315                 320

Gly Tyr Gly Cys Val Cys Val Asn Gly Trp Ser Gly Asp Asp Cys Ser
                325                 330                 335

Glu Asn Ile Asp Asp Cys Ala Phe Ala Ser Cys Thr Pro Gly Ser Thr
            340                 345                 350

Cys Ile Asp Arg Val Ala Ser Phe Ser Cys Met Cys Pro Glu Gly Lys
        355                 360                 365

Ala Gly Leu Leu Cys His Leu Asp Asp Ala Cys Ile Ser Asn Pro Cys
    370                 375                 380

His Lys Gly Ala Leu Cys Asp Thr Asn Pro Leu Asn Gly Gln Tyr Ile
385                 390                 395                 400

Cys Thr Cys Pro Gln Gly Tyr Lys Gly Ala Asp Cys Thr Glu Asp Val
                405                 410                 415

Asp Glu Cys Ala Met Ala Asn Ser Asn Pro Cys Glu His Ala Gly Lys
            420                 425                 430

Cys Val Asn Thr Asp Gly Ala Phe His Cys Glu Cys Leu Lys Gly Tyr
        435                 440                 445

Ala Gly Pro Arg Cys Glu Met Asp Ile Asn Glu Cys His Ser Asp Pro
    450                 455                 460

Cys Gln Asn Asp Ala Thr Cys Leu Asp Lys Ile Gly Gly Phe Thr Cys
465                 470                 475                 480

Leu Cys Met Pro Gly Phe Lys Gly Val His Cys Glu Leu Glu Ile Asn
                485                 490                 495

Glu Cys Gln Ser Asn Pro Cys Val Asn Asn Gly Gln Cys Val Asp Lys
            500                 505                 510

Val Asn Arg Phe Gln Cys Leu Cys Pro Pro Gly Phe Thr Gly Pro Val
        515                 520                 525

Cys Gln Ile Asp Ile Asp Asp Cys Ser Ser Thr Pro Cys Leu Asn Gly
    530                 535                 540

Ala Lys Cys Ile Asp His Pro Asn Gly Tyr Glu Cys Gln Cys Ala Thr
545                 550                 555                 560

Gly Phe Thr Gly Val Leu Cys Glu Glu Asn Ile Asp Asn Cys Asp Pro
```

|     |     |     |     |     | 565 |     |     |     | 570 |     |     |     |     | 575 |     |     |
|-----|-----|-----|-----|-----|-----|-----|-----|-----|-----|-----|-----|-----|-----|-----|-----|-----|
| Asp | Pro | Cys | His | His | Gly | Gln | Cys | Gln | Asp | Gly | Ile | Asp | Ser | Tyr | Thr |     |
|     |     |     | 580 |     |     |     |     | 585 |     |     |     |     | 590 |     |     |     |
| Cys | Ile | Cys | Asn | Pro | Gly | Tyr | Met | Gly | Ala | Ile | Cys | Ser | Asp | Gln | Ile |     |
|     |     | 595 |     |     |     |     | 600 |     |     |     |     | 605 |     |     |     |     |
| Asp | Glu | Cys | Tyr | Ser | Ser | Pro | Cys | Leu | Asn | Asp | Gly | Arg | Cys | Ile | Asp |     |
|     | 610 |     |     |     |     | 615 |     |     |     |     | 620 |     |     |     |     |     |
| Leu | Val | Asn | Gly | Tyr | Gln | Cys | Asn | Cys | Gln | Pro | Gly | Thr | Ser | Gly | Val |     |
| 625 |     |     |     |     | 630 |     |     |     |     | 635 |     |     |     |     | 640 |     |
| Asn | Cys | Glu | Ile | Asn | Phe | Asp | Asp | Cys | Ala | Ser | Asn | Pro | Cys | Ile | His |     |
|     |     |     |     | 645 |     |     |     |     | 650 |     |     |     |     | 655 |     |     |
| Gly | Ile | Cys | Met | Asp | Gly | Ile | Asn | Arg | Tyr | Ser | Cys | Val | Cys | Ser | Pro |     |
|     |     |     | 660 |     |     |     |     | 665 |     |     |     |     | 670 |     |     |     |
| Gly | Phe | Thr | Gly | Gln | Arg | Cys | Asn | Ile | Asp | Ile | Asp | Glu | Cys | Ala | Ser |     |
|     |     | 675 |     |     |     |     | 680 |     |     |     |     | 685 |     |     |     |     |
| Asn | Pro | Cys | Arg | Lys | Gly | Ala | Thr | Cys | Ile | Asn | Gly | Val | Asn | Gly | Phe |     |
|     | 690 |     |     |     |     | 695 |     |     |     |     | 700 |     |     |     |     |     |
| Arg | Cys | Ile | Cys | Pro | Glu | Gly | Pro | His | His | Pro | Ser | Cys | Tyr | Ser | Gln |     |
| 705 |     |     |     |     | 710 |     |     |     |     | 715 |     |     |     |     | 720 |     |
| Val | Asn | Glu | Cys | Leu | Ser | Asn | Pro | Cys | Ile | His | Gly | Asn | Cys | Thr | Gly |     |
|     |     |     |     | 725 |     |     |     |     | 730 |     |     |     |     | 735 |     |     |
| Gly | Leu | Ser | Gly | Tyr | Lys | Cys | Leu | Cys | Asp | Ala | Gly | Trp | Val | Gly | Ile |     |
|     |     |     | 740 |     |     |     |     | 745 |     |     |     |     | 750 |     |     |     |
| Asn | Cys | Glu | Val | Asp | Lys | Asn | Glu | Cys | Leu | Ser | Asn | Pro | Cys | Gln | Asn |     |
|     |     | 755 |     |     |     |     | 760 |     |     |     |     | 765 |     |     |     |     |
| Gly | Gly | Thr | Cys | Asp | Asn | Leu | Val | Asn | Gly | Tyr | Arg | Cys | Thr | Cys | Lys |     |
|     | 770 |     |     |     |     | 775 |     |     |     |     | 780 |     |     |     |     |     |
| Lys | Gly | Phe | Lys | Gly | Tyr | Asn | Cys | Gln | Val | Asn | Ile | Asp | Glu | Cys | Ala |     |
| 785 |     |     |     |     | 790 |     |     |     |     | 795 |     |     |     |     | 800 |     |
| Ser | Asn | Pro | Cys | Leu | Asn | Gln | Gly | Thr | Cys | Phe | Asp | Asp | Ile | Ser | Gly |     |
|     |     |     |     | 805 |     |     |     |     | 810 |     |     |     |     | 815 |     |     |
| Tyr | Thr | Cys | His | Cys | Val | Leu | Pro | Tyr | Thr | Gly | Lys | Asn | Cys | Gln | Thr |     |
|     |     |     | 820 |     |     |     |     | 825 |     |     |     |     | 830 |     |     |     |
| Val | Leu | Ala | Pro | Cys | Ser | Pro | Asn | Pro | Cys | Glu | Asn | Ala | Ala | Val | Cys |     |
|     |     | 835 |     |     |     |     | 840 |     |     |     |     | 845 |     |     |     |     |
| Lys | Glu | Ser | Pro | Asn | Phe | Glu | Ser | Tyr | Thr | Cys | Leu | Cys | Ala | Pro | Gly |     |
| 850 |     |     |     |     | 855 |     |     |     |     | 860 |     |     |     |     |     |     |
| Trp | Gln | Gly | Gln | Arg | Cys | Thr | Ile | Asp | Ile | Asp | Glu | Cys | Ile | Ser | Lys |     |
| 865 |     |     |     |     | 870 |     |     |     |     | 875 |     |     |     |     | 880 |     |
| Pro | Cys | Met | Asn | His | Gly | Leu | Cys | His | Asn | Thr | Gln | Gly | Ser | Tyr | Met |     |
|     |     |     |     | 885 |     |     |     |     | 890 |     |     |     |     | 895 |     |     |
| Cys | Glu | Cys | Pro | Pro | Gly | Phe | Ser | Gly | Met | Asp | Cys | Glu | Glu | Asp | Ile |     |
|     |     |     | 900 |     |     |     |     | 905 |     |     |     |     | 910 |     |     |     |
| Asp | Asp | Cys | Leu | Ala | Asn | Pro | Cys | Gln | Asn | Gly | Gly | Ser | Cys | Met | Asp |     |
|     |     | 915 |     |     |     |     | 920 |     |     |     |     | 925 |     |     |     |     |
| Gly | Val | Asn | Thr | Phe | Ser | Cys | Leu | Cys | Leu | Pro | Gly | Phe | Thr | Gly | Asp |     |
|     | 930 |     |     |     |     | 935 |     |     |     |     | 940 |     |     |     |     |     |
| Lys | Cys | Gln | Thr | Asp | Met | Asn | Glu | Cys | Leu | Ser | Glu | Pro | Cys | Lys | Asn |     |
| 945 |     |     |     |     | 950 |     |     |     |     | 955 |     |     |     |     | 960 |     |
| Gly | Gly | Thr | Cys | Ser | Asp | Tyr | Val | Asn | Ser | Tyr | Thr | Cys | Lys | Cys | Gln |     |
|     |     |     |     | 965 |     |     |     |     | 970 |     |     |     |     | 975 |     |     |
| Ala | Gly | Phe | Asp | Gly | Val | His | Cys | Glu | Asn | Asn | Ile | Asn | Glu | Cys | Thr |     |
|     |     |     | 980 |     |     |     |     | 985 |     |     |     |     | 990 |     |     |     |

-continued

| | | | | | | | | | | | | | | |
|---|---|---|---|---|---|---|---|---|---|---|---|---|---|---|
| Glu | Ser | Ser | Cys | Phe | Asn | Gly | Gly | Thr | Cys | Val | Asp | Gly | Ile | Asn | Ser |
| | | 995 | | | | | 1000 | | | | | 1005 | | |

Phe Ser Cys Leu Cys Pro Val Gly Phe Thr Gly Ser Phe Cys Leu His
　　　1010　　　　　　　　1015　　　　　　　　1020

Glu Ile Asn Glu Cys Ser Ser His Pro Cys Leu Asn Glu Gly Thr Cys
1025　　　　　　　　1030　　　　　　　　1035　　　　　　　　1040

Val Asp Gly Leu Gly Thr Tyr Arg Cys Ser Cys Pro Leu Gly Tyr Thr
　　　　　　　1045　　　　　　　　1050　　　　　　　　1055

Gly Lys Asn Cys Gln Thr Leu Val Asn Leu Cys Ser Arg Ser Pro Cys
　　　　1060　　　　　　　　1065　　　　　　　　1070

Lys Asn Lys Gly Thr Cys Val Gln Lys Lys Ala Glu Ser Gln Cys Leu
　　　1075　　　　　　　　1080　　　　　　　　1085

Cys Pro Ser Gly Trp Ala Gly Ala Tyr Cys Asp Val Pro Asn Val Ser
　　　1090　　　　　　　　1095　　　　　　　　1100

Cys Asp Ile Ala Ala Ser Arg Arg Gly Val Leu Val Glu His Leu Cys
1105　　　　　　　　1110　　　　　　　　1115　　　　　　　　1120

Gln His Ser Gly Val Cys Ile Asn Ala Gly Asn Thr His Tyr Cys Gln
　　　　　　　1125　　　　　　　　1130　　　　　　　　1135

Cys Pro Leu Gly Tyr Thr Gly Ser Tyr Cys Glu Glu Gln Leu Asp Glu
　　　　　　1140　　　　　　　　1145　　　　　　　　1150

Cys Ala Ser Asn Pro Cys Gln His Gly Ala Thr Cys Ser Asp Phe Ile
　　　　　　1155　　　　　　　　1160　　　　　　　　1165

Gly Gly Tyr Arg Cys Glu Cys Val Pro Gly Tyr Gln Gly Val Asn Cys
　　　　1170　　　　　　　　1175　　　　　　　　1180

Glu Tyr Glu Val Asp Glu Cys Gln Asn Gln Pro Cys Gln Asn Gly Gly
1185　　　　　　　　1190　　　　　　　　1195　　　　　　　　1200

Thr Cys Ile Asp Leu Val Asn His Phe Lys Cys Ser Cys Pro Pro Gly
　　　　　　1205　　　　　　　　1210　　　　　　　　1215

Thr Arg Gly Leu Leu Cys Glu Glu Asn Ile Asp Asp Cys Ala Arg Gly
　　　　1220　　　　　　　　1225　　　　　　　　1230

Pro His Cys Leu Asn Gly Gly Gln Cys Met Asp Arg Ile Gly Gly Tyr
　　　1235　　　　　　　　1240　　　　　　　　1245

Ser Cys Arg Cys Leu Pro Gly Phe Ala Gly Glu Arg Cys Glu Gly Asp
　　　1250　　　　　　　　1255　　　　　　　　1260

Ile Asn Glu Cys Leu Ser Asn Pro Cys Ser Ser Glu Gly Ser Leu Asp
1265　　　　　　　　1270　　　　　　　　1275　　　　　　　　1280

Cys Ile Gln Leu Thr Asn Asp Tyr Leu Cys Val Cys Arg Ser Ala Phe
　　　　　　1285　　　　　　　　1290　　　　　　　　1295

Thr Gly Arg His Cys Glu Thr Phe Val Asp Val Cys Pro Gln Met Pro
　　　　1300　　　　　　　　1305　　　　　　　　1310

Cys Leu Asn Gly Gly Thr Cys Ala Val Ala Ser Asn Met Pro Asp Gly
　　　1315　　　　　　　　1320　　　　　　　　1325

Phe Ile Cys Arg Cys Pro Pro Gly Phe Ser Gly Ala Arg Cys Gln Ser
　　　1330　　　　　　　　1335　　　　　　　　1340

Ser Cys Gly Gln Val Lys Cys Arg Lys Gly Glu Gln Cys Val His Thr
1345　　　　　　　　1350　　　　　　　　1355　　　　　　　　1360

Ala Ser Gly Pro Arg Cys Phe Cys Pro Ser Pro Arg Asp Cys Glu Ser
　　　　　　1365　　　　　　　　1370　　　　　　　　1375

Gly Cys Ala Ser Ser Pro Cys Gln His Gly Gly Ser Cys His Pro Gln
　　　　　　1380　　　　　　　　1385　　　　　　　　1390

Arg Gln Pro Pro Tyr Tyr Ser Cys Gln Cys Ala Pro Pro Phe Ser Gly
　　　　1395　　　　　　　　1400　　　　　　　　1405

Ser Arg Cys Glu Leu Tyr Thr Ala Pro Pro Ser Thr Pro Pro Ala Thr
　　　1410　　　　　　　　1415　　　　　　　　1420

| | | | | | | | | | | | | | | |
|---|---|---|---|---|---|---|---|---|---|---|---|---|---|---|
| Cys | Leu | Ser | Gln | Tyr | Cys | Ala | Asp | Lys | Ala | Arg | Asp | Gly | Val | Cys |
| 1425 | | | | 1430 | | | | 1435 | | | | | | 1440 |
| Glu | Ala | Cys | Asn | Ser | His | Ala | Cys | Gln | Trp | Asp | Gly | Gly | Asp | Cys | Ser |
| | | | | 1445 | | | | | 1450 | | | | | 1455 | |
| Leu | Thr | Met | Glu | Asn | Pro | Trp | Ala | Asn | Cys | Ser | Ser | Pro | Leu | Pro | Cys |
| | | | 1460 | | | | | 1465 | | | | | 1470 | | |
| Trp | Asp | Tyr | Ile | Asn | Asn | Gln | Cys | Asp | Glu | Leu | Cys | Asn | Thr | Val | Glu |
| | | | 1475 | | | | 1480 | | | | 1485 | | | | |
| Cys | Leu | Phe | Asp | Asn | Phe | Glu | Cys | Gln | Gly | Asn | Ser | Lys | Thr | Cys | Lys |
| | 1490 | | | | | 1495 | | | | | 1500 | | | | |
| Tyr | Asp | Lys | Tyr | Cys | Ala | Asp | His | Phe | Lys | Asp | Asn | His | Cys | Asn | Gln |
| 1505 | | | | 1510 | | | | 1515 | | | | | | 1520 | |
| Gly | Cys | Asn | Ser | Glu | Glu | Cys | Gly | Trp | Asp | Gly | Leu | Asp | Cys | Ala | Ala |
| | | | | 1525 | | | | 1530 | | | | | 1535 | | |
| Asp | Gln | Pro | Glu | Asn | Leu | Ala | Glu | Gly | Thr | Leu | Val | Ile | Val | Val | Leu |
| | | | 1540 | | | | | 1545 | | | | 1550 | | | |
| Met | Pro | Pro | Glu | Gln | Leu | Leu | Gln | Asp | Ala | Arg | Ser | Phe | Leu | Arg | Ala |
| | | 1555 | | | | | 1560 | | | | | 1565 | | | |
| Leu | Gly | Thr | Leu | Leu | His | Thr | Asn | Leu | Arg | Ile | Lys | Arg | Asp | Ser | Gln |
| | 1570 | | | | | 1575 | | | | 1580 | | | | | |
| Gly | Glu | Leu | Met | Val | Tyr | Pro | Tyr | Tyr | Gly | Glu | Lys | Ser | Ala | Ala | Met |
| 1585 | | | | | 1590 | | | | | 1595 | | | | | 1600 |
| Lys | Lys | Gln | Arg | Met | Thr | Arg | Arg | Ser | Leu | Pro | Gly | Glu | Gln | Glu | Gln |
| | | | | 1605 | | | | | 1610 | | | | | 1615 | |
| Glu | Val | Ala | Gly | Ser | Lys | Val | Phe | Leu | Glu | Ile | Asp | Asn | Arg | Gln | Cys |
| | | | 1620 | | | | | 1625 | | | | 1630 | | | |
| Val | Gln | Asp | Ser | Asp | His | Cys | Phe | Lys | Asn | Thr | Asp | Ala | Ala | Ala | Ala |
| | | | 1635 | | | | 1640 | | | | | 1645 | | | |
| Leu | Leu | Ala | Ser | His | Ala | Ile | Gln | Gly | Thr | Leu | Ser | Tyr | Pro | Leu | Val |
| | 1650 | | | | | 1655 | | | | | 1660 | | | | |
| Ser | Val | Val | Ser | Glu | Ser | Leu | Thr | Pro | Glu | Arg | Thr | Gln | Leu | Leu | Tyr |
| 1665 | | | | | 1670 | | | | | 1675 | | | | | 1680 |
| Leu | Leu | Ala | Val | Ala | Val | Val | Ile | Ile | Leu | Phe | Ile | Ile | Leu | Leu | Gly |
| | | | | 1685 | | | | | 1690 | | | | | 1695 | |
| Val | Ile | Met | Ala | Lys | Arg | Lys | Arg | Lys | His | Gly | Ser | Leu | Trp | Leu | Pro |
| | | | 1700 | | | | | 1705 | | | | | 1710 | | |
| Glu | Gly | Phe | Thr | Leu | Arg | Arg | Asp | Ala | Ser | Asn | His | Lys | Arg | Arg | Glu |
| | | | 1715 | | | | | 1720 | | | | 1725 | | | |
| Pro | Val | Gly | Gln | Asp | Ala | Val | Gly | Leu | Lys | Asn | Leu | Ser | Val | Gln | Val |
| | 1730 | | | | | 1735 | | | | | 1740 | | | | |
| Ser | Glu | Ala | Asn | Leu | Ile | Gly | Thr | Gly | Thr | Ser | Glu | His | Trp | Val | Asp |
| 1745 | | | | | 1750 | | | | | 1755 | | | | | 1760 |
| Asp | Glu | Gly | Pro | Gln | Pro | Lys | Lys | Val | Lys | Ala | Glu | Asp | Glu | Ala | Leu |
| | | | | 1765 | | | | 1770 | | | | | 1775 | | |
| Leu | Ser | Glu | Glu | Asp | Asp | Pro | Ile | Asp | Arg | Arg | Pro | Trp | Thr | Gln | Gln |
| | | | | 1780 | | | | 1785 | | | | | 1790 | | |
| His | Leu | Glu | Ala | Ala | Asp | Ile | Arg | Arg | Thr | Pro | Ser | Leu | Ala | Leu | Thr |
| | | | 1795 | | | | 1800 | | | | | 1805 | | | |
| Pro | Pro | Gln | Ala | Glu | Gln | Glu | Val | Asp | Val | Leu | Asp | Val | Asn | Val | Arg |
| | | 1810 | | | | | 1815 | | | | | 1820 | | | |
| Gly | Pro | Asp | Gly | Cys | Thr | Pro | Leu | Met | Leu | Ala | Ser | Leu | Arg | Gly | Gly |
| 1825 | | | | 1830 | | | | 1835 | | | | | | 1840 | |
| Ser | Ser | Asp | Leu | Ser | Asp | Glu | Asp | Glu | Asp | Ala | Glu | Asp | Ser | Ser | Ala |

```
              1845                  1850                    1855
Asn  Ile  Ile  Thr  Asp  Leu  Val  Tyr  Gln  Gly  Ala  Ser  Leu  Gln  Ala  Gln
              1860                  1865                    1870
Thr  Asp  Arg  Thr  Gly  Glu  Met  Ala  Leu  His  Leu  Ala  Ala  Arg  Tyr  Ser
              1875                  1880                    1885
Arg  Ala  Asp  Ala  Ala  Lys  Arg  Leu  Leu  Asp  Ala  Gly  Ala  Asp  Ala  Asn
              1890                  1895                    1900
Ala  Gln  Asp  Asn  Met  Gly  Arg  Cys  Pro  Leu  His  Ala  Ala  Val  Ala  Ala
1905                    1910                  1915                    1920
Asp  Ala  Gln  Gly  Val  Phe  Gln  Ile  Leu  Ile  Arg  Asn  Arg  Val  Thr  Asp
              1925                  1930                    1935
Leu  Asp  Ala  Arg  Met  Asn  Asp  Gly  Thr  Thr  Pro  Leu  Ile  Leu  Ala  Ala
              1940                  1945                    1950
Arg  Leu  Ala  Val  Glu  Gly  Met  Val  Ala  Glu  Leu  Ile  Asn  Cys  Gln  Ala
              1955                  1960                    1965
Asp  Val  Asn  Ala  Val  Asp  Asp  His  Gly  Lys  Ser  Ala  Leu  His  Trp  Ala
              1970                  1975                    1980
Ala  Ala  Val  Asn  Asn  Val  Glu  Ala  Thr  Leu  Leu  Leu  Leu  Lys  Asn  Gly
1985                    1990                  1995                    2000
Ala  Asn  Arg  Asp  Met  Gln  Asp  Asn  Lys  Glu  Glu  Thr  Pro  Leu  Phe  Leu
              2005                  2010                    2015
Ala  Ala  Arg  Glu  Gly  Ser  Tyr  Glu  Ala  Ala  Lys  Ile  Leu  Leu  Asp  His
              2020                  2025                    2030
Phe  Ala  Asn  Arg  Asp  Ile  Thr  Asp  His  Met  Asp  Arg  Leu  Pro  Arg  Asp
              2035                  2040                    2045
Val  Ala  Arg  Asp  Arg  Met  His  His  Asp  Ile  Val  Arg  Leu  Leu  Asp  Glu
              2050                  2055                    2060
Tyr  Asn  Val  Thr  Pro  Ser  Pro  Pro  Gly  Thr  Val  Leu  Thr  Ser  Ala  Leu
2065                    2070                  2075                    2080
Ser  Pro  Val  Ile  Cys  Gly  Pro  Asn  Arg  Ser  Phe  Leu  Ser  Leu  Lys  His
              2085                  2090                    2095
Thr  Pro  Met  Gly  Lys  Lys  Ser  Arg  Arg  Pro  Ser  Ala  Lys  Ser  Thr  Met
              2100                  2105                    2110
Pro  Thr  Ser  Leu  Pro  Asn  Leu  Ala  Lys  Glu  Ala  Lys  Asp  Ala  Lys  Gly
              2115                  2120                    2125
Ser  Arg  Arg  Lys  Lys  Ser  Leu  Ser  Glu  Lys  Val  Gln  Leu  Ser  Glu  Ser
              2130                  2135                    2140
Ser  Val  Thr  Leu  Ser  Pro  Val  Asp  Ser  Leu  Glu  Ser  Pro  His  Thr  Tyr
2145                    2150                  2155                    2160
Val  Ser  Asp  Thr  Thr  Ser  Ser  Pro  Met  Ile  Thr  Ser  Pro  Gly  Ile  Leu
              2165                  2170                    2175
Gln  Ala  Ser  Pro  Asn  Pro  Met  Leu  Ala  Thr  Ala  Ala  Pro  Pro  Ala  Pro
              2180                  2185                    2190
Val  His  Ala  Gln  His  Ala  Leu  Ser  Phe  Ser  Asn  Leu  His  Glu  Met  Gln
              2195                  2200                    2205
Pro  Leu  Ala  His  Gly  Ala  Ser  Thr  Val  Leu  Pro  Ser  Val  Ser  Gln  Leu
              2210                  2215                    2220
Leu  Ser  His  His  His  Ile  Val  Ser  Pro  Gly  Ser  Gly  Ser  Ala  Gly  Ser
2225                    2230                  2235                    2240
Leu  Ser  Arg  Leu  His  Pro  Val  Pro  Val  Pro  Ala  Asp  Trp  Met  Asn  Arg
              2245                  2250                    2255
Met  Glu  Val  Asn  Glu  Thr  Gln  Tyr  Asn  Glu  Met  Phe  Gly  Met  Val  Leu
              2260                  2265                    2270
```

```
Ala  Pro  Ala  Glu  Gly  Thr  His  Pro  Gly  Ile  Ala  Pro  Gln  Ser  Arg  Pro
               2275                2280                    2285

Pro  Glu  Gly  Lys  His  Ile  Thr  Thr  Pro  Arg  Glu  Pro  Leu  Pro  Pro  Ile
          2290                2295                2300

Val  Thr  Phe  Gln  Leu  Ile  Pro  Lys  Gly  Ser  Ile  Ala  Gln  Pro  Ala  Gly
2305                2310                     2315                          2320

Ala  Pro  Gln  Pro  Gln  Ser  Thr  Cys  Pro  Pro  Ala  Val  Ala  Gly  Pro  Leu
                    2325                2330                          2335

Pro  Thr  Met  Tyr  Gln  Ile  Pro  Glu  Met  Ala  Arg  Leu  Pro  Ser  Val  Ala
               2340                2345                     2350

Phe  Pro  Thr  Ala  Met  Met  Pro  Gln  Gln  Asp  Gly  Gln  Val  Ala  Gln  Thr
               2355                2360                     2365

Ile  Leu  Pro  Ala  Tyr  His  Pro  Phe  Pro  Ala  Ser  Val  Gly  Lys  Tyr  Pro
               2370                2375                2380

Thr  Pro  Pro  Ser  Gln  His  Ser  Tyr  Ala  Ser  Ser  Asn  Ala  Ala  Glu  Arg
2385                2390                     2395                          2400

Thr  Pro  Ser  His  Ser  Gly  His  Leu  Gln  Gly  Glu  His  Pro  Tyr  Leu  Thr
               2405                2410                     2415

Pro  Ser  Pro  Glu  Ser  Pro  Asp  Gln  Trp  Ser  Ser  Ser  Ser  Pro  His  Ser
               2420                2425                     2430

Ala  Ser  Asp  Trp  Ser  Asp  Val  Thr  Thr  Ser  Pro  Thr  Pro  Gly  Gly  Ala
               2435                2440                     2445

Gly  Gly  Gly  Gln  Arg  Gly  Pro  Gly  Thr  His  Met  Ser  Glu  Pro  Pro  His
2450                     2455                          2460

Asn  Asn  Met  Gln  Val  Tyr  Ala
2465                2470
```

( 2 ) INFORMATION FOR SEQ ID NO:17:

( i ) SEQUENCE CHARACTERISTICS:
        ( A ) LENGTH: 2556 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:17:

```
Met  Pro  Pro  Leu  Leu  Ala  Pro  Leu  Leu  Cys  Leu  Ala  Leu  Leu  Pro  Ala
1               5                    10                       15

Leu  Ala  Ala  Arg  Gly  Pro  Arg  Cys  Ser  Gln  Pro  Gly  Glu  Thr  Cys  Leu
               20                 25                      30

Asn  Gly  Gly  Lys  Cys  Glu  Ala  Ala  Asn  Gly  Thr  Glu  Ala  Cys  Val  Cys
               35                 40                      45

Gly  Gly  Ala  Phe  Val  Gly  Pro  Arg  Cys  Gln  Asp  Pro  Asn  Pro  Cys  Leu
          50                 55                      60

Ser  Thr  Pro  Cys  Lys  Asn  Ala  Gly  Thr  Cys  His  Val  Val  Asp  Arg  Arg
65                 70                      75                           80

Gly  Val  Ala  Asp  Tyr  Ala  Cys  Ser  Cys  Ala  Leu  Gly  Phe  Ser  Gly  Pro
               85                 90                      95

Leu  Cys  Leu  Thr  Pro  Leu  Asp  Asn  Ala  Cys  Leu  Thr  Asn  Pro  Cys  Arg
               100                105                     110

Asn  Gly  Gly  Thr  Cys  Asp  Leu  Leu  Thr  Leu  Thr  Glu  Tyr  Lys  Cys  Arg
               115                120                     125

Cys  Pro  Pro  Gly  Trp  Ser  Gly  Lys  Ser  Cys  Gln  Gln  Ala  Asp  Pro  Cys
          130                135                     140

Ala  Ser  Asn  Pro  Cys  Ala  Asn  Gly  Gly  Gln  Cys  Leu  Pro  Phe  Glu  Ala
145                 150                     155                          160
```

```
Ser Tyr Ile Cys His Cys Pro Pro Ser Phe His Gly Pro Thr Cys Trp
                165             170             175
Gln Asp Val Asn Glu Cys Gly Gln Lys Pro Arg Leu Cys Arg His Gly
            180             185             190
Gly Thr Cys His Asn Glu Val Gly Ser Tyr Arg Cys Val Cys Arg Ala
        195             200             205
Thr His Thr Gly Pro Asn Cys Glu Trp Pro Tyr Val Pro Cys Ser Pro
    210             215             220
Ser Pro Cys Gln Asn Gly Gly Thr Cys Arg Pro Thr Gly Asp Val Thr
225             230             235             240
His Glu Cys Ala Cys Leu Pro Gly Phe Thr Gly Gln Asn Cys Glu Glu
            245             250             255
Asn Ile Asp Asp Cys Pro Gly Asn Asn Cys Lys Asn Gly Gly Ala Cys
            260             265             270
Val Asp Gly Val Asn Thr Tyr Asn Cys Pro Cys Pro Pro Glu Trp Thr
            275             280             285
Gly Gln Tyr Cys Thr Glu Asp Val Asp Glu Cys Gln Leu Met Pro Asn
    290             295             300
Ala Cys Gln Asn Gly Gly Thr Cys His Asn Thr His Gly Gly Tyr Asn
305             310             315             320
Cys Val Cys Val Asn Gly Trp Thr Gly Glu Asp Cys Ser Glu Asn Ile
            325             330             335
Asp Asp Cys Ala Ser Ala Ala Cys Phe His Gly Ala Thr Cys His Asp
            340             345             350
Arg Val Ala Ser Phe Tyr Cys Glu Cys Pro His Gly Arg Thr Gly Leu
        355             360             365
Leu Cys His Leu Asn Asp Ala Cys Ile Ser Asn Pro Cys Asn Glu Gly
    370             375             380
Ser Asn Cys Asp Thr Asn Pro Val Asn Gly Lys Ala Ile Cys Thr Cys
385             390             395             400
Pro Ser Gly Tyr Thr Gly Pro Ala Cys Ser Gln Asp Val Asp Glu Cys
            405             410             415
Ser Leu Gly Ala Asn Pro Cys Glu His Ala Gly Lys Cys Ile Asn Thr
            420             425             430
Leu Gly Ser Phe Glu Cys Gln Cys Leu Gln Gly Tyr Thr Gly Pro Arg
        435             440             445
Cys Glu Ile Asp Val Asn Glu Cys Val Ser Asn Pro Cys Gln Asn Asp
    450             455             460
Ala Thr Cys Leu Asp Gln Ile Gly Glu Phe Gln Cys Met Cys Met Pro
465             470             475             480
Gly Tyr Glu Gly Val His Cys Glu Val Asn Thr Asp Glu Cys Ala Ser
            485             490             495
Ser Pro Cys Leu His Asn Gly Arg Cys Leu Asp Lys Ile Asn Glu Phe
            500             505             510
Gln Cys Glu Cys Pro Thr Gly Phe Thr Gly His Leu Cys Gln Tyr Asp
        515             520             525
Val Asp Glu Cys Ala Ser Thr Pro Cys Lys Asn Gly Ala Lys Cys Leu
    530             535             540
Asp Gly Pro Asn Thr Tyr Thr Cys Val Cys Thr Glu Gly Tyr Thr Gly
545             550             555             560
Thr His Cys Glu Val Asp Ile Asp Glu Cys Asp Pro Asp Pro Cys His
            565             570             575
Tyr Gly Ser Cys Lys Asp Gly Val Ala Thr Phe Thr Cys Leu Cys Arg
```

-continued

```
                  580                           585                          590
Pro  Gly  Tyr  Thr  Gly  His  His  Cys  Glu  Thr  Asn  Ile  Asn  Glu  Cys  Ser
               595                           600                          605

Ser  Gln  Pro  Cys  Arg  Leu  Trp  Gly  Thr  Cys  Gln  Asp  Pro  Asp  Asn  Ala
          610                           615                          620

Tyr  Leu  Cys  Phe  Cys  Leu  Lys  Gly  Thr  Thr  Gly  Pro  Asn  Cys  Glu  Ile
625                           630                           635                          640

Asn  Leu  Asp  Asp  Cys  Ala  Ser  Ser  Pro  Cys  Asp  Ser  Gly  Thr  Cys  Leu
                    645                           650                          655

Asp  Lys  Ile  Asp  Gly  Tyr  Glu  Cys  Ala  Cys  Glu  Pro  Gly  Tyr  Thr  Gly
               660                           665                          670

Ser  Met  Cys  Asn  Ser  Asn  Ile  Asp  Glu  Cys  Ala  Gly  Asn  Pro  Cys  His
          675                           680                          685

Asn  Gly  Gly  Thr  Cys  Glu  Asp  Gly  Ile  Asn  Gly  Phe  Thr  Cys  Arg  Cys
          690                           695                          700

Pro  Glu  Gly  Tyr  His  Asp  Pro  Thr  Cys  Leu  Ser  Glu  Val  Asn  Glu  Cys
705                           710                           715                          720

Asn  Ser  Asn  Pro  Cys  Val  His  Gly  Ala  Cys  Trp  Asp  Ser  Leu  Asn  Gly
                    725                           730                          735

Tyr  Lys  Cys  Asp  Cys  Asp  Pro  Gly  Trp  Ser  Gly  Thr  Asn  Cys  Asp  Ile
               740                           745                          750

Asn  Asn  Asn  Glu  Cys  Glu  Ser  Asn  Pro  Cys  Val  Asn  Gly  Gly  Thr  Cys
               755                           760                          765

Lys  Asp  Met  Thr  Ser  Gly  Ile  Val  Cys  Thr  Cys  Trp  Glu  Gly  Phe  Ser
     770                           775                          780

Gly  Pro  Asn  Cys  Gln  Thr  Asn  Ile  Asn  Glu  Cys  Ala  Ser  Asn  Pro  Cys
785                           790                           795                          800

Leu  Asn  Lys  Gly  Thr  Cys  Ile  Asp  Asp  Val  Ala  Gly  Tyr  Lys  Cys  Asn
                    805                           810                          815

Cys  Leu  Leu  Pro  Tyr  Thr  Gly  Ala  Thr  Cys  Glu  Val  Val  Leu  Ala  Pro
               820                           825                          830

Cys  Ala  Pro  Ser  Pro  Cys  Arg  Asn  Gly  Gly  Glu  Cys  Arg  Gln  Ser  Glu
               835                           840                          845

Asp  Tyr  Glu  Ser  Phe  Ser  Cys  Val  Cys  Pro  Thr  Ala  Gly  Ala  Lys  Gly
     850                           855                          860

Gln  Thr  Cys  Glu  Val  Asp  Ile  Asn  Glu  Cys  Val  Leu  Ser  Pro  Cys  Trp
865                           870                           875                          880

His  Gly  Ala  Ser  Cys  Gln  Asn  Thr  His  Gly  Xaa  Tyr  Arg  Cys  His  Cys
               885                           890                          895

Gln  Ala  Gly  Tyr  Ser  Gly  Arg  Asn  Cys  Glu  Thr  Asp  Ile  Asp  Asp  Cys
               900                           905                          910

Trp  Pro  Asn  Pro  Cys  His  Asn  Gly  Gly  Ser  Cys  Thr  Asp  Gly  Ile  Asn
          915                           920                          925

Thr  Ala  Phe  Cys  Asp  Cys  Leu  Pro  Gly  Phe  Trp  Gly  Thr  Phe  Cys  Glu
     930                           935                          940

Glu  Asp  Ile  Asn  Glu  Cys  Ala  Ser  Asp  Pro  Cys  Arg  Asn  Gly  Ala  Asn
945                           950                           955                          960

Cys  Thr  Asp  Cys  Val  Asp  Ser  Tyr  Thr  Cys  Thr  Cys  Pro  Ala  Gly  Phe
                    965                           970                          975

Ser  Gly  Ile  His  Cys  Glu  Asn  Asn  Thr  Pro  Asp  Cys  Thr  Glu  Ser  Ser
               980                           985                          990

Cys  Phe  Asn  Gly  Gly  Thr  Cys  Val  Asp  Gly  Ile  Asn  Ser  Phe  Thr  Cys
               995                          1000                         1005
```

-continued

| | | | | | | | | | | | | | | |
|---|---|---|---|---|---|---|---|---|---|---|---|---|---|---|
|Leu|Cys|Pro|Pro|Gly|Phe|Thr|Gly|Ser|Tyr|Cys|Gln|His|Val|Asn|
| |1010| | | |1015| | | | |1020| | | | |

Glu Cys Asp Ser Arg Pro Cys Leu Leu Gly Gly Thr Cys Gln Asp Gly
1025                  1030                 1035                       1040

Arg Gly Leu His Arg Cys Thr Cys Pro Gln Gly Tyr Thr Gly Pro Asn
             1045                   1050                   1055

Cys Gln Asn Leu Val His Trp Cys Asp Ser Ser Pro Cys Lys Asn Gly
             1060                   1065                   1070

Gly Lys Cys Trp Gln Thr His Thr Gln Tyr Arg Cys Glu Cys Pro Ser
             1075                   1080                   1085

Gly Trp Thr Gly Leu Tyr Cys Asp Val Pro Ser Val Ser Cys Glu Val
             1090                   1095                   1100

Ala Ala Gln Arg Gln Gly Val Asp Val Ala Arg Leu Cys Gln His Gly
1105                  1110                 1115                       1120

Gly Leu Cys Val Asp Ala Gly Asn Thr His His Cys Arg Cys Gln Ala
             1125                   1130                   1135

Gly Tyr Thr Gly Ser Tyr Cys Glu Asp Leu Val Asp Glu Cys Ser Pro
             1140                   1145                   1150

Ser Pro Cys Gln Asn Gly Ala Thr Cys Thr Asp Tyr Leu Gly Gly Tyr
             1155                   1160                   1165

Ser Cys Lys Cys Val Ala Gly Tyr His Gly Val Asn Cys Ser Glu Glu
             1170                   1175                   1180

Ile Asp Glu Cys Leu Ser His Pro Cys Gln Asn Gly Gly Thr Cys Leu
1185                  1190                 1195                       1200

Asp Leu Pro Asn Thr Tyr Lys Cys Ser Cys Pro Trp Gly Thr Gln Gly
             1205                   1210                   1215

Val His Cys Glu Ile Asn Val Asp Asp Cys Asn Pro Pro Val Asp Pro
             1220                   1225                   1230

Val Ser Trp Ser Pro Lys Cys Phe Asn Asn Gly Thr Cys Val Asp Gln
             1235                   1240                   1245

Val Gly Gly Tyr Ser Cys Thr Cys Pro Pro Gly Phe Val Gly Glu Arg
             1250                   1255                   1260

Cys Glu Gly Asp Val Asn Glu Cys Leu Ser Asn Pro Cys Asp Ala Arg
1265                  1270                 1275                       1280

Gly Thr Gln Asn Cys Val Gln Arg Val Asn Asp Phe His Cys Glu Cys
             1285                   1290                   1295

Arg Ala Gly His Thr Gly Arg Arg Cys Glu Ser Val Ile Asn Gly Cys
             1300                   1305                   1310

Lys Gly Lys Pro Cys Lys Asn Gly Gly Thr Cys Ala Val Ala Ser Asn
             1315                   1320                   1325

Thr Ala Arg Gly Phe Ile Cys Lys Cys Pro Ala Gly Phe Glu Gly Ala
             1330                   1335                   1340

Thr Cys Glu Asn Asp Ala Arg Thr Cys Gly Ser Leu Arg Cys Leu Asn
1345                  1350                 1355                       1360

Gly Gly Thr Cys Ile Ser Gly Pro Arg Ser Pro Thr Cys Leu Cys Leu
             1365                   1370                   1375

Gly Pro Phe Thr Gly Pro Glu Cys Gln Phe Pro Ala Ser Ser Pro Cys
             1380                   1385                   1390

Leu Gly Gly Asn Pro Cys Tyr Asn Gln Gly Thr Cys Glu Pro Thr Ser
             1395                   1400                   1405

Glu Ser Pro Phe Tyr Arg Cys Leu Cys Pro Ala Lys Phe Asn Gly Leu
             1410                   1415                   1420

Leu Cys His Ile Leu Asp Tyr Ser Phe Gly Gly Gly Ala Gly Arg Asp
1425                  1430                 1435                       1440

```
Ile  Pro  Pro  Pro  Leu  Ile  Glu  Glu  Ala  Cys  Glu  Leu  Pro  Glu  Cys  Gln
              1445                    1450                    1455

Glu  Asp  Ala  Gly  Asn  Lys  Val  Cys  Ser  Leu  Gln  Cys  Asn  Asn  His  Ala
              1460                    1465                    1470

Cys  Gly  Trp  Asp  Gly  Gly  Asp  Cys  Ser  Leu  Asn  Phe  Asn  Asp  Pro  Trp
              1475                    1480                    1485

Lys  Asn  Cys  Thr  Gln  Ser  Leu  Gln  Cys  Trp  Lys  Tyr  Phe  Ser  Asp  Gly
              1490                    1495                    1500

His  Cys  Asp  Ser  Gln  Cys  Asn  Ser  Ala  Gly  Cys  Leu  Phe  Asp  Gly  Phe
1505                    1510                    1515                    1520

Asp  Cys  Gln  Arg  Ala  Glu  Gly  Gln  Cys  Asn  Pro  Leu  Tyr  Asp  Gln  Tyr
                   1525                    1530                    1535

Cys  Lys  Asp  His  Phe  Ser  Asp  Gly  His  Cys  Asp  Gln  Gly  Cys  Asn  Ser
                   1540                    1545                    1550

Ala  Glu  Cys  Glu  Trp  Asp  Gly  Leu  Asp  Cys  Ala  Glu  His  Val  Pro  Glu
                   1555                    1560                    1565

Arg  Leu  Ala  Ala  Gly  Thr  Leu  Val  Val  Val  Leu  Met  Pro  Pro  Glu
     1570                    1575                    1580

Gln  Leu  Arg  Asn  Ser  Ser  Phe  His  Phe  Leu  Trp  Glu  Leu  Ser  Arg  Val
1585                    1590                    1595                    1600

Leu  His  Thr  Asn  Val  Val  Phe  Lys  Arg  Asp  Ala  His  Gly  Gln  Gln  Met
                    1605                    1610                    1615

Ile  Phe  Pro  Tyr  Tyr  Gly  Arg  Glu  Glu  Leu  Arg  Lys  His  Pro  Ile
                    1620                    1625                    1630

Lys  Arg  Ala  Ala  Glu  Gly  Trp  Ala  Ala  Pro  Asp  Ala  Leu  Leu  Gly  Gln
                    1635                    1640                    1645

Val  Lys  Ala  Ser  Leu  Leu  Pro  Gly  Gly  Ser  Glu  Gly  Gly  Trp  Trp  Trp
     1650                    1655                    1660

Arg  Glu  Leu  Asp  Pro  Met  Asp  Val  Arg  Gly  Ser  Ile  Val  Tyr  Leu  Glu
1665                    1670                    1675                    1680

Ile  Asp  Asn  Trp  Gln  Cys  Val  Gln  Ala  Ser  Ser  Gln  Cys  Phe  Gln  Ser
                    1685                    1690                    1695

Ala  Thr  Asp  Val  Ala  Ala  Phe  Leu  Gly  Ala  Leu  Ala  Ser  Leu  Gly  Ser
                    1700                    1705                    1710

Leu  Asn  Ile  Pro  Tyr  Lys  Ile  Glu  Ala  Val  Gln  Ser  Glu  Thr  Val  Glu
                    1715                    1720                    1725

Pro  Pro  Pro  Pro  Ala  Gln  Leu  His  Phe  Met  Tyr  Val  Ala  Ala  Ala  Ala
     1730                    1735                    1740

Phe  Val  Leu  Leu  Phe  Phe  Val  Gly  Cys  Gly  Val  Leu  Leu  Ser  Arg  Lys
1745                    1750                    1755                    1760

Arg  Trp  Xaa  Gln  His  Gly  Gln  Leu  Trp  Phe  Pro  Glu  Gly  Phe  Lys  Val
                    1765                    1770                    1775

Ser  Glu  Ala  Ser  Lys  Lys  Lys  Trp  Trp  Glu  Xaa  Leu  Gly  Glu  Asp  Ser
               1780                    1785                    1790

Val  Gly  Leu  Lys  Pro  Leu  Lys  Asn  Ala  Ser  Asp  Gly  Ala  Leu  Met  Asp
          1795                    1800                    1805

Asp  Asn  Gln  Asn  Glu  Trp  Gly  Asp  Glu  Asp  Leu  Glu  Thr  Lys  Lys  Phe
     1810                    1815                    1820

Trp  Phe  Glu  Glu  Pro  Val  Val  Leu  Pro  Asp  Leu  Asp  Asp  Gln  Thr  Asp
1825                    1830                    1835                    1840

His  Trp  Gln  Trp  Thr  Gln  Gln  His  Leu  Asp  Ala  Ala  Asp  Leu  Arg  Met
                    1845                    1850                    1855

Ser  Ala  Met  Ala  Pro  Thr  Pro  Pro  Gln  Gly  Glu  Val  Asp  Ala  Asp  Cys
```

|       |       |       | 1860  |       |       |       |       | 1865  |       |       |       |       | 1870  |       |
|-------|-------|-------|-------|-------|-------|-------|-------|-------|-------|-------|-------|-------|-------|-------|
| Met   | Asp   | Val   | Asn   | Val   | Arg   | Gly   | Pro   | Asp   | Gly   | Phe   | Thr   | Pro   | Leu   | Met   | Ile |
|       |       |       | 1875  |       |       |       |       | 1880  |       |       |       |       | 1885  |       |
| Ala   | Ser   | Cys   | Ser   | Gly   | Gly   | Gly   | Leu   | Glu   | Thr   | Gly   | Asn   | Ser   | Glu   | Glu   | Glu |
|       |       |       | 1890  |       |       |       |       | 1895  |       |       |       |       | 1900  |       |
| Glu   | Asp   | Ala   | Pro   | Ala   | Val   | Ile   | Ser   | Asp   | Phe   | Ile   | Tyr   | Gln   | Gly   | Ala   | Ser |
| 1905  |       |       |       |       | 1910  |       |       |       |       | 1915  |       |       |       |       | 1920 |

Met Asp Val Asn Val Arg Gly Pro Asp Gly Phe Thr Pro Leu Met Ile
1875                         1880                         1885

Ala Ser Cys Ser Gly Gly Gly Leu Glu Thr Gly Asn Ser Glu Glu Glu
1890                         1895                         1900

Glu Asp Ala Pro Ala Val Ile Ser Asp Phe Ile Tyr Gln Gly Ala Ser
1905                    1910                    1915                    1920

Leu His Asn Gln Thr Asp Arg Thr Gly Glu Thr Ala Leu His Leu Ala
                    1925                    1930                    1935

Ala Arg Tyr Ser Arg Ser Asp Ala Ala Lys Arg Leu Leu Glu Ala Ser
                    1940                    1945                    1950

Ala Asp Ala Asn Ile Gln Asp Asn Met Gly Arg Thr Pro Leu His Ala
                    1955                    1960                    1965

Ala Val Ser Ala Asp Ala Gln Gly Val Phe Gln Ile Leu Ile Trp Asn
                    1970                    1975                    1980

Arg Ala Thr Asp Leu Asp Ala Arg Met His Asp Gly Thr Thr Pro Leu
1985                    1990                    1995                    2000

Ile Leu Ala Ala Arg Leu Ala Val Glu Gly Met Leu Glu Asp Leu Ile
                    2005                    2010                    2015

Asn Ser His Ala Asp Val Asn Ala Val Asp Asp Leu Gly Lys Ser Ala
                    2020                    2025                    2030

Leu His Trp Ala Ala Ala Val Asn Asn Val Asp Ala Ala Val Val Leu
                    2035                    2040                    2045

Leu Lys Asn Gly Ala Asn Lys Asp Met Gln Asn Asn Arg Glu Glu Thr
                    2050                    2055                    2060

Pro Leu Phe Leu Ala Ala Trp Glu Gly Ser Tyr Glu Thr Ala Lys Val
2065                    2070                    2075                    2080

Leu Leu Asp His Phe Ala Asn Trp Asp Ile Thr Asp His Met Asp Arg
                    2085                    2090                    2095

Leu Pro Arg Asp Ile Ala Gln Glu Arg Met His His Asp Ile Val Arg
                    2100                    2105                    2110

Leu Leu Asp Glu Tyr Asn Leu Val Arg Ser Pro Gln Leu His Gly Ala
                    2115                    2120                    2125

Pro Leu Gly Gly Thr Pro Thr Leu Ser Pro Pro Leu Cys Ser Pro Asn
                    2130                    2135                    2140

Gly Tyr Leu Gly Ser Leu Lys Pro Gly Val Gln Gly Lys Lys Val Arg
2145                    2150                    2155                    2160

Lys Pro Ser Ser Lys Gly Leu Ala Cys Gly Ser Lys Glu Ala Lys Asp
                    2165                    2170                    2175

Leu Lys Ala Trp Arg Lys Lys Ser Gln Asp Gly Lys Gly Cys Leu Leu
                    2180                    2185                    2190

Asp Ser Ser Gly Met Leu Ser Pro Val Asp Ser Leu Glu Ser Pro His
                    2195                    2200                    2205

Gly Tyr Leu Ser Asp Val Ala Ser Pro Pro Leu Leu Pro Ser Pro Phe
                    2210                    2215                    2220

Gln Gln Ser Pro Ser Val Pro Leu Asn His Leu Pro Gly Met Pro Asp
2225                    2230                    2235                    2240

Thr His Leu Gly Ile Gly His Leu Asn Val Ala Ala Lys Pro Glu Met
                    2245                    2250                    2255

Ala Ala Leu Gly Gly Gly Gly Trp Leu Ala Phe Glu Thr Gly Pro Pro
                    2260                    2265                    2270

Arg Leu Ser His Leu Pro Val Ala Ser Gly Thr Ser Thr Val Leu Gly
                    2275                    2280                    2285

| | | | | | | | | | | | | | | |
|---|---|---|---|---|---|---|---|---|---|---|---|---|---|---|
|Ser|Ser|Ser|Gly|Gly|Ala|Leu|Asn|Phe|Thr|Val|Gly|Gly|Ser|Thr|Ser|
| | |2290| | |2295| | | |2300| | | | |
|Leu|Asn|Gly|Gln|Cys|Glu|Trp|Leu|Ser|Trp|Leu|Gln|Ser|Gly|Met|Val|
|2305| | | |2310| | | |2315| | | | | |2320|
|Pro|Asn|Gln|Tyr|Asn|Pro|Leu|Trp|Gly|Ser|Val|Ala|Pro|Gly|Pro|Leu|
| | | |2325| | | | |2330| | | | |2335|
|Ser|Thr|Gln|Ala|Pro|Ser|Leu|Gln|His|Gly|Met|Val|Gly|Pro|Leu|His|
| | | |2340| | | | |2345| | | | |2350|
|Ser|Ser|Leu|Ala|Ala|Ser|Ala|Leu|Ser|Gln|Met|Met|Ser|Tyr|Gln|Gly|
| | |2355| | | |2360| | | | |2365|
|Leu|Pro|Ser|Thr|Trp|Leu|Ala|Thr|Gln|Pro|His|Leu|Val|Gln|Thr|Gln|
| |2370| | | | |2375| | | |2380|
|Gln|Val|Gln|Pro|Gln|Asn|Leu|Gln|Met|Gln|Gln|Gln|Asn|Leu|Gln|Pro|
|2385| | | | |2390| | | |2395| | | | |2400|
|Ala|Asn|Ile|Gln|Gln|Gln|Gln|Ser|Leu|Gln|Pro|Pro|Pro|Pro|Pro|Pro|
| | | |2405| | | | |2410| | | | |2415|
|Gln|Pro|His|Leu|Gly|Val|Ser|Ser|Ala|Ala|Ser|Gly|His|Leu|Gly|Trp|
| | | |2420| | | | |2425| | | | |2430|
|Ser|Phe|Leu|Ser|Gly|Glu|Pro|Ser|Gln|Ala|Asp|Val|Gln|Pro|Leu|Gly|
| | |2435| | | | |2440| | | | |2445|
|Pro|Ser|Ser|Leu|Ala|Val|His|Thr|Ile|Leu|Pro|Gln|Glu|Ser|Pro|Ala|
| |2450| | | | |2455| | | |2460|
|Leu|Pro|Thr|Ser|Leu|Pro|Ser|Ser|Leu|Val|Pro|Pro|Val|Thr|Ala|Ala|
|2465| | | | |2470| | | |2475| | | | |2480|
|Gln|Phe|Leu|Thr|Pro|Pro|Ser|Gln|His|Ser|Tyr|Ser|Ser|Pro|Val|Glu|
| | | | |2485| | | |2490| | | | |2495|
|Asn|Thr|Pro|Ser|His|Gln|Leu|Gln|Val|Pro|Glu|His|Pro|Phe|Leu|Thr|
| | | |2500| | | | |2505| | | | |2510|
|Pro|Ser|Pro|Glu|Ser|Pro|Asp|Gln|Trp|Ser|Ser|Ser|Ser|Pro|His|Ser|
| | |2515| | | | |2520| | | | |2525|
|Asn|Val|Ser|Asp|Trp|Ser|Glu|Gly|Val|Ser|Ser|Pro|Pro|Thr|Ser|Met|
| | |2530| | | | |2535| | | | |2540|
|Gln|Ser|Gln|Ile|Ala|Arg|Ile|Pro|Glu|Ala|Phe|Lys| | | | |
|2545| | | | |2550| | | | |2555|

( 2 ) INFORMATION FOR SEQ ID NO:18:

( i ) SEQUENCE CHARACTERISTICS:
    ( A ) LENGTH: 2523 amino acids
    ( B ) TYPE: amino acid
    ( D ) TOPOLOGY: unknown ( i i ) MOLECULE TYPE: protein ( x i ) SEQUENCE DESCRIPTION: SEQ ID NO:18:

| | | | | | | | | | | | | | | |
|---|---|---|---|---|---|---|---|---|---|---|---|---|---|---|
|Met|Asp|Arg|Ile|Gly|Leu|Ala|Val|Leu|Leu|Cys|Ser|Leu|Pro|Val|Leu|
|1| | | |5| | | | |10| | | | |15|
|Thr|Gln|Gly|Leu|Arg|Cys|Thr|Gln|Thr|Ala|Glu|Met|Cys|Leu|Asn|Gly|
| | | |20| | | | |25| | | | |30|
|Gly|Arg|Cys|Glu|Met|Thr|Pro|Gly|Gly|Thr|Gly|Val|Cys|Leu|Cys|Gly|
| | |35| | | | |40| | | | |45|
|Asn|Leu|Tyr|Phe|Gly|Glu|Arg|Cys|Gln|Phe|Pro|Asn|Pro|Cys|Thr|Ile|
| | |50| | | | |55| | | | |60|
|Lys|Asn|Gln|Cys|Met|Asn|Phe|Gly|Thr|Cys|Glu|Pro|Val|Leu|Gln|Gly|
|65| | | |70| | | | |75| | | | |80|
|Asn|Ala|Ile|Asp|Phe|Ile|Cys|His|Cys|Pro|Val|Gly|Phe|Thr|Asp|Lys|
| | | |85| | | | |90| | | | |95|

-continued

```
Val Cys Leu Thr Pro Val Asp Asn Ala Cys Val Asn Asn Pro Cys Arg
        100             105             110
Asn Gly Gly Thr Cys Glu Leu Leu Asn Ser Val Thr Glu Tyr Lys Cys
        115             120             125
Arg Cys Pro Pro Gly Trp Thr Gly Asp Ser Cys Gln Gln Ala Asp Pro
    130             135             140
Cys Ala Ser Asn Pro Cys Ala Asn Gly Gly Lys Cys Leu Pro Phe Glu
145             150             155             160
Ile Gln Tyr Ile Cys Lys Cys Pro Pro Gly Phe His Gly Ala Thr Cys
                165             170             175
Lys Gln Asp Ile Asn Glu Cys Ser Gln Asn Pro Cys Lys Asn Gly Gly
            180             185             190
Gln Cys Ile Asn Glu Phe Gly Ser Tyr Arg Cys Thr Cys Gln Asn Arg
        195             200             205
Phe Thr Gly Arg Asn Cys Asp Glu Pro Tyr Val Pro Cys Asn Pro Ser
    210             215             220
Pro Cys Leu Asn Gly Gly Thr Cys Arg Gln Thr Asp Asp Thr Ser Tyr
225             230             235             240
Asp Cys Thr Cys Leu Pro Gly Phe Ser Gly Gln Asn Cys Glu Glu Asn
                245             250             255
Ile Asp Asp Cys Pro Ser Asn Asn Cys Arg Asn Gly Gly Thr Cys Val
            260             265             270
Asp Gly Val Asn Thr Tyr Asn Cys Gln Cys Pro Pro Asp Trp Thr Gly
        275             280             285
Gln Tyr Cys Thr Glu Asp Val Asp Glu Cys Gln Leu Met Pro Asn Ala
    290             295             300
Cys Gln Asn Gly Gly Thr Cys His Asn Thr Tyr Gly Gly Tyr Asn Cys
305             310             315             320
Val Cys Val Asn Gly Trp Thr Gly Glu Asp Cys Ser Glu Asn Ile Asp
                325             330             335
Asp Cys Ala Asn Ala Ala Cys His Ser Gly Ala Thr Cys His Asp Arg
            340             345             350
Val Ala Ser Phe Tyr Cys Glu Cys Pro His Gly Arg Thr Gly Leu Leu
        355             360             365
Cys His Leu Asp Asn Ala Cys Ile Ser Asn Pro Cys Asn Glu Gly Ser
    370             375             380
Asn Cys Asp Thr Asn Pro Val Asn Gly Lys Ala Ile Cys Thr Cys Pro
385             390             395             400
Pro Gly Tyr Thr Gly Pro Ala Cys Asn Asn Asp Val Asp Glu Cys Ser
                405             410             415
Leu Gly Ala Asn Pro Cys Glu His Gly Gly Arg Cys Thr Asn Thr Leu
            420             425             430
Gly Ser Phe Gln Cys Asn Cys Pro Gln Gly Tyr Ala Gly Pro Arg Cys
        435             440             445
Glu Ile Asp Val Asn Glu Cys Leu Ser Asn Pro Cys Gln Asn Asp Ser
    450             455             460
Thr Cys Leu Asp Gln Ile Gly Glu Phe Gln Cys Ile Cys Met Pro Gly
465             470             475             480
Tyr Glu Gly Leu Tyr Cys Glu Thr Asn Ile Asp Glu Cys Ala Ser Asn
                485             490             495
Pro Cys Leu His Asn Gly Lys Cys Ile Asp Lys Ile Asn Glu Phe Arg
            500             505             510
Cys Asp Cys Pro Thr Gly Phe Ser Gly Asn Leu Cys Gln His Asp Phe
```

-continued

|     |     |     |     | 515 |     |     |     | 520 |     |     |     | 525 |     |     |
| --- | --- | --- | --- | --- | --- | --- | --- | --- | --- | --- | --- | --- | --- | --- |
| Asp | Glu | Cys | Thr | Ser | Thr | Pro | Cys | Lys | Asn | Gly | Ala | Lys | Cys | Leu | Asp |
|     | 530 |     |     |     |     | 535 |     |     |     | 540 |     |     |     |     |     |
| Gly | Pro | Asn | Ser | Tyr | Thr | Cys | Gln | Cys | Thr | Gly | Phe | Thr | Gly | Arg |
| 545 |     |     |     |     | 550 |     |     |     | 555 |     |     |     |     | 560 |
| His | Cys | Glu | Gln | Asp | Ile | Asn | Glu | Cys | Ile | Pro | Asp | Pro | Cys | His | Tyr |
|     |     |     |     | 565 |     |     |     | 570 |     |     |     | 575 |     |     |
| Gly | Thr | Cys | Lys | Asp | Gly | Ile | Ala | Thr | Phe | Thr | Cys | Leu | Cys | Arg | Pro |
|     |     |     | 580 |     |     |     | 585 |     |     |     |     | 590 |     |     |
| Gly | Tyr | Thr | Gly | Arg | Leu | Cys | Asp | Asn | Ile | Asn | Glu | Cys | Leu | Ser |
|     |     | 595 |     |     |     | 600 |     |     |     | 605 |     |     |     |     |
| Lys | Pro | Cys | Leu | Asn | Gly | Gly | Gln | Cys | Thr | Asp | Arg | Glu | Asn | Gly | Tyr |
|     | 610 |     |     |     |     | 615 |     |     |     | 620 |     |     |     |     |
| Ile | Cys | Thr | Cys | Pro | Lys | Gly | Thr | Thr | Gly | Val | Asn | Cys | Glu | Thr | Lys |
| 625 |     |     |     | 630 |     |     |     | 635 |     |     |     |     |     | 640 |
| Ile | Asp | Asp | Cys | Ala | Ser | Asn | Leu | Cys | Asp | Asn | Gly | Lys | Cys | Ile | Asp |
|     |     |     | 645 |     |     |     | 650 |     |     |     |     | 655 |     |     |
| Lys | Ile | Asp | Gly | Tyr | Glu | Cys | Thr | Cys | Glu | Pro | Gly | Tyr | Thr | Gly | Lys |
|     |     | 660 |     |     |     | 665 |     |     |     |     |     | 670 |     |     |
| Leu | Cys | Asn | Ile | Asn | Ile | Asn | Glu | Cys | Asp | Ser | Asn | Pro | Cys | Arg | Asn |
|     | 675 |     |     |     |     | 680 |     |     |     | 685 |     |     |     |     |
| Gly | Gly | Thr | Cys | Lys | Asp | Gln | Ile | Asn | Gly | Phe | Thr | Cys | Val | Cys | Pro |
|     | 690 |     |     |     |     | 695 |     |     |     | 700 |     |     |     |     |
| Asp | Gly | Tyr | His | Asp | His | Met | Cys | Leu | Ser | Glu | Val | Asn | Glu | Cys | Asn |
| 705 |     |     |     |     | 710 |     |     |     | 715 |     |     |     |     | 720 |
| Ser | Asn | Pro | Cys | Ile | His | Gly | Ala | Cys | His | Asp | Gly | Val | Asn | Gly | Tyr |
|     |     |     |     | 725 |     |     |     | 730 |     |     |     | 735 |     |     |
| Lys | Cys | Asp | Cys | Glu | Ala | Gly | Trp | Ser | Gly | Ser | Asn | Cys | Asp | Ile | Asn |
|     |     |     | 740 |     |     |     | 745 |     |     |     | 750 |     |     |     |
| Asn | Asn | Glu | Cys | Glu | Ser | Asn | Pro | Cys | Met | Asn | Gly | Gly | Thr | Cys | Lys |
|     |     | 755 |     |     |     | 760 |     |     |     | 765 |     |     |     |     |
| Asp | Met | Thr | Gly | Ala | Tyr | Ile | Cys | Thr | Cys | Lys | Ala | Gly | Phe | Ser | Gly |
|     | 770 |     |     |     |     | 775 |     |     |     | 780 |     |     |     |     |
| Pro | Asn | Cys | Gln | Thr | Asn | Ile | Asn | Glu | Cys | Ser | Ser | Asn | Pro | Cys | Leu |
| 785 |     |     |     |     | 790 |     |     |     | 795 |     |     |     |     | 800 |
| Asn | His | Gly | Thr | Cys | Ile | Asp | Asp | Val | Ala | Gly | Tyr | Lys | Cys | Asn | Cys |
|     |     |     |     | 805 |     |     |     | 810 |     |     |     | 815 |     |     |
| Met | Leu | Pro | Tyr | Thr | Gly | Ala | Ile | Cys | Glu | Ala | Val | Leu | Ala | Pro | Cys |
|     |     |     | 820 |     |     |     | 825 |     |     |     | 830 |     |     |     |
| Ala | Gly | Ser | Pro | Cys | Lys | Asn | Gly | Gly | Arg | Cys | Lys | Glu | Ser | Glu | Asp |
|     |     | 835 |     |     |     | 840 |     |     |     | 845 |     |     |     |     |
| Phe | Glu | Thr | Phe | Ser | Cys | Glu | Cys | Pro | Pro | Gly | Trp | Gln | Gly | Gln | Thr |
|     | 850 |     |     |     |     | 855 |     |     |     | 860 |     |     |     |     |
| Cys | Glu | Ile | Asp | Met | Asn | Glu | Cys | Val | Asn | Arg | Pro | Cys | Arg | Asn | Gly |
| 865 |     |     |     |     | 870 |     |     |     | 875 |     |     |     |     | 880 |
| Ala | Thr | Cys | Gln | Asn | Thr | Asn | Gly | Ser | Tyr | Lys | Cys | Asn | Cys | Lys | Pro |
|     |     |     |     | 885 |     |     |     | 890 |     |     |     | 895 |     |     |
| Gly | Tyr | Thr | Gly | Arg | Asn | Cys | Glu | Met | Asp | Ile | Asp | Asp | Cys | Gln | Pro |
|     |     |     | 900 |     |     |     | 905 |     |     |     | 910 |     |     |     |
| Asn | Pro | Cys | His | Asn | Gly | Gly | Ser | Cys | Ser | Asp | Gly | Ile | Asn | Met | Phe |
|     |     |     | 915 |     |     |     | 920 |     |     |     | 925 |     |     |     |
| Phe | Cys | Asn | Cys | Pro | Ala | Gly | Phe | Arg | Gly | Pro | Lys | Cys | Glu | Glu | Asp |
|     |     | 930 |     |     |     | 935 |     |     |     | 940 |     |     |     |     |

| | | | | | | | | | | | | | | |
|---|---|---|---|---|---|---|---|---|---|---|---|---|---|---|
| Ile | Asn | Glu | Cys | Ala | Ser | Asn | Pro | Cys | Lys | Asn | Gly | Ala | Asn | Cys |
| 945 | | | | | 950 | | | | 955 | | | | | 960 |
| Asp | Cys | Val | Asn | Ser | Tyr | Thr | Cys | Thr | Cys | Gln | Pro | Gly | Phe | Ser | Gly |
| | | | | 965 | | | | | 970 | | | | | 975 |
| Ile | His | Cys | Glu | Ser | Asn | Thr | Pro | Asp | Cys | Thr | Glu | Ser | Ser | Cys | Phe |
| | | | 980 | | | | | 985 | | | | | 990 | | |
| Asn | Gly | Gly | Thr | Cys | Ile | Asp | Gly | Ile | Asn | Thr | Phe | Thr | Cys | Gln | Cys |
| | | | 995 | | | | | 1000 | | | | | 1005 | | |
| Pro | Pro | Gly | Phe | Thr | Gly | Ser | Tyr | Cys | Gln | His | Asp | Ile | Asn | Glu | Cys |
| | | 1010 | | | | | 1015 | | | | 1020 | | | | |
| Asp | Ser | Lys | Pro | Cys | Leu | Asn | Gly | Gly | Thr | Cys | Gln | Asp | Ser | Tyr | Gly |
| 1025 | | | | 1030 | | | | | 1035 | | | | | 1040 | |
| Thr | Tyr | Lys | Cys | Thr | Cys | Pro | Gln | Gly | Tyr | Thr | Gly | Leu | Asn | Cys | Gln |
| | | | 1045 | | | | | 1050 | | | | | 1055 | | |
| Asn | Leu | Val | Arg | Trp | Cys | Asp | Ser | Ser | Pro | Cys | Lys | Asn | Gly | Gly | Lys |
| | | | 1060 | | | | | 1065 | | | | | 1070 | | |
| Cys | Trp | Gln | Thr | Asn | Asn | Phe | Tyr | Arg | Cys | Glu | Cys | Lys | Ser | Gly | Trp |
| | | 1075 | | | | | 1080 | | | | | 1085 | | | |
| Thr | Gly | Val | Tyr | Cys | Asp | Val | Pro | Ser | Val | Ser | Cys | Glu | Val | Ala | Ala |
| | 1090 | | | | 1095 | | | | | 1100 | | | | | |
| Lys | Gln | Gln | Gly | Val | Asp | Ile | Val | His | Leu | Cys | Arg | Asn | Ser | Gly | Met |
| 1105 | | | | 1110 | | | | | 1115 | | | | | 1120 | |
| Cys | Val | Asp | Thr | Gly | Asn | Thr | His | Phe | Cys | Arg | Cys | Gln | Ala | Gly | Tyr |
| | | | | 1125 | | | | | 1130 | | | | | 1135 | |
| Thr | Gly | Ser | Tyr | Cys | Glu | Glu | Gln | Val | Asp | Glu | Cys | Ser | Pro | Asn | Pro |
| | | | 1140 | | | | | 1145 | | | | | 1150 | | |
| Cys | Gln | Asn | Gly | Ala | Thr | Cys | Thr | Asp | Tyr | Leu | Gly | Gly | Tyr | Ser | Cys |
| | | 1155 | | | | | 1160 | | | | | 1165 | | | |
| Glu | Cys | Val | Ala | Gly | Tyr | His | Gly | Val | Asn | Cys | Ser | Glu | Glu | Ile | Asn |
| | 1170 | | | | | 1175 | | | | | 1180 | | | | |
| Glu | Cys | Leu | Ser | His | Pro | Cys | Gln | Asn | Gly | Gly | Thr | Cys | Ile | Asp | Leu |
| 1185 | | | | | 1190 | | | | | 1195 | | | | | 1200 |
| Ile | Asn | Thr | Tyr | Lys | Cys | Ser | Cys | Pro | Arg | Gly | Thr | Gln | Gly | Val | His |
| | | | | 1205 | | | | | 1210 | | | | | 1215 | |
| Cys | Glu | Ile | Asn | Val | Asp | Asp | Cys | Thr | Pro | Phe | Tyr | Asp | Ser | Phe | Thr |
| | | | 1220 | | | | | 1225 | | | | | 1230 | | |
| Leu | Glu | Pro | Lys | Cys | Phe | Asn | Asn | Gly | Lys | Cys | Ile | Asp | Arg | Val | Gly |
| | | | 1235 | | | | | 1240 | | | | | 1245 | | |
| Gly | Tyr | Asn | Cys | Ile | Cys | Pro | Pro | Gly | Phe | Val | Gly | Glu | Arg | Cys | Glu |
| | | | 1250 | | | | | 1255 | | | | | 1260 | | |
| Gly | Asp | Val | Asn | Glu | Cys | Leu | Ser | Asn | Pro | Cys | Asp | Ser | Arg | Gly | Thr |
| 1265 | | | | | 1270 | | | | | 1275 | | | | | 1280 |
| Gln | Asn | Cys | Ile | Gln | Leu | Val | Asn | Asp | Tyr | Arg | Cys | Glu | Cys | Arg | Gln |
| | | | | 1285 | | | | | 1290 | | | | | 1295 | |
| Gly | Phe | Thr | Gly | Arg | Arg | Cys | Glu | Ser | Val | Val | Asp | Gly | Cys | Lys | Gly |
| | | | 1300 | | | | | 1305 | | | | | 1310 | | |
| Met | Pro | Cys | Arg | Asn | Gly | Gly | Thr | Cys | Ala | Val | Ala | Ser | Asn | Thr | Glu |
| | | | 1315 | | | | | 1320 | | | | | 1325 | | |
| Arg | Gly | Phe | Ile | Cys | Lys | Cys | Pro | Pro | Gly | Phe | Asp | Gly | Ala | Thr | Cys |
| | | | 1330 | | | | | 1335 | | | | | 1340 | | |
| Glu | Tyr | Asp | Ser | Arg | Thr | Cys | Ser | Asn | Leu | Arg | Cys | Gln | Asn | Gly | Gly |
| 1345 | | | | | 1350 | | | | | 1355 | | | | | 1360 |
| Thr | Cys | Ile | Ser | Val | Leu | Thr | Ser | Ser | Lys | Cys | Val | Cys | Ser | Glu | Gly |
| | | | | 1365 | | | | | 1370 | | | | | 1375 | |

```
Tyr Thr Gly Ala Thr Cys Gln Tyr Pro Val Ile Ser Pro Cys Ala Ser
            1380                1385                1390
His Pro Cys Tyr Asn Gly Gly Thr Cys Gln Phe Phe Ala Glu Glu Pro
        1395                1400                1405
Phe Phe Gln Cys Phe Cys Pro Lys Asn Phe Asn Gly Leu Phe Cys His
    1410                1415                1420
Ile Leu Asp Tyr Glu Phe Pro Gly Gly Leu Gly Lys Asn Ile Thr Pro
1425                1430                1435                1440
Pro Asp Asn Asp Ile Cys Glu Asn Glu Gln Cys Ser Glu Leu Ala
            1445                1450                1455
Asp Asn Lys Val Cys Asn Ala Asn Cys Asn Asn His Ala Cys Gly Trp
        1460                1465                1470
Asp Gly Gly Asp Cys Ser Leu Asn Phe Asn Asp Pro Trp Lys Asn Cys
    1475                1480                1485
Thr Gln Ser Leu Gln Cys Trp Lys Tyr Phe Asn Asp Gly Lys Cys Asp
        1490                1495                1500
Ser Gln Cys Asn Asn Thr Gly Cys Leu Tyr Asp Gly Phe Asp Cys Gln
1505                1510                1515                1520
Lys Val Glu Val Gln Cys Asn Pro Leu Tyr Asp Gln Tyr Cys Lys Asp
            1525                1530                1535
His Phe Gln Asp Gly His Cys Asp Gln Gly Cys Asn Asn Ala Glu Cys
        1540                1545                1550
Glu Trp Asp Gly Leu Asp Cys Ala Asn Met Pro Glu Asn Leu Ala Glu
    1555                1560                1565
Gly Thr Leu Val Leu Val Val Leu Met Pro Pro Glu Arg Leu Lys Asn
    1570                1575                1580
Asn Ser Val Asn Phe Leu Arg Glu Leu Ser Arg Val Leu His Thr Asn
1585                1590                1595                1600
Val Val Phe Lys Lys Asp Ser Lys Gly Glu Tyr Lys Ile Tyr Pro Tyr
            1605                1610                1615
Tyr Gly Asn Glu Glu Glu Leu Lys Lys His His Ile Lys Arg Ser Thr
        1620                1625                1630
Asp Tyr Trp Ser Asp Ala Pro Ser Ala Ile Phe Ser Thr Met Lys Glu
    1635                1640                1645
Ser Ile Leu Leu Gly Arg His Arg Arg Glu Leu Asp Glu Met Glu Val
        1650                1655                1660
Arg Gly Ser Ile Val Tyr Leu Glu Ile Asp Asn Arg Gln Cys Tyr Lys
1665                1670                1675                1680
Ser Ser Ser Gln Cys Phe Asn Ser Ala Thr Asp Val Ala Ala Phe Leu
            1685                1690                1695
Gly Ala Leu Ala Ser Leu Gly Ser Leu Asp Thr Leu Ser Tyr Lys Ile
        1700                1705                1710
Glu Ala Val Lys Ser Glu Asn Met Glu Thr Pro Lys Pro Ser Thr Leu
    1715                1720                1725
Tyr Pro Met Leu Ser Met Leu Val Ile Pro Leu Leu Ile Ile Phe Val
        1730                1735                1740
Phe Met Met Val Ile Val Asn Lys Lys Arg Arg Arg Glu His Asp Ser
1745                1750                1755                1760
Phe Gly Ser Pro Thr Ala Leu Phe Gln Lys Asn Pro Ala Lys Arg Asn
            1765                1770                1775
Gly Glu Thr Pro Trp Glu Asp Ser Val Gly Leu Lys Pro Ile Lys Asn
        1780                1785                1790
Met Thr Asp Gly Ser Phe Met Asp Asp Asn Gln Asn Glu Trp Gly Asp
```

```
                    1795                    1800                    1805
Glu Glu Thr Leu Glu Asn Lys Arg Phe Arg Phe Glu Glu Gln Val Ile
    1810                    1815                    1820
Leu Pro Glu Leu Val Asp Asp Lys Thr Asp Pro Arg Gln Trp Thr Arg
1825                    1830                    1835                    1840
Gln His Leu Asp Ala Ala Asp Leu Arg Ile Ser Ser Met Ala Pro Thr
                    1845                    1850                    1855
Pro Pro Gln Gly Glu Ile Glu Ala Asp Cys Met Asp Val Asn Val Arg
                1860                    1865                    1870
Gly Pro Asp Gly Phe Thr Pro Leu Met Ile Ala Ser Cys Ser Gly Gly
                1875                    1880                    1885
Gly Leu Glu Thr Gly Asn Ser Glu Glu Glu Glu Asp Ala Ser Ala Asn
    1890                    1895                    1900
Met Ile Ser Asp Phe Ile Gly Gln Gly Ala Gln Leu His Asn Gln Thr
1905                    1910                    1915                    1920
Asp Arg Thr Gly Glu Thr Ala Leu His Leu Ala Ala Arg Tyr Ala Arg
                    1925                    1930                    1935
Ala Asp Ala Ala Lys Arg Leu Leu Glu Ser Ser Ala Asp Ala Asn Val
                1940                    1945                    1950
Gln Asp Asn Met Gly Arg Thr Pro Leu His Ala Ala Val Ala Ala Asp
            1955                    1960                    1965
Ala Gln Gly Val Phe Gln Ile Leu Ile Arg Asn Arg Ala Thr Asp Leu
    1970                    1975                    1980
Asp Ala Arg Met Phe Asp Gly Thr Thr Pro Leu Ile Leu Ala Ala Arg
1985                    1990                    1995                    2000
Leu Ala Val Glu Gly Met Val Glu Glu Leu Ile Asn Ala His Ala Asp
                    2005                    2010                    2015
Val Asn Ala Val Asp Glu Phe Gly Lys Ser Ala Leu His Trp Ala Ala
            2020                    2025                    2030
Ala Val Asn Asn Val Asp Ala Ala Ala Val Leu Leu Lys Asn Ser Ala
        2035                    2040                    2045
Asn Lys Asp Met Gln Asn Asn Lys Glu Glu Thr Ser Leu Phe Leu Ala
    2050                    2055                    2060
Ala Arg Glu Gly Ser Tyr Glu Thr Ala Lys Val Leu Leu Asp His Tyr
2065                    2070                    2075                    2080
Ala Asn Arg Asp Ile Thr Asp His Met Asp Arg Leu Pro Arg Asp Ile
                2085                    2090                    2095
Ala Gln Glu Arg Met His His Asp Ile Val His Leu Leu Asp Glu Tyr
        2100                    2105                    2110
Asn Leu Val Lys Ser Pro Thr Leu His Asn Gly Pro Leu Gly Ala Thr
    2115                    2120                    2125
Thr Leu Ser Pro Pro Ile Cys Ser Pro Asn Gly Tyr Met Gly Asn Met
2130                    2135                    2140
Lys Pro Ser Val Gln Ser Lys Lys Ala Arg Lys Pro Ser Ile Lys Gly
2145                    2150                    2155                    2160
Asn Gly Cys Lys Glu Ala Lys Glu Leu Lys Ala Arg Arg Lys Lys Ser
            2165                    2170                    2175
Gln Asp Gly Lys Thr Thr Leu Leu Asp Ser Gly Ser Ser Gly Val Leu
        2180                    2185                    2190
Ser Pro Val Asp Ser Leu Glu Ser Thr His Gly Tyr Leu Ser Asp Val
    2195                    2200                    2205
Ser Ser Pro Pro Leu Met Thr Ser Pro Phe Gln Gln Ser Pro Ser Met
2210                    2215                    2220
```

-continued

```
Pro Leu Asn His Leu Thr Ser Met Pro Glu Ser Gln Leu Gly Met Asn
2225                2230                2235                2240

His Ile Asn Met Ala Thr Lys Gln Glu Met Ala Ala Gly Ser Asn Arg
            2245                2250                2255

Met Ala Phe Asp Ala Met Val Pro Arg Leu Thr His Leu Asn Ala Ser
            2260                2265                2270

Ser Pro Asn Thr Ile Met Ser Asn Gly Ser Met His Phe Thr Val Gly
            2275                2280                2285

Gly Ala Pro Thr Met Asn Ser Gln Cys Asp Trp Leu Ala Arg Leu Gln
            2290                2295                2300

Asn Gly Met Val Gln Asn Gln Tyr Asp Pro Ile Arg Asn Gly Ile Gln
2305                2310                2315                2320

Gln Gly Asn Ala Gln Ala Gln Ala Leu Gln His Gly Leu Met Thr
            2325                2330                2335

Ser Leu His Asn Gly Leu Pro Ala Thr Thr Leu Ser Gln Met Met Thr
            2340                2345                2350

Tyr Gln Ala Met Pro Asn Thr Arg Leu Ala Asn Gln Pro His Leu Met
            2355                2360                2365

Gln Ala Gln Gln Met Gln Gln Gln Gln Asn Leu Gln Leu His Gln Ser
2370                2375                2380

Met Gln Gln Gln His His Asn Ser Ser Thr Thr Ser Thr His Ile Asn
2385                2390                2395                2400

Ser Pro Phe Cys Ser Ser Asp Ile Ser Gln Thr Asp Leu Gln Gln Met
            2405                2410                2415

Ser Ser Asn Asn Ile His Ser Val Met Pro Gln Asp Thr Gln Ile Phe
            2420                2425                2430

Ala Ala Ser Leu Pro Ser Asn Leu Thr Gln Ser Met Thr Thr Ala Gln
            2435                2440                2445

Phe Leu Thr Pro Pro Ser Gln His Ser Tyr Ser Ser Pro Met Asp Asn
            2450                2455                2460

Thr Pro Ser His Gln Leu Gln Val Pro Asp His Pro Phe Leu Thr Pro
2465                2470                2475                2480

Ser Pro Glu Ser Pro Asp Gln Trp Ser Ser Ser Ser Pro His Ser Asn
            2485                2490                2495

Met Ser Asp Trp Ser Glu Gly Ile Ser Ser Pro Pro Thr Ser Met Gln
            2500                2505                2510

Pro Gln Arg Thr His Ile Pro Glu Ala Phe Lys
            2515                2520
```

( 2 ) INFORMATION FOR SEQ ID NO:19:

( i ) SEQUENCE CHARACTERISTICS:
    ( A ) LENGTH: 2703 amino acids
    ( B ) TYPE: amino acid
    ( D ) TOPOLOGY: unknown ( i i ) MOLECULE TYPE: protein ( x i ) SEQUENCE DESCRIPTION: SEQ ID NO:19:

```
Met Gln Ser Gln Arg Ser Arg Arg Arg Ser Arg Ala Pro Asn Thr Trp
1               5                   10                  15

Ile Cys Phe Trp Ile Asn Lys Met His Ala Val Ala Ser Leu Pro Ala
            20                  25                  30

Ser Leu Pro Leu Leu Leu Leu Thr Leu Ala Phe Ala Asn Leu Pro Asn
            35                  40                  45

Ile Val Arg Gly Thr Asp Thr Ala Leu Val Ala Ala Ser Cys Thr Ser
            50                  55                  60
```

```
Val Gly Cys Gln Asn Gly Gly Thr Cys Val Thr Gln Leu Asn Gly Lys
 65              70              75              80
Thr Tyr Cys Ala Cys Asp Ser His Tyr Val Gly Asp Tyr Cys Glu His
             85              90              95
Arg Asn Pro Cys Asn Ser Met Arg Cys Gln Asn Gly Gly Thr Cys Gln
            100             105             110
Val Thr Phe Arg Asn Gly Arg Pro Gly Ile Ser Cys Lys Cys Pro Leu
            115             120             125
Gly Phe Asp Glu Ser Leu Cys Glu Ile Ala Val Pro Asn Ala Cys Asp
    130             135             140
His Val Thr Cys Leu Asn Gly Gly Thr Cys Gln Leu Lys Thr Leu Glu
145             150             155             160
Glu Tyr Thr Cys Ala Cys Ala Asn Gly Tyr Thr Gly Glu Arg Cys Glu
                165             170             175
Thr Lys Asn Leu Cys Ala Ser Ser Pro Cys Arg Asn Gly Ala Thr Cys
            180             185             190
Thr Ala Leu Ala Gly Ser Ser Phe Thr Cys Ser Cys Pro Pro Gly
            195             200             205
Phe Thr Gly Asp Thr Cys Ser Tyr Asp Ile Glu Glu Cys Gln Ser Asn
    210             215             220
Pro Cys Lys Tyr Gly Gly Ile Cys Val Asn Thr His Gly Ser Tyr Gln
225             230             235             240
Cys Met Cys Pro Thr Gly Tyr Thr Gly Lys Asp Cys Asp Thr Lys Tyr
                245             250             255
Lys Pro Cys Ser Pro Ser Pro Cys Gln Asn Ala Gly Ile Cys Arg Ser
            260             265             270
Asn Gly Leu Ser Tyr Glu Cys Lys Cys Pro Lys Gly Phe Glu Gly Lys
            275             280             285
Asn Cys Glu Gln Asn Tyr Asp Asp Cys Leu Gly His Leu Cys Gln Asn
    290             295             300
Gly Gly Thr Cys Ile Asp Gly Ile Ser Asp Tyr Thr Cys Arg Cys Pro
305             310             315             320
Pro Asn Phe Thr Gly Arg Phe Cys Gln Asp Asp Val Asp Glu Cys Ala
                325             330             335
Gln Arg Asp His Pro Val Cys Gln Asn Gly Ala Thr Cys Thr Asn Thr
            340             345             350
His Gly Ser Tyr Ser Cys Ile Cys Val Asn Gly Trp Ala Gly Leu Asp
            355             360             365
Cys Ser Asn Asn Thr Asp Asp Cys Lys Gln Ala Ala Cys Phe Tyr Gly
    370             375             380
Ala Thr Cys Ile Asp Gly Val Gly Ser Phe Tyr Cys Gln Cys Thr Lys
385             390             395             400
Gly Lys Thr Gly Leu Leu Cys His Leu Asp Asp Ala Cys Thr Ser Asn
            405             410             415
Pro Cys His Ala Asp Ala Ile Cys Asp Thr Ser Pro Ile Asn Gly Ser
            420             425             430
Tyr Ala Cys Ser Cys Ala Thr Gly Tyr Lys Gly Val Asp Cys Ser Glu
        435             440             445
Asp Ile Asp Glu Cys Asp Gln Gly Ser Pro Cys Glu His Asn Gly Ile
    450             455             460
Cys Val Asn Thr Pro Gly Ser Tyr Arg Cys Asn Cys Ser Gln Gly Phe
465             470             475             480
Thr Gly Pro Arg Cys Glu Thr Asn Ile Asn Glu Cys Glu Ser His Pro
```

-continued

|   |   |   |   | 485 |   |   |   |   | 490 |   |   |   |   | 495 |   |
|---|---|---|---|---|---|---|---|---|---|---|---|---|---|---|---|
| Cys | Gln | Asn | Glu | Gly | Ser | Cys | Leu | Asp | Asp | Pro | Gly | Thr | Phe | Arg | Cys |
|   |   |   | 500 |   |   |   |   | 505 |   |   |   |   | 510 |   |   |
| Val | Cys | Met | Pro | Gly | Phe | Thr | Gly | Thr | Gln | Cys | Glu | Ile | Asp | Ile | Asp |
|   |   |   | 515 |   |   |   |   | 520 |   |   |   |   | 525 |   |   |
| Glu | Cys | Gln | Ser | Asn | Pro | Cys | Leu | Asn | Asp | Gly | Thr | Cys | His | Asp | Lys |
|   |   |   | 530 |   |   |   |   | 535 |   |   |   |   | 540 |   |   |
| Ile | Asn | Gly | Phe | Lys | Cys | Ser | Cys | Ala | Leu | Gly | Phe | Thr | Gly | Ala | Arg |
| 545 |   |   |   |   | 550 |   |   |   |   | 555 |   |   |   |   | 560 |
| Cys | Gln | Ile | Asn | Ile | Asp | Asp | Cys | Gln | Ser | Gln | Pro | Cys | Arg | Asn | Arg |
|   |   |   |   | 565 |   |   |   |   | 570 |   |   |   |   | 575 |   |
| Gly | Ile | Cys | His | Asp | Ser | Ile | Ala | Gly | Tyr | Ser | Cys | Glu | Cys | Pro | Pro |
|   |   |   |   | 580 |   |   |   |   | 585 |   |   |   |   | 590 |   |
| Gly | Tyr | Thr | Gly | Thr | Ser | Cys | Glu | Ile | Asn | Ile | Asn | Asp | Cys | Asp | Ser |
|   |   |   | 595 |   |   |   |   | 600 |   |   |   |   | 605 |   |   |
| Asn | Pro | Cys | His | Arg | Gly | Lys | Cys | Ile | Asp | Asp | Val | Asn | Ser | Phe | Lys |
|   |   | 610 |   |   |   |   | 615 |   |   |   |   | 620 |   |   |   |
| Cys | Leu | Cys | Asp | Pro | Gly | Tyr | Thr | Gly | Tyr | Ile | Cys | Gln | Lys | Gln | Ile |
| 625 |   |   |   |   | 630 |   |   |   |   | 635 |   |   |   |   | 640 |
| Asn | Glu | Cys | Glu | Ser | Asn | Pro | Cys | Gln | Phe | Asp | Gly | His | Cys | Gln | Asp |
|   |   |   |   | 645 |   |   |   |   | 650 |   |   |   |   | 655 |   |
| Arg | Val | Gly | Ser | Tyr | Tyr | Cys | Gln | Cys | Gln | Ala | Gly | Thr | Ser | Gly | Lys |
|   |   |   | 660 |   |   |   |   | 665 |   |   |   |   | 670 |   |   |
| Asn | Cys | Glu | Val | Asn | Val | Asn | Glu | Cys | His | Ser | Asn | Pro | Cys | Asn | Asn |
|   |   | 675 |   |   |   |   | 680 |   |   |   |   | 685 |   |   |   |
| Gly | Ala | Thr | Cys | Ile | Asp | Gly | Ile | Asn | Ser | Tyr | Lys | Cys | Gln | Cys | Val |
|   | 690 |   |   |   |   | 695 |   |   |   |   | 700 |   |   |   |   |
| Pro | Gly | Phe | Thr | Gly | Gln | His | Cys | Glu | Lys | Asn | Val | Asp | Glu | Cys | Ile |
| 705 |   |   |   |   | 710 |   |   |   |   | 715 |   |   |   |   | 720 |
| Ser | Ser | Pro | Cys | Ala | Asn | Asn | Gly | Val | Cys | Ile | Asp | Gln | Val | Asn | Gly |
|   |   |   |   | 725 |   |   |   |   | 730 |   |   |   |   | 735 |   |
| Tyr | Lys | Cys | Glu | Cys | Pro | Arg | Gly | Phe | Tyr | Asp | Ala | His | Cys | Leu | Ser |
|   |   |   | 740 |   |   |   |   | 745 |   |   |   |   | 750 |   |   |
| Asp | Val | Asp | Glu | Cys | Ala | Ser | Asn | Pro | Cys | Val | Asn | Glu | Gly | Arg | Cys |
|   |   | 755 |   |   |   |   | 760 |   |   |   |   | 765 |   |   |   |
| Glu | Asp | Gly | Ile | Asn | Glu | Phe | Ile | Cys | His | Cys | Pro | Pro | Gly | Tyr | Thr |
|   | 770 |   |   |   |   | 775 |   |   |   |   | 780 |   |   |   |   |
| Gly | Lys | Arg | Cys | Glu | Leu | Asp | Ile | Asp | Glu | Cys | Ser | Ser | Asn | Pro | Cys |
| 785 |   |   |   |   | 790 |   |   |   |   | 795 |   |   |   |   | 800 |
| Gln | His | Gly | Gly | Thr | Cys | Tyr | Asp | Lys | Leu | Asn | Ala | Phe | Ser | Cys | Gln |
|   |   |   |   | 805 |   |   |   |   | 810 |   |   |   |   | 815 |   |
| Cys | Met | Pro | Gly | Tyr | Thr | Gly | Gln | Lys | Cys | Glu | Thr | Asn | Ile | Asp | Asp |
|   |   |   | 820 |   |   |   |   | 825 |   |   |   |   | 830 |   |   |
| Cys | Val | Thr | Asn | Pro | Cys | Gly | Asn | Gly | Thr | Cys | Ile | Asp | Lys | Val |
|   |   | 835 |   |   |   |   | 840 |   |   |   |   | 845 |   |   |   |
| Asn | Gly | Tyr | Lys | Cys | Val | Cys | Lys | Val | Pro | Phe | Thr | Gly | Arg | Asp | Cys |
|   | 850 |   |   |   |   | 855 |   |   |   |   | 860 |   |   |   |   |
| Glu | Ser | Lys | Met | Asp | Pro | Cys | Ala | Arg | Asn | Arg | Cys | Lys | Asn | Glu | Ala |
| 865 |   |   |   |   | 870 |   |   |   |   | 875 |   |   |   |   | 880 |
| Lys | Cys | Thr | Pro | Ser | Ser | Asn | Phe | Leu | Asp | Phe | Ser | Cys | Thr | Cys | Lys |
|   |   |   |   | 885 |   |   |   |   | 890 |   |   |   |   | 895 |   |
| Leu | Gly | Tyr | Thr | Gly | Arg | Tyr | Cys | Asp | Glu | Asp | Ile | Asp | Glu | Cys | Ser |
|   |   |   | 900 |   |   |   |   | 905 |   |   |   |   | 910 |   |   |

```
Leu Ser Ser Pro Cys Arg Asn Gly Ala Ser Cys Leu Asn Val Pro Gly
        915                 920                 925

Ser Tyr Arg Cys Leu Cys Thr Lys Gly Tyr Glu Gly Arg Asp Cys Ala
        930                 935                 940

Ile Asn Thr Asp Asp Cys Ala Ser Phe Pro Cys Gln Asn Gly Arg Thr
945                 950                 955                 960

Cys Leu Asp Gly Ile Gly Asp Tyr Ser Cys Leu Cys Val Asp Gly Phe
                965                 970                 975

Asp Gly Lys His Cys Glu Thr Asp Ile Asn Glu Cys Leu Ser Gln Pro
        980                 985                 990

Cys Gln Asn Gly Ala Thr Cys Ser Gln Tyr Val Asn Ser Tyr Thr Cys
        995                 1000                1005

Thr Cys Pro Leu Gly Phe Ser Gly Ile Asn Cys Gln Thr Asn Asp Glu
        1010                1015                1020

Asp Cys Thr Glu Ser Ser Cys Leu Asn Gly Gly Ser Cys Ile Asp Gly
1025                1030                1035                1040

Ile Asn Gly Tyr Asn Cys Ser Cys Leu Ala Gly Tyr Ser Gly Ala Asn
                1045                1050                1055

Cys Gln Tyr Lys Leu Asn Lys Cys Asp Ser Asn Pro Cys Leu Asn Gly
        1060                1065                1070

Ala Thr Cys His Glu Gln Asn Asn Glu Tyr Thr Cys His Cys Pro Ser
        1075                1080                1085

Gly Phe Thr Gly Lys Gln Cys Ser Glu Tyr Val Asp Trp Cys Gly Gln
        1090                1095                1100

Ser Pro Cys Glu Asn Gly Ala Thr Cys Ser Gln Met Lys His Gln Phe
1105                1110                1115                1120

Ser Cys Lys Cys Ser Ala Gly Trp Thr Gly Lys Leu Cys Asp Val Gln
        1125                1130                1135

Thr Ile Ser Cys Gln Asp Ala Ala Asp Arg Lys Gly Leu Ser Leu Arg
        1140                1145                1150

Gln Leu Cys Asn Asn Gly Thr Cys Lys Asp Tyr Gly Asn Ser His Val
        1155                1160                1165

Cys Tyr Cys Ser Gln Gly Tyr Ala Gly Ser Tyr Cys Gln Lys Glu Ile
        1170                1175                1180

Asp Glu Cys Gln Ser Gln Pro Cys Gln Asn Gly Gly Thr Cys Arg Asp
1185                1190                1195                1200

Leu Ile Gly Ala Tyr Glu Cys Gln Cys Arg Gln Gly Phe Gln Gly Gln
                1205                1210                1215

Asn Cys Glu Leu Asn Ile Asp Asp Cys Ala Pro Asn Pro Cys Gln Asn
        1220                1225                1230

Gly Gly Thr Cys His Asp Arg Val Met Asn Phe Ser Cys Ser Cys Pro
        1235                1240                1245

Pro Gly Thr Met Gly Ile Ile Cys Glu Ile Asn Lys Asp Asp Cys Lys
        1250                1255                1260

Pro Gly Ala Cys His Asn Asn Gly Ser Cys Ile Asp Arg Val Gly Gly
1265                1270                1275                1280

Phe Glu Cys Val Cys Gln Pro Gly Phe Val Gly Ala Arg Cys Glu Gly
                1285                1290                1295

Asp Ile Asn Glu Cys Leu Ser Asn Pro Cys Ser Asn Ala Gly Thr Leu
        1300                1305                1310

Asp Cys Val Gln Leu Val Asn Asn Tyr His Cys Asn Cys Arg Pro Gly
        1315                1320                1325

His Met Gly Arg His Cys Glu His Lys Val Asp Phe Cys Ala Gln Ser
        1330                1335                1340
```

-continued

```
Pro Cys Gln Asn Gly Gly Asn Cys Asn Ile Arg Gln Ser Gly His His
1345                1350                1355                1360

Cys Ile Cys Asn Asn Gly Phe Tyr Gly Lys Asn Cys Glu Leu Ser Gly
            1365                1370                1375

Gln Asp Cys Asp Ser Asn Pro Cys Arg Val Gly Asn Cys Val Val Ala
        1380                1385                1390

Asp Glu Gly Phe Gly Tyr Arg Cys Glu Cys Pro Arg Gly Thr Leu Gly
        1395                1400                1405

Glu His Cys Glu Ile Asp Thr Leu Asp Glu Cys Ser Pro Asn Pro Cys
        1410                1415                1420

Ala Gln Gly Ala Ala Cys Glu Asp Leu Leu Gly Asp Tyr Glu Cys Leu
1425                1430                1435                1440

Cys Pro Ser Lys Trp Lys Gly Lys Arg Cys Asp Ile Tyr Asp Ala Asn
            1445                1450                1455

Tyr Pro Gly Trp Asn Gly Gly Ser Gly Ser Gly Asn Asp Arg Tyr Ala
            1460                1465                1470

Ala Asp Leu Glu Gln Gln Arg Ala Met Cys Asp Lys Arg Gly Cys Thr
        1475                1480                1485

Glu Lys Gln Gly Asn Gly Ile Cys Asp Ser Asp Cys Asn Thr Tyr Ala
        1490                1495                1500

Cys Asn Phe Asp Gly Asn Asp Cys Ser Leu Gly Ile Asn Pro Trp Ala
1505                1510                1515                1520

Asn Cys Thr Ala Asn Glu Cys Trp Asn Lys Phe Lys Asn Gly Lys Cys
            1525                1530                1535

Asn Glu Glu Cys Asn Asn Ala Ala Cys His Tyr Asp Gly His Asp Cys
            1540                1545                1550

Glu Arg Lys Leu Lys Ser Cys Asp Thr Leu Phe Asp Ala Tyr Cys Gln
            1555                1560                1565

Lys His Tyr Gly Asp Gly Phe Cys Asp Tyr Gly Cys Asn Asn Ala Glu
        1570                1575                1580

Cys Ser Trp Asp Gly Leu Asp Cys Glu Asn Lys Thr Gln Ser Pro Val
1585                1590                1595                1600

Leu Ala Glu Gly Ala Met Ser Val Val Met Leu Met Asn Val Glu Ala
            1605                1610                1615

Phe Arg Glu Ile Gln Ala Gln Phe Leu Arg Asn Met Ser His Met Leu
            1620                1625                1630

Arg Thr Thr Val Arg Leu Lys Lys Asp Ala Leu Gly His Asp Ile Ile
        1635                1640                1645

Ile Asn Trp Lys Asp Asn Val Arg Val Pro Glu Ile Glu Asp Thr Asp
        1650                1655                1660

Phe Ala Arg Lys Asn Lys Ile Leu Tyr Thr Gln Gln Val His Gln Thr
1665                1670                1675                1680

Gly Ile Gln Ile Tyr Leu Glu Ile Asp Asn Arg Lys Cys Thr Glu Cys
            1685                1690                1695

Phe Thr His Ala Val Glu Ala Ala Glu Phe Leu Ala Ala Thr Ala Ala
            1700                1705                1710

Lys His Gln Leu Arg Asn Asp Phe Gln Ile His Ser Val Arg Gly Ile
        1715                1720                1725

Lys Asn Pro Gly Asp Glu Asp Asn Gly Glu Pro Pro Ala Asn Val Lys
        1730                1735                1740

Tyr Val Ile Thr Gly Ile Ile Leu Val Ile Ile Ala Leu Ala Phe Phe
1745                1750                1755                1760

Gly Met Val Leu Ser Thr Gln Arg Lys Arg Ala His Gly Val Thr Trp
```

```
                         1765                    1770                     1775
       Phe  Pro  Glu  Gly  Phe  Arg  Ala  Pro  Ala  Ala  Val  Met  Ser  Arg  Arg  Arg
                      1780                    1785                    1790
       Arg  Asp  Pro  His  Gly  Gln  Glu  Met  Arg  Asn  Leu  Asn  Lys  Gln  Val  Ala
                      1795                    1800                    1805
       Met  Gln  Ser  Gln  Gly  Val  Gly  Gln  Pro  Gly  Ala  His  Trp  Ser  Asp  Asp
                      1810                    1815                    1820
       Glu  Ser  Asp  Met  Pro  Leu  Pro  Lys  Arg  Gln  Arg  Ser  Asp  Pro  Val  Ser
       1825                     1830                    1835                    1840
       Gly  Val  Gly  Leu  Gly  Asn  Asn  Gly  Gly  Tyr  Ala  Ser  Asp  His  Thr  Met
                           1845                    1850                    1855
       Val  Ser  Glu  Tyr  Glu  Glu  Ala  Asp  Gln  Arg  Val  Trp  Ser  Gln  Ala  His
                      1860                    1865                    1870
       Leu  Asp  Val  Val  Asp  Val  Arg  Ala  Ile  Met  Thr  Pro  Pro  Ala  His  Gln
                      1875                    1880                    1885
       Asp  Gly  Gly  Lys  His  Asp  Val  Asp  Ala  Arg  Gly  Pro  Cys  Gly  Leu  Thr
                      1890                    1895                    1900
       Pro  Leu  Met  Ile  Ala  Ala  Val  Arg  Gly  Gly  Gly  Leu  Asp  Thr  Gly  Glu
       1905                     1910                    1915                    1920
       Asp  Ile  Glu  Asn  Asn  Glu  Asp  Ser  Thr  Ala  Gln  Val  Ile  Ser  Asp  Leu
                           1925                    1930                    1935
       Leu  Ala  Gln  Gly  Ala  Glu  Leu  Asn  Ala  Thr  Met  Asp  Lys  Thr  Gly  Glu
                      1940                    1945                    1950
       Thr  Ser  Leu  His  Leu  Ala  Ala  Arg  Phe  Ala  Arg  Ala  Asp  Ala  Ala  Lys
                      1955                    1960                    1965
       Arg  Leu  Phe  His  Ala  Gly  Ala  Asp  Ala  Asn  Cys  Gln  Asp  Asn  Thr  Gly
                      1970                    1975                    1980
       Arg  Thr  Pro  Leu  His  Ala  Ala  Val  Ala  Ala  Asp  Ala  Met  Gly  Val  Phe
       1985                     1990                    1995                    2000
       Gln  Ile  Leu  Leu  Arg  Asn  Arg  Ala  Thr  Asn  Leu  Asn  Ala  Arg  Met  His
                           2005                    2010                    2015
       Asp  Gly  Thr  Thr  Pro  Leu  Ile  Leu  Ala  Ala  Arg  Leu  Ala  Ile  Glu  Gly
                      2020                    2025                    2030
       Met  Val  Glu  Asp  Leu  Ile  Thr  Ala  Asp  Ala  Asp  Ile  Asn  Ala  Ala  Asp
                      2035                    2040                    2045
       Asn  Ser  Gly  Lys  Thr  Ala  Leu  His  Trp  Ala  Ala  Ala  Val  Asn  Asn  Thr
       2050                     2055                    2060
       Glu  Ala  Val  Asn  Ile  Leu  Leu  Met  His  His  Ala  Asn  Arg  Asp  Ala  Gln
       2065                     2070                    2075                    2080
       Asp  Asp  Lys  Asp  Glu  Thr  Pro  Leu  Phe  Leu  Ala  Ala  Arg  Glu  Gly  Ser
                      2085                    2090                    2095
       Tyr  Glu  Ala  Cys  Lys  Ala  Leu  Leu  Asp  Asn  Phe  Ala  Asn  Arg  Glu  Ile
                      2100                    2105                    2110
       Thr  Asp  His  Met  Asp  Arg  Leu  Pro  Arg  Asp  Val  Ala  Ser  Glu  Arg  Leu
                      2115                    2120                    2125
       His  His  Asp  Ile  Val  Arg  Leu  Leu  Asp  Glu  His  Val  Pro  Arg  Ser  Pro
                      2130                    2135                    2140
       Gln  Met  Leu  Ser  Met  Thr  Pro  Gln  Ala  Met  Ile  Gly  Ser  Pro  Pro  Pro
       2145                     2150                    2155                    2160
       Gly  Gln  Gln  Gln  Pro  Gln  Leu  Ile  Thr  Gln  Pro  Thr  Val  Ile  Ser  Ala
                      2165                    2170                    2175
       Gly  Asn  Gly  Gly  Asn  Asn  Gly  Asn  Gly  Asn  Ala  Ser  Gly  Lys  Gln  Ser
                      2180                    2185                    2190
```

```
Asn Gln Thr Ala Lys Gln Lys Ala Ala Lys Lys Ala Lys Leu Ile Glu
            2195                2200                2205
Gly Ser Pro Asp Asn Gly Leu Asp Ala Thr Gly Ser Leu Arg Arg Lys
        2210                2215                2220
Ala Ser Ser Lys Lys Thr Ser Ala Ala Ser Lys Lys Ala Ala Asn Leu
2225                2230                2235                2240
Asn Gly Leu Asn Pro Gly Gln Leu Thr Gly Gly Val Ser Gly Val Pro
                2245                2250                2255
Gly Val Pro Pro Thr Asn Ser Ala Val Gln Ala Ala Ala Ala Ala Ala
            2260                2265                2270
Ala Ala Val Ala Ala Met Ser His Glu Leu Glu Gly Ser Pro Val Gly
        2275                2280                2285
Val Gly Met Gly Gly Asn Leu Pro Ser Pro Tyr Asp Thr Ser Ser Met
    2290                2295                2300
Tyr Ser Asn Ala Met Ala Ala Pro Leu Ala Asn Gly Asn Pro Asn Thr
2305                2310                2315                2320
Gly Ala Lys Gln Pro Pro Ser Tyr Glu Asp Cys Ile Lys Asn Ala Gln
                2325                2330                2335
Ser Met Gln Ser Leu Gln Gly Asn Gly Leu Asp Met Ile Lys Leu Asp
            2340                2345                2350
Asn Tyr Ala Tyr Ser Met Gly Ser Pro Phe Gln Gln Glu Leu Leu Asn
        2355                2360                2365
Gly Gln Gly Leu Gly Met Asn Gly Asn Gly Gln Arg Asn Gly Val Gly
    2370                2375                2380
Pro Gly Val Leu Pro Gly Gly Leu Cys Gly Met Gly Gly Leu Ser Gly
2385                2390                2395                2400
Ala Gly Asn Gly Asn Ser Arg Glu Gln Gly Leu Ser Pro Pro Tyr Ser
                2405                2410                2415
Asn Gln Ser Pro Pro His Ser Val Gln Ser Ser Leu Ala Leu Ser Pro
            2420                2425                2430
His Ala Tyr Leu Gly Ser Pro Ser Pro Ala Lys Ser Leu Pro Ser Leu
        2435                2440                2445
Pro Thr Ser Pro Thr His Ile Gln Ala Met Arg His Ala Thr Gln Gln
    2450                2455                2460
Lys Gln Phe Gly Gly Ser Asn Leu Asn Ser Leu Leu Gly Gly Ala Asn
2465                2470                2475                2480
Gly Gly Gly Val Val Gly Gly Gly Gly Gly Gly Gly Gly Val Gly
                2485                2490                2495
Gln Gly Pro Gln Asn Ser Pro Val Ser Leu Gly Ile Ile Ser Pro Thr
            2500                2505                2510
Gly Ser Asp Met Gly Ile Met Leu Ala Pro Pro Gln Ser Ser Lys Asn
        2515                2520                2525
Ser Ala Ile Met Gln Thr Ile Ser Pro Gln Gln Gln Gln Gln Gln Gln
    2530                2535                2540
Gln Gln Gln Gln Gln Gln His Gln Gln Gln Gln Gln Gln Gln Gln Gln
2545                2550                2555                2560
Gln Gln Gln Gln Gln Gln Gln Gln Leu Gly Gly Leu Glu Phe Gly Ser
                2565                2570                2575
Ala Gly Leu Asp Leu Asn Gly Phe Cys Gly Ser Pro Asp Ser Phe His
            2580                2585                2590
Ser Gly Gln Met Asn Pro Pro Ser Ile Gln Ser Ser Met Gly Ser
        2595                2600                2605
Ser Pro Ser Thr Asn Met Leu Ser Pro Ser Ser Gln His Asn Gln Gln
    2610                2615                2620
```

```
Ala Phe Tyr Gln Tyr Leu Thr Pro Ser Ser Gln His Ser Gly Gly His
2625                2630            2635                2640

Thr Pro Gln His Leu Val Gln Thr Leu Asp Ser Tyr Pro Thr Pro Ser
            2645            2650            2655

Pro Glu Ser Pro Gly His Trp Ser Ser Ser Pro Arg Ser Asn Ser
            2660            2665            2670

Asp Trp Ser Glu Gly Val Gln Ser Pro Ala Ala Asn Asn Leu Tyr Ile
        2675            2680            2685

Ser Gly Gly His Gln Ala Asn Lys Gly Ser Glu Ala Ile Tyr Ile
    2690            2695            2700
```

(2) INFORMATION FOR SEQ ID NO:20:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

GCGCATCAGG ATCATATGAA GCACGATGTG GATGCA        36

(2) INFORMATION FOR SEQ ID NO:21:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

GGCCACATCG TCCGGAAATC GATCCATGTG ATC        33

(2) INFORMATION FOR SEQ ID NO:22:

(i) SEQUENCE CHARACTERISTICS:
        (A) LENGTH: 33 amino acids
        (B) TYPE: amino acid
        (D) TOPOLOGY: unknown (ii) MOLECULE TYPE: peptide (ix) FEATURE:
        (A) NAME/KEY: Modified-site
        (B) LOCATION: 17
        (D) OTHER INFORMATION: /note= "X = Ala or Val"

(xi) SEQUENCE DESCRIPTION: SEQ ID NO:22:

```
Ile Asn Ala Ala Asp Asn Ser Gly Lys Thr Ala Leu His Trp Ala Ala
1               5                   10                  15

Xaa Val Asn Asn Thr Glu Ala Val Asn Ile Leu Leu Met His His Ala
            20                  25                  30

Asn
```

(2) INFORMATION FOR SEQ ID NO:23:

(i) SEQUENCE CHARACTERISTICS:
        (A) LENGTH: 3771 base pairs
        (B) TYPE: nucleic acid
        (C) STRANDEDNESS: double
        (D) TOPOLOGY: unknown ( i i ) MOLECULE TYPE: cDNA ( x i ) SEQUENCE DESCRIPTION: SEQ ID NO:23:

| | | | | | |
|---|---|---|---|---|---|
| TTTTTTTTT | TTTTTTGAA | CATGAATGAA | GTTACTTTAT | TTGAACTATA | TATAAATGTA | 60 |
| CTGTATTATA | TATGCGTAAT | ATGCATACAT | AAATGGTGTG | GAATTTGTTG | TGGAATATTC | 120 |
| GTCAAATGAA | CTTTAATAAC | TAATCAGTGC | TAAATACAAC | TTAGTAAAAT | CATATCATAT | 180 |
| CATATCAAAT | ATGGTGGCGC | GGTCAGTAGC | CGCTAGCTGT | CCGTACGATC | TCTACATACT | 240 |
| ATATGCTATA | TATGCTATAT | ATTGGCGATG | TATACGATAG | TTCGTTCGAT | GCTCGATGAT | 300 |
| ATCAATATGA | AAGCAACAAT | TCATCAAATG | TATGCAAGGG | ATTCGATAAA | AAAAATTATT | 360 |
| GTTATGTCGT | ATGGCTATGG | GGCTATGTTA | AAATATGTTT | ATGTATGTAT | GTATATGTAT | 420 |
| ATGTATATGT | ATATGCGTAA | TGGAATATCT | GGCTGCGTTA | CAACTATGCT | TCCTAAATGC | 480 |
| TCCGTTTAAT | AATGAATAAT | TCAAATTAAA | ATCACATCAA | ATTCGCTGAA | TGAAAGAGAT | 540 |
| TAAATGGCCA | AGACAAGTGA | GACAAGTCTA | TCGAATTTAC | CCATCTCCAT | TTCCTCTCTC | 600 |
| AAAATACTAT | TTTAATCCTA | TATAAATCCG | ATATAAAGAA | AATTCACATG | GATCTGATGA | 660 |
| AAGAGACAAA | TTCGAAACCG | AGAGAGATGG | AGAGATGGGC | AATGGTTATA | GCTAGCTATA | 720 |
| TCAACAATAT | ACATATCCTA | TAAACGGGAG | CGCTACGATT | TTGGCACAGC | TTGCACTCGA | 780 |
| ATGGCGTGGC | TTGGCTTGGC | TTGAATCGAA | TCAGGAATCA | AGAATCAGGA | TAATGCCTAA | 840 |
| TACTAGTAGG | TGTCTTGGGT | CAAGATTCTC | TTGGGAACTA | CAGCTACAAC | TAACTAACTA | 900 |
| ACTAACTAAC | TAGCTAATAC | ATATGATGTA | CGCCAACTTA | TTGCGTATGT | GCGTACAAAT | 960 |
| ACGAATTGGA | AGAGCGGAAA | GGAAGCTACA | ATTGCAATTG | TGGTTTGCTG | TTGTTTTAGG | 1020 |
| GTTCGAGCAG | CTCGAACGCT | ATTACAATAT | ATCTATAAAA | AAAATATATC | ATAGTAAACG | 1080 |
| AGGATTGCAC | ACACACTGAG | ATTATGTAGA | AAGTAACTTA | ACGACGAATG | GAAGAGAATG | 1140 |
| ATCGAGGGGA | CTTCGGTGGG | TGGGTGGTTG | ATTGGTTGGT | TGGTAGTTCT | ACTTGGGGAC | 1200 |
| AGGGAACTAA | TCCTTAATCC | GTCACGCCCA | GGTGCACCAG | CTGTTGCATG | GTTCGCTGCA | 1260 |
| AATAGGTGGG | ATCCGGAAAC | ATATTGAACT | GCGTCTTGTG | ATCCACACTG | TTCCAGATCA | 1320 |
| CCACATCCTC | GCGTCCGGTG | GTCACCGATC | GTCCGATCGA | GAAAAGCAGC | CGACGATCGA | 1380 |
| ATGCAATCTT | GAGGAAGCGC | AAAACCTTTC | GCCCCAGCGG | GCAGTCCGGC | AAGTAGCAGA | 1440 |
| TCCGCGGGAA | TCCCACGGCG | AAGAAGGCAC | GACCTGGATG | CGGATGCTCC | TCCGTCTGCA | 1500 |
| GTCCCGATGC | AATGTCGTAA | ACAATCTGTA | TGGTGTTCTG | ACCCTCGTGT | CCTGGCAGAT | 1560 |
| TCTTGCTAAT | TATGCTCCAC | GACATGCTGC | CAATGGGCTG | ATTGCCGACC | TTCTCGCCGT | 1620 |
| AAACGATGCC | GCATACAGGG | CACTCGATGA | AAAGGTTCTT | GTTCATTTCG | TTTTGCTGGG | 1680 |
| CAATTATCAT | CCCATTGAGG | CACTGCAAAT | GCATGAGATG | CTGGCAGCGA | CTCAGCGAAA | 1740 |
| TGGCCGGATT | CTGGGCGGAG | TGCACCAGCT | CCTCCATGCA | CATGGGACAG | GGCTGGGCAT | 1800 |
| TGGGCCACAG | CGGTGGCTCC | ACCACCTTGA | CAAAACGCGA | TATCATATCG | CTGGCCGGGT | 1860 |
| CCACGCCCAC | AATCGAACCG | GCGATTGATT | GCTGCTGCTG | CTGCTGCGCC | TGTTGCTGCT | 1920 |
| GTTGCATCTG | CAGCTGTTGC | TGCTGTTGTT | GCTGCTGCTG | TTGCTGTCGC | GGATGCAGTG | 1980 |
| GTAATGGCGG | CGGCACCGGC | GCCCTTTCGC | CCAGCGACGA | TGGCGGCACG | GAGGGCACAA | 2040 |
| AAACTTCATC | GCTGCCAAGC | GAGCAGTCCA | GCAGATCATT | GACCGAAATG | GCAAAGTTCC | 2100 |
| TGCTGCGCAG | GCTCTCCTTG | CTCTCGTGGC | TGAGGTAAGT | GGACACGGTG | TCCACACTGG | 2160 |
| GTCTCCGCCG | ATGCGATTTC | ACACTGTTCG | TGTCCGTGTC | CGAGGTCCGC | GTTCGCGATC | 2220 |
| TCGAGCGATG | CGAGCCCATC | CGGCTGCTCC | TTTGCGACTG | CAGCGATCCC | TCCGAGCAGC | 2280 |

-continued

| | | | | | | |
|---|---|---|---|---|---|---|
| GACTATGATG | ACTGTTCATC | GAGGCAGTCA | GCATGTTCTT | GGCGTGCGAA | AAGTGCGCAT | 2340 |
| GCGACAGATG | GTTGGCATGG | TGCAGCGAGG | CCGATGAGGA | GGATGAACTG | GCACTGGCCG | 2400 |
| CCGTCGACAT | GTTCGATTGG | TGCTTAGTGC | TGCTGCTGAA | GATGTTTAGG | TTGTTGAGTA | 2460 |
| TCTGGCGTAG | ATTGGTGGTG | GAGATCTCGC | TGTGCTTCTT | GGGCGGCTTC | CTGGCGCCG  | 2520 |
| TCTGATGATG | GATCTGATGG | TGCTGCATCT | GATGTTGCTG | CTGTTGCTGA | TGCTGTTGTT | 2580 |
| GCTGATGCTG | GTGATGATGT | TGCTGCTGCT | GCTGCTGTTG | ATGCTGGAGC | TGATGCTGCT | 2640 |
| GCTGCTGCAC | TTGATGGCTG | GTGGGCAATG | GGTGCTGTTG | CCTGGTCATG | GGCACTCTGT | 2700 |
| GCAGGCTCTT | GGTGTCGCCC | AGTTTGGGTA | GAGTGTTGTA | CTGGCTGCTC | ACGCTGGCGG | 2760 |
| AATTCGACTT | GAGTTGGTTG | GCCTGTTGTG | GCGTTAGTTT | CACCAAGGGA | TACGGCGCCT | 2820 |
| GTTGGGTACG | CCGAATGCTG | CGCATGGGTC | CGCTGGGTTG | GCGCACGTGG | GTGAGATTGC | 2880 |
| AAAAATTAAT | GGTGTACGGC | AGGCCGATGT | GGGTGTTGCA | CAGGTCCAAG | GTTTGTTCGC | 2940 |
| CCCTCGCCCA | GGCGTCCTCG | ATGATGCACT | GGACGTGCAT | GTTGTAGGGC | CGCCAGTCGT | 3000 |
| TGTTGCTATC | GGCACTGCCG | CCCGACCACT | CCCACTTGGT | GCCCTTGCCC | GCCGGCGAGC | 3060 |
| TGGGTGCGTA | TAACATGCGC | CGAACACCGA | TGGTCAGCAG | GCCGGAGCGC | GTTTCCGCCT | 3120 |
| CCGATTCCTG | GGTCATTGTG | CGCACGTTGA | CGTAGTACTG | CTCCAGGCTG | GGATCCGCAT | 3180 |
| CGCTCAGCAT | GACGCGCGTC | AGTTTCTTGG | CGTGGGCGCG | TTCCAAGTGC | TGCGACACCG | 3240 |
| CCGGCGAATA | GGGCAGCCAC | TTGCCGCGCG | ACTCGAACTC | CCACACGCAG | ACGGCGTGGG | 3300 |
| CGTGGTTCAC | GGGCGGCCCA | CCGGATCCGG | CGGTGGACAG | GGCCATGGTG | GCACAACTGG | 3360 |
| AGGCGGCGCT | ACCTCCGCCA | CCGGGAACAA | CGGATCCGGA | TGCCGCACTT | CCGGCGCTGC | 3420 |
| TGGCCATTGC | TTGCAGTTGA | TCCGTTATCC | GTGGAGTGAG | CCCATTGCCA | TATCCATGCC | 3480 |
| CATTTCCATA | TCCAACTCCT | CCTGCGCTCT | CTTCACTAGC | TCTCACTCAC | TCACTCTCTC | 3540 |
| TCTCGCTCTC | TCTTGCTGTT | GCTGTCGCGC | TATCTCGCTC | GCTCGCGAAG | ATGGGCACAA | 3600 |
| AATAAACAAA | GAAATTAAAA | ATGGTGGACC | CGCTGCCAGC | GTTAGTTATC | CCTGATTTTC | 3660 |
| CCTGGCTTCC | ATTTTCCCGA | AGTTTTCGTT | CTGGTTCTTT | AGTCACTCGG | TTTCGTTTAG | 3720 |
| GCGCAGCTTA | AGAATTCACG | TTTGATGGTA | AAAACGGTTT | TTCTAGCATT | T          | 3771 |

DELTEX PROTEINS

This invention was made with government support under grant numbers GM29093 and NS26084 awarded by the National Institutes of Health. The government has certain rights in the invention.

TABLE OF CONTENTS
1. INTRODUCTION
2. BACKGROUND OF THE INVENTION
3. SUMMARY OF THE INVENTION
4. DESCRIPTION OF THE FIGURES
5. DETAILED DESCRIPTION OF THE INVENTION
   5.1. ISOLATION OF THE DELTEX NUCLEIC ACIDS
   5.2. EXPRESSION OF DELTEX NUCLEIC ACIDS
   5.3. IDENTIFICATION AND PURIFICATION THE DELTEX GENE PRODUCTS
   5.4. STRUCTURE OF THE DELTEX GENES AND PROTEINS
      5.4.1. GENETIC ANALYSIS
      5.4.2. PROTEIN ANALYSIS
   5.5. GENERATION OF ANTIBODIES TO DELTEX PROTEINS AND DERIVATIVES THEREOF
   5.6. DELTEX PROTEINS, DERIVATIVES AND ANALOGS
      5.6.1. DERIVATIVES OF DELTEX CONTAINING ONE OR MORE DOMAINS OF THE PROTEIN
   5.7. IN VITRO ASSAYS OF DELTEX PROTEINS, DERIVATIVES AND ANALOGS
   5.8. THERAPEUTIC USES
      5.8.1. MALIGNANCIES
      5.8.2. NERVOUS SYSTEM DISORDERS
      5.8.3. TISSUE REPAIR AND REGENERATION
   5.9. PROPHYLACTIC USES
      5.9.1. MALIGNANCIES
      5.9.2. OTHER DISORDERS
   5.10. DEMONSTRATION OF THERAPEUTIC OR PROPHYLACTIC UTILITY
   5.11. ANTISENSE REGULATION OF DELTEX EXPRESSION
      5.11.1. DELTEX ANTISENSE NUCLEIC ACIDS
      5.11.2. THERAPEUTIC UTILITY OF DELTEX ANTISENSE NUCLEIC ACIDS
   5.12. THERAPEUTIC/PROPHYLACTIC ADMINISTRATION AND COMPOSITIONS
   5.13. DIAGNOSTIC UTILITY
6. EXAMPLE: A MEMBER OF THE NOTCH GROUP OF INTERACTING LOCI, DELTEX ENCODES A CYTOPLASMIC BASIC PROTEIN
   6.1. RESULTS
      6.1.1. MOLECULAR CLONING OF THE DELTEX LOCUS
      6.1.2. TRANSCRIPTIONAL ACTIVITY OF THE 6A REGION
      6.1.3. ALL DELTEX ADULT PHENOTYPES CAN BE RESCUED BY A 10-KB GENOMIC FRAGMENT
      6.1.4. DELTEX ENCODES A BASIC PROTEIN RICH IN GLUTAMINE, HISTIDINE, AND SERINE RESIDUES
      6.1.5. THE DELTEX PROTEIN IS LOCALIZED WITHIN THE CYTOPLASM
      6.1.6. THE GENETIC SUPPRESSION OF DELTEX
      6.1.7. SUPPRESSION OF THE PHENOTYPIC INTERACTIONS BETWEEN DELTEX AND NOTCH, DELTA AND MASTERMIND
   6.2. DISCUSSION
   6.3. MATERIAL AND METHODS
      6.3.1. ISOLATION OF NUCLEIC ACIDS
      6.3.2. P-MEDIATED TRANSFORMATION
      6.3.3. SEQUENCE DETERMINATION AND ANALYSIS
      6.3.4. EXPRESSION CONSTRUCTS AND IMMUNOLOGICAL PROCEDURES
      6.3.5. STRAINS AND CROSSES
      6.3.6. PHENOTYPIC REVERSION OF DX$^P$
      6.3.7. COMPLEMENTATION OF DELTEX ALLELES BY THE DELTEX TRANSPOSONS TX05B AND TX012G
      6.3.8. ORIGIN OF SU(DX)$^{SP}$
      6.3.9. CROSSES BETWEEN SU(DX) MUTATIONS AND DELTEX ALLELES
      6.3.10. CROSSES BETWEEN SU(DX) AND MUTATIONS OF THE NOTCH LOCUS
      6.3.11. CROSSES INVOLVING SU(DX), DELTEX, DELTA AND MASTERMIND
      6.3.12. CROSSES COMPARING SU(DX) MUTATIONS
      6.3.13. CROSSES INVOLVING DUPLICATIONS OF THE DELTEX LOCUS
7. DELTEX IMPLICATED IN NOTCH-MEDIATED SIGNAL TRANSDUCTION: EVIDENCE FOR CYTOSOLIC INTERACTION WITH NOTCH CDC10/SWI6/ANKYRIN REPEATS
   7.1. DELTEX INTERACTS WITH NOTCH INTRACELLULAR DOMAIN
   7.2. NOTCH AND DELTEX CO-LOCALIZATION IN VIVO
   7.3. NOTCH ANKYRIN REPEATS ARE BOTH NECESSARY AND SUFFICIENT FOR DELTEX ASSOCIATION
   7.4. DIRECT NOTCH/DELTEX INTERACTION INDICATED BY YEAST EXPRESSION STUDIES
   7.5. INTRAGENIC SUPPRESSOR MUTATION MAPS WITHIN ANK REPEAT
   7.6. DISCUSSION
8. EXAMPLE: PORTIONS OF DELTEX WHICH MEDIATE HETEROTYPIC AND HOMOTYPIC BINDING
9. EXAMPLE: DELTEX CONTAINS A PUTATIVE SH3-BINDING DOMAIN
10. DEPOSIT OF MICROORGANISMS

1. INTRODUCTION

The present invention relates to deltex genes and their encoded protein products, as well as derivatives and analogs thereof. The invention further relates to production of deltex proteins, derivatives and antibodies. Related therapeutic compositions and methods of therapy and diagnosis are also provided.

2. BACKGROUND OF THE INVENTION

In *Drosophila melanogaster*, the so called "Notch group" of genes has been implicated in events crucial for the correct developmental choices of a wide variety of precursor cells (for review, see Fortini and Artavanis-Tsakonas, 1993, Cell 75:1245–1247; Artavanis-Tsakonas and Simpson, 1991, Trends Genet. 7:403–408). The accumulated genetic and molecular studies suggest that these genes encode elements of a cell communication mechanism which includes cell surface, cytoplasmic, and nuclear components.

Very little is known about the mechanisms underlying cell fate choices in higher organisms such as vertebrates; a knowledge of such mechanisms could provide insights into pathologies associated with abnormal differentiation events. Thus, a need exists in the art to obtain and characterize the human members of the "Notch group" of genes, including deltex, since these genes appear to play crucial roles in the determination of cell fate.

Numerous developmental genetic studies in recent years have shown that the Notch locus plays a central role in regulative events influencing cell fate decisions in Drosophila in a very broad spectrum of developing tissues (reviewed in Artavanis-Tsakonas and Simpson, 1991, Trends Genet. 7:403–408; and in Artavanis-Tsakonas et al., 1991, Ann. Rev. Cell Biol. 7:427–452). This pleiotropy of Notch function is revealed by mutations affecting all stages of development and a variety of tissues (e.g., Welshons, 1965, Science 150:1122–1229; Welshons, 1971, Genetics 68:259–268; Shellenbarger and Mohler, 1978, Dev Biol. 62:432–446). A dramatic illustration of Notch function is seen in the development of the embryonic nervous system, whereby loss of function mutations cause the misrouting of epithelial precursor cells into a neural developmental pathway and result in what has been termed a 'neurogenic' phenotype (Poulson, 1937, Proc. Natl. Acad. Sci. USA, 23:133–137; Lehman et al., 1983, Roux's Arch. Dev. Biol. 192:62–74).

In attempts to understand the molecular contexts by which the Notch protein communicates signals from the cell surface to the nucleus to effect changes in cell fate, genetic means have been used to identify loci that interact phenotypically with various Notch alleles. These genetic studies led to the definition of a small group of interacting loci, which has been operationally termed the 'Notch group' (Artavanis-Tsakonas and Simpson, 1991, Trends Genet. 7:403–408). The other members of the Notch group are deltex (Xu and Artavanis-Tsakonas, 1991, Genetics 126:665–677), Enhancer of (split) [E(spl)] (Knust et al., 1987, EMBO J. 6:4113–4123; Hartley et al., 1988, Cell 55:785–795; Preiss et al., 1988, EMBO J. 7:3917–3927; Klambt et al., 1989, EMBO J. 8:203–210), and mastermind (mam) (Smoller et al., 1990, Genes Dev. 4:1688–1700). mastermind and Enhancer of (split) encode nuclear proteins (Smoller et al., 1990, Genes Dev. 4:1688–1700; Delidakis et al., 1991, Genetics 129:803–823). deltex mutations suppress the pupal lethality conferred by certain heteroallelic combinations of the Abruptex class of Notch alleles (Xu et al., 1990, Genes Dev. 4:464–475). From this same genetic screen, the genes Delta and mastermind were also identified, both of which belong to the same 'neurogenic' class of genes as Notch because of the similar mutant phenotypes they produce. Moreover, subsequent analysis has shown that alleles of deltex exhibit genetic interactions with those of Delta and mastermind, a further suggestion of functional links among these loci (Xu and Artavanis-Tsakonas, 1990, Genetics 126:665–677).

The manner by which Notch is thought to influence determinative events is indirect, that is, not through the direct specification of cellular fates. Instead, recent experimental studies (Coffman et al, 1993, Cell 73:659–671; Fortini et al, Nature, in press) indicate that Notch activity delays differentiation, and in this manner renders precursor cells competent to receive and/or interpret any number of specific developmental cues (Cagan and Ready, 1989, Genes Dev. 3:1099–1112). In loss of function mutants, this inhibition is lost and cells assume default pathways of differentiation. For example, during the development of the Drosophila nervous system, cells that normally would become epidermis instead adopt a neural fate in the absence of Notch function. However, a salient feature of Notch activity is its pleiotropy. Notch is required for the proper specification of many other cell types, including those of the compound eye (Cagan and Ready, 1989, Genes Dev. 3:1099–1112), ovary (Ruohola et al, 1991, Cell 66:433–449; Xu et al., 1992, Development 115:913–922), and mesoderm (Corbin et al., 1991, Cell 67:311–323). Similarly, the widespread expression patterns exhibited by vertebrate Notch cognates suggest also a broad-based functional role in these species (Coffman et al, 1993, Cell 73:659–671; Coffman et al., 1990, Science 249:1438–1441; Weinmaster et al., 1991, Development 113:199–205; Weinmaster et al., 1992, Development 116:931–941; Kopan and Weintraub, 1993, J. Cell Biol. 121:631–641; Franco del Amo et al., 1992, Development 115:737–744; Ellisen et al., 1991, Cell 66:649–661; Stifani et al., 1992, Nature Genetics 2:119–127).

Notch homologs have been isolated from a variety of vertebrate species and have been shown to be remarkably similar to their Drosophila counterpart in terms of structure, expression pattern and ligand binding properties (Rebay et al., 1991, Cell 67:687–699; Coffman et al., 1990, Science 249:1438–1441; Ellisen et al, 1991, Cell 66:649–661; Weinmaster et al., 1991, Development 113:199–205). Two human Notch homologs have been isolated (PCT Publication No. WO 92/19737 dated Nov. 12, 1992), termed hN and TAN-1. A human Notch (TAN-1) malfunction has been associated with a lymphatic cancer (Ellisen et al., 1991, Cell 66:649–661).

Notch encodes a large, structurally-complex transmembrane protein, consistent with an involvement in cell-cell communication (Wharton et al., 1985, Cell 43:567–581; Kidd et al., 1986, Mol. Cell. Biol. 6:3094–3108). Notch has an extracellular domain containing 36 tandem EGF-like repeats and 3 Notch/lin12 repeats. The intracellular domain bears several common structural motifs including 6 cdc10SW16/ankyrin repeats ("ANK" repeats) (Lux et al., 1990, Nature 344:36–42; Breeden and Nasmyth, 1987, Nature 329:651–654; Michaely and Bennett, 1992, Trends Cell Biol. 2:127–129; Blank et al., 1992, Trends Biochem. Sci. 17:135–140; Bennett, 1992, J. Biol. Chem. 267:8703–8706)), a polyglutamine stretch known as 'opa', and a PEST motif (Stifani et al., 1992, Nature Genetics 2:119–127). The remarkable degree to which these motifs have been conserved in homologs isolated from mice (Weinmaster et al., 1991, Development 113:199–205; Weinmaster et al., 1992, Development 116:931–941; Kopan and Weintraub, 1993, J. Cell Biol. 121:631–641), rats (Kopan and Weintraub, 1993, J. Cell Biol. 121:631–641; Franco del Amo et al., 1993, Genomics 15:259–264), humans (Ellisen et al., 1991, Cell 66:649–661; Stifani et al., 1992, Nature Genetics 2:119–127; PCT Publication No. WO 92/19737 dated Nov. 12, 1992), and Xenopus (Coffman et al, 1993, Cell 73:659–671; Coffman et al., 1990, Science 249:1438–1441) implies that they will have a common biochemical mode of action. In particular, ANK repeats, which constitute the most conserved region (~70% amino acid identity) between Notch and its vertebrate counterparts (Stifani et al., 1992, Nature Genetics 2:119–127), are thought to mediate protein-protein interactions among diverse groups of proteins, including those involved in signal transduction processes and cytoskeletal interactions (Lux et al., 1990, Nature 344:36–42; Breeden and Nasmyth, 1987, Nature 329:651–654; Michaely and Bennett, 1992, Trends Cell Biol. 2:127–129; Blank et al., 1992, Trends Biochem. Sci. 17:135–140; Bennett, 1992, J. Biol. Chem. 267:8703–8706). Indeed, Rebay et al. (1993, Cell 74:319–329) have recently demonstrated that the ANK repeats are crucial for Notch-mediated signaling events. Both EGF-like repeats and ankyrin motifs are found in a variety of proteins known to interact with other protein molecules. Indeed, evidence has shown a direct interaction between Notch and the products of the Delta and Serrate loci, which also encode transmembrane proteins containing EGF-like repeats (Fehon et al., 1990, Cell 61:523–534; Rebay et al., 1991, Cell 67:687–699). Despite the evidence to suggest that Notch functions as a cell surface receptor, few biochemical details of Notch function are known.

It has been demonstrated that dominant 'activated' phenotypes result from in vivo overexpression of a Notch protein lacking most extracellular, ligand-binding sequences, while 'dominant-negative' phenotypes result from overexpression of a protein lacking most intracellular sequences (Rebay et al., 1993, Cell 74:319–329). Despite this evidence further implicating Notch as a cell surface receptor of extracellular signals, the intracellular nature of the signal transduction cascade is unknown.

Citation of a reference herein shall not be construed as an admission that such reference is prior art to the present invention.

3. SUMMARY OF THE INVENTION

The present invention relates to nucleotide sequences of deltex genes, and amino acid sequences of the encoded deltex proteins. The invention further relates to fragments and other derivatives, and analogs, of deltex proteins, as well as antibodies thereto. Nucleic acids encoding such fragments or derivatives are also within the scope of the invention. Production of the foregoing proteins and derivatives, e.g., by recombinant methods, is provided.

In a specific embodiment, the invention relates to Drosophila deltex nucleic acids and proteins. In another embodiment, the invention relates to human deltex nucleic acids and proteins.

In specific embodiments, the invention relates to deltex protein derivatives and analogs of the invention which are functionally active, or which comprise one or more domains of a deltex protein, including but not limited to the Gln-rich clusters, SH3 binding domains, domains which mediate binding to Notch or to a Notch derivative containing Notch cdc10/SW16/ankyrin ("ANK") repeats, or any combination of the foregoing.

The present invention also relates to therapeutic and diagnostic methods and compositions based on deltex proteins and nucleic acids. The invention provides for treatment of disorders of cell fate or differentiation by administration of a therapeutic compound of the invention. Such therapeutic compounds (termed herein "Therapeutics") include: deltex proteins and analogs and derivatives (including fragments) thereof; antibodies thereto; nucleic acids encoding the deltex proteins, analogs, or derivatives; and deltex antisense nucleic acids. In a preferred embodiment, a Therapeutic of the invention is administered to treat a cancerous condition, or to prevent progression from a pre-neoplastic or non-malignant state into a neoplastic or a malignant state. In other specific embodiments, a Therapeutic of the invention is administered to treat a nervous system disorder or to promote tissue regeneration and repair.

In one embodiment, Therapeutics which antagonize, or inhibit, Notch and/or deltex function (hereinafter "Antagonist Therapeutics") are administered for therapeutic effect. In another embodiment, Therapeutics which promote Notch and/or deltex function (hereinafter "Agonist Therapeutics") are administered for therapeutic effect.

Disorders of cell fate, in particular hyperproliferative (e.g., cancer) or hypoproliferative disorders, involving aberrant or undesirable levels of expression or activity or localization of Notch and/or deltex protein can be diagnosed by detecting such levels, as described more fully infra.

In a preferred aspect, a Therapeutic of the invention is a protein consisting of at least a fragment (termed herein "adhesive fragment") of deltex which mediates binding to a Notch protein or a fragment thereof.

4. DESCRIPTION OF THE FIGURES

FIG. 1. Map of cloned genomic sequences and alignment of deltex cDNA clones. A). Coordinates are indicated in kilobasepairs, 0 corresponding to the P element insertion site of $dx^P$. The positions of EcoRI (R) and SalI (S) restriction sites are shown. Recombinant phages λA25 and λA28 derive from $dx^P$ genomic DNA library (see Section 6.3). Wild-type Canton S clones are represented by λI1, λI2 and λI3. DNA fragments cloned into the Bluescript plasmid vector are denoted with the prefix pd. B). Detail of genomic interval −5 to +6.5. XbaI (X) restriction sites are also shown. Below the map, open bars represent the cDNAs cBE30 and cBE8; thin lines delineate intronic sequences. deltex mRNA sequences represented by the cDNAs are shown as a solid line; broken line depicts the remaining 5' end of the mRNA as inferred from genomic sequencing. Within schematic of the predicted protein, black boxes denote relative position of opa repeats. Stippled bar to left of deltex transcription unit indicates genomic fragments that hybridize to partial cDNAs representing a ribosomal protein gene.

Figure 2B:
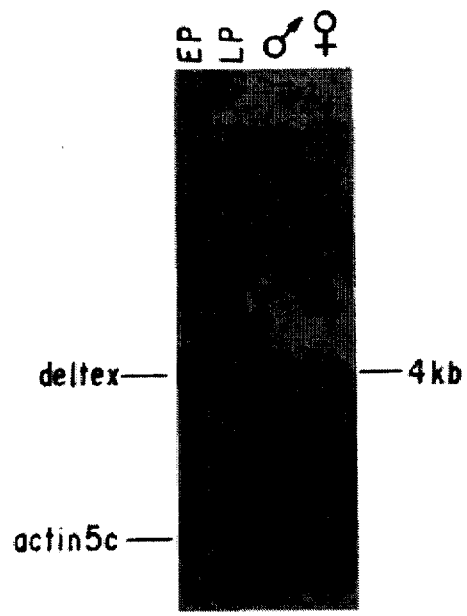

FIG. 2. Developmental Northern blot. Each lane contains 5 μg size-fractionated poly (A)⁺ RNA isolated from developmentally staged animals. Left: embryonic mRNA, hours (h) after egg laying; (L1–3) first, second and third larval instars. Right: early-(E) and late (L)-staged pupae (P) and adult male and female mRNA. Length of deltex mRNA is indicated in kilobases (kb). Band of deltex hybridization present in adult male lane is due to contaminating female flies. Pattern of actin 5c mRNA accumulation is shown as control.

Figure 3A:
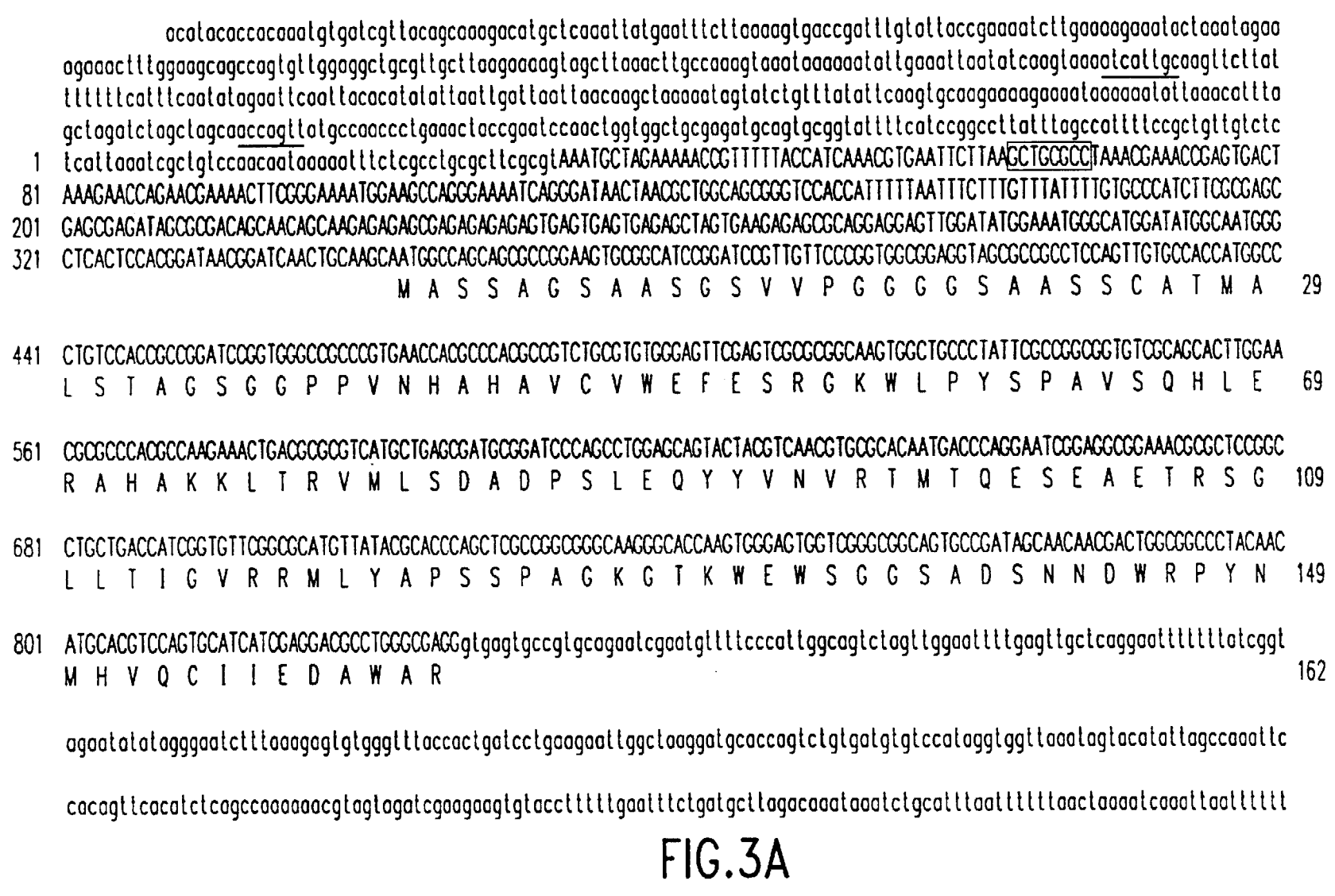

FIG. 3. Composite nucleotide sequence (SEQ ID NO:1) and deduced amino acid sequence (SEQ ID NO:2) of the deltex locus. DNA sequences in uppercase letters are derived from the cDNAs cBE30 (nucleotide 1 to 1299) and cBE8 (nucleotides 1116 to 3764); lowercase letters refer to genomic sequence from the $dx^P$ strain. The predicted amino acid sequence is depicted below the DNA sequence, with the opa repeats shown in bold letters. Numbers along left margin refer to the cDNA sequence; numbers on the right refer to the predicted amino acid sequence. Duplicated nucleotides resulting from insertion of the P element of $dx^P$ are shown boxed. A potential polyadenylation signal is underlined twice; a stretch of 17 A's is found in cDNA cBE8 just after nucleotide 3764 (the last uppercase letter). 5' to the cDNA sequence, two groups of seven nucleotides (underlined) are homologous to a transcription initiation consensus sequence.

Figure 4:
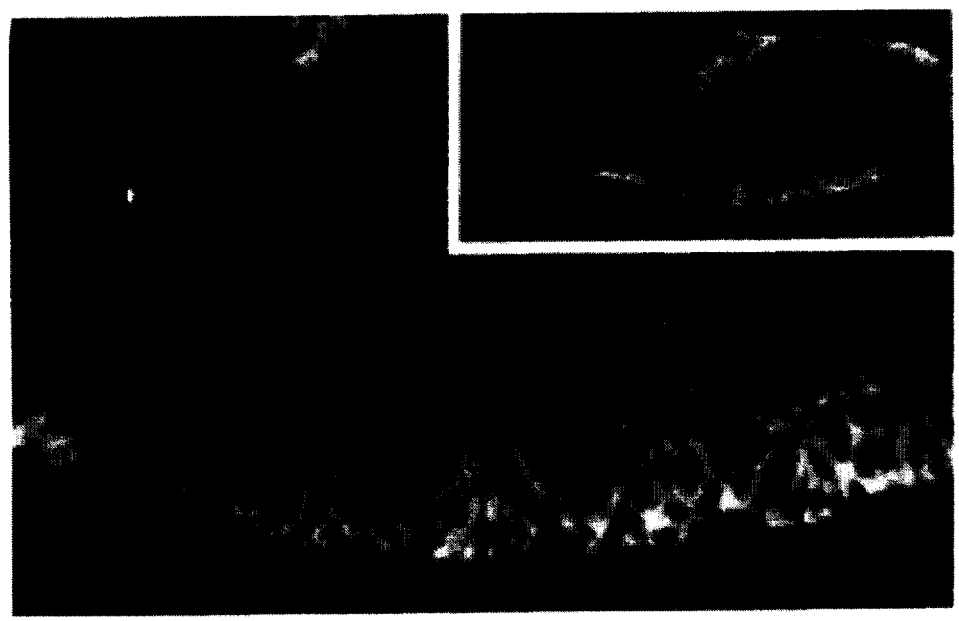
Figure 6A:
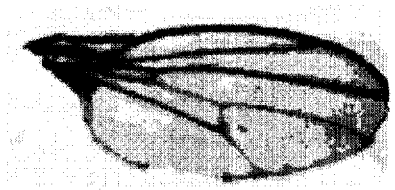
Figure 6B:
Figure 6C:
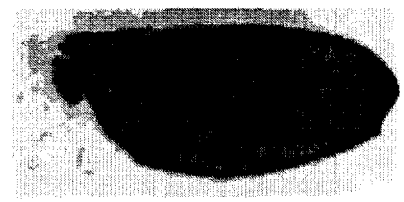
Figure 6D:
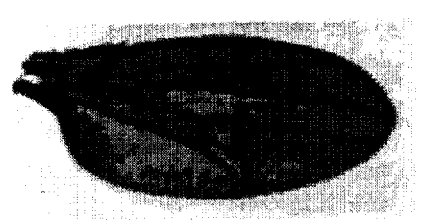
Figure 6E:
Figure 6F:
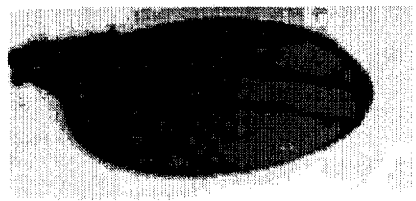
Figure 7A:
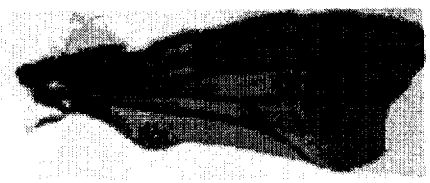
Figure 7B:
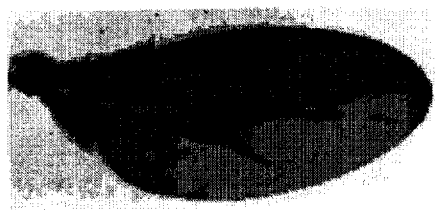
Figure 7C:
Figure 7D:

FIG. 4. Subcellular pattern of induced deltex protein expression. Confocal microscope images of a stage-10 embryo (lateral view: anterior is to the left; dorsal is up) after immunofluorescent staining with monoclonal antibody C645.17A. Embryo contains a transposon (line 142A$^D$) of deltex coding sequences under the control of the Drosophila Hsp70 promoter and was stained after heat shock induction (see Section 6.3). Upper right: whole embryo; lower left: high magnification of same image detailing ventral region.

FIG. 5. The effects of the Su(dx) mutations on various deltex alleles are summarized. The top row indicates the genetic constitution of the second chromosome and the left column indicates the genetic makeup of the X chromosome in the male. (+++): the deltex wing and ocellar phenotypes are completely suppressed. (++): the deltex wing and ocellar phenotypes are almost completely suppressed; only a trace of extra wing vein material is present at the margin of the fifth longitudinal veins. (+): the deltex wing and ocellar phenotypes are partially suppressed.

FIG. 6. Suppression of deltex wing phenotypes by the Su(dx) mutations. a). Wing of y dx$^{ENU}$ sn$^3$/Y male: note notches and extra vein material. b). Wing of y dx$^{ENU}$ sn$^3$/Y. Su(dx)$^{sp}$/+ male: the dx$^{ENU}$ wing phenotype is completely suppressed by one copy of the Su(dx)$^{sp}$ mutation. c). Wing of dx$^{SM}$t$^2$ v/Y male: notches and extra vein material are evident along the veins. d). Wing of dx$^{SM}$t$^2$v/Y; Su(dx)$^{sp}$+ male: the phenotype of this strong dx allele is completely suppressed by one copy of the Su(dx)$^{sp}$ mutation, but is only partially suppressed by the Su(dx)$^2$ mutation. e). Wing of dx$^P$ sn$^3$/Y male: this weak allele displays a mild extra-vein-material phenotype on the ends of the longitudinal veins. f). Wing of dx$^P$ sn$^3$/Y, Su(dx)$^{sp}$+ male: the phenotype of the dx$^P$ mutation is only partially suppressed by Su(dx)$^{sp}$ (and also by the other two Su(dx) mutations).

FIG. 7. a). Wing of nd dx$^{ENU}$/Y fly. Note the severe deltex wing-notching and the suppressed Abruptex gapped-vein phenotype. b). Wing of Ax$^{E2}$ dx$^{ENU}$/Y; Su(dx)/+ fly. Note the suppression of the deltex phenotype and the reemergence of the Abruptex gapped-vein phenotype. c). Dorsal view of Ax$^{E2}$sn$^3$/Y, Su(dx)$^{sp}$/+ fly. d). Dorsal view of Ax$^{E2}$ dx$^{ENU}$/Y, Su(dx)$^{sp}$/+ fly. Arrow points to region exhibiting a severe loss of micro- and macro-chaetae.

FIG. 8. deltex interacts with Notch cdc10/SW16/ankyrin ("ANK") repeats. Confocal microscope images of Drosophila S2 cells (a–d and f–l) and distal portion of imaginal wing disc (e) are presented as split images (except k) with Notch expression shown in green and deltex in red. For S2 cells, each panel represents a co-transfection experiment involving the deltex expression plasmid pCaSpeR hs-dx (see Section 6) and each of the expression constructs depicted in FIG. 9 or described elsewhere: a and b, pMtNcDNA (full-length Notch; Rebay et al., 1993, Cell 74:319–329); c, pMTD11 (Delta; Fehon et al., 1990, Cell 61:523–534); d, Ser-mtn (Serrate; Rebay et al., 1991, Cell 67:687–699); f, pMTΔB-S; g, pMTΔS-S; h, pMTECN; i, pMTΔcdc10; j and k, pMTDl/NANK; l, pMTDl/CANK. Cell surface 'capping' was induced (except in b) as described (Fehon et al., 1990, Cell 61:523–534; Rebay et al., 1991, Cell 67:687–699). Immunofluorescent labeling of cells was performed as described (Fehon et al., 1990, Cell 61:523–534) using mouse anti-Notch monoclonal antibody (line C458.2H) specific for the extracellular domain and rat anti-deltex polyclonal or monoclonal (line C645.17A) antibodies (see Section 6) directed against the entire coding region. Extraneous cytoplasmic Notch expression was minimized by reacting cells with anti-Notch antibody prior to cell permeabilization and incubation with anti-deltex antibodies. Delta and Serrate expression (c and d) are viewed indirectly through their co-capping with Notch. In some instances, aggregated cell partners were torn apart during manipulation. The diameter of S2 cells is 7–10 microns.

FIG. 9. Plasmid expression constructs used in S2 cell transfections. a, Notch intracellular domain (top; drawn to scale); extracellular domain is not shown but is intact (TM, transmembrane region). Structural motifs and restriction sites used to generate deletion constructs (black bars) are indicated. Deleted amino acids are presented in parentheses (numbering from Wharton et al., 1985, Cell 43:567–581). b, Intracellular domains of Delta-based expression constructs (same scale as in a). NdeI site adjacent to translational stop codon was used as insertion site for Notch-(pMTDl/NANK) and cactus-(pMTDl/CANK) ANK repeat coding sequences. Results of deltex binding are summarized. c, Immunoblot analysis of 52 cell lysates after transfection and expression of plasmid constructs depicted in b (NT, non-transfected cells). Integrity of other expression constructs (a) was also confirmed by immunoblot analysis (not shown).

Figure 10:
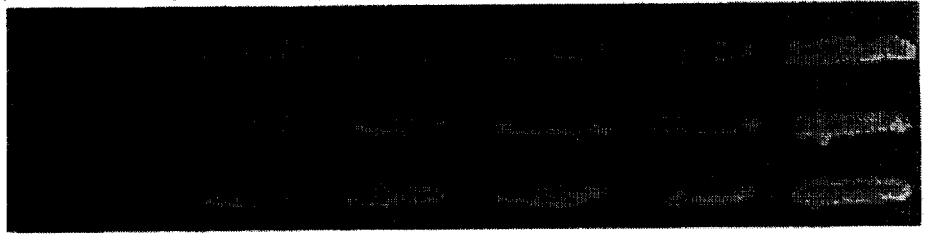

FIG. 10. Direct Notch/deltex interaction in yeast. Each column lists Drosophila genes that were fused to sequences encoding a LexA DNA-binding domain or an acidic transcription activation domain. These were co-transformed into yeast containing a LexA operator-lacZ reporter gene plasmid (pSH18-34; S. Hanes and R. Brent, unpublished) and were plated onto glucose- and galactose-Ura⁻His⁻Trp⁻X-gal-indicator plates. Three independent yeast isolates are shown for each experiment. Only transformations involving LexA-Notch ICN1 and deltex-ACT resulted in detectable β-galactosidase activity.

Figure 11A:
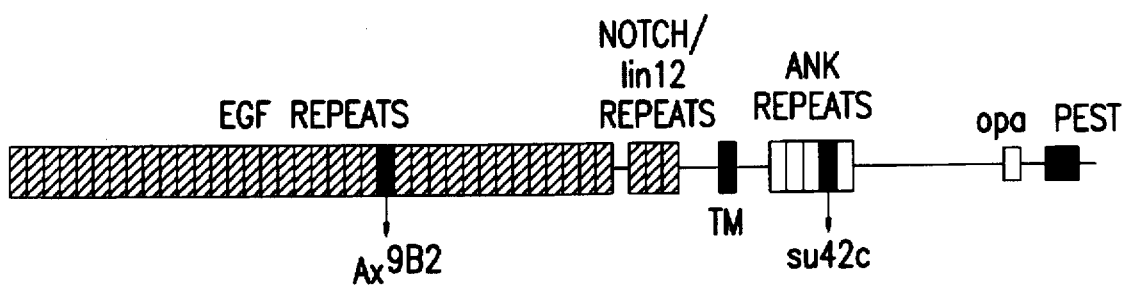
Figure 11B:
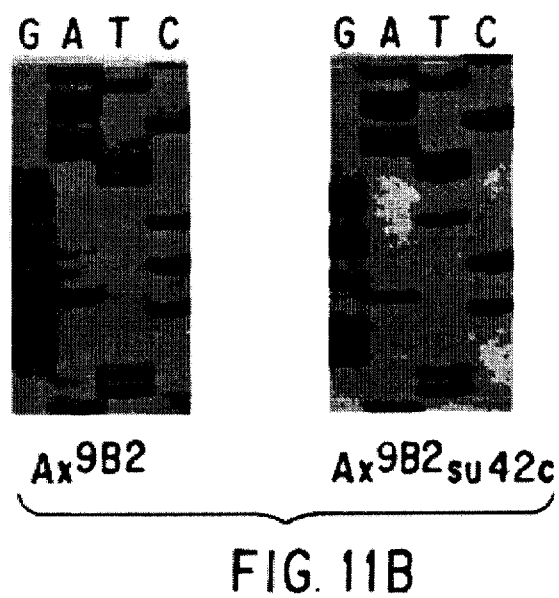
Figure 11C:

FIG. 11. Intragenic suppressor mutation maps within fifth Notch ANK repeat. a, Diagram of Notch protein. The su42c mutation was induced in flies containing the Ax$^{9B2}$ mutation (Xu et al., 1990, Genes Dev. 4:464–475). b, DNA sequencing gels showing C to T transition in Ax$^{9B2}$ su42c genomic DNA. This residue is unaffected (i.e., wild-type) in the parental Ax$^{9B2}$ DNA. c, Amino acid sequence (single letter code) (SEQ ID NO:22) of fifth ANK repeat showing alanine to valine substitution resulting from the su42c mutation (numbering based on Wharton et al., 1985 Cell 43:567–581).

FIG. 12. Nucleotide sequence (SEQ ID NO:3), complimentary strand (SEQ ID NO:23), and deduced amino acid sequence (SEQ ID NO:4) of deltex cDNA.

Figure 13:
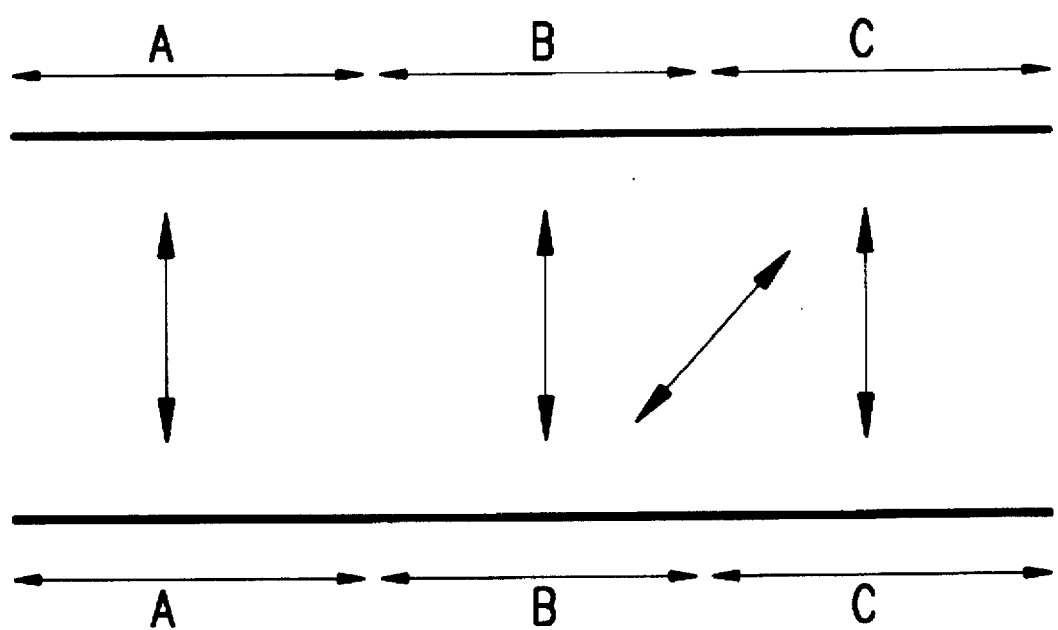

FIG. 13. Schematic diagram of deltex fragments mediating deltex—deltex interactions.

FIG. 14. Amino acid sequence of Drosophila deltex (SEQ ID NO:2; SEQ ID NO:4) and designated fragments implicated in protein—protein interactions. Fragments A–D (SEQ ID NOS:5–8, respectively) are shown.

Figure 15:
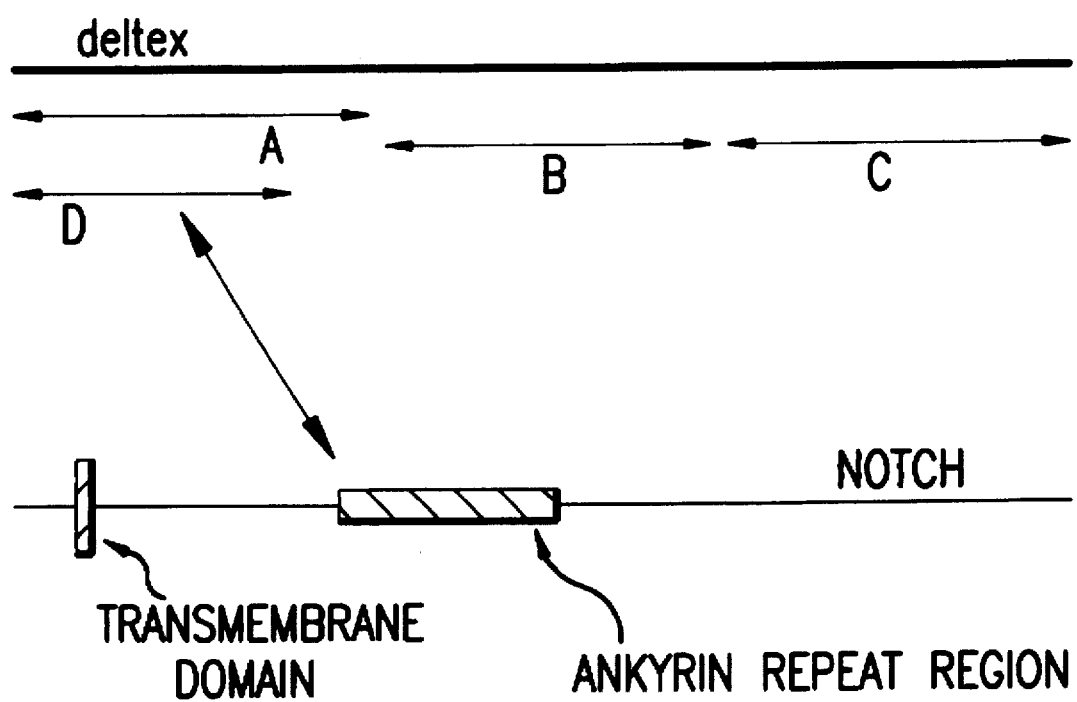

FIG. 15. Schematic diagram of the deltex and Notch fragments mediating deltex-Notch interactions.

FIG. 16. Putative SH3-binding domains in Drosophila (fly). The sequence of the mouse GAP SH3-binding domain (SEQ ID NO:9) is shown, with the putative SH3 binding domains of the Drosophila proteins deltex (SEQ ID NO:10 and SEQ ID NO:11), son of Sevenless (SEQ ID NO:12 and SEQ ID NO:13), hairless (SEQ ID NO:14), and disabled (SEQ ID NO:15).

Figure 17B:
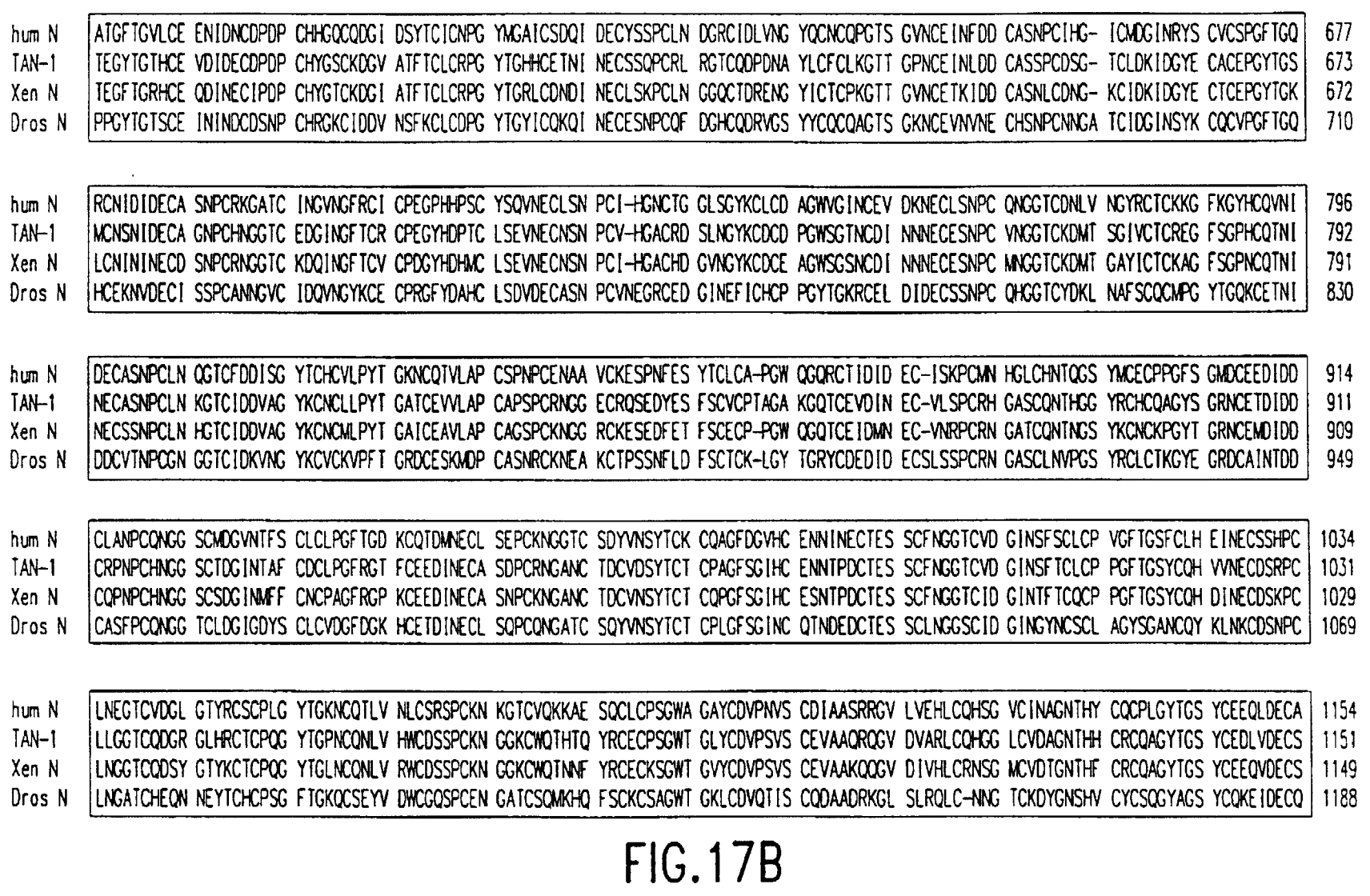
Figure 17D:
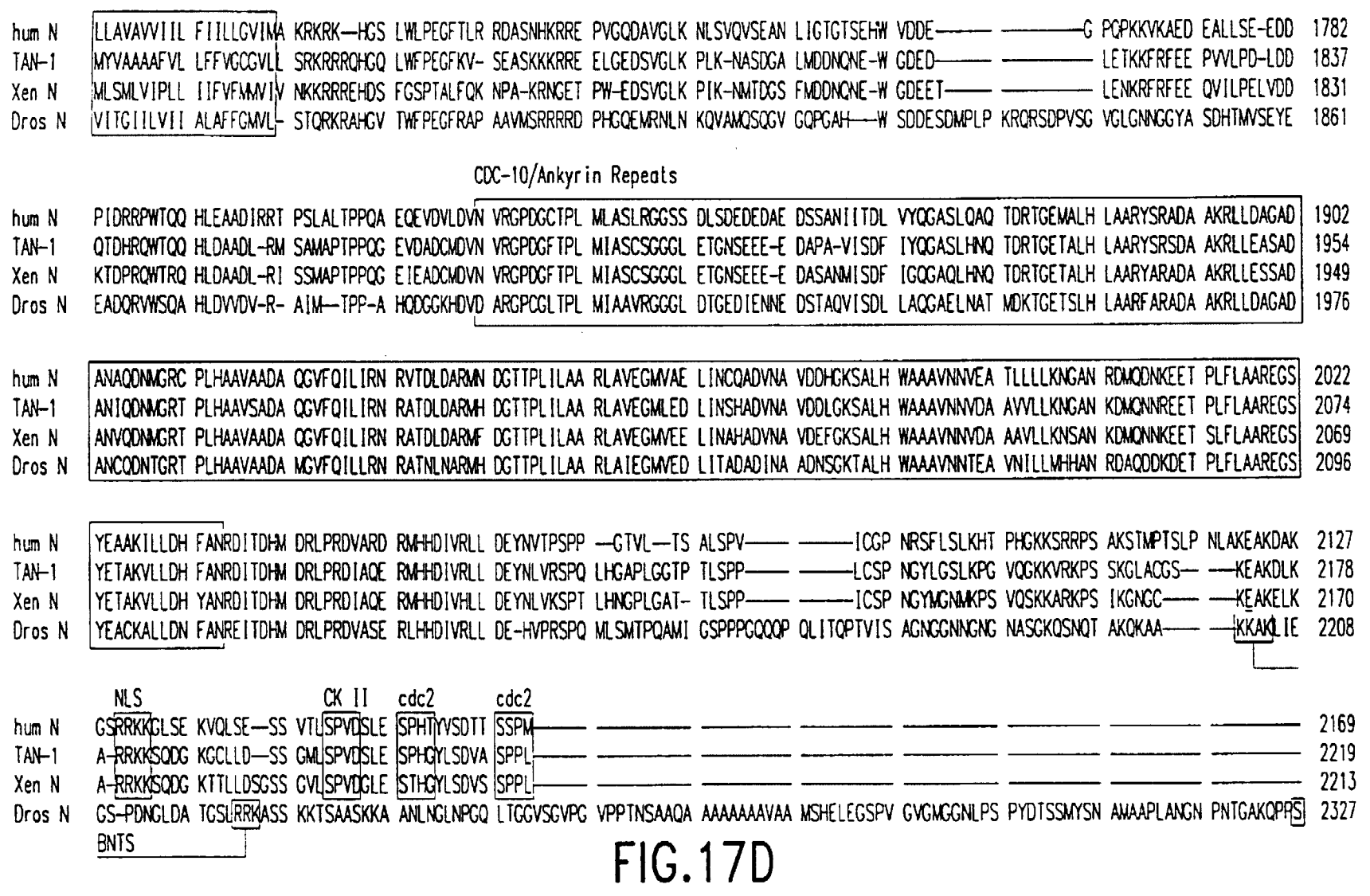

FIG. 17. Aligned amino acid sequences of Notch proteins of various species. humN: the human Notch protein encoded by the hN homolog (SEQ ID NO:16). TAN-1: the human Notch protein encoded by the TAN-1 homolog (SEQ ID NO:17) (the sequence shown is derived partly from work by Artavanis-Tsakonas et al. (see PCT Publication No. WO 92/19737 dated Nov. 12, 1992) and partly from the TAN-1 sequence as published by Ellisen et al., 1991, Cell 66:649–661); Xen N: Xenopus Notch protein (Coffman et al., 1990, Science 249:1438–1441 (SEQ ID NO:18)). Dros N: Drosophila Notch protein (Wharton et al., 1985, Cell 43:567–581 (SEQ ID NO:19)). Structural domains are indicated.

5. DETAILED DESCRIPTION OF THE INVENTION

The present invention relates to nucleotide sequences of deltex genes, and amino acid sequences of their encoded deltex proteins. The invention further relates to fragments and other derivatives, and analogs, of deltex proteins. Nucleic acids encoding such fragments or derivatives are also within the scope of the invention. Production of the foregoing proteins and derivatives, e.g., by recombinant methods, is provided.

In particular, the invention relates to the Drosophila deltex gene and protein. In another embodiment, the invention relates to the human deltex gene and protein.

The invention also relates to deltex protein derivatives and analogs of the invention which are functionally active, i.e., they are capable of displaying one or more known functional activities associated with a full-length (wild-type) deltex protein. Such functional activities include but are not limited to antigenicity [ability to bind (or compete with a deltex protein for binding) to an anti-deltex protein antibody], immunogenicity (ability to generate antibody which binds to a deltex protein), ability to bind (or compete with a deltex protein for binding) to Notch or a second deltex protein or other proteins or fragments thereof, ability to bind (or compete with a deltex protein for binding) to a receptor or ligand for a deltex protein.

The invention further relates to fragments (and derivatives and analogs thereof) of a deltex protein which comprise one or more domains of a deltex protein (see infra), including but not limited to the Gln-rich clusters, SH3 binding domains, domains which mediate binding to Notch (or a derivative thereof containing the Notch ANK repeats) or to a second deltex molecule or fragment thereof, or any combination of the foregoing.

Antibodies to deltex proteins, their derivatives and analogs, are additionally provided.

deltex plays a critical role in development and other physiological processes, in particular, in the signaling pathway of Notch which is involved in cell fate (differentiation) determination. Our results presented by way of example below indicate that deltex mediates the intracellular portion of the signal transduction cascade involved in Notch function. As described therein (see Section 6), our results show that deltex is localized within the cytoplasm, that it is a protein of unique sequence, and that it displays direct molecular interaction with the Notch intracellular ANK repeats, motifs shared by many proteins and implicated in protein-protein interactions (Lux et al., 1990, Nature 344:36–42, Thompson et al., 1991, Science 253:762–768, reviewed in Bennett, 1992, J. Biol. Chem. 267:8703–8706, Blank et al., 1992, Trends Biochem. Sci. 17:135–140, Rebay et al., 1993, Cell 74:319–329). Moreover, an in vivo functional analysis of various truncated forms of Notch has implicated these ANK repeats in downstream signaling events (Rebay et al., 1993, Cell, 74:319–329). Furthermore, deltex displays genetic interactions with Notch and Delta, both transmembrane proteins, and with mastermind, a nuclear localized protein (Smoller et al., 1990, Genes Dev. 4:1688–1700). This makes deltex the first identified cytoplasmic component of the Notch group of interacting loci. We further examined the functional characteristics of deltex by analyzing its genetic interactions with another locus, Suppressor of deltex [Su(dx)]. This analysis implicates Suppressor of deltex in the genetic circuitry of Notch and suggests a three way interaction between Su(dx), deltex and Notch.

The deltex nucleic acid and amino acid sequences and antibodies thereto of the invention can be used for the detection and quantitation of deltex mRNA and protein, to study expression thereof, to produce deltex proteins, fragments and other derivatives, and analogs thereof, in the study, assay, and manipulation of differentiation and other physiological processes, and are of therapeutic and diagnostic use, as described infra. The deltex nucleic acids and antibodies can also be used to clone deltex homologs of other species, as described infra. Such deltex homologs are expected to exhibit significant homology to each other, and encode proteins which exhibit the ability to bind to a Notch protein.

The present invention also relates to therapeutic and diagnostic methods and compositions based on deltex proteins and nucleic acids. The invention provides for treatment of disorders of cell fate or differentiation by administration of a therapeutic compound of the invention. Such therapeutic compounds (termed herein "Therapeutics") include: deltex proteins and analogs and derivatives (including fragments) thereof; antibodies thereto; nucleic acids encoding the deltex proteins, analogs, or derivatives; and deltex antisense nucleic acids. In a preferred embodiment, a Therapeutic of the invention is administered to treat a cancerous condition, or to prevent progression from a pre-neoplastic or non-malignant state into a neoplastic or a malignant state. In other specific embodiments, a Therapeutic of the invention is administered to treat a nervous system disorder or to promote tissue regeneration and repair.

In one embodiment, Therapeutics which antagonize, or inhibit, Notch and/or deltex function (hereinafter "Antagonist Therapeutics") are administered for therapeutic effect. In another embodiment, Therapeutics which promote Notch and/or deltex function (hereinafter "Agonist Therapeutics") are administered for therapeutic effect.

Disorders of cell fate, in particular hyperproliferative (e.g., cancer) or hypoproliferative disorders, involving aberrant or undesirable levels of expression or activity or localization of Notch and/or deltex protein can be diagnosed by detecting such levels, as described more fully infra.

In a preferred aspect, a Therapeutic of the invention is a protein consisting of at least a fragment (termed herein "adhesive fragment") of deltex that mediates binding to a Notch protein, a second deltex protein, or a fragment of Notch or deltex.

The invention is illustrated by way of examples infra which disclose, inter alia, the cloning and sequencing of D. melanogaster deltex; the construction and recombinant expression of deltex chimeric/fusion derivatives, production of anti-deltex antibodies, and the identification of regions of deltex which bind to the ANK repeats of Notch, or which bind to regions of deltex.

For clarity of disclosure, and not by way of limitation, the detailed description of the invention is divided into the subsections set forth below.

5.1. Isolation of the Deltex Nucleic Acids

The invention relates to the nucleotide sequences of deltex nucleic acids. In specific embodiments, Drosophila deltex nucleic acids comprise the genomic sequence shown in FIG. 3 (SEQ ID NO:1), or the cDNA sequence shown in FIG. 12 (SEQ ID NO:3), or the coding regions thereof, or nucleic acids encoding a deltex protein (e.g., having the sequence of SEQ ID NO:4). The invention provides nucleic acids consisting of at least 8 nucleotides (i.e., a hybridizable portion) of a deltex sequence; in other embodiments, the nucleic acids consist of at least 25 (continuous) nucleotides, 50 nucleotides, 100 nucleotides, 150 nucleotides, or 200 nucleotides of a deltex sequence, or a full-length deltex coding sequence. The invention also relates to nucleic acids hybridizable to or complementary to the foregoing sequences. In specific aspects, nucleic acids are provided which comprise a sequence complementary to at least 10, 25, 50, 100, or 200 nucleotides or the entire coding region of a deltex gene. In a specific embodiment, a nucleic acid which is hybridizable to a deltex nucleic acid (e.g., having sequence SEQ ID NO:3), or to a nucleic acid encoding a deltex derivative, under conditions of low stringency is provided. By way of example and not limitation, procedures using such conditions of low stringency are as follows (see also Shilo and Weinberg, 1981, Proc. Natl. Acad. Sci. USA 78:6789–6792): Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° C. in a solution containing 2× SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65°–68° C. and reexposed to film. Other conditions of low stringency which may be used are well known in the art (e.g., as employed for cross-species hybridizations).

In another specific embodiment, a nucleic acid which is hybridizable to a deltex nucleic acid under conditions of high stringency is provided. By way of example and not limitation, procedures using such conditions of high stringency are as follows: Prehybridization of filters containing DNA is carried out for 8 h to overnight at 65° C. in buffer composed of 6× SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5–20×10$^6$ cpm of $^{32}$P-labeled probe. Washing of filters is done at 37° C. for 1 h in a solution containing 2× SSC, 0.01% PVP, 0.01% Ficoll, and 0.01% BSA. This is followed by a wash in 0.1× SSC at 50° C. for 45 min before autoradiography. Other conditions of high stringency which may be used are well known in the art.

Nucleic acids encoding fragments and derivatives of deltex proteins (see Section 5.6), and deltex antisense nucleic acids (see Section 5.11) are additionally provided. As is readily apparent, as used herein, a "nucleic acid encoding a fragment or portion of a deltex protein" shall be construed as referring to a nucleic acid encoding only the recited fragment or portion of the deltex protein and not the other contiguous portions of the deltex protein as a continuous sequence.

Specific embodiments for the cloning of a deltex gene, e.g., a human deltex gene, presented as a particular example but not by way of limitation, follows:

For expression cloning (a technique commonly known in the art), an expression library is obtained or is constructed by methods known in the art. For example, mRNA (e.g., human) is isolated, cDNA is made and ligated into an expression vector (e.g., a bacteriophage derivative) such that it is capable of being expressed by the host cell into which it is then introduced. Various screening assays can then be used to select for the expressed deltex product. In a preferred aspect, anti-deltex antibodies can be used to select the recombinant host cell expressing a cloned deltex gene.

In another specific embodiment, PCR is used to amplify the desired deltex sequence in a genomic or cDNA library, prior to selection. Oligonucleotide primers representing known deltex sequences can be used as primers in PCR. The synthetic oligonucleotides may be utilized as primers to amplify by PCR sequences from a source (RNA or DNA), preferably a cDNA library, of potential interest. PCR can be carried out, e.g., by use of a Perkin-Elmer Cetus thermal cycler and Taq polymerase (Gene Amp™). The DNA being amplified can include human mRNA or cDNA or genomic DNA. One can choose to synthesize several different degenerate primers, for use in the PCR reactions. It is also possible to vary the stringency of hybridization conditions used in priming the PCR reactions, to allow for greater or lesser degrees of nucleotide sequence similarity between the known deltex nucleotide sequence and the nucleic acid homolog being isolated. For cross species hybridization, low stringency conditions are preferred (see supra). For same species hybridization, moderately stringent conditions are preferred (see supra). After successful amplification of a segment of a deltex gene homolog, that segment may be molecularly cloned and sequenced, and utilized as a probe to isolate a complete cDNA or genomic clone. This, in turn, will permit the determination of the gene's complete nucleotide sequence, the analysis of its expression, and the production of its protein product for functional analysis, as described infra. In a preferred aspect, human genes encoding deltex proteins may be identified in this fashion. Alternatively to selection by hybridization, the PCR-amplified DNA can be inserted into an expression vector for expression cloning as described above.

In the event that it is desired to isolate a deltex gene by cross-species hybridization (either by direct hybridization to a deltex probe representing all or a part of a deltex gene of an evolutionarily distant, different species, or by PCR using oligonucleotide primers derived from the sequence of a deltex gene of a different, evolutionarily distant species), and no hybridizing deltex genes are detected or amplified when hybridization is carried out, the desired deltex gene can be isolated by a more gradual method via first isolating a deltex gene from a more closely related species, identifying the portions of deltex which are conserved cross-species, and then screening with a probe or priming for PCR with a nucleic acid containing the conserved sequence. This method, while more cumbersome, is straightforward and can be readily carried out by routine methods. For example, in a specific aspect directed toward isolating a human deltex gene, first a gene from another species of fly (e.g., Drosophila hidei, Drosophila pseudoobscura, mosquito, or housefly) can be isolated, and the conserved portions of the sequence identified, and used to screen or amplify a human cDNA library. One may also, prior to screening or amplifying the human library, isolate "intermediate" deltex genes, e.g., from fish, rat, cow, or other species, to further define regions of sequence conserved across species.

The above-methods are not meant to limit the following general description of methods by which clones of deltex may be obtained.

Any eukaryotic cell can potentially serve as the nucleic acid source for the molecular cloning of the deltex gene. The DNA may be obtained by standard procedures known in the art from cloned DNA (e.g., a DNA "library"), by chemical synthesis, by cDNA cloning, or by the cloning of genomic DNA, or fragments thereof, purified from the desired human cell (see, for example Sambrook et al., 1989, Molecular Cloning, A Laboratory Manual, Cold Spring Harbor Laboratory, 2d. Ed., Cold Spring Harbor, N.Y.; Glover, D.

M. (ed.), 1985, DNA Cloning: A Practical Approach, MRL Press, Ltd., Oxford, U.K. Vol. I, II.) Clones derived from genomic DNA may contain regulatory and intron DNA regions in addition to coding regions; clones derived from cDNA will contain only exon sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene may be accomplished in a number of ways. For example, if an amount of a portion of a deltex (of any species) gene or its specific RNA, or a fragment thereof e.g., the adhesive domain, is available and can be purified and labeled, the generated DNA fragments may be screened by nucleic acid hybridization to the labeled probe (Benton, W. and Davis, R., 1977, Science 196, 180; Grunstein, M. And Hogness, D., 1975, Proc. Natl. Acad. Sci. U.S.A. 72, 3961). Those DNA fragments with substantial homology to the probe will hybridize. For cross species hybridization, low stringency conditions are preferred (see supra). For same species hybridization, moderately stringent conditions are preferred (see supra). It is also possible to identify the appropriate fragment by restriction enzyme digestion(s) and comparison of fragment sizes with those expected according to a known restriction map if such is available. Further selection can be carried out on the basis of the properties of the gene. Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isolectric focusing behavior, proteolytic digestion maps, in vitro aggregation activity ("adhesiveness") or antigenic properties as known for deltex. If an antibody to deltex is available, the deltex protein may be identified by binding of labeled antibody to the putatively deltex synthesizing clones, in an ELISA (enzyme-linked immunosorbent assay)-type procedure.

The deltex gene can also be identified by mRNA selection by nucleic acid hybridization followed by in vitro translation. In this procedure, fragments are used to isolate complementary mRNAs by hybridization. Such DNA fragments may represent available, purified deltex DNA of another species (e.g., Drosophila). Immunoprecipitation analysis or functional assays (e.g., aggregation ability in vitro; see examples infra) of the in vitro translation products of the isolated products of the isolated mRNAs identifies the mRNA and, therefore, the complementary DNA fragments that contain the desired sequences. In addition, specific mRNAs may be selected by adsorption of polysomes isolated from cells to immobilized antibodies specifically directed against deltex protein. A radiolabelled deltex cDNA can be synthesized using the selected mRNA (from the adsorbed polysomes) as a template. The radiolabelled mRNA or cDNA may then be used as a probe to identify the deltex DNA fragments from among other genomic DNA fragments.

Alternatives to isolating the deltex genomic DNA include, but are not limited to, chemically synthesizing the gene sequence itself from a known sequence or making cDNA to the mRNA which encodes the deltex gene. For example, RNA for cDNA cloning of the deltex gene can be isolated from cells which express deltex. Other methods are possible and within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 or pUC plasmid derivatives. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and deltex gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionization, can be done before insertion into the cloning vector.

In specific embodiments, transformation of host cells with recombinant DNA molecules that incorporate the isolated deltex gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The deltex sequences provided by the instant invention include those nucleotide sequences encoding substantially the same amino acid sequences as found in native deltex protein, and those encoded amino acid sequences with functionally equivalent amino acids, all as described in Section 5.6 infra for deltex derivatives.

5.2. Expression of Deltex Nucleic Acids

The nucleic acid coding for a deltex protein or a functionally active fragment or other derivative thereof can be inserted into an appropriate expression vector, i.e., a vector which contains the necessary elements for the transcription and translation of the inserted protein-coding sequence. The necessary transcriptional and translational signals can also be supplied by the native deltex gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. In a specific embodiment, a molecule comprising a portion of a deltex gene which encodes a protein that binds to Notch or a molecule comprising the Notch ANK repeats is expressed. In another embodiment, a molecule comprising a portion of a deltex gene which encodes a protein that binds to a fragment of a deltex protein is expressed. In other specific embodiments, the human deltex gene is expressed, or a sequence encoding a functionally active portion of human deltex. In a specific embodiment, a chimeric protein comprising a Notch-binding domain of a deltex protein is expressed. In other specific embodiments, a full-length deltex cDNA is expressed, or a sequence encoding a functionally active portion of a deltex protein. In yet another embodiment, a fragment of a deltex protein comprising a domain of the protein, or other derivative, or analog of a deltex protein is expressed.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of a nucleic acid sequence encoding a deltex protein or peptide fragment may be regulated by a second nucleic acid sequence so that the deltex protein or peptide is expressed in a host transformed with the recombinant DNA molecule. For example, expression of a deltex protein may be controlled by any promoter/enhancer element known in the art. Promoters which may be used to control deltex gene expression include, but are not limited to, the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase (Villa-Kamaroff et al., 1978, Proc. Natl. Acad. Sci. U.S.A. 75:3727–3731), tac (DeBoer et al., 1983, Proc. Natl. Acad. Sci. U.S.A. 80:21–25), $\lambda P_L$, or trc promoters; see also "Useful proteins from recombinant bacteria" in Scientific American, 1980, 242:74–94; plant expression vectors comprising the nopaline synthetase promoter region or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58; alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94; myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Expression vectors containing deltex gene inserts can be identified by three general approaches: (a) nucleic acid hybridization, (b) presence or absence of "marker" gene functions, and (c) expression of inserted sequences. In the first approach, the presence of a foreign gene inserted in an expression vector can be detected by nucleic acid hybridization using probes comprising sequences that are homologous to an inserted deltex gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the deltex gene is inserted within the marker gene sequence of the vector, recombinants containing the deltex insert can be identified by the absence of the marker gene function. In the third approach, recombinant expression vectors can be identified by assaying the foreign gene product expressed by the recombinant. Such assays can be based, for example, on the physical or functional properties of the deltex gene product in in vitro assay systems, e.g., binding to Notch, binding with antibody.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered deltex protein may be controlled. Furthermore, different host cells have characteristic and specific mechanisms for the translational and post-translational processing and modification (e.g., phosphorylation, cleavage) of proteins. Appropriate cell lines or host systems can be chosen to ensure the desired modification and processing of the foreign protein expressed.

In other specific embodiments, the deltex protein, fragment, analog, or derivative may be expressed as a fusion, or chimeric protein product (comprising the protein, fragment, analog, or derivative joined via a peptide bond to a heterologous protein sequence (of a different protein)). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

Both cDNA and genomic sequences can be cloned and expressed.

In other embodiments, a deltex cDNA sequence may be chromosomally integrated and expressed. Homologous recombination procedures known in the art may be used.

5.3. Identification and Purification of the Deltex Gene Products

In particular aspects, the invention provides amino acid sequences of deltex, preferably human deltex, and fragments and derivatives thereof which comprise an antigenic determinant (i.e., can be recognized by an antibody) or which are functionally active, as well as nucleic acid sequences encoding the foregoing. "Functionally active" material as used herein refers to that material displaying one or more known functional activities associated with the full-length (wild-type) deltex protein product, e.g., binding to Notch or a portion thereof, binding to another deltex molecule or portion thereof, binding to any other deltex ligand, antigenicity (binding to an anti-deltex antibody), Notch intracellular signal transduction, etc.

In specific embodiments, the invention provides fragments of a deltex protein consisting of at least 6 amino acids, 10 amino acids, 50 amino acids, or of at least 75 amino acids. In other embodiments, the proteins comprise or consist essentially of one or more Gln-rich clusters (e.g., amino acids 261–302 and amino acids 488–513 of SEQ ID NO:4); one or more of the SH3 binding domains (e.g., SEQ ID NOS:11 and 12 of FIG. 16), or a portion which binds to Notch (e.g., comprising the first approximately 200 amino acids of deltex), or any combination of the foregoing, of a deltex protein. Fragments, or proteins comprising fragments, lacking some or all of the foregoing regions of deltex are also provided. Nucleic acids encoding the foregoing are provided.

Once a recombinant which expresses a deltex gene sequence is identified, the gene product can be analyzed. This is achieved by assays based on the physical or functional properties of the product, including radioactive labelling of the product followed by analysis by gel electrophoresis, immunoassay, etc. Chemically synthesized proteins, derivatives, and analogs can be similarly analyzed.

Once a deltex protein is identified, it may be isolated and purified by standard methods including chromatography (e.g., ion exchange, affinity, and sizing column chromatography), centrifugation, differential solubility, or by any other standard technique for the purification of proteins. The functional properties may be evaluated using any suitable assay (see Section 5.7).

Alternatively, the amino acid sequence of a deltex protein can be deduced from the nucleotide sequence of the chimeric gene contained in the recombinant. Once the amino acid sequence is thus known, the protein can be synthesized by standard chemical methods known in the art (e.g., see Hunkapiller et al., 1984, Nature 310:105–111).

By way of example, the deduced amino acid sequence (SEQ ID NOS:2 or 4 (which are identical to each other) of a Drosophila deltex protein is presented in FIG. 12.

5.4. Structure of the Deltex Genes and Proteins

The structure of the deltex genes and proteins can be analyzed by various methods known in the art.

5.4.1. Genetic Analysis

The cloned DNA or cDNA corresponding to the deltex gene can be analyzed by methods including but not limited to Southern hybridization (Southern, 1975, J. Mol. Biol. 98:503–517), Northern hybridization (see e.g., Freeman et al., 1983, Proc. Natl. Acad. Sci. U.S.A. 80:4094–4098, and Section 6.1.3, infra), restriction endonuclease mapping (Maniatis, 1982, Molecular Cloning, A Laboratory, Cold Spring Harbor, N.Y.), and DNA sequence analysis (see Section 6.3.1 and FIGS. 1–4). Polymerase chain reaction (PCR; U.S. Pat. Nos. 4,683,202, 4,683,195 and 4,889,818; Gyllenstein et al., 1988, Proc. Natl. Acad. Sci. U.S.A. 85:7652–7656; Ochman et al., 1988, Genetics 120:621–623; Loh et al., 1989, Science 243:217–220) followed by Southern hybridization with a deltex-specific probe can allow the detection of the deltex genes in DNA from various cell types. In one embodiment, Southern hybridization can be used to determine the genetic linkage of deltex. Northern hybridization analysis can be used to determine the expression of the deltex genes. Various cell types, at various states of development or activity can be tested for deltex gene expression. The stringency of the hybridization conditions for both Southern and Northern hybridization can be manipulated to ensure detection of nucleic acids with the desired degree of relatedness to the specific deltex probe used.

Restriction endonuclease mapping can be used to roughly determine the genetic structure of the deltex gene. Restriction maps derived by restriction endonuclease cleavage can be confirmed by DNA sequence analysis. Alternatively, restriction maps can be deduced, once the nucleotide sequence is known.

DNA sequence analysis can be performed by any techniques known in the art, including but not limited to the method of Maxam and Gilbert (1980, Meth. Enzymol. 65:499–560), the Sanger dideoxy method (Sanger et al., 1977, Proc. Natl. Acad. Sci. U.S.A. 74:5463), the use of T7 DNA polymerase (Tabor and Richardson, U.S. Pat. No. 4,795,699; Sequenase, U.S. Biochemical Corp.), or Taq polymerase, or use of an automated DNA sequenator (e.g., Applied Biosystems, Foster City, Calif.). The cDNA sequence of a *Drosophila melanogaster* deltex gene is shown in FIG. 12 (SEQ ID NO:3) and is described in Section 6, infra.

5.4.2. Protein Analysis

The amino acid sequence of a deltex protein can be derived by deduction from the DNA sequence, or alternatively, by direct sequencing of the protein, e.g., with an automated amino acid sequencer. The amino acid sequence of a representative deltex protein comprises the sequence substantially as depicted in FIG. 12 (SEQ ID NO:4), and detailed in Section 6, infra.

The deltex protein sequence can be further characterized by a hydrophilicity analysis (Hopp and Woods, 1981, Proc. Natl. Acad. Sci. U.S.A. 78:3824). A hydrophilicity profile can be used to identify the hydrophobic and hydrophilic regions of a deltex protein and the corresponding regions of the gene sequence which encode such regions.

Secondary, structural analysis (Chou and Fasman, 1974, Biochemistry 13:222) can also be done, to identify regions of a deltex protein that assume specific secondary structures.

Manipulation, translation, and secondary structure prediction, as well as open reading frame prediction and plotting, can also be accomplished using computer software programs available in the art.

Other methods of structural analysis can also be employed. These include but are not limited to X-ray crystallography (Engstom, 1974, Biochem. Exp. Biol. 11:7–13) and computer modeling (Fletterick and Zoller (eds.), 1986, Computer Graphics and Molecular Modeling, in Current Communications in Molecular Biology, Cold Spring Harbor Laboratory, Cold Spring Harbor, N.Y.).

5.5. Generation of Antibodies to Deltex Proteins and Derivatives Thereof

According to the invention, a deltex protein, its fragments or other derivatives, or analogs thereof, may be used as an immunogen to generate antibodies which recognize such an immunogen. Such antibodies include but are not limited to polyclonal, monoclonal, chimeric, single chain, Fab fragments, and an Fab expression library. In a preferred embodiment, antibodies which specifically bind to deltex proteins are produced. In another embodiment, antibodies to a particular domain of a deltex protein are produced. In a specific embodiment, an antibody is produced which binds to a fragment of deltex which binds to Notch; in another embodiment, an antibody binds to a molecule comprising the first 204 amino-terminal amino acids of deltex. In another embodiment the antibody binds to an amino-terminal fragment of deltex containing not more than the first 200 amino acids of deltex. In yet another embodiment, an antibody binds to a fragment of deltex which binds to a second deltex molecule.

Various procedures known in the art may be used for the production of polyclonal antibodies to a deltex protein or derivative or analog. In a particular embodiment, rabbit polyclonal antibodies to an epitope of the deltex protein having a sequence depicted in FIG. 12 or a subsequence thereof, can be obtained. For the production of antibody, various host animals can be immunized by injection with a native deltex protein, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

In a preferred embodiment, polyclonal or monoclonal antibodies are produced by use of a hydrophilic portion of a deltex peptide (e.g., identified by the procedure of Hopp and Woods (1981, Proc. Natl. Acad. Sci. U.S.A. 78:3824)).

For preparation of monoclonal antibodies directed toward a deltex protein sequence or analog thereof, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in *Monoclonal Antibodies and Cancer Therapy*, Alan R. Liss, Inc., pp. 77–96) can be used. In an additional embodiment of the invention, monoclonal antibodies can be produced in germ-free animals (PCT Publication No. WO 89/12690 dated Dec. 28, 1989). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96), or by other methods known in the art. In fact, according to the invention, techniques developed for the production of "chimeric antibodies" (Morrison et al., 1984, Proc. Natl. Acad. Sci. U.S.A. 81:6851–6855; Neuberger et al., 1984, Nature 312:604–608; Takeda et al., 1985, Nature 314:452–454) by splicing the genes from a mouse antibody molecule specific for a deltex protein together with genes from a human antibody molecule of appropriate biological activity can be used; such antibodies are within the scope of this invention.

According to the invention, techniques described for the production of single chain antibodies (U.S. Pat. No. 4,946,778) can be adapted to produce deltex protein-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for deltex proteins, derivatives, or analogs.

Antibody fragments and other derivatives which contain the idiotype (binding domain) of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g. ELISA (enzyme-linked immunosorbent assay). For example, to select antibodies which recognize a specific domain of a deltex protein, one may assay generated hybridomas for a product which binds to a deltex fragment containing such domain. For selection of an antibody specific to human deltex protein(s), one can select on the basis of positive binding to a human deltex protein and a lack of binding to Drosophila deltex protein.

In a specific embodiment, antibodies specific to a phosphorylated epitope of deltex are produced.

The foregoing antibodies can be used in methods known in the art relating to the localization and activity of the protein sequences of the invention e.g., for imaging these proteins, measuring levels thereof in appropriate physiological samples, etc. Antibodies to deltex (since it normally colocalizes with Notch) can be used to determine the intracellular distribution of Notch and/or deltex, in diagnostic methods such as described infra. The antibodies also have use in immunoassays. In another embodiment of the invention (see infra), anti-deltex antibodies and fragments thereof containing the binding domain are Therapeutics.

5.6. Deltex Proteins, Derivatives and Analogs

The invention further provides deltex proteins, and derivatives (including but not limited to fragments) and analogs of deltex proteins. Nucleic acids encoding deltex protein derivatives and protein analogs are also provided. In one embodiment, the deltex proteins are encoded by the deltex nucleic acids described in Section 5.1 supra. In particular aspects, the proteins, derivatives, or analogs are of fly, frog, mouse, rat, pig, cow, dog, monkey, or human deltex proteins.

The production and use of derivatives and analogs related to deltex are within the scope of the present invention. In a specific embodiment, the derivative or analog is functionally active, i.e., capable of exhibiting one or more functional activities associated with a full-length, wild-type deltex protein.

In particular, deltex derivatives can be made by altering deltex sequences by substitutions, additions or deletions that provide for functionally equivalent molecules. Due to the degeneracy of nucleotide coding sequences, other DNA sequences which encode substantially the same amino acid sequence as a deltex gene may be used in the practice of the present invention. These include but are not limited to nucleotide sequences comprising all or portions of deltex genes which are altered by the substitution of different codons that encode a functionally equivalent amino acid residue within the sequence, thus producing a silent change. Likewise, the deltex derivatives of the invention include, but are not limited to, those containing, as a primary amino acid sequence, all or part of the amino acid sequence of a deltex protein including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In a specific embodiment of the invention, proteins consisting of or comprising a fragment of a deltex protein consisting of at least 10 (continuous) amino acids of the deltex protein is provided. In other embodiments, the fragment consists of at least 20 or 50 amino acids of the deltex protein. In specific embodiments, such fragments are not larger than 35, 100 or 200 amino acids. Derivatives or analogs of deltex include but are not limited to those peptides which are substantially homologous to deltex or fragments thereof (e.g., at least 30% identity over an amino acid sequence of identical size) or whose encoding nucleic acid is capable of hybridizing to a coding deltex sequence.

The deltex protein derivatives and analogs of the invention can be produced by various methods known in the art. The manipulations which result in their production can occur at the gene or protein level. For example, the cloned deltex gene sequence can be modified by any of numerous strategies known in the art (Sambrook et al., 1990, Molecular Cloning, A Laboratory Manual, 2d ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. In the production of the gene encoding a derivative or analog of a deltex protein, care should be taken to ensure that the modified gene remains within the same translational reading frame as the deltex gene, uninterrupted by translational stop signals, in the gene region where the desired deltex activity is encoded.

Additionally, the deltex-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson et al., 1978, J. Biol. Chem 253:6551), use of TAB® linkers (Pharmacia), etc.

Manipulations of the deltex sequence may also be made at the protein level. Included within the scope of the invention are deltex protein fragments or other derivatives or analogs which are differentially modified during or after translation, e.g., by acetylation, phosphorylation, carboxylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, NaBH$_4$, acetylation, formylation, oxidation, reduction, etc.

In a preferred aspect, phosphorylation or, alternatively, dephosphorylation is carried out, which can be to various extents, on the purified deltex protein or derivative thereof. The phosphorylation state of the molecule may be important to its role in intracellular signal transduction of Notch function. Phosphorylation can be carried out by reaction with an appropriate kinase (e.g., possibly cdc2 or CK II). Dephosphorylation can be carried out by reaction with an appropriate phosphatase.

In addition, analogs and derivatives of deltex proteins can be chemically synthesized. For example, a peptide corresponding to a portion of a deltex protein which comprises the desired domain, or which mediates the desired activity in vitro, can be synthesized by use of a peptide synthesizer. Furthermore, if desired, nonclassical amino acids or chemical amino acid analogs can be introduced as a substitution or addition into the deltex protein sequence. Non-classical amino acids include but are not limited to the D-isomers of the common amino acids, α-amino isobutyric acid, 4-aminobutyric acid, hydroxyproline, sarcosine, citrulline, cysteic acid, t-butylglycine, t-butylalanine, phenylglycine, cyclohexylalanine, β-alanine, designer amino acids such as β-methyl amino acids, Cα-methyl amino acids, and Nα-methyl amino acids.

In a specific embodiment, the deltex derivative is a chimeric, or fusion, protein comprising a deltex protein or fragment thereof (preferably consisting of at least a domain or motif of the deltex protein, or at least 10 amino acids of the deltex protein) joined at its amino or carboxy-terminus via a peptide bond to an amino acid sequence of a different protein. In one embodiment, such a chimeric protein is produced by recombinant expression of a nucleic acid encoding the protein (comprising a deltex-coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. A specific embodiment relates to a chimeric protein comprising a fragment of a deltex protein which comprises a domain or motif of the deltex protein, e.g., a Gln-rich cluster, portion which binds to a Notch protein or to a second deltex protein, an SH3 binding domain, etc. In a particular embodiment, a chimeric nucleic acid can be constructed, encoding a fusion protein consisting of a deltex Notch-binding fragment joined to a non-deltex protein. As another example, and not by way of limitation, a recombinant molecule can be constructed according to the invention, comprising coding portions of both a deltex gene and another gene which is a member of the "Notch group." Another specific embodiment relates to a chimeric protein comprising a fragment of a deltex protein of at least six amino acids. Particular examples of the construction and expression of fusion proteins comprising deltex or various deltex fragments, are described in Sections 7 and 8 hereof.

Other specific embodiments of derivatives and analogs are described in the subsection below and examples sections infra.

5.6.1. Derivatives of Deltex Containing One or More Domains of the Protein

In a specific embodiment, the invention provides deltex derivatives and analogs, in particular deltex fragments and derivatives of such fragments, that comprise or consist of one or more domains of the deltex protein, including but not limited to a Gln-rich cluster, a region which binds to a Notch protein (or a molecule comprising the ANK repeats thereof), a region which binds to a second deltex protein or portion thereof, or an SH3-binding domain. In specific embodiments, the deltex derivative may lack all or a portion of one or more of the foregoing domains.

In specific embodiments directed to the domains of the *D. melanogaster* deltex protein, the aforesaid domains consist of approximately the following amino-acid sequences:
Gln-rich clusters amino acids 261–302 of FIG. 12 (part of SEQ ID NO:4);

amino acids 488–513 of FIG. 12 (part of SEQ ID NO:4);
SH3 binding domain

SEQ ID NO:10 of FIG. 16

SEQ ID NO:11 of FIG. 16
Notch-binding fragment

Fragment D (SEQ ID NO:8) of FIG. 14
Deltex-binding fragments

Fragment A (SEQ ID NO:5) of FIG. 14

Fragment B (SEQ ID NO:6) of FIG. 14

Fragment C (SEQ ID NO:7) of FIG. 14
Other binding fragments, e.g., smaller than those set forth above, can be identified by routine methods, e.g., by construction of nucleic acids encoding such fragments and assays for binding (e.g. via the interaction trap method, S2 cell expression assay) such as described in Sections 7 and 8 infra.

In a specific embodiment, relating to a deltex protein of a species other than *D. melanogaster*, preferably human, fragments comprising specific domains of deltex are those comprising domains in the respective deltex protein most homologous to the specific domain of the *Drosophila melanogaster* deltex protein.

In specific embodiments, deltex fragments which homotypically bind to an identical deltex fragment (e.g. fragment A (SEQ ID NO:5), fragment B (SEQ ID NO:6), and fragment C (SEQ ID NO:7) shown in FIG. 14) or to a distinct deltex fragment (e.g., fragment B (SEQ ID NO:6) and fragment C (SEQ ID NO:7) shown in FIG. 14) are provided. Examples of such fragments and assays for their selection are described in Section 8 infra.

Also provided are inhibitors (e.g., peptide inhibitors) of the foregoing protein interactions with Notch or with a second deltex protein.

The ability to bind to a Notch protein or a deltex protein (or derivative thereof) can be demonstrated by in vitro assays such as described in Sections 7 and 8 infra, e.g., by S2 cell expression assay (Section 7.3), interaction trap technique (Sections 7.4, 8), etc.

The nucleic acid sequences encoding Notch or deltex proteins or fragments thereof, for use in such assays, can be isolated from human, porcine, bovine, feline, avian, equine, canine, or insect, as well as primate sources and any other species in which homologs of known genes can be identified. For example, the Notch protein or portion thereof comprising the ANK repeats which can be expressed and assayed for binding to deltex or a deltex derivative can be or be derived from any of the Notch homologs shown in FIG. 17 (human hN, human TAN-1, Xenopus, and Drosophila; SEQ ID NOS:16–19, respectively).

Due to the degeneracy of nucleotide coding sequences, other DNA sequences which encode substantially the same amino acid sequence as the aforesaid domains may be used in the practice of the present invention. These include but are not limited to nucleotide sequences comprising all or portions of the deltex genes which are altered by the substitution of different codons that encode a functionally equivalent amino acid residue within the sequence, thus producing a silent change. Likewise, the deltex proteins, fragments or derivatives thereof, of the invention include, but are not limited to, those containing, as a primary amino acid sequence, all or part of the amino acid sequence of the domains including altered sequences in which functionally equivalent amino acid residues are substituted for residues within the sequence ("conservative" changes).

The derivatives, analogs, and peptides of the invention can be produced by various methods known in the art. The manipulations which result in their production can occur at the gene or protein level.

Additionally, the nucleic acid sequence can be mutated in vitro or in vivo; and manipulations of the sequence may also be made at the protein level.

In addition, analogs and peptides can be chemically synthesized.

5.7. In Vitro Assays of Deltex Proteins, Derivatives and Analogs

The functional activity of deltex proteins, derivatives and analogs, can be assayed in vitro by various methods.

For example, in one embodiment, where one is assaying for the ability to bind or compete with wild-type deltex for binding to anti-deltex antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled.

Many means are known in the art for detecting binding in an immunoassay and are within the scope of the present invention.

In another embodiment, where one is assaying for the ability to mediate binding to Notch or to a second deltex protein or portions thereof, one can carry out assays such as described infra in Section 7 or 8.

Other methods will be known to the skilled artisan and are within the scope of the invention.

5.8. Therapeutic Uses

The invention provides for treatment of disorders of cell fate or differentiation by administration of a therapeutic compound of the invention. Such therapeutic compounds (termed herein "Therapeutics") include: deltex proteins and analogs and derivatives (including fragments) thereof (e.g., as described hereinabove); antibodies thereto (as described hereinabove); nucleic acids encoding the deltex proteins, analogs, or derivatives (e.g., as described hereinabove); and deltex antisense nucleic acids. As stated supra, the Antagonist Therapeutics of the invention are those Therapeutics which antagonize, or inhibit, a deltex function and/or Notch function (since the data (see Sections 6-9) indicates that deltex functions in intracellular signal transduction from Notch). Such Antagonist Therapeutics are most preferably identified by use of known convenient in vitro assays, e.g., based on their ability to inhibit binding of deltex to another protein (e.g., a Notch protein), or inhibit any known Notch or deltex function as preferably assayed in vitro or in cell culture, although genetic assays (e.g., in Drosophila) may also be employed. In a preferred embodiment, the Antagonist Therapeutic is a protein or derivative thereof comprising a functionally active fragment such as a fragment of deltex which mediates binding to Notch, or an antibody thereto. In other specific embodiments, such an Antagonist Therapeutic is a nucleic acid capable of expressing a molecule comprising a fragment of deltex which binds to Notch, or a deltex antisense nucleic acid (see Section 5.11 herein). It should be noted that preferably, suitable in vitro or in vivo assays, as described infra, should be utilized to determine the effect of a specific Therapeutic and whether its administration is indicated for treatment of the affected tissue, since the developmental history of the tissue may determine whether an Antagonist or Agonist Therapeutic is desired.

In another embodiment of the invention, a nucleic acid containing a portion of a deltex gene is used, as an Antagonist Therapeutic, to promote deltex inactivation by homologous recombination (Koller and Smithies, 1989, Proc. Natl. Acad. Sci. USA 86:8932-8935; Zijlstra et al., 1989, Nature 342:435-438).

The Agonist Therapeutics of the invention, as described supra, promote deltex function. Such Agonist Therapeutics include but are not limited to proteins and derivatives comprising the portions of Notch that mediate binding to deltex, i.e., the ANK repeats, and nucleic acids encoding the foregoing (which can be administered to express their encoded products in vivo).

Further descriptions and sources of Therapeutics of the inventions are found in Sections 5.1 through 5.7 herein.

Molecules which retain, or alternatively inhibit, a desired deltex property, e.g., binding to Notch, binding to an intracellular ligand, can be used therapeutically as inducers, or inhibitors, respectively, of such property and its physiological correlates. In a specific embodiment, a peptide (e.g., in the range of 6-50 or 15-25 amino acids; and particularly of about 10, 15, 20 or 25 amino acids) containing the sequence of a portion of deltex which binds to Notch is used to antagonize Notch function. In a specific embodiment, such an Antagonist Therapeutic is used to treat or prevent human or other malignancies associated with increased Notch expression (e.g., cervical cancer, colon cancer, breast cancer, squamous adenocarcimas (see infra)). Derivatives or analogs of deltex can be tested for the desired activity by procedures known in the art, including but not limited to the assays described in the examples infra. For example, molecules comprising deltex fragments which bind to Notch ANK repeats and which are smaller than deltex fragment D (see FIG. 14 and Section 8), can be obtained and selected by expressing deletion mutants of fragment D (or of a nucleotide sequence of another species encoding the amino-terminal ~204 amino acids of deltex) and assaying for binding of the expressed product to Notch by any of the several methods (e.g., interaction trap system) described in the Examples Sections infra. In one specific embodiment, peptide libraries can be screened to select a peptide with the desired activity; such screening can be carried out by assaying, e.g., for binding to Notch or a molecule containing the Notch ANK repeats.

The Agonist and Antagonist Therapeutics of the invention have therapeutic utility for disorders of cell fate. The Agonist Therapeutics are administered therapeutically (including prophylactically): (1) in diseases or disorders involving an absence or decreased (relative to normal, or desired) levels of Notch or deltex function, for example, in patients where Notch or deltex protein is lacking, genetically defective, biologically inactive or underactive, or underexpressed; and (2) in diseases or disorders wherein in vitro (or in vivo) assays (see infra) indicate the utility of deltex agonist administration. The absence or decreased levels in Notch or deltex function can be readily detected, e.g., by obtaining a patient tissue sample (e.g., from biopsy tissue) and assaying it in vitro for protein levels, structure and/or activity of the expressed Notch or deltex protein. Many methods standard in the art can be thus employed, including but not limited to immunoassays to detect and/or visualize Notch or deltex protein (e.g., Western blot, immunoprecipitation followed by sodium dodecyl sulfate polyacrylamide gel electrophoresis, immunocytochemistry, etc.) and/or hybridization assays to detect Notch or deltex expression by detecting and/or visualizing respectively Notch or deltex mRNA (e.g., Northern assays, dot blots, in situ hybridization, etc.)

In vitro assays which can be used to determine whether administration of a specific Agonist Therapeutic or Antagonist Therapeutic is indicated, include in vitro cell culture assays in which a patient tissue sample is grown in culture, and exposed to or otherwise administered a Therapeutic, and the effect of such Therapeutic upon the tissue sample is observed. In one embodiment, where the patient has a malignancy, a sample of cells from such malignancy is plated out or grown in culture, and the cells are then exposed to a Therapeutic. A Therapeutic which inhibits survival or growth of the malignant cells (e.g., by promoting terminal differentiation) is selected for therapeutic use in vivo. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, etc. In a specific aspect, the malignant cell cultures are separately exposed to (1) an Agonist Therapeutic, and (2) an Antagonist Therapeutic; the result of the assay can indicate which type of Therapeutic has therapeutic efficacy.

In another embodiment, a Therapeutic is indicated for use which exhibits the desired effect, inhibition or promotion of cell growth, upon a patient cell sample from tissue having or suspected of having a hyper- or hypoproliferative disorder, respectively. Such hyper- or hypoproliferative disorders include but are not limited to those described in Sections 5.8.1 through 5.8.3 infra.

In another specific embodiment, a Therapeutic is indicated for use in treating nerve injury or a nervous system degenerative disorder (see Section 5.8.2) which exhibits in vitro promotion of nerve regeneration/neurite extension from nerve cells of the affected patient type.

In addition, administration of an Antagonist Therapeutic of the invention is also indicated in diseases or disorders determined or known to involve a Notch or deltex dominant activated phenotype ("gain of function" mutations.) Administration of an Agonist Therapeutic is indicated in diseases or disorders determined or known to involve a Notch or deltex dominant negative phenotype ("loss of function" mutations). The functions of various structural domains of the Notch protein have been investigated in vivo, by ectopically expressing a series of Drosophila Notch deletion mutants under the hsp70 heat-shock promoter, as well as eye-specific promoters (see Rebay et al., 1993, Cell 74:319–329). Two classes of dominant phenotypes were observed, one suggestive of Notch loss-of function mutations and the other of Notch gain-of-function mutations. Dominant "activated" phenotypes resulted from overexpression of a protein lacking most extracellular sequences, while dominant "negative" phenotypes resulted from overexpression of a protein lacking most intracellular sequences. The results indicated that Notch functions as a receptor whose extracellular domain mediates ligand-binding, resulting in the transmission of developmental signals by the cytoplasmic domain. The phenotypes observed also suggested that the ANK repeat region within the intracellular domain plays an essential role in Notch mediated signal transduction events (intracellular function). We have shown that deltex binds to the Notch ANK repeat region (see Sections 6–8).

In various specific embodiments, in vitro assays can be carried out with representative cells of cell types involved in a patient's disorder, to determine if a Therapeutic has a desired effect upon such cell types.

In another embodiment, cells of a patient tissue sample suspected of being pre-neoplastic are similarly plated out or grown in vitro, and exposed to a Therapeutic. The Therapeutic which results in a cell phenotype that is more normal (i.e., less representative of a pre-neoplastic state, neoplastic state, malignant state, or transformed phenotype) is selected for therapeutic use. Many assays standard in the art can be used to assess whether a pre-neoplastic state, neoplastic state, or a transformed or malignant phenotype, is present. For example, characteristics associated with a transformed phenotype (a set of in vitro characteristics associated with a tumorigenic ability in vivo) include a more rounded cell morphology, looser substratum attachment, loss of contact inhibition, loss of anchorage dependence, release of proteases such as plasminogen activator, increased sugar transport, decreased serum requirement, expression of fetal antigens, disappearance of the 250,000 dalton surface protein, etc. (see Luria et al., 1978, General Virology, 3d Ed., John Wiley & Sons, New York pp. 436–446).

In other specific embodiments, the in vitro assays described supra can be carried out using a cell line, rather than a cell sample derived from the specific patient to be treated, in which the cell line is derived from or displays characteristic(s) associated with the malignant, neoplastic or pre-neoplastic disorder desired to be treated or prevented, or is derived from the neural or other cell type upon which an effect is desired, according to the present invention.

The Antagonist Therapeutics are administered therapeutically (including prophylactically): (1) in diseases or disorders involving increased (relative to normal, or desired) levels of Notch or deltex function, for example, where the Notch or deltex protein is overexpressed or overactive; and (2) in diseases or disorders wherein in vitro (or in vivo) assays indicate the utility of deltex antagonist administration. The increased levels of Notch or deltex function can be readily detected by methods such as those described above, by quantifying protein and/or RNA. In vitro assays with cells of patient tissue sample or the appropriate cell line or cell type, to determine therapeutic utility, can be carried out as described above.

5.8.1. Malignancies

Malignant and pre-neoplastic conditions which can be tested as described supra for efficacy of intervention with Antagonist or Agonist Therapeutics, and which can be treated upon thus observing an indication of therapeutic utility, include but are not limited to those described below in Sections 5.8.1 and 5.9.1.

Malignancies and related disorders, cells of which type can be tested in vitro (and/or in vivo), and upon observing the appropriate assay result, treated according to the present invention, include but are not limited to those listed in Table 1 (for a review of such disorders, see Fishman et al., 1985, Medicine, 2d Ed., J. B. Lippincott Co., Philadelphia):

TABLE 1

MALIGNANCIES AND RELATED DISORDERS

Leukemia
  acute leukemia
    acute lymphocytic leukemia
    acute myelocytic leukemia
      myeloblastic
      promyelocytic
      myelomonocytic
      monocytic
      erythroleukemia
  chronic leukemia
    chronic myelocytic (granulocytic) leukemia
    chronic lymphocytic leukemia
Polycythemia vera
Lymphoma
  Hodgkin's disease
  non-Hodgkin's disease
Multiple myeloma
Waldenström's macroglobulinemia
Heavy chain disease
Solid tumors
  sarcomas and carcinomas
    fibrosarcoma
    myxosarcoma
    liposarcoma
    chondrosarcoma
    osteogenic sarcoma
    chordoma
    angiosarcoma
    endotheliosarcoma
    lymphangiosarcoma
    lymphangioendotheliosarcoma
    synovioma
    mesothelioma
    Ewing's tumor

TABLE 1-continued

MALIGNANCIES AND RELATED DISORDERS leiomyosarcoma
rhabdomyosarcoma
colon carcinoma
pancreatic cancer
breast cancer
ovarian cancer
prostate cancer
squamous cell carcinoma
basal cell carcinoma
adenocarcinoma
sweat gland carcinoma
sebaceous gland carcinoma
papillary carcinoma
papillary adenocarcinomas
cystadenocarcinoma
medullary carcinoma
bronchogenic carcinoma
renal cell carcinoma
hepatoma
bile duct carcinoma
choriocarcinoma
seminoma
embryonal carcinoma
Wilms' tumor
cervical cancer
testicular tumor
lung carcinoma
small cell lung carcinoma
bladder carcinoma
epithelial carcinoma
glioma
astrocytoma
medulloblastoma
craniopharyngioma
ependymoma
pinealoma
hemangioblastoma
acoustic neuroma
oligodendroglioma
menangioma
melanoma
neuroblastoma
retinoblastoma In specific embodiments, malignancy or dysproliferative changes (such as metaplasias and dysplasias) are treated or prevented in epithelial tissues such as those in the cervix, esophagus, and lung.

Malignancies of the colon and cervix exhibit increased expression of human Notch relative to such non-malignant tissue (see copending U.S. application Ser. No. 08/083.590 filed Jun. 25, 1993, incorporated by reference herein in its entirety; PCT application no. PCT/US93/09338 filed Sep. 30, 1993, incorporated by reference herein in its entirety). Thus, in specific embodiments, malignancies of the colon or cervix are treated or prevented by administering an effective amount of an Antagonist Therapeutic of the invention. The presence of increased Notch expression in colon, and cervical cancer suggests that many more cancerous and hyperproliferative conditions exhibit upregulated Notch. Thus, in specific embodiments, various cancers, e.g., breast cancer, squamous adenocarcinoma, seminoma, melanoma, and lung cancer, as well as other hyperproliferative disorders, can be treated or prevented by administration of an Antagonist Therapeutic.

5.8.2. Nervous System Disorders

Nervous system disorders, involving cell types which can be tested as described supra for efficacy of intervention with Antagonist or Agonist Therapeutics, and which can be treated upon thus observing an indication of therapeutic utility, include but are not limited to nervous system injuries, and diseases or disorders which result in either a disconnection of axons, a diminution or degeneration of neurons, or demyelination. Nervous system lesions which may be treated in a patient (including human and non-human mammalian patients) according to the invention include but are not limited to the following lesions of either the central (including spinal cord, brain) or peripheral nervous systems:

(i) traumatic lesions, including lesions caused by physical injury or associated with surgery, for example, lesions which sever a portion of the nervous system, or compression injuries;

(ii) ischemic lesions, in which a lack of oxygen in a portion of the nervous system results in neuronal injury or death, including cerebral infarction or ischemia, or spinal cord infarction or ischemia;

(iii) malignant lesions, in which a portion of the nervous system is destroyed or injured by malignant tissue which is either a nervous system associated malignancy or a malignancy derived from non-nervous system tissue;

(iv) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis;

(v) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis;

(vi) lesions associated with nutritional diseases or disorders, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;

(vii) neurological lesions associated with systemic diseases including but not limited to diabetes (diabetic neuropathy, Bell's palsy), systemic lupus erythematosus, carcinoma, or sarcoidosis;

(viii) lesions caused by toxic substances including alcohol, lead, or particular neurotoxins; and (ix) demyelinated lesions in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

Therapeutics which are useful according to the invention for treatment of a nervous system disorder may be selected by testing for biological activity in promoting the survival or differentiation of neurons (see also Section 5.8). For example, and not by way of limitation, Therapeutics which elicit any of the following effects may be useful according to the invention:

(i) increased survival time of neurons in culture;

(ii) increased sprouting of neurons in culture or in vivo;

(iii) increased production of a neuron-associated molecule in culture or in vivo, e.g., choline acetyltransferase or acetylcholinesterase with respect to motor neurons; or (iv) decreased symptoms of neuron dysfunction in vivo. Such effects may be measured by any method known in the art. In preferred, non-limiting embodiments, increased survival of neurons may be measured by the method set forth in Arakawa et al. (1990, J. Neurosci. 10:3507–3515); increased sprouting of neurons may be detected by methods set forth in Pestronk et al. (1980, Exp. Neurol. 70:65–82) or Brown et al. (1981, Ann. Rev. Neurosci. 4:17–42); increased production of neuron-associated molecules may be measured by bioassay, enzymatic assay, antibody binding, Northern blot assay, etc., depending on the molecule to be measured; and motor neuron dysfunction may be measured by assessing the physical manifestation of motor neuron disorder, e.g., weakness, motor neuron conduction velocity, or functional disability.

In a specific embodiments, motor neuron disorders that may be treated according to the invention include but are not limited to disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including but not limited to progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

5.8.3. Tissue Repair and Regeneration

In another embodiment of the invention, a Therapeutic of the invention is used for promotion of tissue regeneration and repair, including but not limited to treatment of benign dysproliferative disorders. Specific embodiments are directed to treatment of cirrhosis of the liver (a condition in which scarring has overtaken normal liver regeneration processes), treatment of keloid (hypertrophic scar) formation (disfiguring of the skin in which the scarring process interferes with normal renewal), psoriasis (a common skin condition characterized by excessive proliferation of the skin and delay in proper cell fate determination), and baldness (a condition in which terminally differentiated hair follicles (a tissue rich in Notch) fail to function properly).

5.9. Prophylactic Uses

5.9.1. Malignancies

The Therapeutics of the invention can be administered to prevent progression to a neoplastic or malignant state, including but not limited to those disorders listed in Table 1. Such administration is indicated where the Therapeutic is shown in assays, as described supra, to have utility for treatment or prevention of such disorder. Such prophylactic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W. B. Saunders Co., Philadelphia, pp. 68–79.) Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/therapeutic administration of a Therapeutic of the invention. As mentioned supra, such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84–90 for characteristics associated with a transformed or malignant phenotype).

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention.

In other embodiments, a patient which exhibits one or more of the following predisposing factors for malignancy is treated by administration of an effective amount of a Therapeutic: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), and a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, Basic Pathology, 2d Ed., W. B. Saunders Co., Philadelphia, pp. 112–113) etc.) In another specific embodiment, an Antagonist Therapeutic of the invention is administered to a human patient to prevent progression to breast, colon, or cervical cancer.

5.9.2. Other Disorders

In other embodiments, a Therapeutic of the invention can be administered to prevent a nervous system disorder

5.10 Demonstration of Therapeutic or Prophylactic Utility

The Therapeutics of the invention can be tested in vivo for the desired therapeutic or prophylactic activity. For example, such compounds can be tested in suitable animal model systems prior to testing in humans, including but not limited to rats, mice, chicken, cows, monkeys, rabbits, etc. For in vivo testing, prior to administration to humans, any animal model system known in the art may be used.

5.11. Antisense Regulation of Deltex Expression

The present invention provides the therapeutic or prophylactic use of nucleic acids of at least six nucleotides that are antisense to a gene or cDNA encoding deltex or a portion thereof. "Antisense" as used herein refers to a nucleic acid capable of hybridizing to a portion of a deltex RNA (preferably mRNA) by virtue of some sequence complementarity. Such antisense nucleic acids have utility as Antagonist Therapeutics of the invention, and can be used in the treatment or prevention of disorders as described supra in Section 5.8 and its subsections.

The antisense nucleic acids of the invention can be oligonucleotides that are double-stranded or single-stranded, RNA or DNA or a modification or derivative thereof, which can be directly administered to a cell, or which can be produced intracellularly by transcription of exogenous, introduced sequences.

In a specific embodiment, the deltex antisense nucleic acids provided by the instant invention can be used for the treatment of tumors or other disorders, the cells of which tumor type or disorder can be demonstrated (in vitro or in vivo) to express a deltex gene or a Notch gene. Such demonstration can be by detection of RNA or of protein.

The invention further provides pharmaceutical compositions comprising an effective amount of the deltex antisense nucleic acids of the invention in a pharmaceutically acceptable carrier, as described infra in Section 5.12. Methods for treatment and prevention of disorders (such as those described in Sections 5.8 and 5.9) comprising administering the pharmaceutical compositions of the invention are also provided.

In another embodiment, the invention is directed to methods for inhibiting the expression of a deltex nucleic acid sequence in a prokaryotic or eukaryotic cell comprising providing the cell with an effective amount of a composition comprising an antisense deltex nucleic acid of the invention.

deltex antisense nucleic acids and their uses are described in detail below.

5.11.1. Deltex Antisense Nucleic Acids

The deltex antisense nucleic acids are of at least six nucleotides and are preferably oligonucleotides (ranging from 6 to about 50 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO 88/09810, published Dec. 15, 1988) or blood-brain barrier (see, e.g., PCT Publication No. WO 89/10134, published Apr. 25, 1988), hybridization-triggered cleavage agents (see, e.g., Krol et al., 1988, BioTechniques 6:958–976) or intercalating agents (see, e.g., Zon, 1988, Pharm. Res. 5:539–549).

In a preferred aspect of the invention, a deltex antisense oligonucleotide is provided, preferably of single-stranded DNA. In a most preferred aspect, such an oligonucleotide comprises a sequence antisense to the sequence encoding an SH3 binding domain or a Notch-binding domain of deltex, most preferably, of human deltex. The oligonucleotide may be modified at any position on its structure with substituents generally known in the art.

The deltex antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

In another embodiment, the oligonucleotide comprises at least one modified sugar moiety selected from the group including but not limited to arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641).

The oligonucleotide may be conjugated to another molecule, e.g., a peptide, hybridization triggered cross-linking agent, transport agent, hybridization-triggered cleavage agent, etc.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

In a specific embodiment, the deltex antisense oligonucleotide comprises catalytic RNA, or a ribozyme (see, e.g., PCT International Publication WO 90/11364, published Oct. 4, 1990; Sarver et al., 1990, Science 247:1222–1225). In another embodiment, the oligonucleotide is a 2'-O-methylribonucleotide (Inoue et al., 1987, Nucl. Acids Res. 15:6131–6148), or a chimeric RNA-DNA analogue (Inoue et al., 1987, FEBS Lett. 215:327–330).

In an alternative embodiment, the deltex antisense nucleic acid of the invention is produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the deltex antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the deltex antisense RNA can be by any promoter known in the art to act in mammalian, preferably human, cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc.

The antisense nucleic acids of the invention comprise a sequence complementary to at least a portion of an RNA transcript of a deltex gene, preferably a human deltex gene. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded deltex antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a deltex RNA it may contain and still form a stable duplex (or triplex, as the case may be). One skilled in the art can ascertain a tolerable degree of mismatch by use of standard procedures to determine the melting point of the hybridized complex.

5.11.2. Therapeutic Utility of Deltex Antisense Nucleic Acids

The deltex antisense nucleic acids can be used to treat (or prevent) malignancies or other disorders, of a cell type which has been shown to express deltex or Notch. In specific embodiments, the malignancy is cervical, breast, or colon cancer, or squamous adenocarcinoma. Malignant, neoplastic, and pre-neoplastic cells which can be tested for such expression include but are not limited to those described supra in Sections 5.8.1 and 5.9.1. In a preferred embodiment, a single-stranded DNA antisense deltex oligonucleotide is used.

Malignant (particularly, tumor) cell types which express deltex or Notch RNA can be identified by various methods known in the art. Such methods include but are not limited to hybridization with a deltex or Notch-specific nucleic acid (e.g. by Northern hybridization, dot blot hybridization, in situ hybridization), observing the ability of RNA from the cell type to be translated in vitro into Notch or Deltex, immunoassay, etc. In a preferred aspect, primary tumor tissue from a patient can be assayed for Notch or deltex expression prior to treatment, e.g., by immunocytochemistry or in situ hybridization.

Pharmaceutical compositions of the invention (see Section 5.12), comprising an effective amount of a deltex antisense nucleic acid in a pharmaceutically acceptable carrier, can be administered to a patient having a malignancy which is of a type that expresses Notch or deltex RNA or protein.

The amount of deltex antisense nucleic acid which will be effective in the treatment of a particular disorder or condition will depend on the nature of the disorder or condition, and can be determined by standard clinical techniques. Where possible, it is desirable to determine the antisense cytotoxicity of the tumor type to be treated in vitro, and then in useful animal model systems prior to testing and use in humans.

In a specific embodiment, pharmaceutical compositions comprising deltex antisense nucleic acids are administered via liposomes, microparticles, or microcapsules. In various embodiments of the invention, it may be useful to use such compositions to achieve sustained release of the deltex antisense nucleic acids. In a specific embodiment, it may be desirable to utilize liposomes targeted via antibodies to specific identifiable tumor antigens (Leonetti et al., 1990, Proc. Natl. Acad. Sci. U.S.A. 87:2448–2451; Renneisen et al., 1990, J. Biol. Chem. 265:16337–16342).

5.12. Therapeutic/Prophylactic Administration and Compositions

The invention provides methods of treatment (and prophylaxis) by administration to a subject of an effective amount of a Therapeutic of the invention. In a preferred aspect, the Therapeutic is substantially purified. The subject is preferably an animal, including but not limited to animals such as cows, pigs, chickens, etc., and is preferably a mammal, and most preferably human.

Various delivery systems are known and can be used to administer a Therapeutic of the invention, e.g., encapsulation in liposomes, microparticles, microcapsules, expression by recombinant cells, receptor-mediated endocytosis (see, e.g., Wu and Wu, 1987, J. Biol. Chem. 262:4429–4432), construction of a Therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In another embodiment, the Therapeutic can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the Therapeutic can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Florida (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

In a specific embodiment, administration of a Therapeutic into a Notch-expressing cell is accomplished by linkage of the Therapeutic to a Delta (or other toporythmic) protein or portion thereof capable of mediating binding to Notch. Contact of a Notch-expressing cell with the linked Therapeutic results in binding of the linked Therapeutic via its Delta portion to Notch on the surface of the cell, followed by uptake of the linked Therapeutic into the Notch-expressing cell.

In a specific embodiment, the Therapeutic is delivered intracellularly (e.g., by expression from a nucleic acid vector, or by linkage to a Delta protein capable of binding to Notch followed by binding and internalization, or by receptor-mediated or diffusion mechanisms).

In a specific embodiment where the Therapeutic is a nucleic acid encoding a protein Therapeutic, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864–1868), etc. Alternatively, a nucleic acid Therapeutic can be introduced intracellularly and incorporated within host cell DNA for expression, by homologous recombination.

In specific embodiments directed to treatment or prevention of particular disorders, preferably the following forms of administration are used:

| Disorder | Preferred Forms of Administration |
| --- | --- |
| Cervical cancer | Topical |
| Gastrointestinal cancer | Oral; intravenous |
| Lung cancer | Inhaled; intravenous |
| Leukemia | Intravenous; extracorporeal |
| Metastatic carcinomas | Intravenous; oral |
| Brain cancer | Targeted; intravenous; intrathecal |
| Liver cirrhosis | Oral; intravenous |
| Psoriasis | Topical |
| Keloids | Topical |
| Baldness | Topical |
| Spinal cord injury | Targeted; intravenous; intrathecal |
| Parkinson's disease | Targeted; intravenous; intrathecal |
| Motor neuron disease | Targeted; intravenous; intrathecal |
| Alzheimer's disease | Targeted; intravenous; intrathecal |

The present invention also provides pharmaceutical compositions. Such compositions comprise a therapeutically effective amount of a Therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

5.13. Diagnostic Utility deltex proteins, analogues, derivatives, and subsequences thereof, deltex nucleic acids (and sequences complementary thereto), anti-deltex antibodies, have uses in diagnostics. Such molecules can be used in assays, such as immunoassays, to detect, prognose, diagnose, or monitor various conditions, diseases, and disorders affecting deltex expression, or monitor the treatment thereof. In particular, such an immunoassay is carried out by a method comprising contacting a sample derived from a patient with an anti-deltex antibody under conditions such that immunospecific binding can occur, and detecting or measuring the amount of any immunospecific binding by the antibody. In a specific aspect, such binding of antibody, in tissue sections, preferably in conjunction with binding of anti-Notch can be used to detect aberrant Notch and/or deltex localization or aberrant levels of Notch-deltex colocalization in a disease state. In a specific embodiment, antibody to deltex can be used to assay in a patient tissue or serum sample for the presence of deltex where an aberrant level of deltex is an indication of a diseased condition. Aberrant levels of deltex binding ability in an endogenous Notch protein, or aberrant levels of binding ability to Notch (or other deltex ligand) in an endogenous deltex protein may be indicative of a disorder of cell fate (e.g., cancer, etc.) By "aberrant levels," is meant increased or decreased levels relative to that present, or a standard level representing that present, in an analogous sample from a subject not having the disorder.

The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few.

deltex genes and related nucleic acid sequences and subsequences, including complementary sequences, and other toporythmic gene sequences, can also be used in hybridization assays. deltex nucleic acid sequences, or subsequences thereof comprising about at least 8 nucleotides, can be used as hybridization probes. Hybridization assays can be used to detect, prognose, diagnose, or monitor conditions, disorders, or disease states associated with aberrant changes in deltex expression and/or activity as described supra. In particular, such a hybridization assay is carried out by a method comprising contacting a sample containing nucleic acid with a nucleic acid probe capable of hybridizing to deltex DNA or RNA, under conditions such that hybridization can occur, and detecting or measuring any resulting hybridization.

6. EXAMPLE: A MEMBER OF THE NOTCH GROUP OF INTERACTING LOCI, DELTEX ENCODES A CYTOPLASMIC BASIC PROTEIN

As described herein, we have proceeded with a molecular characterization of Drosophila deltex. We report the cloning and sequencing of deltex, and that deltex encodes a maternally and zygotically expressed transcript that results in the production of a basic protein of novel sequence. Expression of the deltex protein appears ubiquitous and at low levels within the cytoplasm. By ectopically expressing deltex under the control of a heatshock promoter, we confirm the cytoplasmic subcellular localization of deltex. Moreover, this overexpression does not result in any obvious phenotypic abnormalities in the fly. Finally, we examine genetically the functional effects of several Suppressor of deltex mutations upon the various deltex interactions. We demonstrate that in addition to suppressing all adult morphological defects of deltex alleles, these suppressors also are capable of suppressing most synergistic effects involving deltex and Notch, Delta, and mastermind.

6.1. Results

6.1.1. Molecular Cloning of the Deltex Locus

The deltex allele $dx^P$ was isolated during a P element-induced mutagenesis screen (Golubovsky, 1983, Dros. Inf.

Ser. 59:42–43; Maine et al., 1985, Cell 43:521–529). In situ hybridization of P element sequences to polytene chromosomes revealed that the stock carrying the dx$^P$ mutation (dx$^P$sn3) contained four P elements in regions 2A, 5C, 5D and 6A, respectively, on the X chromosome (data not shown). Because the cytological position of the deltex locus was previously assigned within the polytene interval 6A3,4 and 6F10,11 (Demerec et al., 1942, Yearbook-Carnegie Institution 41:191; Gorman and Girton, 1992, Genetics 131:99–112), these observations suggested that the deltex phenotype of dx$^P$ was associated with the P element insertion at 6A.

We proceeded to isolate genomic DNA clones representing the 6A chromosomal region by constructing a genomic library of partial Sau3A digests of dx$^P$ DNA and screening it with a P element DNA probe. The overlapping clones, 1A25 and 1A28, both of which carry P element homologous sequences (FIG. 1A), were shown by in situ hybridization on polytene chromosomes to derive from the 6A region (data not shown). Using DNA fragments from these clones to screen a wild-type genomic library, we obtained three wild-type clones (III1, III2, III3) that covered ~35 kb around the P element insertion site (FIG. 1A). That the P element in 6A is causative of the deltex phenotype is suggested by an examination of genomic DNA from seven phenotypic revertants of dx$^P$, which were generated by genetic mobilization of the P element: In all cases the P elements were excised from the cloned region (data not shown).

6.1.2. Transcriptional Activity of the 6A Region

The transcriptional activity within the 35-kb cloned region was examined by Northern analysis: RNA samples from various developmental stages were probed with DNA fragments covering the entire cloned region. Only two transcription units were revealed by this analysis. The first one encoded a single size-class RNA of 1.1 kb that was detectable with both probes pdA8.5 and pdA703 (FIG. 1A). This RNA accumulated at high levels during all stages of development. Limited sequencing of a cDNA clone representing this transcription unit revealed homology to mammalian ribosomal protein L7a (not shown). The second transcription unit, detectable with probes pdA4.8 and pdA702 but not pdA703, encoded a single-sized RNA species of ~4 kb. Its accumulation profile appeared to be regulated throughout development (FIG. 2): RNA was most abundant in adult females and during the first half of embryogenesis and accumulated at lower levels during the larval and pupal stages. The fact that the P element associated with the dx$^P$ mutation was localized within this 4-kb transcript (see below) provided further evidence that this was the deltex transcription unit.

6.1.3. All Deltex Adult Phenotypes Can Be Rescued by a 10-KB Genomic Fragment In order to confirm that this transcription unit encoded deltex sequences, we transformed Drosophila embryos with cloned DNA spanning coordinates −+6 to −4 (FIG. 1) and tested the ability of the introduced DNA to complement deltex mutations (see Section 6.3). The 10-kb XbaI genomic fragment used for this study contained the putative deltex transcription unit but interrupted the neighboring ribosomal protein transcription unit (FIG. 1B). We obtained two independent transformant lines, denoted TX05B and TX012G, both of which carried insertions of the transposon on the second chromosome. In genetic complementation tests using all four deltex alleles, both TX005B and TX012G rescued all the adult mutant phenotypes, including the wing, ocellar and rough eye defects (Xu and Artavanis-Tsakonas, 1990, Genetics 126:665–677). This rescue was complete for TX05B, whereas in the case of TX012G, a small percentage of flies displayed a weak delta at the tip of the fifth longitudinal wing vein for all four deltex alleles (data not shown).

We previously reported that although deltex mutations are viable, about 40% of the eggs laid by homozygous deltex females (dx$^{ENU}$ failed to hatch (Xu and Artavanis-Tsakonas, 1990, Genetics 126:665–677). During the course of the present work it was noticed that this particular phenotype appeared more variable than previously encountered: between 12 and 48% of dx$^{ENU}$ embryos produced by homozygous dx$^{ENU}$ females failed to hatch. Neither TX05B nor TX012G improved this statistic: the exact same percentage of eggs failed to hatch whether or not their mutant mothers contained one copy of the transposon (see also below), suggesting that the observed lethality is not solely linked to deltex function.

Double mutant combinations between dx$^{ENU}$ and the Notch allele notchoid (nd) are lethal (Xu and Artavanis-Tsakonas, 1990, Genetics 126:665–677). TX05B and TX012G are capable of rescuing this lethality: nd dx$^{ENU}$ homozygous or hemizygous animals are rescued by one copy of the 10-kb XbaI transposon, although the transformant females are sterile (eggs are laid but never hatch). Two copies of the transposon do not improve this sterility. Additionally, the rescued animals display a wing phenotype (very thick veins ending in deltas and large nicks in the wing margin) very similar to that previously described for nd dx$^{ENU}$/nd+ females (see Xu and Artavanis-Tsakonas, 1990, Genetics 126:665–677), though it is less severe with two copies of the transposon. On the one hand, these results clearly indicate that the 10-kb XbaI genomic fragment contains sequences encoding deltex information. On the other hand, they suggest that these transformant lines are failing to provide the entire adult complement of deltex function and/or that activity necessary for normal maternal function. It should be emphasized, however, that the semi-lethal phenotype associated with what appears to be deltex maternal function is not understood and the possibility that it reflects some aspect of the genetic background has not been excluded.

6.1.4. Deltex Encodes a Basic Protein Rich in Glutamine, Histidine, and Serine Residues Two cDNA clones homologous to the 4-kb deltex transcript were isolated from an embryonic cDNA library (see Section 6.3) and their complete nucleotide sequence determined. These cDNAs, denoted cBE30 and cBE8, are 1299 bp and 2648 bp long, respectively, and overlap by 183 bp (FIGS. 1B,3). The composite nucleotide sequence (SEQ ID NO:1) is 3763 bp, which is a few hundred base pairs shorter than the length of the RNA (~4 kb) as measured on RNA blots. Because a poly A tail and a poly A addition signal appear in the cDNA sequence, the 5' extent of the deltex transcript appears not to be represented by the cDNAs. From limited sequencing of corresponding dx$^P$ genomic DNA, we detect two short sequences approximately 150 bp and 300 bp upstream of the cDNA sequence that are highly homologous to a conserved sequence found at the cap site of other insect genes (Hultmark et al., 1986, Cell 44:429–438; FIG. 3). There is no obvious TATA box, although parts of this region are A/T rich. Genomic sequencing of dx$^P$ DNA also revealed two small introns of 594 and 68 bp, as well as the location of the P element insertion site to within the 5' untranslated region (see FIG. 1B).

Within the 3763-bp cDNA sequence there is a single open reading frame (ORF) of 2211 bp. The first AUG codon is within a sequence context that is consistent with the translation initiation consensus sequence determined for Drosophila (Cavener, 1987, Nucl. Acids Res. 15:1353–1361). Assuming that translation starts at that AUG, the deltex mRNA contains an untranslated leader sequence of at least 344 bp and an untranslated 3' sequence of 1200 bp (FIG. 3). The predicted protein product (SEQ ID NO:2) has 737 amino acids and an estimated molecular mass of 82 kDa (FIG. 3). Computer database searches (see Section 6.3) failed to provide significant homologies to any known proteins.

The predicted deltex protein is rather basic, with an estimated pI of 9.8. One feature of this protein is the high percentage of the amino acids glutamine, histidine and serine: 11.26%, 5.97% and 11.94% respectively, compared to 5.0%, 2.8%, and 7.6% for the average Drosophila protein (Smoller et al., 1990, Genes Dev. 4:1688–1700). Most of the glutamine residues are concentrated in two clusters: the first one, extending between residues 261 and 302, is rich both in glutamine and histidine. The second one, starting at residue 488 and ending at residue 513, is composed mainly of glutamine. Such glutamine rich stretches are found in many proteins and are often referred to as opa or M repeats (Wharton et al., 1985, Cell 40:55–62; McGinnis et al., 1984, Nature 308:428–433). Their significance is unknown. Hydropathy plot analysis of the protein sequence failed to identify a putative signal sequence or transmembrane domain (Kyte and Doolittle, 1982, J. Mol. Biol. 157:105–132).

6.1.5. The Deltex Protein Is Localized within the Cytoplasm

To assess the spatial distribution and subcellular localization of the deltex protein, we raised mono- and polyclonal antibodies against bacterially expressed deltex fusion proteins (see Section 6.3). The specificity of the antibodies was routinely tested by immunoblot analysis and by immunofluorescent observation of Schneider 2 (S2) tissue culture cells (Schneider, 1972, J. Embryol. Exp. Morph. 27:353–365) transfected with deltex expression constructs. On immunoblots (not shown) the antibodies recognized an ~80 kDa protein, in agreement with that predicted from the DNA sequence.

The immunological staining of embryos and imaginal tissues with these antibodies revealed an apparently ubiquitous non-nuclear distribution.

However, because this generalized pattern was also of low intensity, it presented difficulties in interpretation. To increase our confidence in this apparently cytoplasmic localization, we overexpressed the deltex protein in flies containing a P element transposon of deltex coding sequences under the control of the Hsp70 promoter (see Section 6.3). Using the antisera to compare the staining patterns of heat-shocked embryos containing or lacking the transposon, we observed a dramatic increase in staining intensity in embryos containing the transposon.

FIG. 4 shows that deltex is localized within the cytoplasm. However, because the Hsp70 promoter is ubiquitously expressed, we are not able to confidently assess the normal overall spatial pattern of deltex expression.

We examined further whether overexpression of deltex from this transposon was capable of rescuing deltex mutant defects and also whether additional phenotypic consequences might result from this over—and possibly ectopic—expression of deltex (see Section 6.3). Under the conditions we have tested, the $124A^P$ transposon is capable of completely rescuing, albeit with variable penetrance, the defects associated with deltex mutations. Additionally, various heat shock regimens of wild-type animals carrying the transposon revealed no obvious phenotypic consequences of overexpression compared to control animals.

6.1.6. The Genetic Suppression of Deltex

During the course of characterizing deltex we recovered a spontaneous suppressor of deltex, which we denote $Su(dx)^{sp}$. Meiotic mapping placed this mutation on the second chromosome. This prompted us to examine two other second chromosome mutations, $Su(dx)$ and $Su(dx)^2$, which were described by Morgan et al., 1931, Year book—Carnegie Institution 30:410 to suppress the adult phenotypes of deltex mutations.

FIG. 5 summarizes the effects of these mutations on four deltex mutations, $dx^{ENU}$, $dx^{SM}$, dx, $dx^P$. All three $Su(dx)$ mutations suppress in a dominant fashion the adult mutant phenotypes (wing, ocelli and eye) of these deltex alleles, although with differences in expressivity. $Su(dx)$ and $Su(dx)^{sp}$ are the most efficient suppressors, suppressing completely the wing and ocellar defects of $dx^{ENU}$ and $dx^{SM}$, and partially suppressing their rough eye phenotype. $Su(dx)^2$ has a weaker effect, suppressing only partially the wing phenotype of $dx^{SM}$ (FIG. 6).

Although the genetic behavior of the three second chromosome suppressors is similar with regard to deltex, the fact that they act in a dominant fashion and as homozygotes display no obvious mutant phenotype by themselves precludes us from concluding they are allelic. However, one line of genetic evidence to suggest that they may be allelic makes use of the observation that homozygous $Su(dx)$ or $Su(dx)^{sp}$ animals in an $Ax^{E2}$ $dx^{ENU}$ background do not survive. This contrasts with flies of the genotype $Ax^{E2}dx^{ENU}$; $Su(dx)/+$, which are viable (Xu and Artavanis-Tsakonas, 1990, Genetics 126:665–677). We find that any heterozygous combination of the suppressor mutations in combination with $Ax^{E2}dx^{ENU}$ results in lethality. Thus, these results are consistent with the notion that the three suppressor mutations are allelic.

6.1.7. Suppression of the Phenotypic Interactions between Deltex and Notch, Delta and Mastermind Characteristic of the genetic behavior of deltex is its interactions with Notch, Delta, and mastermind (Xu and Artavanis-Tsakonas, 1990, Genetics 126:665–677). We were therefore interested in examining further the effects of the $Su(dx)$ loci upon these interactions.

The deltex locus first caught our attention by virtue of its ability to suppress, in a dominant fashion, the lethality conferred by certain transheterozygous combinations of the Abruptex alleles of the Notch locus (e.g., $Ax^{E2}/Ax^{9B2}$; Xu and Artavanis-Tsakonas, 1990, Genetics 126:665–677). This lethality is restored in the presence of $Su(dx)$, that is, animals that are $Ax^{E2}$ $dx^{ENU}/AX^{9B2}+$; $Su(dx)/+$ are no longer viable. Similarly, in the presence of $Su(dx)$, the normally lethal nd $dx^{ENU}$ double mutation (Xu and Artavanis-Tsakonas, 1990, Genetics 126:665–677) now results in a viable combination, although these animals exhibit a severe loss of wing blade material such that only a narrow strip of blade remains (not shown).

A characteristic pupal lethality is displayed by deltex mutants bearing one copy of N, Dl, or mam (Xu and Artavanis-Tsakonas, 1990, Genetics 126:665–677). With Notch this lethality is complete, whereas with Dl and mam the condition is semi-lethal (Xu and Artavanis-Tsakonas, 1990, Genetics 126:665–677). We found that one copy of Su(dx) can partially suppress these interactions: a few animals of the genotype $N^{5419}$ $dx^{ENU}/+$ $dx^{ENU}$; Su(dx)/+ are able to escape lethality, although they display the same small, rough-eye defect as their dead siblings (see also Xu and Artavanis-Tsakonas, 1990, Genetics 126:665–677); animals that are $dx^{ENU}/Y$; Su(dx)+/+mam$^{IL115}$ or $dx^{ENU}/Y$; Su(dx)/+; Dl$^{9P39}/+$ are perfectly viable, but display clear deltex mutant phenotypes (ocelli and wing).

Previously, we reported that in the wing of $Ax^{E2}dx^{ENU}$ homozygous or hemizygous animals there is a suppression of the Abruptex mutant phenotype concomitant with an enhancement of the deltex mutant phenotype (Xu and Artavanis-Tsakonas, 1990, Genetics 126:665–677). As indicated above, animals homozygous for Su(dx) in this background do not survive. However, with one copy of Su(dx) the wing defects are similar to those of $Ax^{E2}$ single mutants. That is, with the addition of a single copy of Su(dx) there is a suppression of the effect of deltex upon $AX^{E2}$. In addition, the triple mutants display a novel phenotype never observed in animals carrying any two of these mutations: many micro- and macrochaetae on the thoracic region are missing (FIG. 7).

6.2. Discussion

Genes that individually share similar mutant phenotypes or that combinatorially show a synergistic enhancement of a mutant phenotype are often regarded as integrated within a common developmental pathway. While not constituting proof of such integration, these observations nonetheless provide a powerful means for identifying potentially interacting components of complex developmental processes. This premise has formed the basis of genetic screens we have performed and has led to the identification of deltex as an interacting partner of Notch. Moreover, this finding has been strengthened by the demonstration that deltex also interacts with Delta and mastermind, two genes that not only share similar null phenotypes with those of Notch, but also display phenotypic interactions with Notch (Xu et al., 1990, Genes Dev. 4:464–475; Xu and Artavanis-Tsakonas, 1990, Genetics 126:665–677).

In this paper, we present our initial molecular characterization of the deltex locus. We have ultimately identified the deltex transcription unit by showing via germline-mediated transformation experiments that a 10-kb genomic fragment containing a ~5 kb transcription unit is capable of complementing most deltex mutant defects. Moreover, this genomic fragment rescues the normally lethal genetic interaction that results when flies are doubly mutant for deltex and nd. Finally, Northern analysis indicates a maternal loading of deltex transcripts into the developing oocyte, a finding that is consistent with the maternal effect observed upon embryogenesis in eggs laid by homozygous mutant mothers (Xu and Artavanis-Tsakonas, 1990, Genetics 126:665–677).

The phenotypic consequences of null mutations of deltex are not known. The only known deficiency (Df(1) G4e$^L$H24i$^R$) of the chromosomal region in which deltex resides was generated synthetically (Stephenson and Mahowald, 1987, Dev. Biol. 124:1–8; see also Gorman and Girton, 1992, Genetics 131:99–112) and because of its size uncovers multiple loci. Moreover, the placement of a Minute locus within this deficiency has complicated the genetic analysis of deltex. Minutes exhibit a dominant haplo-insufficient phenotype of reduced fertility, long generation times and shortened and thin bristles. Numerous Minute loci are found within the Drosophila genome and in at least one case has been shown to encode a ribosomal protein gene (Kongsuwan et al., 1985, Nature 317:555–558; see also Burns et al., 1984, Mol. Cell. Biol. 4:2643–2652). In the course of our molecular characterization of deltex, we discovered a ribosomal protein (rp) transcription unit that resides ~2 kb from the 5' end of the deltex transcription unit. We have shown that P element transformation of a genomic fragment containing this rp transcription unit rescues fully the Minute phenotype of Df(1)G4e$^L$H24i$^R$. Thus, the proximity of the rp gene to deltex appears likely to have contributed to the difficulty in recovering deltex deficiencies (see also Lefevre, 1974, Cold Spring Harbor Symp. Quant. Biol. 38 591–599).

We have extended the genetic analysis of deltex by examining three second chromosome mutations that are effective suppressors of the deltex phenotype, though their allelism has not been established. That the relationship of Su(dx) to deltex and Notch reflects not a simple suppression of deltex is suggested by the synergistic effects that are displayed in triple mutants [i.e., $Ax^{E2}dx^{ENU}$;Su(dx)]: a novel phenotype of missing bristles is observed (FIG. 7). Because homozygous $Ax^{E2}dx^{ENU}$ animals carrying a duplication of the deltex locus do not display this novel phenotype (not shown), the Su(dx) loci cannot be mere duplications of the deltex locus. Moreover, whereas animals homozygous for all three mutations are not viable, homozygotes for any two mutations are viable. Thus, there is the suggestion that the effects of Su(dx) mutations are the result of a three-way interaction between Notch, deltex and Su(dx).

We have established by several criteria the specificity of the antibodies for the deltex protein, although immunological staining of tissues has been complicated by the low levels and apparently ubiquitous distribution of the protein product. These results have been consistent with our efforts to detect the embryonic distribution of deltex mRNA in situ using appropriate nucleic acid probes. However, the use of a transposon to overexpress deltex in embryos has afforded us a view of deltex in vivo and to demonstrate a cytoplasmic distribution of the protein, in agreement with conceptual translation of the gene. Additionally, the ability of this transposon to rescue deltex mutant phenotypes without producing overt mutant consequences in wild-type animals is consistent with the evidence showing a generalized distribution of the gene product.

Two observations raise the possibility that the in vivo level of deltex protein accumulation is under translational control. First, in the 5' non-coding region preceding the long ORF, there is an unusual arrangement of five ATG codons that are part of a short ORF of 14 codons (FIG. 3). This organization is reminiscent of genes known to be under translational control (Abastado et al., 1991, Mol. Cell. Biol. 11:486–496; see also Kozak, 1986, Cell 44(2):283–292). Second, we have shown that in plasmid expression constructs, removal of these upstream initiator codons significantly increases the level of deltex protein accumulation in transfected S2 cells, as detected by immunofluorescence. Thus, this may account for the low levels of protein accumulation we detect in vivo, although artificially overexpressing deltex appears not to have any deleterious consequences (see above).

Biochemical and genetic studies have identified Delta and Serrate as ligands of Notch and have provided insights into the nature of their interactions with the Notch extracellular domain (Fehon et al., 1990, Cell 61:523–534; Rebay et al., 1991, Cell 67:687–699; PCT Publication No. WO 92/19737 dated Nov. 12, 1992).

6.3. Material and Methods

6.3.1. Isolation of Nucleic Acids

Isolation of Drosophila genomic DNA was performed as described by Preiss et al. (1988, EMBO J. 7:3917–3927). Total embryonic and larval RNAs from a Canton S strain were prepared according to the procedure of Chirgwin et al. (1979, Biochemistry 18(24)5294–5299). Pupal and adult RNAs were generously provided by A. Preiss (Preiss et al., 1988, EMBO J. 7:3917–3927). Poly (A)$^+$ RNA was selected by serial passage over oligo(dT)-cellulose (Stratagene) according to Maniatis et al. (1989, Molecular Cloning: A Laboratory Manual. Cold Spring Harbor, Cold Spring Harbor Laboratory, N.Y.). $^{32}$P-labelled DNA probes were prepared by random oligonucleotide priming (Feinberg and Vogelstein, 1984, Anal. Biochem. 137:266–267). Enzymes were used as instructed by the manufacturers. All other procedures were carried out according to standard protocols (Sambrook et al., 1989, Molecular Cloning: A Laboratory Manual, 2d Ed., Cold Spring Harbor Laboratory, Cold Spring Harbor, N.Y.).

The genomic library of $dx^P$ DNA was prepared as follows: 60 mg of DNA from $dx^P$ flies were digested with 2 units of Sau3A in a reaction volume of 320 ml for 1 h, and then fractionated by centrifugation on a continuous 10–40% sucrose gradient for 22 h at 22,000 rpm (rotor SW40, Beckman). Fractions containing DNA of 15 kb or more were collected, dialysed, precipitated with ethanol, and ligated to 1 mg of BamHI cut arms of λEMBL3 (Frischauf et al., 1983, J. Mol. Biol. 170:827–842) in a reaction volume of 10 ml. Half of the ligation mixture was used in a standard in vitro lambda packaging reaction (kit from Amersham), yielding a total of 2×10$^6$ recombinant phages. The Drosophila wild-type genomic library in λEMBL3 was provided by J. Tamkun (Tamkun et al., 1992, Cell 68:561–572). The cDNAs cBE8 and cBE30 were recovered from a λgt10 cDNA library made from 3–12 h embryonic mRNA and donated by Larry Kauvar (Poole et al., 1985, Cell 40:37–43).

6.3.2. P-MEDIATED TRANSFORMATION

For the genomic rescue experiments, a 10-kb XbaI genomic fragment (FIG. 1) encompassing the ~5-kb deltex transcription unit was cloned into the XbaI site of the P transformation vector pDM23, which carries the rosy gene as a selection marker (G. Rubin, unpublished). This DNA was co-injected with the Δ2-3 helper plasmid (to provide transposase; Robertson et al., 1988, Genetics 118:461–470) into cn; ry$^{506}$ embryos using essentially the procedure described by Spradling (1986, in Glover, D. M. (ed.), Drosophila—A Practical Approach, IRL Press, Oxford, pp. 175–197). Three phenotypically cn and ry$^+$ G1 females were recovered and mated to cn; ry$^{506}$ males. One of the insertions was X-linked and male lethal and not used further. The other two insertions were localized to chromosome 2 and single lines were established using the balancer strain. Bc Elp/CyO, ry506.

For experiments involving overexpression of deltex in vivo, we used the pCaSpeR-hs transformation vector (Thummel and Pirrotta, 1991, DIS 71:150), which was kindly provided by C. Thummel. cDNA sequences extending from 33 nucleotides 5' of the translational start site to a sole SpeI site within the 3' non-coding region were ligated into the EcoRI-XbaI digested vector. DNAs were injected into W$^{1118}$ embryos; 9 w$^+$ transformant fly lines were recovered, one of which, 124A$^D$, was chosen for this study. When crossed to deltex mutants, this transgenic line significantly improved deltex mutant defects in the absence of heat shock and produced wild-type appearing flies with the application of daily 1 hour heat shocks at 37° C. For the immunofluorescent staining pictured in FIG. 4 (see also below), we applied the following heat shock regimen to an overnight collection of embryos produced from homozygous 124A$^D$ flies: 50 min at 37° C., 50 min at 25° C., 50 min at 37° C. After a 4 hour recovery at 25° C., the embryos were fixed in 4% paraformaldehyde/phosphate-buffered saline (PBS) solution.

6.3.3. SEQUENCE DETERMINATION AND ANALYSIS

The EcoRI-cDNA insert from cBE8 was subcloned directly in both orientations into Bluescript KS-, M13mp18 and M13mp19 vectors. Overlapping deletions were produced on the inserts using the Exonuclease III-Mung Bean Nuclease system (kit from Stratagene). Additional deletions were obtained through the use of restriction sites within the vector polylinker and the cDNA inserts. The cDNA insert of cBE30 contains two internal EcoRI sites but no HindIII site: it was cloned into M13mp18 and M13mp19 vectors as three separate EcoRI pieces, and into Bluescript KS- vector as a HindIII fragment containing sequences from λgt10 on both sides. Single-stranded cDNAs were produced according to the manufacturer's instructions. Both strands of the cDNAs were sequenced using the dideoxynucleotide chain termination method (Sanger et al., 1977, Proc. Natl. Acad. Sci. USA 74:5463–5467) and the Sequenase kit (U.S. Biochemical Corp.), with the M13 universal and reverse primers. cDNA sequences that were not accessible by these methods were obtained using synthetic primers complementary to part of a previously determined sequence. Genomic sequences of interest from phages A25 or I2 were subcloned into convenient restriction sites of Bluescript KS- and sequenced using synthetic primers.

DNA sequence manipulations were performed using Intelligenetic's PC-GENE software. Open reading frame prediction and plotting were performed using the University of Wisconsin program CODONPREFERENCE (Gribshov et al., 1984, Nucl. Acids Res. 12:539–549). The GenPept and SWISS-PROT databases were searched with all or part of the deduced amino acid sequence using the FASTA program (Pearson and Lipman, 1988, Proc. Natl. Acad. Sci. USA, 85:2444–2448) available by the GenBank FASTA server through BITNET.

6.3.4. EXPRESSION CONSTRUCTS AND IMMUNOLOGICAL PROCEDURES cDNA representing the entire deltex coding region was inserted into the pGex1 expression vector and expressed in E. coli XL1-Blue (see Smith and Johnson, 1988, Gene 67:31–40). The bacterial pellet was washed first in ice-cold 50 mM Tris pH 8.0, 50 mM EDTA, 50 mM NaCl before being resuspended in ice-cold 50 mM Tris pH 8.0, 150 mM NaCl, 1 mM EDTA, 1 mg/ml lysozyme, 1 mM phenylmethylsulfonylfluoride (PMSF). After ~1 hour on ice, the cells were lysed by the addition of Triton X-100 to 1% final concentration. The lysate was sonicated briefly to shear DNA and then cleared by centrifugation. After overnight incubation at 4° C. with glutathione-agarose beads (Sigma), the fusion protein was eluted from the PBS-washed beads with 5 mM reduced glutathione, 50 mM Tris pH 8.0 (see Smith and Johnson, 1988, Gene 67:31–40). Standard procedures were used to immunize Sprague-Dawley rats with soluble fusion protein (Harlow and Lane, 1988, Antibodies:

*A Laboratory Manual*, Cold Spring Harbor, Cold Spring Harbor Laboratory, N.Y.). Immune sera was tested for positive reactivity by immunofluorescent staining of transiently-transfected S2 tissue culture cells (see Fehon et al., 1990, Cell 61:523–534) and by immunostaining of protein blots (Harlow and Lane, 1988, *Antibodies: A Laboratory Manual*, Cold Spring Harbor, Cold Spring Harbor Laboratory, N.Y.). The expression vector used in the transfections was pRmHa-3 (Bunch et al., 1988, Nucl. Acids Res. 16:1043–1061), into which deltex cDNA sequences were inserted. Hybridoma fusions were performed by the Howard Hughes Medical Institute's Hybridoma Facility at Yale University. The antibody supernatant used in this study derived from the cell line C645.17A. Immunofluorescent staining and confocal imaging of embryos was essentially as described by Fehon et al. (1991, J. Cell Biol. 113:657–669).

6.3.5. STRAINS AND CROSSES

Stocks were maintained and crosses were performed using standard procedures described previously (Xu and Artavanis-Tsakonas, 1990, Genetics 126:665–677). Genetic markers and strains not specifically mentioned here can be found in Lindsley and Grell (1968, Genetic Variations of Drosophila melanogaster, Publication number 627, Carnegie Institute of Washington, Washington D.C.) or Lindsley and Zimm (1985, Dros. Inf. Serv. 62), Lindsley and Zimm (1986, Dros. Inf. Serv. 64), Lindsley and Zimm (1987, Dros. Inf. Serv. 67), and Lindsley and Zimm (1990, Dros. Inf. Serv. 68).

6.3.6. PHENOTYPIC REVERSION OF $dx^P$

Homozygous $dx^P$ $sn^3$ females were mated to cn; $P(ry^+$; D2-3) $ry^{506}$ Sb/TM6 males, which provide a stable source of P transposase (Robertson et al., 1988, Genetics 118:461–470). $dx^P$ $sn^3$/Y; cn/+; $P(ry^+;D2-3)ry^{506}$ Sb/+F1 males were then mated to C(1)A, y females. From ~3000 males scored in the F2 generation, we recovered seven phenotypically wild-type males. These were mated to C(1) A, y females to establish single lines and their genomic DNA was analyzed further by standard Southern blot procedures (Maniatis et al., 1989, Molecular Cloning: A Laboratory Manual, Cold Spring Harbor, Cold Spring Harbor Laboratory, N.Y.)

6.3.7. COMPLEMENTATION OF DELTEX ALLELES BY THE DELTEX TRANSPOSONS TX05B AND TX012G y $dx^{ENU}$ $sn^3$, $dx^{SM}$ $t^2$v, ec dx and $dx^P$ $sn^3$ females were mated to cn TX05B/cn+; $ry^{506}$ males and to cn TX012G/cn+; $ry^{506}$ males to assess effects on adult phenotypes. To assess the effects on embryonic lethality, y $dx^{ENU}$ $sn^3$ females were crossed to y $dx^{ENU}$ $sn^3$/Y, cn TX05B/+ males and to $dx^{ENU}$ $sn^3$/Y; cn TX012G/+ males; $dx^{SM}$ $t^2$ v females were crossed to $dx^{SM}$ $t^2$ v/Y; cn TX012G/+ males. From this cross both sibling progeny containing or lacking the transposon were mated to males of identical X chromosome genotype and the percentage of unhatched embryos was calculated.

6.3.8. ORIGIN OF $Su(dx)^{SP}$

The mutation $(Su(dx)^{sp})$ was found in a homozygous $Ax^{E2}$ $dx^{ENU}$ stock maintained in our laboratory and was shown to segregate with the second chromosome. The following crosses were performed: An $Ax^{E2}$ $dx^{ENU}$; $Su(dx)^{sp}$/+female was mated to FM6/Y; Adv/SM1 males. Individual F1 $Ax^{E2}$ $dx^{ENU}$/FM6; $Su(dx)^{sp}$/SM1 or $Ax^{E2}$ $dx^{ENU}$/FM6; +/SM1 females were mated to individual F1 $Ax^{E2}$ $dx^{ENU}$/Y; $Su(dx)^{sp}$/SM1 males. The individual F2 $Ax^{E2}$ $dx^{ENU}$/$Ax^{E2}$ $dx^{ENU}$; $Su(dx)^{sp}$/SM1 females were then mated to individual $Ax^{E2}$ $dx^{ENU}$/Y; $Su(dx)^{sp}$/SM1 males to establish stock lines. No homozygous $Su(dx)^{sp}$ animals were found in the F3 offsprings from these crosses, indicating that the triple homozygous mutants were lethal. $Su(dx)^{sp}$ homozygotes and $Su(dx)^{sp}$/$Su(dx)$ heterozygotes were viable and displayed no obvious mutant phenotypes.

6.3.9. CROSSES BETWEEN SU(DX) MUTATIONS AND DELTEX ALLELES y $dx^{ENU}$ $sn^3$, $dx^{SM}$ $t^2$ v, ec dx and $dx^P$ $sn^3$ females were mated to $Su(dx)^{sp}$, $Su(dx)$ and ed $Su(dx)^2$ males to observe double mutant effects of dx and $Su(dx)$. y dx $sn^{ENU}$ $sn^3$; +/SM1 females were mated to y $dx^{ENU}$ $sn^3$/Y, $Su(dx)$/+ males. F1: y $dx^{ENU}$ $sn^3$; $Su(dx)$/SM1 females x y $dx^{ENU}$ $sn^3$/Y; $Su(dx)$/SM1 male. F2: y $dx^{ENU}$ $sn^3$, $Su(dx)$ females x y $dx^{ENU}$ $sn^3$/Y; $Su(dx)$ males.

6.3.10. CROSSES BETWEEN SU(DX) AND MUTATIONS OF THE NOTCH LOCUS y w $Ax^{9B2}$/FM7C×$Ax^{E2}$ $dx^{ENU}$/Y; $Su(dx)$SM1. F1 female progeny: y w $Ax^{9B2}$/$Ax^{E2}$ $dx^{ENU}$; $Su(dx)$/+, y w $Ax^{9B2}$/$Ax^{E2}$ $dx^{ENU}$; SM1/+, FM7C/$Ax^{E2}$ $dx^{ENU}$; $Su(dx)$/+, FM7C/$Ax^{E2}$ $dx^{ENU}$; SM1/+.

y $Ax^{9B2}$ sn3×$Ax^{E2}$ $dx^{ENU}$/Y; $Su(dx)^{sp}$/Adv. F1 female progeny: y $Ax^{9B2}$ $sn^3$/$Ax^{E2}$ $dx^{ENU}$; $Su(dx)$/+ and y $Ax^{9B2}$ $sn^3$/$Ax^{E2}$ $dx^{ENU}$; SM1/+.

y w $Ax^{9B2}$/FM7C×$Ax^{E2}$ $dx^{ENU}$/Y. F1 female progeny: y w $Ax^{9B2}$/$Ax^{E2}$ $dx^{ENU}$ and FM7C/$Ax^{E2}$ $dx^{ENU}$.

$Ax^{E2}$ $dx^{ENU}$ females×$Su(dx)^{sp}$, $Su(dx)$ or ed $Su(dx)^2$ males.

$w^a$ nd $dx^{ENU}$ $sn^3$/FM7C×$Su(dx)$. F1 male progeny: $w^a$ nd $dx^{ENU}$ $sn^3$/Y; $Su(dx)$/+ and FM7C/Y; $Su(dx)$/+.

$w^a$ nd $dx^{ENU}$ $sn^3$/FM7C×$Su(dx)^{sp}$/Y. F1 male progeny: $w^a$ nd $dx^{ENU}$ $sn^3$/Y; $Su(dx)^{sp}$/+ and FM7C/Y; $Su(dx)^{sp}$/+.

$nd^2$ $dx^{ENU}$ $sn^3$/FM7C×$Su(dx)$/Y. F1 male progeny: $nd^2$ $dx^{ENU}$ $sn^3$/Y; $Su(dx)$/+ and FM7C/Y; $Su(dx)$/+.

$nd^2$ $dx^{ENU}$ $sn^3$/FM7C×$Su(dx)^{sp}$/Y. F1 male progeny: $nd^2$ $dx^{ENU}$ $sn^3$/Y; $Su(dx)^{sp}$/+ and FM7C/Y; $Su(dx)^{sp}$/+.

$nd^2$ $dx^{ENU}$ $sn^3$/FM7C×ed $Su(dx)^2$/Y. F1 male progeny: $nd^2$ $dx^{ENU}$ $sn^3$/Y; ed $Su(dx)^2$/+ and FM7C/Y; ed $Su(dx)^2$/+.

y $w^a$ $N^{5419}$ $dx^{ENU}$ $sn^3$/FM7C×y $dx^{ENU}$ $sn^3$/Y; $Su(dx)$. F1 female progeny: y $w^a$ $N^{5419}$ $dx^{ENU}$ $sn^3$/y++$dx^{ENU}$ $sn^3$; $Su(dx)$/+, FM7C/y $dx^{ENU}$ $sn^3$; $Su(dx)$/+ and y $w^a$ $N^{5419}$ $dx^{ENU}$ $sn^3$/FM7C; $Su(dx)$/+.

$Ax^{E2}$ $sn^3$; $Su(dx)^{sp}$/SM1 females×ed $Su(dx)^2$, $Su(dx)$ and $Ax^{E2}$ $sn^3$/Y; $Su(dx)^{sp}$/SM1 males.

6.3.11. CROSSES INVOLVING SU(DX), DELTEX, DELTA AND MASTERMIND y $dx^{ENU}$ $sn^3$; $Su(dx)$ females×$D1^{9P39}$/TM1 males. F1 male progeny: y $dx^{ENU}$ $sn^3$/Y; $Su(dx)$/+; $D1^{9P39}$/+ and y $dx^{ENU}$ $sn^3$/Y; $Su(dx)$/+; TM1/+.

y $dx^{ENU}$ $sn^3$; $Su(dx)$ females×cn bw sp mam$^{IL115}$/Cyo males. F1 male progeny: y $dx^{ENU}$ $sn^3$/Y; $Su(dx)$++++/+ cn bw sp mam$^{IL115}$ and y $dx^{ENU}$ $sn^3$/Y; $Su(dx)$/Cyo.

6.3.12. CROSSES COMPARING SU(DX) MUTATIONS $Ax^{E2}$ $dx^{ENU}$; $Su(dx)^{sp}$/Cyo females×$Ax^{E2}$ $dx^{ENU}$/Y; $Su(dx)^{sp}$/Cyo.

Ax$^{E2}$ dx$^{ENU}$/FM7C; Su(dx)/Sm1 females×Ax$^{E2}$ dx$^{ENU}$/Y; Su(dx)SM1.

Ax$^{E2}$ dx$^{ENU}$; Su(dx)$^{sp}$/Cyo females×Ax$^{E2}$ dx$^{ENU}$/Y; Su(dx)/SM1. F1 progeny: Ax$^{E2}$ dx$^{ENU}$/Y; Cyo or SM1/Su (dx)$^{sp}$ or Su(dx). Ax$^{E2}$ dx$^{ENU}$/Ax$^{E2}$ dx$^{ENU}$; Cyo or SM1/Su (dx)$^{sp}$ or Su(dx).

Ax$^{E2}$ dx$^{ENU}$; Su(dx)$^{sp}$/Cyo females×ed Su(dx)$^{2}$ males. F1 progeny: Ax$^{E2}$ dx$^{ENU}$/++; Su(dx)$^{sp}$/ed Su(dx)$^{2}$, Ax$^{E2}$ dx$^{ENU}$/Y; Cyoled Su(dx)$^{2}$, Ax$^{E2}$ dx$^{ENU}$/Ax$^{E2}$ dx$^{ENU}$; Cyoled Su(dx)$^{2}$.

6.3.13. CROSSES INVOLVING DUPLICATIONS OF THE DELTEX LOCUS y w$^{a}$ N$^{5419}$/FM6 females×Tp(1:Y) J104 y B$^{5}$;Yy$^{+}$(6E; Y$^{6}$) males. F1: y w$^{a}$ N$^{5419}$/Tp(1:Y) J104 y B$^{5}$; Yy$^{+}$(6E; Y$^{6}$) females×FM7C/Y males. F2: Tp(1:Y) J104 y w$^{a}$ N$^{5419}$B$^{5}$; Yy$^{+}$(6E; Y$^{6}$)/FM7C individual females×Ax$^{E2}$ dx$^{ENU}$/Y males. F3: Tp(1:Y) J104 y w$^{a}$ N$^{5419}$B$^{5}$; Yy$^{+}$(6E; Y$^{6}$)/Ax$^{E2}$ dx$^{ENU}$/Y virgins×Ax$^{E2}$ dx$^{ENU}$/Y males. F4: Ax$^{E2}$ dx$^{ENU}$/Ax$^{E2}$ dx$^{ENU}$/DpJ104 y w$^{a}$ N$^{5419}$B$^{5}$ (1A; 6E) animals.

7. DELTEX IMPLICATED IN NOTCH-MEDIATED SIGNAL TRANSDUCTION: EVIDENCE FOR CYTOSOLIC INTERACTION WITH NOTCH CDC10/SW16/ANKYRIN REPEATS

As described herein, we have demonstrated a direct interaction between the novel cytoplasmic protein encoded by the deltex locus and the transmembrane receptor encoded by Notch, by expression studies conducted in cultured cells, in yeast, and in the imaginal wing disc. deltex binds specifically to the Notch cdc10/SW16/ankyrin ("ANK") repeats, a region that is crucial for Notch signaling and that constitutes the most conserved domain among Notch family members. In addition, we describe a new class of viable Notch allele that is associated with a missense mutation within the ANK repeat region and that, like mutations of deltex, behaves as a dominant intragenic suppressor of the Abruptex 'negative complementation'.

7.1. DELTEX INTERACTS WITH NOTCH INTRACELLULAR DOMAIN

Figure 8A:
Figure 8B:
Figure 9A:
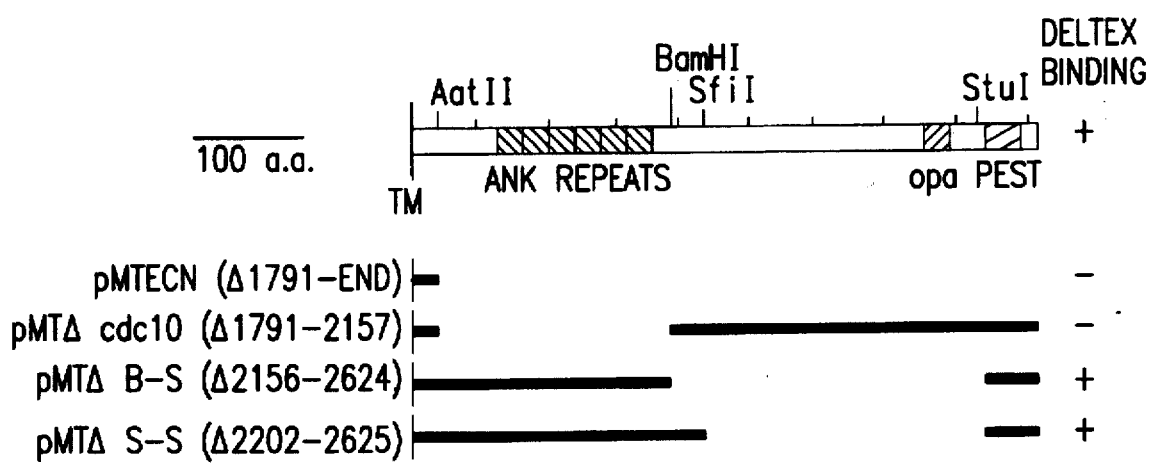

We explored the possibility of protein-protein interactions between deltex and Notch by examining the relative subcellular localization of the two proteins after co-expressing them in Drosophila Schneider 2 (S2) cultured cells (Schneider, 1972, J. Embryol. Exp. Morph. 27:353–365). S2 cells were co-transfected with plasmid expression constructs that placed Notch and deltex under the inducible control of the Drosophila metallothionein and Hsp70 promoters, respectively. S2 cells do not express endogenous Notch (Fehon et al., 1990, Cell 61:523–534) and express deltex at levels too low for reliable immunofluorescent detection (see Section 6 hereinabove and data not shown). Notch expression was induced prior to heat-shock induction of deltex to ensure proper cell surface localization of Notch. By aggregating cells expressing both Notch and deltex with cells expressing Delta, a presumptive membrane-bound ligand of Notch (Fehon et al., 1990, Cell 61:523–534; Heitzler and Simpson, 1991, Cell 64:1083–1092), a dramatic co-capping of these proteins was induced at the point of cellular contact. FIG. 8a shows co-localization between deltex and Notch, indicating molecular interaction between the two proteins. Moreover, this co-localization was evident even in the absence of capping with Delta, although in this case Notch and deltex were mis-localized within peri-nuclear regions of the cell (FIG. 8b). This latter result suggests that there is no ligand dependency of deltex association with Notch.

Figure 8C:
Figure 8D:
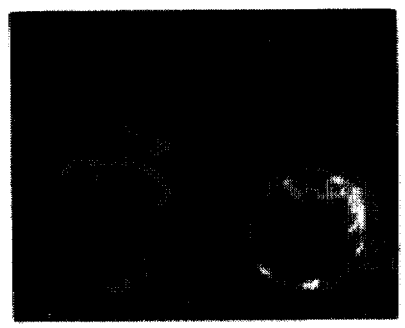

When the same aggregation experiment was performed using plasmids expressing deltex in combination with others expressing either Delta or Serrate (another presumptive ligand of Notch; Rebay et al., 1991, Cell 67:687–699), no co-localization was observed between deltex and these transmembrane proteins (FIG. 8c, d). This indicates that overexpression itself is not causing deltex to concentrate in the regions of cellular contact where Notch and Delta accumulate (Fehon et al., 1990, Cell 61:523–534). Moreover, the results indicate that the genetic interaction previously noted between deltex and Delta (Xu and Artavanis-Tsakonas, 1990, Genetics 126:665–677) is likely an indirect reflection of a direct Notch/deltex interaction.

FIG. 8 Methods: Cell culture conditions and media were as described (Fehon et al., 1990, Cell 61:523–534). For transfections, cells were transferred in fresh media to 6-well plates (Falcon) and allowed to attach to plastic for 1–3 h (cell density ~¾ confluent). Ten micrograms total plasmid DNA in 0.5 ml serum-free media (SFM) were mixed with 0.5 ml SFM containing 50 ml LipofectACE™ (Life Technologies, Inc.). After 15–30 min. mixture was added to cells previously rinsed with SFM. After ~6 h incubation, transfection mixture was replaced with media plus serum. Expression from the metallothionein promoter was induced ~24 h later by CuSO$_4$ addition as described (Fehon et al., 1990, Cell 61:523–534), followed 12–18 h later with induction of the Hsp 70 promoter that consisted of two 30 min incubations at 37° C. with an intervening 30 min at 25° C. Three to five hours later, cells were incubated with anti-Notch antibody for 30 min and fixed in PLP fixative (Tomlinson and Ready, 1987, Dev. Biol. 120:336–376). Antibody incubations and cell mounting were as described (Fehon et al., 1990, Cell 61:523–534) using anti-deltex antibodies followed by FITC- and Texas Red-conjugated goat anti-mouse and anti-rat antibodies (Jackson ImmunoResearch Laboratories, Inc.). Third instar larvae from transgenic line 124A$^D$ (see Section 6) were heat shocked as above to induce deltex expression and dissected wing discs were fixed and incubated with antibodies as outlined above. Confocal images were obtained as described (Xu et al., 1992, Development 115:913–922); cropping and pseudo-coloring were performed using Adobe Photoshop (Adobe Systems, Inc.) computer program.

7.2. NOTCH AND DELTEX CO-LOCALIZATION IN VIVO

Figure 8E:

The above demonstration of Notch/deltex interaction in transfected cells prompted us to explore whether such interaction was detectable in vivo. We examined the imaginal wing disc, a tissue that requires both proteins for its proper development (Xu and Artavanis-Tsakonas, 1990, Genetics 126:665–677). In addition, Notch displays a polarized distribution to the apical surface of the disc epithelium (Fehon et al., 1991, J. Cell Biol. 113:657–669). Because the endogenous level of deltex protein accumulation is below the threshold necessary for confident immunofluorescent detection (see Section 6 hereinabove), we used a transformant fly line carrying an inducible deltex construct to elevate transiently the in vivo pool of deltex protein. Over- and/or ectopic-expression from this transposon rescues deltex mutant defects and has no obvious phenotypic consequences in otherwise wild-type animals (see Section 6 hereinabove). FIG. 8e shows a coincidence of deltex and Notch proteins at the apical surface of the wing disc epithelium, confirming the co-localization data of the S2 cell culture assay and suggesting that Notch/deltex interactions normally occur in vivo.

7.3. NOTCH ANKYRIN REPEATS ARE BOTH NECESSARY AND SUFFICIENT FOR DELTEX ASSOCIATION

Figure 8F:
Figure 8G:
Figure 8H:
Figure 8I:
Figure 8J:
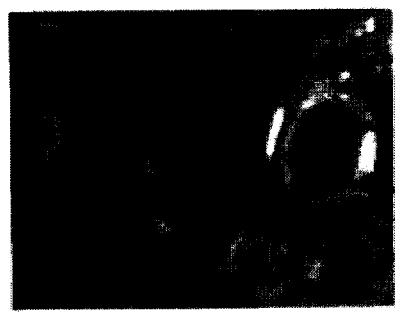
Figure 8K:
Figure 8L:

The 938-amino-acid intracellular domain of Notch contains several structural motifs (Stifani et al., 1992, Nature Genetics 2:119–127; Wharton et al., 1985, Cell 43:567–581; Kidd et al., 1986, Mol. Cell. Biol. 6:3094–3108; Breeden and Nasmyth, 1987, Nature 329:651–654). To identify those regions involved in deltex binding, we expressed deltex along with a set of Notch deletion constructs (FIG. 9a) in the S2 cell culture assay. The phenotypic consequences of expressing these same deletions of Notch were also recently examined in transgenic flies (Rebay et al., 1993, Cell 74:319–329). The constructs ΔB-S and A S-S, which delete sequences C-terminal of the ANK repeats, did not visibly impede deltex association (FIG. 8f, g). Overexpression of these deletions within the fly produced only mild phenotypes similar to those resulting from overexpression of an intact version of Notch (Rebay et al., 1993, Cell 74:319–329). This stands in contrast to the results obtained with deletions that removed the ANK repeats (ECN or Δcdc10). In the S2 cell assay, we detected no association of deltex with these versions of Notch (FIG. 8h, i). In the fly, overexpression of both the ECN and Δcdc10 constructs resulted in severe dominant-negative phenotypes, demonstrating an essential role for the ANK repeats in Notch signal transduction (Rebay et al., 1993, Cell 74:319–329). Combined, these results not only implicate the ANK repeats in mediating Notch/deltex interaction (see below), but also suggest a role for deltex in intracellular signaling events.

Figure 9B:
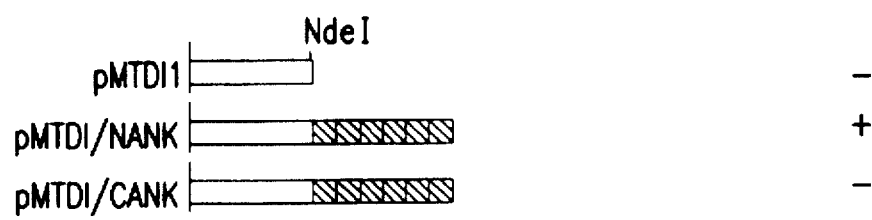

To determine whether the ANK repeats alone were sufficient to promote deltex binding, we produced an expression construct, pMTD1/NANK, that affixed the Notch ANK repeats to the cytoplasmic domain of Delta (FIG. 9b). Because Delta shows no physical association with deltex (FIG. 8c), co-localization of the two proteins at the cell surface would be a consequence of the Notch ANK repeats. FIG. 8, panels j and k show this to be the case. Indeed, the deltex/Notch-ANK-repeat interaction is emphasized in FIG. 8k, which is an electronic merging of the side-by-side image displayed in FIG. 8j. Unlike the staining patterns obtained from other transfection experiments, this shows that the co-localization is offset, i.e., not coincident, reflecting the labeling of Notch in one cell and that of deltex (through hybrid Delta/Notch-ANK-repeat protein) in an adjacent cell. Thus, the Notch ANK repeats are both necessary and sufficient for deltex binding to occur.

Figure 9C:
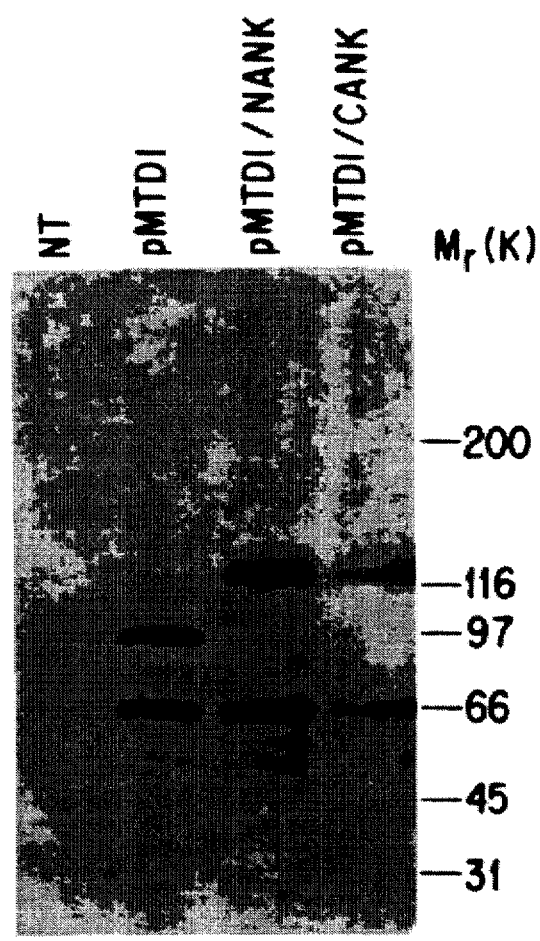

Because ANK repeats, in general, are a conserved feature of many proteins, we sought to address the specificity of deltex binding for those repeats of Notch. We replaced the ANK repeats of pMTD1/NANK with those of the Drosophila gene, cactus, to produce the expression plasmid, pMTD1/CANK (FIG. 9b). cactus encodes an I-κB cognate that has been shown to bind, via ANK repeats, a Drosophila NF-κB cognate, dorsal (Geisler et al., 1992, Cell 71:613–621; Kidd, 1992, Cell 71:623–635). In the S2 cell expression assay, no association of deltex for the ANK repeats of cactus was observed (FIG. 8l), although immunoblot analysis indicated a hybrid Delta/cactus protein of proper size was expressed in these cells (FIG. 9c). This result indicates a specific association of deltex for the ANK repeats of Notch and serves as a control for the concern that overexpression of ANK repeats, per se, promotes deltex association.

FIG. 9 Methods: All constructs were based on the expression vector pRmHa-3 (Bunch et al., 1988, Nucl. Acids Res. 16:1043–1061), which uses the inducible Drosophila metallothionein promoter to drive expression. a. Details of plasmid construction have been described (Rebay et al., 1993, Cell 74:319–329). b. Encoded Notch ANK repeats were isolated as a PCR-derived DNA fragment containing artificial NdeI and BspEI sites. The following synthetic oligonucleotide primers (H.H.M.I. facility, Yale University) were used: 5' GCG CAT CAG GAT CAT ATG AAG CAC GAT GTG GAT GCA 3' (SEQ ID NO:20) and 5' GGC CAC ATC GTC CGG AAA TCG ATC CAT GTG ATC 3' (SEQ ID NO:21). To generate pMTD1/NANK, the following three-piece ligation was performed: a 2.6-kb EcoRI-NdeI DNA fragment from pMTD11 (Fehon et al., 1990, Cell 61:523–534) and the NdeI/BspEI-digested PCR fragment were inserted into the EcoRI and XmaI sites of pRmHa-3. The resulting construct encoded Notch protein sequences beginning four residues before the first ANK repeat and ending nine residues after the sixth ANK repeat. For pMTD1/CANK, the same three-piece ligation was performed except a 0.7-kb AseI-BspEI DNA fragment from the cactus cDNA pcact5B (Geisler et al., 1992, Cell 71:613–621) replaced the fragment encoding the Notch ANK repeats. The resulting construct encoded eight residues of cactus before the first ANK repeat and five residues of cactus after the sixth ANK repeat. For both constructs, a TAG stop codon was provided by the XbaI site within the vector polylinker sequence. c. Standard procedures (Harlow and Lane, 1988, in Antibodies: A Laboratory Manual, Cold Spring Harbor Laboratory Press, New York) were used for the preparation of cell lysates, PAGE-electrophoresis (3–15% gel) and immunoblot analysis. The anti-Delta monoclonal antibody C584.9B was used in conjunction with goat anti-mouse peroxidase-conjugated secondary antibodies (Jackson ImmunoResearch Laboratories, Inc.) and the LumiGLO™ (Kirkegaard & Perry Laboratories, Inc.) chemiluminescent detection kit according to manufacturer's instructions.

7.4. DIRECT NOTCH/DELTEX INTERACTION INDICATED BY YEAST EXPRESSION STUDIES

The above demonstration of a specific association between deltex and Notch ANK repeats leaves open the question of whether the interaction is mediated directly or through other cellular components. To address this question, we have conducted similar expression studies in yeast using the so-called 'interaction trap' technique (Zervos et al., 1993, Cell 72:223–232). The "interaction trap" system involves three plasmids co-transfected in a yeast cell. The first plasmid is designed to express a fusion protein with a DNA binding domain of a yeast transcription factor LexA. The second plasmid is designed to produce a fusion protein with an acidic activation transcription domain (ACT). The third plasmid is a lacZ reporter gene which is activated by the binding of functional LexA protein to its upstream elements. Since the LexA fusion protein does not have an acidic transcription activation domain, it cannot activate the lacZ reporter gene. However, if there is a protein-protein interaction between a LexA fusion and an ACT fusion, a functional LexA protein is reconstructed which activates lacZ reporter gene transcription (resulting in synthesis of β-galactosidase).

Two expression plasmids were constructed. One (LexA-Notch ICN1) encoded a LexA DNA-binding domain fused to a portion of the Notch intracellular domain (amino acids 1827–2258; Wharton et al., 1985, Cell 43:567–581) that included the ANK repeats. The other plasmid (pJG4-5- deltex) encoded the entire deltex protein fused to an acidic transcription activation domain (ACT-deltex). These were co-transformed into yeast carrying a reporter gene (LexAoperator-lacZ) plasmid. Notch/deltex interactions would be expected to mediate the formation of a complex between the LexA-Notch ICN1 and ACT-deltex proteins resulting in the restoration of transcriptional activity. This would be detected as a blue yeast colony due to induced β-galactosidase synthesis. As presented in FIG. 10, a specific interaction was indeed detected between Notch and deltex within the yeast cell. This result suggests that the Notch/deltex interaction observed within Drosophila cells is the consequence of a direct protein-protein interaction.

FIG. 10 Methods: The 'interaction trap' method was as described (Zervos et al., 1993, Cell 72:223–232). R. Finley and R. Brent generously provided yeast strain EGY40 and plasmids LEX202+PL (to make LexA fusions), pJG4-5 (to make acidic activation domain fusions), pSH18-34 (LexAop-lacZ reporter gene) and pRFHMI (LexA-bicoid fusion). The entire groucho coding region (Delidakis et al., 1991, Genetics 129:803–823) was isolated by PCR and inserted into the EcoRI restriction sites of LEX202+PL and pJG4-5 to create LexA-groucho and pJG4-5-groucho. A PCR-derived DNA fragment containing artificial EcoRI and SalI sites and encoding amino acids 1827–2258 of Notch was inserted into LEX202+PL to create LexA-Notch ICN1. The entire coding region of deltex was recovered by PCR and inserted into the XhoI site of pJG4-5 to create pJG4-5-deltex. Yeast transformations were performed as described (Gietz et al., 1992, Nucl. Acids Res. 20:1425).

7.5. INTRAGENIC SUPPRESSOR MUTATION MAPS WITHIN ANK REPEAT

In the same genetic screen (Xu et al., 1990, Genes Dev. 4:464–475; Xu and Artavanis-Tsakonas, 1990, Genetics 126:665–677) that identified deltex as a potentially interacting partner of Notch, an unusual allele of Notch was also recovered. This allele, denoted $N^{su42c}$, is homozygous viable, and like mutations of deltex, Delta or mastermind, suppresses completely the pupal lethality associated with the $Ax^{E2}/Ax^{9B2}$ 'negative complementation'.

Intra-genic recombination analyses indicated that the $N^{su42c}$ lesion was positioned centromere-proximal, and thus 3', to the $Ax^{9B2}$ mutation located within the genomic region encoding the 23rd EGF-like repeat. We have sequenced $Ax^{9B2}$ su42c genomic DNA encompassing the 17th EGF-like repeat to the C-terminal end of the protein and find a missense mutation that results in an alanine to valine substitution within the fifth ANK repeat (FIG. 11). This alanine is conserved among all Notch homologs in mice, rats, humans and Xenopus (Coffman et al., 1990, Science 249:1438–1441; Weinmaster et al., 1991, Development 113:199–205; Weinmaster et al., 1992, Development 116:931–941; Kopan and Weintraub, 1993, J. Cell Biol. 121:631–641; Ellisen et al., 1991, Cell 66:649–661; Stifani et al., 1992, Nature Genetics 2:119–127; Franco del Amo et al., 1993, Genomics 15:259–264), but does not fall within a conserved position in the consensus sequence compiled for ANK repeats in general (Lux et al., 1990, Nature 344:36–42; Breeden and Nasmyth, 1987, Nature 329:651–654; Michaely and Bennett, 1992, Trends Cell Biol. 2:127–129; Blank et al., 1992, Trends Biochem. Sci. 17:135–140; Robbins et al., 1992, J. Virol. 66:2594–2599).

Interestingly, the su42c mutation, which is the first mutation known to affect the ANK region of Notch, confers upon adult flies a subset of deltex-like mutant phenotypes (not shown). These include outstretched wings and variably-fused ocelli (Gorman and Girton, 1992, Genetics 131:99–112; Xu and Artavanis-Tsakonas, 1990, Genetics 126:665–677) which are not displayed by the parental $Ax^{9B2}$ mutant. Thus, both the genetic behavior of this mutation as well as its position within the ANK domain implicate this region in Notch/deltex interactions. Biochemical studies should provide insights into whether this mutation alters the affinity of deltex binding and/or interferes with requisite protein conformational changes.

FIG. 11 Methods: Genomic DNA was obtained by PCR and subcloned into Bluescript KS-(Stratagene). Several clones of at least two different PCR reactions were sequenced (both strands) by the dideoxy chain termination method (Sanger et al., 1977, Proc. Natl. Acad. Sci. U.S.A. 74:5463–5467) and covered nucleotides 2850 to 8880 (numbering based on Wharton et al., 1985, Cell 43:567–581). Eleven base-pair changes were discovered, three of which predicted amino acid substitutions. Of these, one at position 3584 corresponded to the previously described $Ax^{9B2}$ mutation (Kelly et al., 1987, Cell 51:539–548; Hartley et al., 1987, EMBO J. 6:3407–3417) and another at 7510 coincided with a formerly described strain polymorphism (Kidd et al., 1986, Mol. Cell. Biol. 6:3094–3108). A third base-pair change at position 6920 was taken to be the su42c mutation and was confirmed by direct sequencing of the PCR product.

7.6. DISCUSSION

We present three independent lines of evidence, the S2 cell assay, in vivo co-localization data, and the yeast 'interaction trap' assay, to demonstrate a specific interaction between deltex and the ANK repeats of the Notch intracellular domain. This reveals deltex to be the first cytoplasmic component of a postulated Notch signal transducing complex that also includes Delta and Serrate.

Although we have demonstrated that the ANK repeats are both necessary and sufficient to promote deltex binding, other regions of the intracellular domain may influence the Notch/deltex protein complex. This possibility is raised by the lethal interaction that results when deltex mutants also contain the Notch mutation notchoid[1](nd[1]), which is associated with missense mutations near the C terminus (Xu et al., 1990, Genes Dev. 4:464–475). Such influence would be reminiscent of that which occurs in the binding of cactus and dorsal, which are Drosophila counterparts of IκB and NF-κB, respectively. Although the ANK repeats of cactus bind to the centrally located Rel homology domain of dorsal, deletion analyses indicate that a region near the carboxy terminus of dorsal also is necessary to keep dorsal sequestered in the cytoplasm when it is bound to cactus (Kidd, 1992, Cell 71:623–635; Robbins et al., 1992, J. Virol. 66:2594–2599; Rushlow et al., 1989, Cell 59:1165–1177; Isoda et al., 1992, Genes Dev. 6:619–630; Norris and Manley, 1992, Genes Dev. 6:1657–1667).

Models analogous to those which have emerged from studies of IκB and NF-κB have been proposed recently to explain the activity of Notch family members (Kidd, 1992, Cell 71:623–635; LaMarco et al., 1991, Science 253:789–792; Kodoyianni et al., 1992, Molec. Biol. Cell 3:1199–1213): Notch may represent a novel IκB-like protein that, in response to an external stimulus, causes the dissociation of an ANK repeat-bound transcription factor, which is then transported into the nucleus. However, we find no evidence to support the possibility that deltex may be such a factor. In S2 cells expressing either the ECN or Δcdc10 deletion constructs (FIG. 8h, i) or in embryos and imaginal tissues over-expressing the deltex protein (see Section 6 and data not shown), we see no nuclear accumulation of deltex at the level of resolution provided by immunofluorescent microscopy (not shown). Truncations of Notch that delete the extracellular and transmembrane regions result in the production of an intracellular domain ($N^{nucl}$); that localizes within the nucleus (Fortini et al. Nature, in press; Struhl et al., 1993, Cell 74:331–345). Co-expression of deltex with $N^{nucl}$ in S2 cells did not prevent $N^{nucl}$ from translocating into the nucleus and deltex remained in the cytoplasm (not shown).

Molecular analyses have shown that the Abruptex alleles of Notch represent single amino acid substitutions clustering within six adjacent EGF-like repeats (Kelly et al., 1987, Cell 51:539–548; Hartley et al., 1987, EMBO 6:3407–3417). The phenotype produced by these gain-of-function alleles results in the differentiation of greater numbers of epidermal cells at the expense of neural cells (Heitzler and Simpson, 1993, Development 117:1113–1123) (so-called 'anti-neurogenic' phenotype (Palka et al., 1990, Development 109:167–175)), and contrasts with the opposite phenotype produced by loss-of-function Notch mutations. The underlying basis for the dominant phenotype produced by the Abruptex mutations is uncertain, although the phenotype is mimicked by truncated forms of Notch (Rebay et al., 1993, Cell 74:319–329; Struhl et al., 1993, Cell 74:331–345), suggesting that this is an activated form of the receptor. On the basis of genetic mosaic studies, Heitzler and Simpson (Heitzler and Simpson, 1993, Development 117:1113–1123) have suggested that Abruptex molecules may have an increased affinity for Delta, but do not constitute constitutively active forms of the receptor, as evidenced by their dependency upon the Delta ligand.

The mechanism by which certain heteroallelic combinations of Abruptex alleles 'negatively complement' to result in pupal lethality is uncertain. The conventional interpretation of this phenomenon is that Notch polypeptides interact with one another either as dimers or as part of multiprotein complexes (Foster, 1975, Genetics 81:99–120; Kelly et al., 1987, Cell 51:539–548), a notion that has precedents in a number of other receptor proteins (Ullrich and Schlessinger, 1990, Cell 61:203–212). Pupae of the negatively complementing genotype exhibit a severe loss of sensory bristles compared with Abruptex homozygotes (Foster, 1975, Genetics 81:99–120), which are fully viable. This would seem to suggest an even greater gain-of-function activity or 'antineurogenic' effect on the part of the negatively complementing alleles, the consequence of which is inviability. Reducing the gene dosage of either Delta, mastermind, or deltex suppresses both this lethality (Xu et al., 1990, Genes Dev. 4:464–475; Xu and Artavanis-Tsakonas, 1990, Genetics 126:665–677) and the sensory bristle loss. In the case of Delta and mastermind, both of which are neurogenic genes, restoration of viability and sensory bristles may result from a countervailing shift in the developmental equilibrium towards neural differentiation.

In light of our demonstration of a physical Notch/deltex interaction, the finding that lowering the gene dosage of deltex also attenuates the apparent 'hyperactivity' of the negatively complementing genotypes implies that deltex normally functions as a positive regulator of Notch activity. This notion is supported by other genetic evidence, namely, the lethal interactions that result from deltex and $nd^1$ (a hypomorphic allele) double mutants and from deltex mutants bearing only one wild-type copy of Notch (Xu and Artavanis-Tsakonas, 1990, Genetics 126:665–677). Also consistent with this idea is the observation that overexpression of deltex in wild-type flies reveals no apparent phenotypic consequences (see Section 6).

The fact that the deltex protein is of unique sequence (see Section 6) raises the possibility that deltex may define a new class of proteins implicated in cell signaling events. Given that the ANK repeats constitute the most conserved (~70% identity) portion among the various Notch homologs (Stifani et al., 1992, Nature Genetics 2:119–127) and that deltex interacts with these repeats, we expect that deltex cognates will exist in higher eukaryotes and that these may function through similar biochemical modes of action.

8. EXAMPLE: PORTIONS OF DELTEX WHICH MEDIATE HETEROTYPIC AND HOMOTYPIC BINDING

Using the interaction trap system as our assay (see Section 7.4) we systematically examined, by deletion analysis, the domains of Notch and deltex which are responsible for protein-protein interactions. Both deltex-deltex as well as deltex-Notch interactions were detected. Deletion constructs encoding various fragments (described below) of Drosophila deltex, Drosophila Notch and human Notch were expressed as fusion constructs (LexA or ACT fusions), and assayed.

The sequences of the fragments A–D (SEQ ID NOS:5, 6, 7, and 8, respectively) of Drosophila deltex which were expressed are shown in FIG. 14.

FIG. 13 summarizes the deltex-deltex interactions we have detected. Fragment A interacts with Fragment A (homotypic interactions). Fragment B interacts with Fragment B (homotypic interactions). Fragment C interacts with Fragment C (homotypic interactions). In addition, we detected interactions between fragments C and B. However, we can only detect the fragment C-B interaction if fragment C is tested as the "bait" (i.e., as the LexA fusion). If Fragment B is the bait, this interaction is not detected. All the other aforesaid interactions occur irrespective of which fragment is used as the bait. Fragment A consists of amino acids 1–303. Fragment B consists of amino acids 306–486. Fragment C consists of amino acids 514–737.

The heterotypic interaction between Notch and deltex is occurred between the ANK repeat region of Notch and fragment D of deltex (which is part of fragment A and includes amino acids 1–204). Drosophila Notch ANK repeats as well as the ANK repeats of both human Notch proteins (encoded by TAN-1 and hN) were tested in this interaction assay and showed positive binding to fragment D. The following fragments containing the ANK repeat region were used: Drosophila Notch amino acids: 1889–2076 (numbering per Wharton et al., 1985, Cell 43:567–581; see FIG. 17); Human Notch TAN-1 amino acids: 1826–2146 (see FIG. 17); Human Notch hN amino acids: 1772–2093 (see FIG. 17). All displayed interactions with fragment D. FIG. 15 summarizes schematically this interaction.

9. EXAMPLE: DELTEX CONTAINS A PUTATIVE SH3-BINDING DOMAIN

SH2 and SH3 domains are conserved protein modules so named based on their homology to the oncogene Src (Src Homology). These motifs have been implicated in mediating protein-protein interactions in a number of signal transduction pathways (reviewed in Cell 71:359–362; Science 252:668–674; Trends Cell Biol. 3:8–13; FEBS 307:55–61). Recently, a complementary motif that binds to the SH3 domain has been identified and called simply an 'SH3-binding domain' ("SH3-BD") (Science 259:1157–1161). The core binding region of SH3-BD is proline-rich and approximately ten residues in length. As shown in FIG. 16, this motif, as defined from a mouse protein that experimentally bound an SH3 domain, is shown aligned to two regions (separated by 58 residues) of deltex that may represent Drosophila versions of this motif. These regions are located centrally in the deltex protein, approximately 280 residues C-terminal to the region of deltex that has been shown to bind to the ANK repeats of Notch. For reference, regions of selected Drosophila proteins, which may also contain SH3-BD, are shown. The Son of sevenless (Sos) gene, in particular, is worth noting. The encoded protein, a putative guanine nucleotide exchange factor (GNEF), has been shown to bind to an 'adaptor' protein (drk) containing only SH2 and SH3 modules, although the actual residues that mediate binding have not been accurately defined (Cell 73:169–177 and 179–191).

There are currently only six SH3-containing proteins identified in Drosophila, any one of which may be a direct binding partner of deltex, and thus an indirect partner of Notch. These include the proteins encoded by the genes drk, src1, src2, abl, spectrin, and dlg. With the exception of spectrin, all encode signalling molecules. Spectrin encodes a protein associated with the cytoskeleton. Thus deltex may 'tie-in' Notch to already identified signalling components or to the cytoskeleton.

10. DEPOSIT OF MICROORGANISMS

Plasmid pCaSpeR hs-dx containing a cDNA insert encoding a full-length *Drosophila melanogaster* deltex was deposited on Jan. 20, 1994 with the American Type Culture Collection, 1201 Parklawn Drive, Rockville, Md. 20852, under the provisions of the Budapest Treaty on the International Recognition of the Deposit of Microorganisms for the Purposes of Patent Procedures and was assigned accession number 75640.

The present invention is not to be limited in scope by the microorganism deposited or the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A substantially purified deltex protein having the amino acid sequence depicted in FIG. 12 (SEQ ID NO:4).

2. A substantially purified protein comprising a fragment of a deltex protein, said deltex protein having the amino acid sequence depicted in FIG. 12 (SEQ ID NO:4), said fragment consisting of at least 20 continuous amino acids of the deltex protein.

3. A fragment of a deltex protein consisting of at least 10 continuous amino acids of a deltex protein, said deltex protein having the amino acid sequence depicted in FIG. 12 (SEQ ID NO:4), which fragment displays one or more functional activities associated with a full-length deltex protein.

4. The fragment of claim 3 which consists of at least 20 continuous amino acids of the deltex protein.

5. The substantially purified protein of claim 2 which is able to be bound by an antibody to said deltex protein.

6. The fragment of claim 3 which is able to be bound by an antibody to said deltex protein.

7. A substantially purified protein comprising a fragment of at least 20 continuous amino acids of a deltex protein, said deltex protein having the amino acid sequence depicted in FIG. 12 (SEQ ID NO:4), which fragment comprises a glutamine-rich cluster of the deltex protein.

8. A substantially purified protein comprising a fragment of a deltex protein, said deltex protein having the amino acid sequence depicted in FIG. 12 (SEQ ID NO:4), which fragment binds to a Notch protein or to a molecule comprising the cdc10/SW16/ankyrin repeats of a Notch protein.

9. A substantially purified protein comprising a fragment of a first deltex protein, which fragment binds to a second deltex protein or to a molecule comprising a fragment of a second deltex protein, said first and second deltex proteins each having the amino acid sequence depicted in FIG. 12 (SEQ ID NO:4).

10. A substantially purified protein comprising a fragment of a deltex protein, said deltex protein having the amino acid sequence depicted in FIG. 12 (SEQ ID NO:4), which fragment comprises a SH3 binding domain of the deltex protein.

11. A chimeric protein comprising a functionally active fragment of at least 20 continuous amino acids of a deltex protein joined via a peptide bond to an amino acid sequence of a protein other than the deltex protein, said deltex protein having the amino acid sequence depicted in FIG. 12 (SEQ ID NO:4).

12. The protein of claim 11 in which the fragment binds to a Notch protein or to a molecule comprising the cdc10/SW16/ankyrin repeats of a Notch protein.

13. The protein of claim 11 in which the fragment comprises an SH3 binding domain.

14. A derivative or analog of the protein of claim 1, which is characterized by the ability to be bound by an antibody to the protein of claim 1, wherein said antibody does not bind a glutamine-rich cluster of the protein of claim 1.

15. A peptide having an amino acid sequence in the range of 15-25 amino acids, said sequence being a portion of a deltex protein having the amino acid sequence depicted in FIG. 12 (SEQ ID NO:4).

16. A derivative or analog of the protein of claim 1, consisting of at least 20 continuous amino acids of the deltex protein, which is able to display one or more functional activities of the protein of claim 1.

17. A composition comprising a deltex protein having the amino acid sequence depicted in FIG. 12 (SEQ ID NO:4); and a pharmaceutically acceptable carrier.

18. A composition comprising the fragment of claim 3, and a pharmaceutically acceptable carrier.

19. A composition comprising the substantially purified protein of claim 8, and a pharmaceutically acceptable carrier.

20. A composition comprising the substantially purified protein of claim 9, and a pharmaceutically acceptable carrier.

21. A composition comprising the substantially purified protein of claim 10, and a pharmaceutically acceptable carrier.

22. A composition comprising the chimeric protein of claim 11, and a pharmaceutically acceptable carrier.

23. A composition comprising a derivative or analog of a deltex protein, said deltex protein having the amino acid sequence depicted in FIG. 12 (SEQ ID NO:4), which derivative or analog is characterized by the ability to bind to a Notch protein or to a molecule comprising the cdc10/SW16/ankyrin repeats of a Notch protein.

24. The fragment of claim 3 or 4 which is substantially purified.

25. The derivative or analog of claim 14 or 16 which is substantially purified.

26. The composition of claim 18 in which the fragment is substantially purified.

27. The composition of claim 23 in which the derivative or analog is substantially purified.

* * * * *